US011739134B2

(12) United States Patent
Blackwell et al.

(10) Patent No.: US 11,739,134 B2
(45) Date of Patent: Aug. 29, 2023

(54) LONG ACTING PEPTIDE TYROSINE TYROSINE (PYY) ANALOGS AND METHODS OF USE

(71) Applicant: Intarcia Therapeutics, Inc., Boston, MA (US)

(72) Inventors: William Blackwell, Boston, MA (US); Ved P. Srivastava, Boston, MA (US); James M. Way, Boston, MA (US)

(73) Assignee: Intarcia Therapeutics, Inc., Boston, MA (US)

( * ) Notice: Subject to any disclaimer, the term of this patent is extended or adjusted under 35 U.S.C. 154(b) by 0 days.

(21) Appl. No.: 17/233,111

(22) Filed: Apr. 16, 2021

(65) Prior Publication Data

US 2022/0002371 A1 Jan. 6, 2022

Related U.S. Application Data

(60) Provisional application No. 63/076,459, filed on Sep. 10, 2020, provisional application No. 63/011,649, filed on Apr. 17, 2020.

(51) Int. Cl.

*C07K 14/575* (2006.01)
*A61P 3/04* (2006.01)
*A61K 38/00* (2006.01)

(52) U.S. Cl.

CPC .............. *C07K 14/575* (2013.01); *A61P 3/04* (2018.01); *A61K 38/00* (2013.01)

(58) Field of Classification Search

None

See application file for complete search history.

(56) References Cited

FOREIGN PATENT DOCUMENTS

| | | | | |
|---|---|---|---|---|
| CN | 101065133 A | 10/2007 | | |
| WO | WO 2004/089279 A2 | 10/2004 | | |
| WO | WO 2006/066024 A2 | 6/2006 | | |
| WO | WO 2011/092473 A1 | 8/2011 | | |
| WO | WO 2012/101413 A1 | 8/2012 | | |
| WO | WO-2014178018 A1 | * 11/2014 | ......... A61K 38/1709 | |
| WO | WO 2015/177572 A1 | 11/2015 | | |
| WO | WO 2015/177573 A1 | 11/2015 | | |

OTHER PUBLICATIONS

Balasubramaniam et al., "Structure—Activity Studies Including a $\Psi(CH_2\text{-}NH)$ Scan of Peptide YY (PYY) Active Site, PYY(22-36), for Interaction with Rat Intestinal PYY Receptors: Development of Analogues with Potent in Vivo Activity in the Intestine", Journal of Medicinal Chemistry 43(18):3420-3427 (2000).

International Search Report and Written Opinion received for PCT Patent Application No. PCT/US2021/027759, dated Oct. 6, 2021, 14 pages.

* cited by examiner

*Primary Examiner* — Christina Bradley

(74) *Attorney, Agent, or Firm* — Lathrop GPM LLP; Brian C. Trinque

(57) ABSTRACT

This invention relates to isolated polypeptides that are long acting analogs of human PYY. The disclosed PYY analog polypeptides have beneficial physicochemical properties relative to endogenous PYY and known synthetic PYY analog polypeptides, such as longer (i.e., "long-acting") elimination half-lives ($t_{1/2}$), and improved solubility and thermal stability. This invention also relates to methods of using presently disclosed PYY analog polypeptides in a variety of therapeutic indications, as well as methods of producing the same. The disclosed PYY analog polypeptides are particularly useful in methods of treating metabolic diseases or disorders, such as type 2 diabetes, treating obesity, and providing weight loss, and in methods of treating nonalcoholic fatty liver disease (NAFLD) and/or nonalcoholic steatohepatitis (NASH).

20 Claims, 9 Drawing Sheets

Specification includes a Sequence Listing.

```
                        SEQUENCE LISTING


<160> NUMBER OF SEQ ID NOS: 814

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr


<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr


<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Pro Lys Pro Glu Ala Pro Gly Lys Asp Ala Ser Pro Glu Glu Trp Asn
1               5                   10                  15
```

Arg Tyr Tyr Ala Asp Leu Arg His Tyr Leu Asn Trp Leu Thr Arg Gln
20 25 30

Arg Tyr

<210> SEQ ID NO 4
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (35)..(35)
<223> OTHER INFORMATION: n-methylY

<400> SEQUENCE: 4

Lys Pro Lys Pro Glu Ala Pro Gly Lys Asp Ala Ser Pro Glu Glu Trp
1 5 10 15

Asn Arg Tyr Tyr Ala Asp Ala Arg His Tyr Leu Asn Trp Leu Thr Arg
20 25 30

Gln Arg Tyr
35

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: n-methylY

<400> SEQUENCE: 5

Pro Lys Pro Glu Ala Pro Gly Lys Asp Ala Ser Pro Glu Glu Trp Asn
1 5 10 15

Arg Tyr Tyr Ala Asp Ala Arg His Tyr Leu Asn Trp Leu Thr Arg Gln
20 25 30

Arg Tyr

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: n-methylY

<400> SEQUENCE: 6

Pro Lys Pro Lys Ala Pro Gly Lys Asp Ala Ser Pro Glu Glu Trp Asn
1 5 10 15

Arg Tyr Tyr Ala Asp Ala Arg His Tyr Leu Asn Trp Leu Thr Arg Gln
20 25 30

Arg Tyr

<210> SEQ ID NO 7
<211> LENGTH: 34
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (34)..(34)
<223> OTHER INFORMATION: n-methylY

<400> SEQUENCE: 7

```
Pro Lys Pro Glu Ala Pro Lys Lys Asp Ala Ser Pro Glu Glu Trp Asn
1               5                   10                  15

Arg Tyr Tyr Ala Asp Ala Arg His Tyr Leu Asn Trp Leu Thr Arg Gln
            20                  25                  30

Arg Tyr
```

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (34)..(34)
<223> OTHER INFORMATION: n-methylY

<400> SEQUENCE: 8

```
Pro Lys Pro Glu Ala Pro Gly Lys Asp Ala Ser Pro Lys Glu Trp Asn
1               5                   10                  15

Arg Tyr Tyr Ala Asp Ala Arg His Tyr Leu Asn Trp Leu Thr Arg Gln
            20                  25                  30

Arg Tyr
```

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (34)..(34)
<223> OTHER INFORMATION: n-methylY

<400> SEQUENCE: 9

```
Pro Lys Pro Glu Ala Pro Gly Lys Asp Ala Ser Pro Glu Glu Trp Lys
1               5                   10                  15

Arg Tyr Tyr Ala Asp Ala Arg His Tyr Leu Asn Trp Leu Thr Arg Gln
            20                  25                  30

Arg Tyr
```

<210> SEQ ID NO 10
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (34)..(34)
<223> OTHER INFORMATION: n-methylY

<400> SEQUENCE: 10

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr


<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Homotyrosine

<400> SEQUENCE: 11

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr


<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: D-amino acid

<400> SEQUENCE: 12

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr


<210> SEQ ID NO 13
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe


<210> SEQ ID NO 14
<211> LENGTH: 34
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: D-amino acid

<400> SEQUENCE: 14

Pro Lys Pro Glu Ala Pro Gly Lys Asp Ala Ser Pro Glu Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 15
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: D-amino acid

<400> SEQUENCE: 15

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe


<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Pro Lys Pro Glu Ala Pro Gly Lys Asp Ala Ser Pro Glu Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 17
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe
```

```
<210> SEQ ID NO 18
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: D-amino acid

<400> SEQUENCE: 18

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe


<210> SEQ ID NO 19
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Pro Lys Pro Glu Lys Pro Gly Lys Asp Ala Ser Pro Glu Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 20
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Pro Lys Pro Glu Ala Pro Gly Lys Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: D-amino acid

<400> SEQUENCE: 21

Pro Lys Pro Glu Ala Pro Gly Lys Asp Ala Ser Pro Glu Glu Trp Asn
1               5                   10                  15
```

```
Arg Tyr Tyr Lys Asp Leu Arg His Tyr Leu Asn Trp Leu Thr Arg Gln
            20                  25                  30

Arg Phe


<210> SEQ ID NO 22
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Dap

<400> SEQUENCE: 22

Pro Lys Pro Glu Ala Pro Gly Lys Asp Ala Ser Pro Glu Glu Trp Asn
1               5                   10                  15

Arg Tyr Tyr Xaa Asp Leu Arg His Tyr Leu Asn Trp Leu Thr Arg Gln
            20                  25                  30

Arg Phe


<210> SEQ ID NO 23
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Pro Lys Pro Glu Ala Pro Gly Lys Asp Ala Ser Pro Glu Glu Trp Gln
1               5                   10                  15

Arg Tyr Tyr Lys Asp Leu Arg His Tyr Leu Asn Trp Leu Thr Arg Gln
            20                  25                  30

Arg Phe


<210> SEQ ID NO 24
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 25
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Pro Lys Pro Glu Ala Pro Gly Lys Asp Ala Ser Pro Glu Glu Trp Ser
1               5                   10                  15
```

```
Arg Tyr Tyr Lys Asp Leu Arg His Tyr Leu Asn Trp Leu Thr Arg Gln
            20                  25                  30

Arg Phe


<210> SEQ ID NO 26
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Pro Lys Pro Glu Ala Pro Gly Lys Asp Ala Ser Pro Glu Glu Trp Thr
1               5                   10                  15

Arg Tyr Tyr Lys Asp Leu Arg His Tyr Leu Asn Trp Leu Thr Arg Gln
            20                  25                  30

Arg Phe


<210> SEQ ID NO 27
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Pro Lys Pro Glu Lys Pro Gly Lys Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 28
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Pro Lys Pro Glu Lys Pro Gly Lys Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 29
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Pro Lys Pro Glu Lys Pro Gly Glu Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30
```

```
Arg Phe


<210> SEQ ID NO 30
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: homoSer

<400> SEQUENCE: 30

Pro Lys Pro Glu Ala Pro Gly Lys Asp Ala Ser Pro Glu Glu Trp Ser
1               5                   10                  15

Arg Tyr Tyr Lys Asp Leu Arg His Tyr Leu Asn Trp Leu Thr Arg Gln
            20                  25                  30

Arg Phe


<210> SEQ ID NO 31
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: alpha-methyl-Ser

<400> SEQUENCE: 31

Pro Lys Pro Glu Ala Pro Gly Lys Asp Ala Ser Pro Glu Glu Trp Ser
1               5                   10                  15

Arg Tyr Tyr Lys Asp Leu Arg His Tyr Leu Asn Trp Leu Thr Arg Gln
            20                  25                  30

Arg Phe


<210> SEQ ID NO 32
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 33
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33
```

```
Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 34
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Pro Lys Pro Glu Lys Pro Gly Glu Asp Ala Ser Pro Lys Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 35
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Pro Lys Pro Glu Lys Pro Gly Glu Asp Ala Ser Pro Lys Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Pro Lys Pro Glu Lys Pro Gly Glu Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 37
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Pro Lys Pro Glu Lys Pro Gly Lys Asp Ala Ser Pro Lys Glu Trp Asn
1               5                   10                  15
```

```
Arg Tyr Tyr Lys Asp Leu Arg His Tyr Leu Asn Trp Leu Thr Arg Gln
            20                  25                  30

Arg Phe


<210> SEQ ID NO 38
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Pro Lys Pro Glu Lys Pro Gly Glu Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 39
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Pro Lys Pro Glu Lys Pro Gly Lys Asp Ala Ser Pro Lys Glu Trp Glu
1               5                   10                  15

Arg Tyr Tyr Lys Asp Leu Arg His Tyr Leu Asn Trp Leu Thr Arg Gln
            20                  25                  30

Arg Phe


<210> SEQ ID NO 40
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Pro Lys Pro Glu Lys Pro Gly Lys Asp Ala Ser Pro Lys Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 41
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Pro Lys Pro Glu Ala Pro Gly Lys Asp Ala Ser Pro Glu Glu Trp Glu
1               5                   10                  15

Arg Tyr Tyr Lys Asp Leu Arg His Tyr Leu Asn Trp Leu Thr Arg Gln
            20                  25                  30
```

Arg Phe

<210> SEQ ID NO 42
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Pro Lys Pro Glu Ala Pro Gly Lys Asp Ala Ser Pro Glu Glu Trp Asp
1 5 10 15

Arg Tyr Tyr Lys Asp Leu Arg His Tyr Leu Asn Trp Leu Thr Arg Gln
20 25 30

Arg Phe

<210> SEQ ID NO 43
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

Pro Lys Pro Glu Ala Pro Gly Lys Asp Ala Ser Pro Glu Glu Trp Lys
1 5 10 15

Arg Tyr Tyr Glu Asp Leu Arg His Tyr Leu Asn Trp Leu Thr Arg Gln
20 25 30

Arg Phe

<210> SEQ ID NO 44
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

Pro Lys Pro Glu Ala Pro Gly Lys Asp Ala Ser Pro Glu Glu Trp Lys
1 5 10 15

Arg Tyr Tyr Asp Asp Leu Arg His Tyr Leu Asn Trp Leu Thr Arg Gln
20 25 30

Arg Phe

<210> SEQ ID NO 45
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Pro Lys Pro Glu Ala Pro Gly Lys Asp Ala Ser Pro Lys Glu Trp Asp
1 5 10 15

Arg Tyr Tyr Lys Asp Leu Arg His Tyr Leu Asn Trp Leu Thr Arg Gln
20 25 30

Arg Phe

<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Pro Lys Pro Glu Ala Pro Gly Lys Lys Ala Ser Pro Glu Glu Trp Asp
1 5 10 15

Arg Tyr Tyr Lys Asp Leu Arg His Tyr Leu Asn Trp Leu Thr Arg Gln
20 25 30

Arg Phe

<210> SEQ ID NO 47
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Pro Lys Pro Glu Ala Pro Gly Lys Asp Ala Ser Pro Glu Glu Trp Asp
1 5 10 15

Arg Tyr Tyr Lys Asp Asp Arg His Tyr Lys Asn Trp Leu Thr Arg Gln
20 25 30

Arg Phe

<210> SEQ ID NO 48
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Pro Lys Pro Glu Ala Pro Gly Lys Asp Ala Ser Pro Glu Glu Trp Asp
1 5 10 15

Arg Tyr Tyr Lys Asp Lys Arg His Tyr Glu Asn Trp Leu Thr Arg Gln
20 25 30

Arg Phe

<210> SEQ ID NO 49
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: Beta-homo-Tyr

<400> SEQUENCE: 49

Pro Lys Pro Glu Ala Pro Gly Lys Asp Ala Ser Pro Glu Glu Trp Asn
1 5 10 15

Arg Tyr Tyr Ala Asp Leu Arg His Tyr Leu Asn Trp Leu Thr Arg Gln
20 25 30

Arg Tyr

<210> SEQ ID NO 50
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Lys
            20                  25                  30

Arg Phe
```

<210> SEQ ID NO 51
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Lys Trp Leu Thr Arg Gln
            20                  25                  30

Arg Phe
```

<210> SEQ ID NO 52
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Pro Lys Pro Glu Ala Pro Gly Lys Asp Ala Ser Pro Glu Glu Trp Asn
1               5                   10                  15

Arg Tyr Tyr Ala Asp Leu Arg His Lys Leu Asn Trp Leu Thr Arg Gln
            20                  25                  30

Arg Phe
```

<210> SEQ ID NO 53
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Pro Lys Pro Glu Ala Pro Gly Lys Asp Ala Ser Pro Glu Glu Trp Asn
1               5                   10                  15

Arg Tyr Tyr Ala Asp Leu Lys His Tyr Leu Asn Trp Leu Thr Arg Gln
            20                  25                  30

Arg Phe
```

<210> SEQ ID NO 54
<211> LENGTH: 34

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Pro Lys Pro Glu Ala Pro Gly Lys Asp Ala Ser Pro Glu Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 55
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Pro Lys Pro Glu Ala Pro Gly Lys Asp Ala Ser Pro Glu Glu Trp Lys
1               5                   10                  15

Arg Tyr Tyr Ala Asp Leu Arg His Tyr Leu Asn Trp Leu Thr Arg Gln
            20                  25                  30

Arg Phe


<210> SEQ ID NO 56
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: 4-pyridylAla

<400> SEQUENCE: 56

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Ala


<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: 3-pyridylAla

<400> SEQUENCE: 57

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30
```

Arg Ala

<210> SEQ ID NO 58
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: 4-methylPhe

<400> SEQUENCE: 58

Pro Lys Pro Glu Ala Pro Gly Lys Asp Ala Ser Pro Glu Glu Trp Asn
1 5 10 15

Arg Tyr Tyr Ala Asp Leu Arg His Tyr Leu Asn Trp Leu Thr Arg Gln
20 25 30

Arg Phe

<210> SEQ ID NO 59
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: 4-carboxyPhe

<400> SEQUENCE: 59

Pro Lys Pro Glu Ala Pro Gly Lys Asp Ala Ser Pro Glu Glu Trp Asn
1 5 10 15

Arg Tyr Tyr Ala Asp Leu Arg His Tyr Leu Asn Trp Leu Thr Arg Gln
20 25 30

Arg Phe

<210> SEQ ID NO 60
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: 4-fluoroPhe

<400> SEQUENCE: 60

Pro Lys Pro Glu Ala Pro Gly Lys Asp Ala Ser Pro Glu Glu Trp Asn
1 5 10 15

Arg Tyr Tyr Ala Asp Leu Arg His Tyr Leu Asn Trp Leu Thr Arg Gln
20 25 30

Arg Phe

<210> SEQ ID NO 61
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

```
<220> FEATURE:
<221> NAME/KEY: MOD_RES
<222> LOCATION: (34)..(34)
<223> OTHER INFORMATION: Homo-Phe

<400> SEQUENCE: 61

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe


<210> SEQ ID NO 62
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: n-methylPhe

<400> SEQUENCE: 62

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe


<210> SEQ ID NO 63
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: n-methylTyr

<400> SEQUENCE: 63

Pro Lys Pro Glu Ala Pro Lys Lys Asp Ala Ser Pro Glu Glu Leu Asn
1               5                   10                  15

Arg Tyr Tyr Ala Asp Ala Arg His Tyr Leu Asn Trp Leu Thr Arg Gln
            20                  25                  30

Arg Tyr


<210> SEQ ID NO 64
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Pro Lys Pro Glu Ala Pro Lys Lys Asp Ala Ser Pro Glu Glu Leu Asn
1               5                   10                  15

Arg Tyr Tyr Ala Asp Ala Arg His Tyr Leu Asn Trp Leu Thr Arg Gln
            20                  25                  30

Arg Phe
```

<210> SEQ ID NO 65
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (20)..(20)
<223> OTHER INFORMATION: D-amino acid

<400> SEQUENCE: 65

```
Pro Lys Pro Glu Ala Pro Gly Lys Asp Ala Ser Pro Glu Glu Trp Asn
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 66
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Pro Lys Pro Glu Ala Pro Gly Lys Asp Lys Ser Pro Glu Glu Trp Asn
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 67
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Pro Lys Pro Glu Ala Pro Gly Lys Asp Ala Ser Pro Glu Lys Trp Asn
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 68
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Pro Lys Pro Glu Ala Pro Gly Lys Asp Ala Ser Pro Glu Glu Trp Asn
1               5                   10                  15

Arg Lys Tyr Lys Asp Leu Arg His Tyr Leu Asn Trp Leu Thr Arg Gln
            20                  25                  30
```

Arg Phe

<210> SEQ ID NO 69
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Pro Lys Pro Glu Ala Pro Gly Lys Asp Ala Ser Pro Glu Glu Trp Asn
1               5                   10                  15

Arg Tyr Lys Lys Asp Leu Arg His Tyr Leu Asn Trp Leu Thr Arg Gln
            20                  25                  30

Arg Phe

<210> SEQ ID NO 70
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Pro Lys Pro Glu Lys Pro Gly Lys Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe

<210> SEQ ID NO 71
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Pro Lys Pro Glu Lys Pro Gly Lys Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe

<210> SEQ ID NO 72
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

Pro Lys Pro Glu Lys Pro Gly Glu Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe

<210> SEQ ID NO 73
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Pro Lys Pro Glu Ala Pro Gly Lys Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 74
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Pro Lys Pro Glu Lys Pro Gly Lys Asp Ala Ser Pro Glu Glu Trp Asn
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 75
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Pro Lys Pro Glu Lys Pro Gly Lys Asp Ala Ser Pro Glu Glu Trp Ser
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 76
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Pro Lys Pro Glu Ala Pro Gly Lys Asp Ala Ser Pro Lys Glu Trp Asp
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 77
<211> LENGTH: 34
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 77

Pro Lys Pro Glu Lys Pro Gly Glu Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 78
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Pro Lys Pro Glu Lys Pro Gly Glu Asp Ala Ser Pro Lys Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 79

<400> SEQUENCE: 79

000


<210> SEQ ID NO 80

<400> SEQUENCE: 80

000


<210> SEQ ID NO 81

<400> SEQUENCE: 81

000


<210> SEQ ID NO 82

<400> SEQUENCE: 82

000


<210> SEQ ID NO 83

<400> SEQUENCE: 83

000


<210> SEQ ID NO 84

<400> SEQUENCE: 84

000


<210> SEQ ID NO 85
```

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: K or absent
<220> FEATURE:
<221> NAME/KEY: MOD_RES
<222> LOCATION: (5)..(5)
<223> OTHER INFORMATION: E or K
<220> FEATURE:
<221> NAME/KEY: MOD_RES
<222> LOCATION: (6)..(6)
<223> OTHER INFORMATION: A or K
<220> FEATURE:
<221> NAME/KEY: MOD_RES
<222> LOCATION: (8)..(8)
<223> OTHER INFORMATION: G or K
<220> FEATURE:
<221> NAME/KEY: MOD_RES
<222> LOCATION: (9)..(9)
<223> OTHER INFORMATION: E, K, or k
<220> FEATURE:
<221> NAME/KEY: MOD_RES
<222> LOCATION: (10)..(10)
<223> OTHER INFORMATION: D or K
<220> FEATURE:
<221> NAME/KEY: MOD_RES
<222> LOCATION: (11)..(11)
<223> OTHER INFORMATION: A or K
<220> FEATURE:
<221> NAME/KEY: MOD_RES
<222> LOCATION: (14)..(14)
<223> OTHER INFORMATION: E or K
<220> FEATURE:
<221> NAME/KEY: MOD_RES
<222> LOCATION: (15)..(15)
<223> OTHER INFORMATION: E or K
<220> FEATURE:
<221> NAME/KEY: MOD_RES
<222> LOCATION: (16)..(16)

```
<223> OTHER INFORMATION: L or W
<220> FEATURE:
<221> NAME/KEY: MOD_RES
<222> LOCATION: (17)..(17)
<223> OTHER INFORMATION: D, E, K, N, Q, S, T, alpha-methylserine, or
      homoserine
<220> FEATURE:
<221> NAME/KEY: MOD_RES
<222> LOCATION: (19)..(19)
<223> OTHER INFORMATION: K or Y
<220> FEATURE:
<221> NAME/KEY: MOD_RES
<222> LOCATION: (20)..(20)
<223> OTHER INFORMATION: K or Y
<220> FEATURE:
<221> NAME/KEY: MOD_RES
<222> LOCATION: (21)..(21)
<223> OTHER INFORMATION: A, D, E, K, k, or Dap
<220> FEATURE:
<221> NAME/KEY: MOD_RES
<222> LOCATION: (23)..(23)
<223> OTHER INFORMATION: A, D, K, or L
<220> FEATURE:
<221> NAME/KEY: MOD_RES
<222> LOCATION: (24)..(24)
<223> OTHER INFORMATION: K or R
<220> FEATURE:
<221> NAME/KEY: MOD_RES
<222> LOCATION: (26)..(26)
<223> OTHER INFORMATION: K or Y
<220> FEATURE:
<221> NAME/KEY: MOD_RES
<222> LOCATION: (27)..(27)
<223> OTHER INFORMATION: E, K, or L
<220> FEATURE:
<221> NAME/KEY: MOD_RES
<222> LOCATION: (28)..(28)
<223> OTHER INFORMATION: K or N
<220> FEATURE:
<221> NAME/KEY: MOD_RES
<222> LOCATION: (33)..(33)
<223> OTHER INFORMATION: K or Q
<220> FEATURE:
<221> NAME/KEY: MOD_RES
<222> LOCATION: (35)..(35)
<223> OTHER INFORMATION: F, y, 3-pyridinylalanine, 4-pyridinylalanine,
      4-carboxyphenylalanine, 4-fluorophenylalanine,
      4-methylphenylalanine, N-methylphenylalanine,
      homophenylalanine, beta-homotyrosine,
<220> FEATURE:
<221> NAME/KEY: MOD_RES
<222> LOCATION: (35)..(35)
<223> OTHER INFORMATION: CONT. FROM ABOVE: homotyrosine, or
      N-methyltyrosine
<220> FEATURE:
<223> OTHER INFORMATION: See specification as filed for detailed
      description of substitutions and preferred embodiments

<400> SEQUENCE: 90

Xaa Pro Lys Pro Xaa Xaa Pro Xaa Xaa Xaa Xaa Ser Pro Xaa Xaa Xaa
1               5                   10                  15

Xaa Arg Xaa Xaa Xaa Asp Xaa Xaa His Xaa Xaa Xaa Trp Leu Thr Arg
            20                  25                  30

Xaa Arg Xaa
        35


<210> SEQ ID NO 91
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

<222> LOCATION: (5)..(5)
<223> OTHER INFORMATION: A or K
<220> FEATURE:
<221> NAME/KEY: MOD_RES
<222> LOCATION: (7)..(7)
<223> OTHER INFORMATION: G or K
<220> FEATURE:
<221> NAME/KEY: MOD_RES
<222> LOCATION: (8)..(8)
<223> OTHER INFORMATION: E, K, or k
<220> FEATURE:
<221> NAME/KEY: MOD_RES
<222> LOCATION: (13)..(13)
<223> OTHER INFORMATION: E or K
<220> FEATURE:
<221> NAME/KEY: MOD_RES
<222> LOCATION: (15)..(15)
<223> OTHER INFORMATION: L or W
<220> FEATURE:
<221> NAME/KEY: MOD_RES
<222> LOCATION: (16)..(16)
<223> OTHER INFORMATION: D, E, K, N, S, alpha-methylserine, or homoserine
<220> FEATURE:
<221> NAME/KEY: MOD_RES
<222> LOCATION: (20)..(20)
<223> OTHER INFORMATION: A, D, E, K, or k,
<220> FEATURE:
<221> NAME/KEY: MOD_RES
<222> LOCATION: (22)..(22)
<223> OTHER INFORMATION: A or L
<220> FEATURE:
<221> NAME/KEY: MOD_RES
<222> LOCATION: (34)..(34)
<223> OTHER INFORMATION: F, 3-pyridinylalanine, 4-pyridinylalanine, 4-carboxyphenylalanine, 4-fluorophenylalanine, 4-methylphenylalanine, N-methylphenylalanine, homophenylalanine, beta-homotyrosine,
<220> FEATURE:
<221> NAME/KEY: MOD_RES
<222> LOCATION: (34)..(34)
<223> OTHER INFORMATION: CONT. FROM ABOVE: homotyrosine, or N-methyltyrosine
<220> FEATURE:
<223> OTHER INFORMATION: See specification as filed for detailed description of substitutions and preferred embodiments

<400> SEQUENCE: 91

```
Pro Lys Pro Glu Xaa Pro Xaa Xaa Asp Ala Ser Pro Xaa Glu Xaa Xaa
1               5                   10                  15

Arg Tyr Tyr Xaa Asp Xaa Arg His Tyr Leu Asn Trp Leu Thr Arg Gln
            20                  25                  30

Arg Xaa
```

<210> SEQ ID NO 92
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (5)..(5)
<223> OTHER INFORMATION: A or K
<220> FEATURE:
<221> NAME/KEY: MOD_RES
<222> LOCATION: (7)..(7)
<223> OTHER INFORMATION: G or K
<220> FEATURE:
<221> NAME/KEY: MOD_RES
<222> LOCATION: (8)..(8)
<223> OTHER INFORMATION: E, K, or k
<220> FEATURE:
<221> NAME/KEY: MOD_RES
<222> LOCATION: (13)..(13)
<223> OTHER INFORMATION: E or K
<220> FEATURE:
<221> NAME/KEY: MOD_RES
<222> LOCATION: (15)..(15)
<223> OTHER INFORMATION: L or W
<220> FEATURE:
<221> NAME/KEY: MOD_RES
<222> LOCATION: (16)..(16)
<223> OTHER INFORMATION: D, E, K, S, alpha-methylserine, or homoserine
<220> FEATURE:
<221> NAME/KEY: MOD_RES
<222> LOCATION: (20)..(20)
<223> OTHER INFORMATION: A, D, E, K, or k
<220> FEATURE:
<221> NAME/KEY: MOD_RES
<222> LOCATION: (22)..(22)
<223> OTHER INFORMATION: A or L
<220> FEATURE:
<221> NAME/KEY: MOD_RES
<222> LOCATION: (34)..(34)
<223> OTHER INFORMATION: F, 3-pyridinylalanine, 4-pyridinylalanine, 4-carboxyphenylalanine, 4-fluorophenylalanine, 4-methylphenylalanine, N-methylphenylalanine, homophenylalanine, beta-homotyrosine,
<220> FEATURE:
<221> NAME/KEY: MOD_RES
<222> LOCATION: (34)..(34)
<223> OTHER INFORMATION: CONT. FROM ABOVE: homotyrosine, or N-methyltyrosine
<220> FEATURE:
<223> OTHER INFORMATION: See specification as filed for detailed description of substitutions and preferred embodiments

<400> SEQUENCE: 92

```
Pro Lys Pro Glu Xaa Pro Xaa Xaa Asp Ala Ser Pro Xaa Glu Xaa Xaa
1               5                   10                  15

Arg Tyr Tyr Xaa Asp Xaa Arg His Tyr Leu Asn Trp Leu Thr Arg Gln
            20                  25                  30

Arg Xaa
```

<210> SEQ ID NO 93
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (5)..(5)
<223> OTHER INFORMATION: A or K
<220> FEATURE:
<221> NAME/KEY: MOD_RES
<222> LOCATION: (7)..(7)
<223> OTHER INFORMATION: G or K
<220> FEATURE:
<221> NAME/KEY: MOD_RES
<222> LOCATION: (8)..(8)
<223> OTHER INFORMATION: E, K, or k
<220> FEATURE:
<221> NAME/KEY: MOD_RES
<222> LOCATION: (13)..(13)
<223> OTHER INFORMATION: E or K
<220> FEATURE:
<221> NAME/KEY: MOD_RES
<222> LOCATION: (15)..(15)
<223> OTHER INFORMATION: L or W
<220> FEATURE:
<221> NAME/KEY: MOD_RES
<222> LOCATION: (16)..(16)
<223> OTHER INFORMATION: D, E, K, N, S, alpha-methylserine, or homoserine
<220> FEATURE:
<221> NAME/KEY: MOD_RES
<222> LOCATION: (20)..(20)
<223> OTHER INFORMATION: D, E, K, or k,
<220> FEATURE:
<221> NAME/KEY: MOD_RES
<222> LOCATION: (22)..(22)
<223> OTHER INFORMATION: A or L
<220> FEATURE:
<221> NAME/KEY: MOD_RES
<222> LOCATION: (34)..(34)
<223> OTHER INFORMATION: F, 3-pyridinylalanine, 4-pyridinylalanine, 4-carboxyphenylalanine, 4-fluorophenylalanine, 4-methylphenylalanine, N-methylphenylalanine, homophenylalanine, beta-homotyrosine,
<220> FEATURE:
<221> NAME/KEY: MOD_RES
<222> LOCATION: (34)..(34)
<223> OTHER INFORMATION: CONT. FROM ABOVE: homotyrosine, or N-methyltyrosine
<220> FEATURE:
<223> OTHER INFORMATION: See specification as filed for detailed description of substitutions and preferred embodiments

<400> SEQUENCE: 93

Pro Lys Pro Glu Xaa Pro Xaa Xaa Asp Ala Ser Pro Xaa Glu Xaa Xaa
1 5 10 15

Arg Tyr Tyr Xaa Asp Xaa Arg His Tyr Leu Asn Trp Leu Thr Arg Gln
20 25 30

Arg Xaa

<210> SEQ ID NO 94
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (5)..(5)
<223> OTHER INFORMATION: A or K
<220> FEATURE:
<221> NAME/KEY: MOD_RES
<222> LOCATION: (8)..(8)
<223> OTHER INFORMATION: E, K, or k
<220> FEATURE:
<221> NAME/KEY: MOD_RES
<222> LOCATION: (13)..(13)
<223> OTHER INFORMATION: E or K
<220> FEATURE:
<221> NAME/KEY: MOD_RES
<222> LOCATION: (16)..(16)
<223> OTHER INFORMATION: D, E, K, or N
<220> FEATURE:
<221> NAME/KEY: MOD_RES
<222> LOCATION: (20)..(20)
<223> OTHER INFORMATION: A, D, E, K, or k,
<220> FEATURE:
<221> NAME/KEY: MOD_RES
<222> LOCATION: (22)..(22)
<223> OTHER INFORMATION: A or L
<220> FEATURE:
<221> NAME/KEY: MOD_RES
<222> LOCATION: (34)..(34)
<223> OTHER INFORMATION: F or N-methyltyrosine
<220> FEATURE:
<223> OTHER INFORMATION: See specification as filed for detailed description of substitutions and preferred embodiments

<400> SEQUENCE: 94

Pro Lys Pro Glu Xaa Pro Gly Xaa Asp Ala Ser Pro Xaa Glu Trp Xaa
1 5 10 15

Arg Tyr Tyr Xaa Asp Xaa Arg His Tyr Leu Asn Trp Leu Thr Arg Gln
20 25 30

Arg Xaa

<210> SEQ ID NO 95
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (5)..(5)
<223> OTHER INFORMATION: A or K
<220> FEATURE:
<221> NAME/KEY: MOD_RES
<222> LOCATION: (13)..(13)
<223> OTHER INFORMATION: E or K
<220> FEATURE:
<221> NAME/KEY: MOD_RES
<222> LOCATION: (16)..(16)
<223> OTHER INFORMATION: D, E, K, or N
<220> FEATURE:
<221> NAME/KEY: MOD_RES
<222> LOCATION: (20)..(20)
<223> OTHER INFORMATION: A, D, E, K, or k
<220> FEATURE:
<223> OTHER INFORMATION: See specification as filed for detailed description of substitutions and preferred embodiments

<400> SEQUENCE: 95

```
Pro Lys Pro Glu Xaa Pro Gly Lys Asp Ala Ser Pro Xaa Glu Trp Xaa
1               5                   10                  15

Arg Tyr Tyr Xaa Asp Leu Arg His Tyr Leu Asn Trp Leu Thr Arg Gln
            20                  25                  30

Arg Phe
```

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 34

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr
```

<210> SEQ ID NO 102

<400> SEQUENCE: 102

000

<210> SEQ ID NO 103

<400> SEQUENCE: 103

000

<210> SEQ ID NO 104
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: n-methylY

<400> SEQUENCE: 104

```
Lys Pro Lys Pro Glu Ala Pro Gly Lys Asp Ala Ser Pro Glu Glu Trp
1               5                   10                  15

Asn Arg Tyr Tyr Ala Asp Ala Arg His Tyr Leu Asn Trp Leu Thr Arg
            20                  25                  30

Gln Arg Tyr
        35
```

<210> SEQ ID NO 105
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: n-methylY

<400> SEQUENCE: 105

```
Pro Lys Pro Glu Ala Pro Gly Lys Asp Ala Ser Pro Glu Glu Trp Asn
1               5                   10                  15

Arg Tyr Tyr Ala Asp Ala Arg His Tyr Leu Asn Trp Leu Thr Arg Gln
            20                  25                  30

Arg Tyr
```

<210> SEQ ID NO 106

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: n-methylY

<400> SEQUENCE: 106

Pro Lys Pro Lys Ala Pro Gly Lys Asp Ala Ser Pro Glu Glu Trp Asn
1               5                   10                  15

Arg Tyr Tyr Ala Asp Ala Arg His Tyr Leu Asn Trp Leu Thr Arg Gln
            20                  25                  30

Arg Tyr


<210> SEQ ID NO 107
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: n-methylY

<400> SEQUENCE: 107

Pro Lys Pro Glu Ala Pro Lys Lys Asp Ala Ser Pro Glu Glu Trp Asn
1               5                   10                  15

Arg Tyr Tyr Ala Asp Ala Arg His Tyr Leu Asn Trp Leu Thr Arg Gln
            20                  25                  30

Arg Tyr


<210> SEQ ID NO 108
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: n-methylY

<400> SEQUENCE: 108

Pro Lys Pro Glu Ala Pro Gly Lys Asp Ala Ser Pro Lys Glu Trp Asn
1               5                   10                  15

Arg Tyr Tyr Ala Asp Ala Arg His Tyr Leu Asn Trp Leu Thr Arg Gln
            20                  25                  30

Arg Tyr


<210> SEQ ID NO 109
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: n-methylY
```

<400> SEQUENCE: 109

```
Pro Lys Pro Glu Ala Pro Gly Lys Asp Ala Ser Pro Glu Glu Trp Lys
1               5                   10                  15

Arg Tyr Tyr Ala Asp Ala Arg His Tyr Leu Asn Trp Leu Thr Arg Gln
            20                  25                  30

Arg Tyr
```

<210> SEQ ID NO 110
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: n-methylY

<400> SEQUENCE: 110

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr
```

<210> SEQ ID NO 111
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: Homotyrosine

<400> SEQUENCE: 111

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr
```

<210> SEQ ID NO 112
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: D-amino acid

<400> SEQUENCE: 112

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr
```

<210> SEQ ID NO 113
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe
```

<210> SEQ ID NO 114
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (20)..(20)
<223> OTHER INFORMATION: D-amino acid

<400> SEQUENCE: 114

```
Pro Lys Pro Glu Ala Pro Gly Lys Asp Ala Ser Pro Glu Glu Trp Asn
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 115
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (8)..(8)
<223> OTHER INFORMATION: D-amino acid

<400> SEQUENCE: 115

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe
```

<210> SEQ ID NO 116
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

```
Pro Lys Pro Glu Ala Pro Gly Lys Asp Ala Ser Pro Glu Glu Trp Asn
1               5                   10                  15
```

```
Arg Tyr Tyr Lys Asp Leu Arg His Tyr Leu Asn Trp Leu Thr Arg Gln
            20                  25                  30

Arg Phe


<210> SEQ ID NO 117

<400> SEQUENCE: 117

000


<210> SEQ ID NO 118

<400> SEQUENCE: 118

000


<210> SEQ ID NO 119
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Pro Lys Pro Glu Lys Pro Gly Lys Asp Ala Ser Pro Glu Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 120
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Pro Lys Pro Glu Ala Pro Gly Lys Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 121

<400> SEQUENCE: 121

000


<210> SEQ ID NO 122
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Dap

<400> SEQUENCE: 122
```

```
Pro Lys Pro Glu Ala Pro Gly Lys Asp Ala Ser Pro Glu Glu Trp Asn
1               5                   10                  15

Arg Tyr Tyr Xaa Asp Leu Arg His Tyr Leu Asn Trp Leu Thr Arg Gln
            20                  25                  30

Arg Phe


<210> SEQ ID NO 123
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Pro Lys Pro Glu Ala Pro Gly Lys Asp Ala Ser Pro Glu Glu Trp Gln
1               5                   10                  15

Arg Tyr Tyr Lys Asp Leu Arg His Tyr Leu Asn Trp Leu Thr Arg Gln
            20                  25                  30

Arg Phe


<210> SEQ ID NO 124
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 125
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Pro Lys Pro Glu Ala Pro Gly Lys Asp Ala Ser Pro Glu Glu Trp Ser
1               5                   10                  15

Arg Tyr Tyr Lys Asp Leu Arg His Tyr Leu Asn Trp Leu Thr Arg Gln
            20                  25                  30

Arg Phe


<210> SEQ ID NO 126
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Pro Lys Pro Glu Ala Pro Gly Lys Asp Ala Ser Pro Glu Glu Trp Thr
1               5                   10                  15
```

```
Arg Tyr Tyr Lys Asp Leu Arg His Tyr Leu Asn Trp Leu Thr Arg Gln
            20                  25                  30

Arg Phe


<210> SEQ ID NO 127
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Pro Lys Pro Glu Lys Pro Gly Lys Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 128

<400> SEQUENCE: 128

000


<210> SEQ ID NO 129
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Pro Lys Pro Glu Lys Pro Gly Glu Asp Ala Ser Pro Lys Glu Trp Asn
1               5                   10                  15

Arg Tyr Tyr Lys Asp Leu Arg His Tyr Leu Asn Trp Leu Thr Arg Gln
            20                  25                  30

Arg Phe


<210> SEQ ID NO 130
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: HomoSer

<400> SEQUENCE: 130

Pro Lys Pro Glu Ala Pro Gly Lys Asp Ala Ser Pro Glu Glu Trp Ser
1               5                   10                  15

Arg Tyr Tyr Lys Asp Leu Arg His Tyr Leu Asn Trp Leu Thr Arg Gln
            20                  25                  30

Arg Phe


<210> SEQ ID NO 131
<211> LENGTH: 34
<212> TYPE: PRT
<213> ORGANISM: Artificial Sequence
```

<220> FEATURE:
<223> OTHER INFORMATION: Description of Artificial Sequence: Synthetic polypeptide
<220> FEATURE:
<221> NAME/KEY: MOD_RES
<222> LOCATION: (16)..(16)
<223> OTHER INFORMATION: alpha-methyl-Ser

<400> SEQUENCE: 131

```
Pro Lys Pro Glu Ala Pro Gly Lys Asp Ala Ser Pro Glu Glu Trp Ser
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 132

<400> SEQUENCE: 132

000

<210> SEQ ID NO 133

<400> SEQUENCE: 133

000

<210> SEQ ID NO 134
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

```
Pro Lys Pro Glu Lys Pro Gly Glu Asp Ala Ser Pro Lys Glu Trp Asp
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 139

Pro Lys Pro Glu Lys Pro Gly Lys Asp Ala Ser Pro Lys Glu Trp Glu
1 5 10 15

Arg Tyr Tyr Lys Asp Leu Arg His Tyr Leu Asn Trp Leu Thr Arg Gln
20 25 30

Arg Phe

<210> SEQ ID NO 140
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 140

Pro Lys Pro Glu Lys Pro Gly Lys Asp Ala Ser Pro Lys Glu Trp Asp
1 5 10 15

Arg Tyr Tyr Lys Asp Leu Arg His Tyr Leu Asn Trp Leu Thr Arg Gln
20 25 30

Arg Phe

<210> SEQ ID NO 141
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 141

Pro Lys Pro Glu Ala Pro Gly Lys Asp Ala Ser Pro Glu Glu Trp Glu
1 5 10 15

Arg Tyr Tyr Lys Asp Leu Arg His Tyr Leu Asn Trp Leu Thr Arg Gln
20 25 30

Arg Phe

<210> SEQ ID NO 142

<400> SEQUENCE: 142

000

<210> SEQ ID NO 143
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 143

Pro Lys Pro Glu Ala Pro Gly Lys Asp Ala Ser Pro Glu Glu Trp Lys
1 5 10 15

Arg Tyr Tyr Glu Asp Leu Arg His Tyr Leu Asn Trp Leu Thr Arg Gln

```
            20                  25                  30

Arg Phe


<210> SEQ ID NO 144
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Pro Lys Pro Glu Ala Pro Gly Lys Asp Ala Ser Pro Glu Glu Trp Lys
1               5                   10                  15

Arg Tyr Tyr Asp Asp Leu Arg His Tyr Leu Asn Trp Leu Thr Arg Gln
            20                  25                  30

Arg Phe


<210> SEQ ID NO 145
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Pro Lys Pro Glu Ala Pro Gly Lys Asp Ala Ser Pro Lys Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 146
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Pro Lys Pro Glu Ala Pro Gly Lys Lys Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 147
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Pro Lys Pro Glu Ala Pro Gly Lys Asp Ala Ser Pro Glu Glu Trp Asp
1               5                   10                  15

Arg Tyr Tyr Lys Asp Asp Arg His Tyr Lys Asn Trp Leu Thr Arg Gln
            20                  25                  30

Arg Phe
```

<210> SEQ ID NO 148
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

```
Pro Lys Pro Glu Ala Pro Gly Lys Asp Ala Ser Pro Glu Glu Trp Asp
1               5                   10                  15

Arg Tyr Tyr Lys Asp Lys Arg His Tyr Glu Asn Trp Leu Thr Arg Gln
            20                  25                  30

Arg Phe
```

<210> SEQ ID NO 149
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: Beta-homoTyr

<400> SEQUENCE: 149

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr
```

<210> SEQ ID NO 150
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Lys
            20                  25                  30

Arg Phe
```

<210> SEQ ID NO 151
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Lys Trp Leu Thr Arg Gln
            20                  25                  30
```

```
Arg Phe


<210> SEQ ID NO 152
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Pro Lys Pro Glu Ala Pro Gly Lys Asp Ala Ser Pro Glu Glu Trp Asn
1               5                   10                  15

Arg Tyr Tyr Ala Asp Leu Arg His Lys Leu Asn Trp Leu Thr Arg Gln
            20                  25                  30

Arg Phe


<210> SEQ ID NO 153
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Pro Lys Pro Glu Ala Pro Gly Lys Asp Ala Ser Pro Glu Glu Trp Asn
1               5                   10                  15

Arg Tyr Tyr Ala Asp Leu Lys His Tyr Leu Asn Trp Leu Thr Arg Gln
            20                  25                  30

Arg Phe


<210> SEQ ID NO 154

<400> SEQUENCE: 154

000


<210> SEQ ID NO 155
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Pro Lys Pro Glu Ala Pro Gly Lys Asp Ala Ser Pro Glu Glu Trp Lys
1               5                   10                  15

Arg Tyr Tyr Ala Asp Leu Arg His Tyr Leu Asn Trp Leu Thr Arg Gln
            20                  25                  30

Arg Phe


<210> SEQ ID NO 156
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: 4-pyridylAla
```

<400> SEQUENCE: 156

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Ala
```

<210> SEQ ID NO 157
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: 3-pyridylAla

<400> SEQUENCE: 157

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Ala
```

<210> SEQ ID NO 158
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: 4-methylPhe

<400> SEQUENCE: 158

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe
```

<210> SEQ ID NO 159
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: 4-carboxyPhe

<400> SEQUENCE: 159

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe
```

<210> SEQ ID NO 160
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (34)..(34)
<223> OTHER INFORMATION: 4-fluoroPhe

<400> SEQUENCE: 160

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe
```

<210> SEQ ID NO 161
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (34)..(34)
<223> OTHER INFORMATION: homoPhe

<400> SEQUENCE: 161

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe
```

<210> SEQ ID NO 162
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (34)..(34)
<223> OTHER INFORMATION: n-methylPhe

<400> SEQUENCE: 162

```
Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Phe
```

<210> SEQ ID NO 163
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (34)..(34)
<223> OTHER INFORMATION: n-methylTyr

<400> SEQUENCE: 163

Pro Lys Pro Glu Ala Pro Lys Lys Asp Ala Ser Pro Glu Glu Leu Asn
1 5 10 15

Arg Tyr Tyr Ala Asp Ala Arg His Tyr Leu Asn Trp Leu Thr Arg Gln
20 25 30

Arg Tyr

<210> SEQ ID NO 164
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

Pro Lys Pro Glu Ala Pro Lys Lys Asp Ala Ser Pro Glu Glu Leu Asn
1 5 10 15

Arg Tyr Tyr Ala Asp Ala Arg His Tyr Leu Asn Trp Leu Thr Arg Gln
20 25 30

Arg Phe

<210> SEQ ID NO 165

<400> SEQUENCE: 165

000

<210> SEQ ID NO 166
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 166

Pro Lys Pro Glu Ala Pro Gly Lys Asp Lys Ser Pro Glu Glu Trp Asn
1 5 10 15

Arg Tyr Tyr Lys Asp Leu Arg His Tyr Leu Asn Trp Leu Thr Arg Gln
20 25 30

Arg Phe

<210> SEQ ID NO 167
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

Pro Lys Pro Glu Ala Pro Gly Lys Asp Ala Ser Pro Glu Lys Trp Asn
1 5 10 15

Arg Tyr Tyr Lys Asp Leu Arg His Tyr Leu Asn Trp Leu Thr Arg Gln
20 25 30

Arg Phe

<210> SEQ ID NO 168

<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 168

Pro Lys Pro Glu Ala Pro Gly Lys Asp Ala Ser Pro Glu Glu Trp Asn
1 5 10 15

Arg Lys Tyr Lys Asp Leu Arg His Tyr Leu Asn Trp Leu Thr Arg Gln
20 25 30

Arg Phe

<210> SEQ ID NO 169
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 169

Pro Lys Pro Glu Ala Pro Gly Lys Asp Ala Ser Pro Glu Glu Trp Asn
1 5 10 15

Arg Tyr Lys Lys Asp Leu Arg His Tyr Leu Asn Trp Leu Thr Arg Gln
20 25 30

Arg Phe

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 175

```
Pro Lys Pro Glu Lys Pro Gly Lys Asp Ala Ser Pro Glu Glu Trp Ser
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 176

<400> SEQUENCE: 176

000

<210> SEQ ID NO 177
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 177

```
Pro Lys Pro Glu Lys Pro Gly Glu Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 178

<400> SEQUENCE: 178

000

<210> SEQ ID NO 179
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

```
Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Tyr
```

<210> SEQ ID NO 180
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

```
Pro Lys Pro Glu Ala Pro Gly Asp Ala Ser Pro Glu Glu Trp Asp Arg
1               5                   10                  15

Tyr Tyr Lys Asp Leu Arg His Tyr Leu Asn Trp Leu Thr Arg Gln Arg
            20                  25                  30
```

Phe

<210> SEQ ID NO 181
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 181

Pro Lys Pro Glu Ala Pro Gly Asp Ala Ser Pro Glu Glu Trp Lys Arg
1 5 10 15

Tyr Tyr Glu Asp Leu Arg His Tyr Leu Asn Trp Leu Thr Arg Gln Arg
20 25 30

Phe

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

```
<400> SEQUENCE: 235

000


<210> SEQ ID NO 236

<400> SEQUENCE: 236

000


<210> SEQ ID NO 237

<400> SEQUENCE: 237

000


<210> SEQ ID NO 238

<400> SEQUENCE: 238

000


<210> SEQ ID NO 239
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Pro Lys Pro Glu Lys Pro Gly Lys Asp Ala Ser Pro Lys Glu Trp Glu
1               5                   10                  15

Arg Tyr Tyr Lys Asp Leu Arg His Tyr Leu Asn Trp Leu Thr Arg Gln
            20                  25                  30

Arg Phe


<210> SEQ ID NO 240
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Pro Lys Pro Glu Lys Pro Gly Lys Asp Ala Ser Pro Lys Glu Trp Asp
1               5                   10                  15

Arg Tyr Tyr Lys Asp Leu Arg His Tyr Leu Asn Trp Leu Thr Arg Gln
            20                  25                  30

Arg Phe


<210> SEQ ID NO 241
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Pro Lys Pro Glu Ala Pro Gly Lys Asp Ala Ser Pro Glu Glu Trp Glu
1               5                   10                  15

Arg Tyr Tyr Lys Asp Leu Arg His Tyr Leu Asn Trp Leu Thr Arg Gln
```

20 25 30

Arg Phe

<210> SEQ ID NO 242
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 242

Pro Lys Pro Glu Ala Pro Gly Lys Asp Ala Ser Pro Glu Glu Trp Asp
1 5 10 15

Arg Tyr Tyr Lys Asp Leu Arg His Tyr Leu Asn Trp Leu Thr Arg Gln
20 25 30

Arg Phe

<210> SEQ ID NO 243
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 243

Pro Lys Pro Glu Ala Pro Gly Lys Asp Ala Ser Pro Glu Glu Trp Lys
1 5 10 15

Arg Tyr Tyr Glu Asp Leu Arg His Tyr Leu Asn Trp Leu Thr Arg Gln
20 25 30

Arg Phe

<210> SEQ ID NO 244
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 244

Pro Lys Pro Glu Ala Pro Gly Lys Asp Ala Ser Pro Glu Glu Trp Lys
1 5 10 15

Arg Tyr Tyr Asp Asp Leu Arg His Tyr Leu Asn Trp Leu Thr Arg Gln
20 25 30

Arg Phe

<210> SEQ ID NO 245
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 245

Pro Lys Pro Glu Ala Pro Gly Lys Asp Ala Ser Pro Lys Glu Trp Asp
1 5 10 15

Arg Tyr Tyr Lys Asp Leu Arg His Tyr Leu Asn Trp Leu Thr Arg Gln
20 25 30

Arg Phe

<210> SEQ ID NO 246
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 246

Pro Lys Pro Glu Ala Pro Gly Lys Lys Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe

<210> SEQ ID NO 247
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 247

Pro Lys Pro Glu Ala Pro Gly Lys Asp Ala Ser Pro Glu Glu Trp Asp
1               5                   10                  15

Arg Tyr Tyr Lys Asp Asp Arg His Tyr Lys Asn Trp Leu Thr Arg Gln
            20                  25                  30

Arg Phe

<210> SEQ ID NO 248
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 248

Pro Lys Pro Glu Ala Pro Gly Lys Asp Ala Ser Pro Glu Glu Trp Asp
1               5                   10                  15

Arg Tyr Tyr Lys Asp Lys Arg His Tyr Glu Asn Trp Leu Thr Arg Gln
            20                  25                  30

Arg Phe

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 280

```
Pro Lys Pro Glu Ala Pro Gly Asp Ala Ser Pro Glu Glu Trp Asp Arg
1               5                   10                  15

Tyr Tyr Lys Asp Leu Arg His Tyr Leu Asn Trp Leu Thr Arg Gln Arg
            20                  25                  30

Phe
```

<210> SEQ ID NO 281
<211> LENGTH: 33
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 281

```
Pro Lys Pro Glu Ala Pro Gly Asp Ala Ser Pro Glu Glu Trp Lys Arg
1               5                   10                  15

Tyr Tyr Glu Asp Leu Arg His Tyr Leu Asn Trp Leu Thr Arg Gln Arg
            20                  25                  30

Phe
```

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 324

```
Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 342

```
Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 343
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 343

```
Pro Lys Pro Glu Ala Pro Gly Lys Asp Ala Ser Pro Glu Glu Trp Lys
1               5                   10                  15

Arg Tyr Tyr Glu Asp Leu Arg His Tyr Leu Asn Trp Leu Thr Arg Gln
            20                  25                  30

Arg Phe
```

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371
<400> SEQUENCE: 371
000

<210> SEQ ID NO 372
<400> SEQUENCE: 372
000

<210> SEQ ID NO 373
<400> SEQUENCE: 373
000

<210> SEQ ID NO 374
<400> SEQUENCE: 374
000

<210> SEQ ID NO 375
<400> SEQUENCE: 375
000

<210> SEQ ID NO 376
<400> SEQUENCE: 376
000

<210> SEQ ID NO 377
<400> SEQUENCE: 377
000

<210> SEQ ID NO 378
<400> SEQUENCE: 378
000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

```
<210> SEQ ID NO 390
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: K or absent
<220> FEATURE:
<221> NAME/KEY: MOD_RES
<222> LOCATION: (5)..(5)
<223> OTHER INFORMATION: E or K
<220> FEATURE:
<221> NAME/KEY: MOD_RES
<222> LOCATION: (6)..(6)
<223> OTHER INFORMATION: A or K
<220> FEATURE:
<221> NAME/KEY: MOD_RES
<222> LOCATION: (8)..(8)
<223> OTHER INFORMATION: G or K
<220> FEATURE:
<221> NAME/KEY: MOD_RES
<222> LOCATION: (9)..(9)
<223> OTHER INFORMATION: E, K, or k
<220> FEATURE:
<221> NAME/KEY: MOD_RES
<222> LOCATION: (10)..(10)
<223> OTHER INFORMATION: D or K
<220> FEATURE:
<221> NAME/KEY: MOD_RES
<222> LOCATION: (11)..(11)
<223> OTHER INFORMATION: A or K
<220> FEATURE:
<221> NAME/KEY: MOD_RES
<222> LOCATION: (14)..(14)
<223> OTHER INFORMATION: E or K
<220> FEATURE:
<221> NAME/KEY: MOD_RES
<222> LOCATION: (15)..(15)
<223> OTHER INFORMATION: E or K
<220> FEATURE:
<221> NAME/KEY: MOD_RES
<222> LOCATION: (16)..(16)
<223> OTHER INFORMATION: L or W
<220> FEATURE:
<221> NAME/KEY: MOD_RES
<222> LOCATION: (17)..(17)
<223> OTHER INFORMATION: D, E, K, N, Q, S, T, alpha-methylserine, or
      homoserine
<220> FEATURE:
<221> NAME/KEY: MOD_RES
<222> LOCATION: (19)..(19)
<223> OTHER INFORMATION: K or Y
<220> FEATURE:
<221> NAME/KEY: MOD_RES
<222> LOCATION: (20)..(20)
<223> OTHER INFORMATION: K or Y
<220> FEATURE:
<221> NAME/KEY: MOD_RES
<222> LOCATION: (21)..(21)
<223> OTHER INFORMATION: A, D, E, K, k, or Dap
<220> FEATURE:
<221> NAME/KEY: MOD_RES
<222> LOCATION: (23)..(23)
<223> OTHER INFORMATION: A, D, K, or L
<220> FEATURE:
<221> NAME/KEY: MOD_RES
<222> LOCATION: (24)..(24)
<223> OTHER INFORMATION: K or R
<220> FEATURE:
<221> NAME/KEY: MOD_RES
<222> LOCATION: (26)..(26)
<223> OTHER INFORMATION: K or Y
<220> FEATURE:
<221> NAME/KEY: MOD_RES
<222> LOCATION: (27)..(27)
```

```
<223> OTHER INFORMATION: E, K, or L
<220> FEATURE:
<221> NAME/KEY: MOD_RES
<222> LOCATION: (28)..(28)
<223> OTHER INFORMATION: K or N
<220> FEATURE:
<221> NAME/KEY: MOD_RES
<222> LOCATION: (33)..(33)
<223> OTHER INFORMATION: K or Q
<220> FEATURE:
<221> NAME/KEY: MOD_RES
<222> LOCATION: (35)..(35)
<223> OTHER INFORMATION: F, y, 3-pyridinylalanine, 4-pyridinylalanine,
      4-carboxyphenylalanine, 4-fluorophenylalanine,
      4-methylphenylalanine, N-methylphenylalanine,
      homophenylalanine, beta-homotyrosine,
<220> FEATURE:
<221> NAME/KEY: MOD_RES
<222> LOCATION: (35)..(35)
<223> OTHER INFORMATION: CONT. FROM ABOVE: homotyrosine, or
      N-methyltyrosine
<220> FEATURE:
<223> OTHER INFORMATION: See specification as filed for detailed
      description of substitutions and preferred embodiments

<400> SEQUENCE: 390

Xaa Pro Lys Pro Xaa Xaa Pro Xaa Xaa Xaa Xaa Ser Pro Xaa Xaa Xaa
1               5                   10                  15

Xaa Arg Xaa Xaa Xaa Asp Xaa Xaa His Xaa Xaa Xaa Trp Leu Thr Arg
            20                  25                  30

Xaa Arg Xaa
        35


<210> SEQ ID NO 391

<400> SEQUENCE: 391

000


<210> SEQ ID NO 392

<400> SEQUENCE: 392

000


<210> SEQ ID NO 393

<400> SEQUENCE: 393

000


<210> SEQ ID NO 394
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: A or K
<220> FEATURE:
<221> NAME/KEY: MOD_RES
<222> LOCATION: (8)..(8)
<223> OTHER INFORMATION: E, K, or k
<220> FEATURE:
<221> NAME/KEY: MOD_RES
<222> LOCATION: (13)..(13)
<223> OTHER INFORMATION: E or K
<220> FEATURE:
<221> NAME/KEY: MOD_RES
```

```
<222> LOCATION: (16)..(16)
<223> OTHER INFORMATION: D, E, K, or N
<220> FEATURE:
<221> NAME/KEY: MOD_RES
<222> LOCATION: (20)..(20)
<223> OTHER INFORMATION: A, D, E, K, or k,
<220> FEATURE:
<221> NAME/KEY: MOD_RES
<222> LOCATION: (22)..(22)
<223> OTHER INFORMATION: A or L
<220> FEATURE:
<221> NAME/KEY: MOD_RES
<222> LOCATION: (34)..(34)
<223> OTHER INFORMATION: F or N-methyltyrosine
<220> FEATURE:
<223> OTHER INFORMATION: See specification as filed for detailed
      description of substitutions and preferred embodiments

<400> SEQUENCE: 394

Pro Lys Pro Glu Xaa Pro Gly Xaa Asp Ala Ser Pro Xaa Glu Trp Xaa
1               5                   10                  15

Arg Tyr Tyr Xaa Asp Xaa Arg His Tyr Leu Asn Trp Leu Thr Arg Gln
            20                  25                  30

Arg Xaa


<210> SEQ ID NO 395

<400> SEQUENCE: 395

000


<210> SEQ ID NO 396

<400> SEQUENCE: 396

000


<210> SEQ ID NO 397

<400> SEQUENCE: 397

000


<210> SEQ ID NO 398

<400> SEQUENCE: 398

000


<210> SEQ ID NO 399

<400> SEQUENCE: 399

000


<210> SEQ ID NO 400

<400> SEQUENCE: 400

000


<210> SEQ ID NO 401

<400> SEQUENCE: 401

000


<210> SEQ ID NO 402
```

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424
<211> LENGTH: 34
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 424

```
Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 442

```
Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 443
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 443

Pro Lys Pro Glu Ala Pro Gly Lys Asp Ala Ser Pro Glu Glu Trp Lys
1 5 10 15

Arg Tyr Tyr Glu Asp Leu Arg His Tyr Leu Asn Trp Leu Thr Arg Gln
20 25 30

Arg Phe

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501

<400> SEQUENCE: 501

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (8)..(8)
<223> OTHER INFORMATION: K(alloc)

<400> SEQUENCE: 524

```
Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (8)..(8)
<223> OTHER INFORMATION: K(ivDde)

<400> SEQUENCE: 542

Pro Lys Pro Glu Ala Pro Gly Lys Asp Ala Ser Pro Glu Glu Trp Asp
1 5 10 15

Arg Tyr Tyr Lys Asp Leu Arg His Tyr Leu Asn Trp Leu Thr Arg Gln
20 25 30

Arg Phe

<210> SEQ ID NO 543
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (8)..(8)
<223> OTHER INFORMATION: K(ivDde)

<400> SEQUENCE: 543

Pro Lys Pro Glu Ala Pro Gly Lys Asp Ala Ser Pro Glu Glu Trp Lys
1 5 10 15

Arg Tyr Tyr Glu Asp Leu Arg His Tyr Leu Asn Trp Leu Thr Arg Gln
20 25 30

Arg Phe

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (8)..(8)
<223> OTHER INFORMATION: K(ivDde)

<400> SEQUENCE: 642

```
Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 643
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (8)..(8)
<223> OTHER INFORMATION: K(ivDde)

<400> SEQUENCE: 643

```
Pro Lys Pro Glu Ala Pro Gly Lys Asp Ala Ser Pro Glu Glu Trp Lys
1               5                   10                  15

Arg Tyr Tyr Glu Asp Leu Arg His Tyr Leu Asn Trp Leu Thr Arg Gln
            20                  25                  30

Arg Phe
```

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (8)..(8)
<223> OTHER INFORMATION: K(ivDde)
<220> FEATURE:
<221> NAME/KEY: MOD_RES
<222> LOCATION: (16)..(16)
<223> OTHER INFORMATION: D(allyl)
<220> FEATURE:
<221> NAME/KEY: MOD_RES
<222> LOCATION: (20)..(20)
<223> OTHER INFORMATION: K(alloc)

<400> SEQUENCE: 742

```
Pro Lys Pro Glu Ala Pro Gly Lys Asp Ala Ser Pro Glu Glu Trp Asp
1               5                   10                  15

Arg Tyr Tyr Lys Asp Leu Arg His Tyr Leu Asn Trp Leu Thr Arg Gln
            20                  25                  30

Arg Phe
```

<210> SEQ ID NO 743
<211> LENGTH: 34

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: K(ivDde)
<220> FEATURE:
<221> NAME/KEY: MOD_RES
<222> LOCATION: (16)..(16)
<223> OTHER INFORMATION: K(alloc)
<220> FEATURE:
<221> NAME/KEY: MOD_RES
<222> LOCATION: (20)..(20)
<223> OTHER INFORMATION: E(allyl)

<400> SEQUENCE: 743

Pro Lys Pro Glu Ala Pro Gly Lys Asp Ala Ser Pro Glu Glu Trp Lys
1               5                   10                  15

Arg Tyr Tyr Glu Asp Leu Arg His Tyr Leu Asn Trp Leu Thr Arg Gln
            20                  25                  30

Arg Phe

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

<400> SEQUENCE: 759

000

<210> SEQ ID NO 760

<400> SEQUENCE: 760

000

<210> SEQ ID NO 761

<400> SEQUENCE: 761

000

<210> SEQ ID NO 762

<400> SEQUENCE: 762

000

<210> SEQ ID NO 763

<400> SEQUENCE: 763

000

<210> SEQ ID NO 764

<400> SEQUENCE: 764

000

<210> SEQ ID NO 765

<400> SEQUENCE: 765

000

<210> SEQ ID NO 766

<400> SEQUENCE: 766

000

<210> SEQ ID NO 767

<400> SEQUENCE: 767

000

<210> SEQ ID NO 768

<400> SEQUENCE: 768

000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800
<211> LENGTH: 36
<212> TYPE: PRT
<213> ORGANISM: Unknown
<220> FEATURE:
<223> OTHER INFORMATION: Description of Unknown:
PYY peptide sequence

<400> SEQUENCE: 800

```
Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35
```

<210> SEQ ID NO 801
<211> LENGTH: 30
<212> TYPE: PRT
<213> ORGANISM: Unknown
<220> FEATURE:
<223> OTHER INFORMATION: Description of Unknown:
GLP-1 sequence

<400> SEQUENCE: 801

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

<210> SEQ ID NO 802
<211> LENGTH: 39
<212> TYPE: PRT
<213> ORGANISM: Unknown
<220> FEATURE:
<223> OTHER INFORMATION: Description of Unknown:
Exenatide sequence

<400> SEQUENCE: 802

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

```
Ser Gly Ala Pro Pro Pro Ser
        35


<210> SEQ ID NO 803

<400> SEQUENCE: 803

000


<210> SEQ ID NO 804

<400> SEQUENCE: 804

000


<210> SEQ ID NO 805
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (20)..(20)
<223> OTHER INFORMATION: diacid-gamma-Glu
<220> FEATURE:
<221> NAME/KEY: MOD_RES
<222> LOCATION: (21)..(21)
<223> OTHER INFORMATION: (AEEA)2-Lys

<400> SEQUENCE: 805

Tyr Xaa Glu Gly Thr Phe Thr Ser Asp Tyr Ser Ile Xaa Leu Asp Lys
1               5                   10                  15

Ile Ala Gln Glu Lys Ala Phe Val Gln Trp Leu Ile Ala Gly Gly Pro
            20                  25                  30

Ser Ser Gly Ala Pro Pro Pro Ser
        35                  40


<210> SEQ ID NO 806
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: K or absent
<220> FEATURE:
<221> NAME/KEY: MOD_RES
<222> LOCATION: (5)..(5)
<223> OTHER INFORMATION: E or K
<220> FEATURE:
<221> NAME/KEY: MOD_RES
<222> LOCATION: (6)..(6)
<223> OTHER INFORMATION: A or K
<220> FEATURE:
<221> NAME/KEY: MOD_RES
<222> LOCATION: (8)..(8)
<223> OTHER INFORMATION: G or K
<220> FEATURE:
<221> NAME/KEY: MOD_RES
```

```
<222> LOCATION: (9)..(9)
<223> OTHER INFORMATION: E, K, or k
<220> FEATURE:
<221> NAME/KEY: MOD_RES
<222> LOCATION: (11)..(11)
<223> OTHER INFORMATION: A or K
<220> FEATURE:
<221> NAME/KEY: MOD_RES
<222> LOCATION: (14)..(14)
<223> OTHER INFORMATION: E or K
<220> FEATURE:
<221> NAME/KEY: MOD_RES
<222> LOCATION: (15)..(15)
<223> OTHER INFORMATION: E or K
<220> FEATURE:
<221> NAME/KEY: MOD_RES
<222> LOCATION: (16)..(16)
<223> OTHER INFORMATION: L or W
<220> FEATURE:
<221> NAME/KEY: MOD_RES
<222> LOCATION: (17)..(17)
<223> OTHER INFORMATION: D, E, K, N, Q, S, T, alpha-methylserine, or
      homoserine
<220> FEATURE:
<221> NAME/KEY: MOD_RES
<222> LOCATION: (19)..(19)
<223> OTHER INFORMATION: K or Y
<220> FEATURE:
<221> NAME/KEY: MOD_RES
<222> LOCATION: (20)..(20)
<223> OTHER INFORMATION: K or Y
<220> FEATURE:
<221> NAME/KEY: MOD_RES
<222> LOCATION: (21)..(21)
<223> OTHER INFORMATION: A, D, E, K, k, or Dap
<220> FEATURE:
<221> NAME/KEY: MOD_RES
<222> LOCATION: (23)..(23)
<223> OTHER INFORMATION: A, D, K, or L
<220> FEATURE:
<221> NAME/KEY: MOD_RES
<222> LOCATION: (24)..(24)
<223> OTHER INFORMATION: K or R
<220> FEATURE:
<221> NAME/KEY: MOD_RES
<222> LOCATION: (26)..(26)
<223> OTHER INFORMATION: K or Y
<220> FEATURE:
<221> NAME/KEY: MOD_RES
<222> LOCATION: (28)..(28)
<223> OTHER INFORMATION: K or N
<220> FEATURE:
<221> NAME/KEY: MOD_RES
<222> LOCATION: (33)..(33)
<223> OTHER INFORMATION: K or Q
<220> FEATURE:
<221> NAME/KEY: MOD_RES
<222> LOCATION: (35)..(35)
<223> OTHER INFORMATION: F, y, 3-pyridinylalanine, 4-pyridinylalanine,
      4-carboxyphenylalanine, 4-fluorophenylalanine,
      4-methylphenylalanine, N-methylphenylalanine,
      homophenylalanine, beta-homotyrosine,
<220> FEATURE:
<221> NAME/KEY: MOD_RES
<222> LOCATION: (35)..(35)
<223> OTHER INFORMATION: CONT. FROM ABOVE: homotyrosine, or
      N-methyltyrosine
<220> FEATURE:
<223> OTHER INFORMATION: See specification as filed for detailed
      description of substitutions and preferred embodiments

<400> SEQUENCE: 806

Xaa Pro Lys Pro Xaa Xaa Pro Xaa Xaa Asp Xaa Ser Pro Xaa Xaa Xaa
1               5                   10                  15

Xaa Arg Xaa Xaa Xaa Asp Xaa Xaa His Xaa Leu Xaa Trp Leu Thr Arg
            20                  25                  30
```

```
Xaa Arg Xaa
        35


<210> SEQ ID NO 807
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 807

Trp Asp Arg Tyr Tyr Lys Asp
1               5


<210> SEQ ID NO 808
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Gamma-Glu
<220> FEATURE:
<221> NAME/KEY: SITE
<222> LOCATION: (1)..(10)
<223> OTHER INFORMATION: This sequence may encompass 1-10 residues

<400> SEQUENCE: 808

Glu Glu Glu Glu Glu Glu Glu Glu Glu Glu
1               5                   10


<210> SEQ ID NO 809
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Gamma-Glu
<220> FEATURE:
<221> NAME/KEY: SITE
<222> LOCATION: (1)..(10)
<223> OTHER INFORMATION: This sequence may encompass 1-10 “Glu” residues

<400> SEQUENCE: 809

Glu Glu Glu Glu Glu Glu Glu Glu Glu Glu Gly
1               5                   10


<210> SEQ ID NO 810
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Gamma-Glu

<400> SEQUENCE: 810

Glu Glu Glu Glu
1
```

<210> SEQ ID NO 811
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(5)
<223> OTHER INFORMATION: Gamma-Glu

<400> SEQUENCE: 811

Glu Glu Glu Glu Glu
1 5

<210> SEQ ID NO 812
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(3)
<223> OTHER INFORMATION: Gamma-Glu

<400> SEQUENCE: 812

Glu Glu Glu Gly
1

<210> SEQ ID NO 813
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(11)
<223> OTHER INFORMATION: Gamma-Glu
<220> FEATURE:
<221> NAME/KEY: SITE
<222> LOCATION: (2)..(11)
<223> OTHER INFORMATION: This sequence may encompass 1-10 "Glu" residues

<400> SEQUENCE: 813

Gly Glu Glu Glu Glu Glu Glu Glu Glu Glu Glu
1 5 10

<210> SEQ ID NO 814
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 814

Glu Glu Glu Glu
1

LONG ACTING PEPTIDE TYROSINE TYROSINE (PYY) ANALOGS AND METHODS OF USE

RELATED APPLICATION

This application claims the benefit of U.S. Provisional Patent Application No. 63/011,649, filed Apr. 17, 2020, and U.S. Provisional Patent Application No. 63/076,459, filed Sep. 10, 2020, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 13, 2021, is named 717075_102487-058_SL.txt and is 115,023 bytes in size.

FIELD

The present invention relates to compounds that are peptide tyrosine tyrosine (PYY) analogs and methods of preparing the same. The invention also provides pharmaceutically acceptable compositions comprising compounds of the present invention and methods of using said compositions in the treatment of various disorders.

BACKGROUND

Peptide YY (PYY) also known as peptide tyrosine tyrosine is a peptide that in humans is encoded by the PYY gene. Peptide YY is a short (36-amino acid) peptide released from cells in the ileum and colon in response to feeding. In the blood, gut, and other elements of periphery, PYY acts to reduce appetite; similarly, when injected directly into the central nervous system, PYY is also anorexigenic, i.e., it reduces appetite.

SUMMARY

It has now been found that compounds of this disclosure, and pharmaceutically acceptable compositions thereof, are effective as PYY analogs. Such compounds have a general formula as follows:

an isolated polypeptide, comprising the amino acid sequence of SEQ ID NO: 806:

$X_0PX_2PX_4X_5PX_7X_8DX_{10}SPX_{13}X_{14}X_{15}X_{16}RX_{18}X_{19}X_{20}DX_{22}X_{23}HX_{25}LX_{27}WLTRX_{32}RX_{34}$-(OH/$NH_2$) (SEQ ID NO: 806), or a pharmaceutically acceptable salt thereof;

wherein each variable is as defined and described herein.

Such exemplary compounds are provided in Table 3 herein.

Compounds of the present invention have been designed to attain long elimination half-lives ($t_{1/2}$) and are thus described herein as "long-acting" PYY analogs.

Compounds of the present invention, and pharmaceutically acceptable compositions thereof, are useful for treating a variety of diseases, disorders or conditions, associated with PYY receptors. Such diseases, disorders, or conditions include metabolic diseases or disorders such as type 2 diabetes, obesity and the need to attain weight loss. In certain embodiments, the invention also relates to methods of treating nonalcoholic fatty liver disease (NAFLD) and/or nonalcoholic steatohepatitis (NASH).

DETAILED DESCRIPTION

Figure 1:
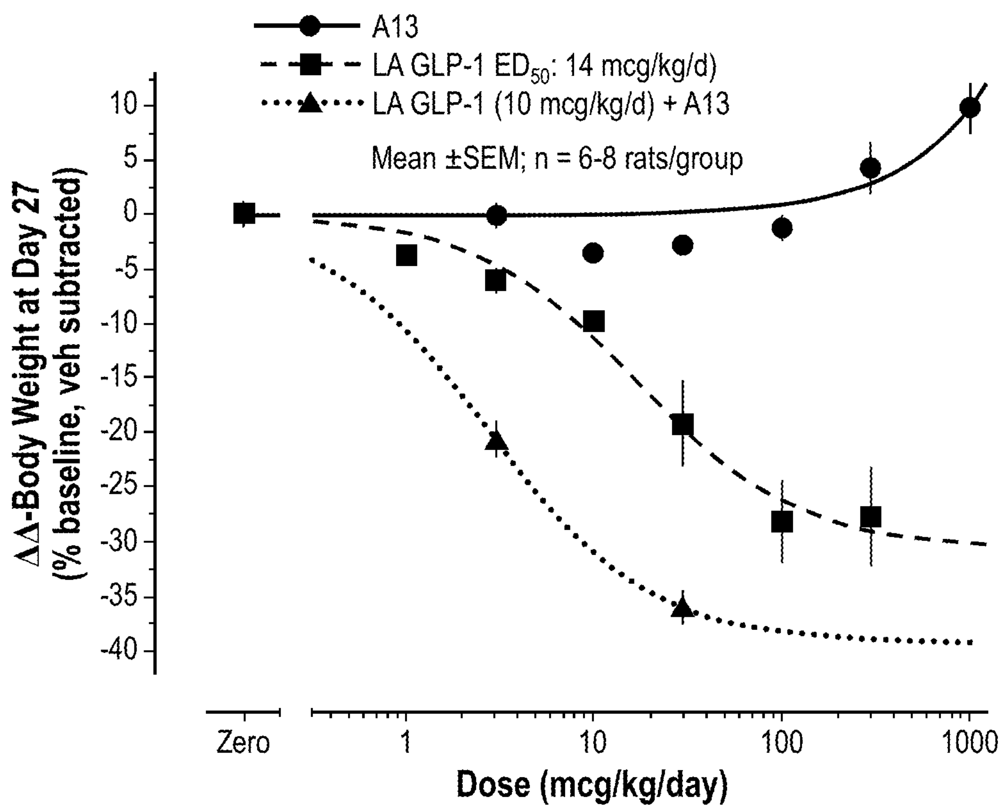
FIG. 1 depicts mean weight loss (%) from baseline and vehicle control (ΔΔ %) of a long acting PYY analog in combination with a long acting GLP-1 analog.

General description of certain embodiments of the invention Compounds of the present invention, and pharmaceutical compositions thereof, are useful as agonists of PYY receptors, particularly as agonists of human PYY receptors, including NPY1R, NPY2R, NPY4R, and NPY5R. This invention also relates to methods of producing and using such compounds, i.e., PYY analog polypeptides. Compounds of the present invention are long-acting PYY analogs. These PYY analog polypeptides are particularly useful in methods of treating metabolic diseases or disorders, such as type 2 diabetes, obesity, and in methods of providing weight loss. In certain embodiments, the invention also relates to methods of treating nonalcoholic fatty liver disease (NAFLD) and/or nonalcoholic steatohepatitis (NASH).

In certain embodiments, the present disclosure provides an isolated polypeptide comprising the amino acid sequence of SEQ ID NO: 806:

$X_0PX_2PX_4X_5PX_7X_8DX_{10}SPX_{13}X_{14}X_{15}X_{16}RX_{18}X_{19}X_{20}DX_{22}X_{23}HX_{25}LX_{27}WLTRX_{32}RX_{34}$-(OH/$NH_2$) (SEQ ID NO: 806), or a pharmaceutically acceptable salt thereof.

Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a peptide" includes one or more peptides, or mixtures of peptides, reference to "a drug" includes one or more drugs, reference to "an osmotic delivery device" includes one or more osmotic delivery devices, and the like. Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the term "substantially" is understood as within a narrow range of variation or otherwise normal tolerance in the art. Substantially can be understood as within 5%, 4%, 3%, 2%, 1%, 0.5%, 0.1%, 0.05%, 0.01% or 0.001% of the stated value.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The terms "drug," "therapeutic agent," and "beneficial agent" are used interchangeably to refer to any therapeutically active substance that is delivered to a subject to produce a desired beneficial effect. In one embodiment of the present invention, the drug is a polypeptide. In another embodiment of the present invention, the drug is a small molecule, for example, hormones such as androgens or estrogens. The devices and methods of the present invention are well suited for the delivery of proteins, small molecules and combinations thereof.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogs, and amino acid mimetics).

In some embodiments, naturally-occurring L-amino acids, are represented by either conventional three-letter, or capitalized one-letter, amino acid designations of Table 1. In other embodiments, naturally-occurring L-amino acids and D-amino acids, are both represented by either conventional three-letter, or capitalized one-letter, amino acid designations of Table 1. In still other embodiments, D-amino acids, are represented by lower-case one-letter amino acid designations corresponding to one-letter designations of Table 2, i.e., a, 1, m, f, w, k, q, e, s, p, v, i, c, y, h, r, n, d, and t.

TABLE 1

| Naturally-occurring amino acids | | |
|---|---|---|
| G | Glycine | Gly |
| A | Alanine | Ala |
| L | Leucine | Leu |
| M | Methionine | Met |
| F | Phenylalanine | Phe |
| W | Tryptophan | Trp |
| K | Lysine | Lys |
| Q | Glutamine | Gln |
| E | Glutamic Acid | Glu |
| S | Serine | Ser |
| P | Proline | Pro |
| V | Valine | Val |
| I | Isoleucine | Ile |
| C | Cysteine | Cys |
| Y | Tyrosine | Tyr |
| H | Histidine | His |
| R | Arginine | Arg |
| N | Asparagine | Asn |
| D | Aspartic Acid | Asp |
| T | Threonine | Thr |

TABLE 2

| Lower case designations refer to D stereoisomers of amino acids | | |
|---|---|---|
| a | D- Alanine | D-Ala |
| l | D-Leucine | D-Leu |
| m | D-Methionine | D-Met |
| f | D-Phenylalanine | D-Phe |
| w | D-Tryptophan | D-Trp |
| k | D-Lysine | D-Lys |
| q | D-Glutamine | D-Gln |
| e | D-Glutamic Acid | D-Glu |
| s | D-Serine | D-Ser |
| p | Proline | D-Pro |
| v | D-Valine | D-Val |
| i | D-Isoleucine | D-Ile |
| c | D-Cysteine | D-Cys |
| y | D-Tyrosine | D-Tyr |
| h | D-Histidine | D-His |
| r | D-Arginine | D-Arg |
| n | D-Asparagine | D-Asn |
| d | D-Aspartic Acid | D-Asp |
| t | D-Threonine | D-Thr |

Peptides may be naturally occurring, synthetically produced, or recombinantly expressed. Peptides may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxy terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). The term peptide also includes modifications, such as but not limited to those described above, of amino acids falling between the amino and carboxy termini. In one embodiment, a peptide may be modified by addition of a small-molecule drug.

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

The phrase "amino acid residue" as used herein refers to an amino acid that is incorporated into a peptide by an amide bond or an amide bond mimetic.

The term "insulinotropic" as used herein typically refers to the ability of a compound, e.g., a peptide, to stimulate or affect the production and/or activity of insulin (e.g., an insulinotropic hormone). Such compounds typically stimulate or otherwise affect the secretion or biosynthesis of insulin in a subject. Thus, an "insulinotropic peptide" is an amino acid-containing molecule capable of stimulating or otherwise affecting secretion or biosynthesis of insulin.

The term "acylated" as used herein, in relation to disclosed polypeptides, means the disclosed polypeptide is substituted with one or more lipophilic substituents each optionally via a spacer, wherein "lipophilic substituent" and "spacer" are defined herein. Certain lipophilic substituents, each optionally via a spacer, can bind albumin and confer affinity to albumin to the resulting acylated polypeptide. The extent is variable, and depending on numerous factors, to which lipophilic substituents, each optionally via a spacer, bind albumin and confer affinity to albumin to the resulting acylated polypeptide. Numerous factors include identities of the lipophilic substituent, optional spacer, polypeptide, and the site of covalent attachment to the polypeptide.

The terms "linear" or "liner polypeptide" as used herein, refer to a "non-acylated" polypeptide, in other words, a disclosed PYY analog polypeptide without a lipophilic substituents each optionally via a spacer, wherein "lipophilic substituent" and "spacer" are defined herein.

The terms "conjugated" or conjugated polypeptide" as used herein, refer to an "acylated" polypeptide, in other words, a disclosed PYY analog polypeptide having one or more lipophilic substituents each optionally via a spacer, wherein "lipophilic substituent" and "spacer" are defined herein.

As used herein, the term "pharmaceutically acceptable salts" refers to derivatives of the disclosed polypeptides wherein the parent polypeptide is modified by converting an existing acid or base moiety to its salt form. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The term "vehicle" as used herein refers to a medium used to carry a compound, e.g., a drug or a particle containing a drug. Vehicles of the present invention typically comprise components such as polymers and solvents. The suspension vehicles of the present invention typically comprise solvents and polymers that are used to prepare suspension formulations further comprising drug particle formulations.

The phrase "phase separation" as used herein refers to the formation of multiple phases (e.g., liquid and gel phases) in the suspension vehicle, such as when the suspension vehicle contacts the aqueous environment. In some embodiments of the present invention, the suspension vehicle is formulated to exhibit phase separation upon contact with an aqueous environment having less than approximately 10% water.

The phrase "single-phase" as used herein refers to a solid, semisolid, or liquid homogeneous system that is physically and chemically uniform throughout.

The term "dispersed" as used herein refers to dissolving, dispersing, suspending, or otherwise distributing a compound, for example, a drug particle formulation, in a suspension vehicle.

The phrase "chemically stable" as used herein refers to formation in a formulation of an acceptable percentage of degradation products produced over a defined period of time by chemical pathways, such as deamidation (usually by hydrolysis), aggregation, or oxidation.

The phrase "physically stable" as used herein refers to formation in a formulation of an acceptable percentage of aggregates (e.g., dimers and other higher molecular weight products). Further, a physically stable formulation does not change its physical state as, for example, from liquid to solid, or from amorphous to crystal form.

The term "viscosity" as used herein typically refers to a value determined from the ratio of shear stress to shear rate (see, e.g., Considine, D. M. & Considine, G. D., Encyclopedia of Chemistry, 4th Edition, Van Nostrand, Reinhold, N.Y., 1984) essentially as follows:

$$F/A=\mu*V/L \qquad \text{(Equation 1)}$$

where F/A=shear stress (force per unit area),

μ=a proportionality constant (viscosity), and

V/L=the velocity per layer thickness (shear rate).

From this relationship, the ratio of shear stress to shear rate defines viscosity. Measurements of shear stress and shear rate are typically determined using parallel plate rheometry performed under selected conditions (for example, a temperature of about 37° C.). Other methods for the determination of viscosity include, measurement of a kinematic viscosity using viscometers, for example, a Cannon-Fenske viscometer, an Ubbelohde viscometer for the Cannon-Fenske opaque solution, or an Ostwald viscometer. Generally, suspension vehicles of the present invention have a viscosity sufficient to prevent a particle formulation suspended therein from settling during storage and use in a method of delivery, for example, in an implantable, drug delivery device.

The term "non-aqueous" as used herein refers to an overall moisture content, for example, of a suspension formulation, typically of less than or equal to about 10 wt %, for example, less than or equal to about 7 wt %, less than or equal to about 5 wt %, and/or less than about 4 wt %. Also, a particle formulation of the present invention comprises less than about 10 wt %, for example, less than about 5 wt %, residual moisture.

The term "subject" as used herein refers to any member of the subphylum Chordata, including, without limitation, humans and other primates, including non-human primates such as rhesus macaques and other monkey species and chimpanzees and other ape species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age or gender. Thus, both adult and newborn individuals are intended to be covered.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "osmotic delivery device" as used herein typically refers to a device used for delivery of a drug (e.g., a disclosed PYY analog polypeptide) to a subject, wherein the device comprises, for example, a reservoir (made, e.g., from a titanium alloy) having a lumen that contains a suspension formulation comprising a drug (e.g., a disclosed PYY analog polypeptide) and an osmotic agent formulation. A piston assembly positioned in the lumen isolates the suspension formulation from the osmotic agent formulation. A semi-permeable membrane is positioned at a first distal end of the reservoir adjacent the osmotic agent formulation and a diffusion moderator (which defines a delivery orifice through which the suspension formulation exits the device) is positioned at a second distal end of the reservoir adjacent the suspension formulation. Typically, the osmotic delivery device is implanted within the subject, for example, subdermally or subcutaneously (e.g., in the inside, outside, or back of the upper arm and in the abdominal area). An exemplary osmotic delivery device is the DUROS® (ALZA Corporation, Mountain View, Calif.) delivery device. Examples of terms synonymous to "osmotic delivery device" include but are not limited to "osmotic drug delivery device", "osmotic drug delivery system", "osmotic device", "osmotic delivery device", "osmotic delivery system", "osmotic pump", "implantable drug delivery device", "drug delivery system", "drug delivery device", "implantable osmotic pump", "implantable drug delivery system", and "implantable delivery system". Other terms for "osmotic delivery device" are known in the art.

The term "continuous delivery" as used herein typically refers to a substantially continuous release of drug from an osmotic delivery device and into tissues near the implantation site, e.g., subdermal and subcutaneous tissues. For example, an osmotic delivery device releases drug essentially at a predetermined rate based on the principle of osmosis. Extracellular fluid enters the osmotic delivery device through the semi-permeable membrane directly into the osmotic engine that expands to drive the piston at a slow and consistent rate of travel. Movement of the piston forces the drug formulation to be released through the orifice of the diffusion moderator. Thus, release of the drug from the osmotic delivery device is at a slow, controlled, consistent rate.

The term "substantial steady-state delivery" as used herein typically refers to delivery of a drug at or near a target concentration over a defined period of time, wherein the amount of the drug being delivered from an osmotic delivery device is substantially zero-order delivery. Substantial zero-order delivery of an active agent (e.g., a disclosed PYY analog polypeptide) means that the rate of drug delivered is constant and is independent of the drug available in the delivery system; for example, for zero-order delivery, if the rate of drug delivered is graphed against time and a line is fitted to the data the line has a slope of approximately zero, as determined by standard methods (e.g., linear regression).

The phrase "drug half-life" as used herein refers how long it takes a drug to be eliminated from blood plasma by one half of its concentration. A drug's half-life is usually measured by monitoring how a drug degrades when it is administered via injection or intravenously. A drug is usually detected using, for example, a radioimmunoassay (RIA), a chromatographic method, an electrochemiluminescent (ECL) assay, an enzyme linked immunosorbent assay (ELISA) or an immunoenzymatic sandwich assay (IEMA).

The terms "μg" and "mcg" and "ug" are understood to mean "micrograms". Similarly, the terms "μl" and "uL" are understood to mean "microliter", and the terms "μM" and "uM" are understood to mean "micromolar".

The term "serum" is meant to mean any blood product from which a substance can be detected. Thus, the term serum includes at least whole blood, serum, and plasma. For example, "an amount of [a substance] in a subject's serum" would cover "an amount of [the substance] in a subject's plasma".

Baseline is defined as the last assessment on or before the day of the initial placement of an osmotic delivery device (containing drug or placebo).

Peptide YY (PYY) is a 36 amino acid residue peptide amide having the amino acid sequence of (YPIKPEAPGEDASPEELNRYYASLRHYLNLVTRQRY-$NH_2$), SEQ ID NO: 800. PYY inhibits gut motility and blood flow (Laburthe, M., Trends Endocrinol Metab. 1(3):168-74 (1990), mediates intestinal secretion (Cox, H. M., et al., Br J Pharmacol 101(2):247-52 (1990); Playford, R. J., et al., Lancet 335(8705):1555-7 (1990)), and stimulate net absorption (MacFayden, R. J., et al., Neuropeptides 7(3):219-27 (1986)). Two major in vivo variants, PYY(1-36) and PYY (3-36), have been identified (e.g., Eberlein, G. A., et al., Peptides 10(4), 797-803 (1989)). The sequence of PYY, as well as peptide analogs and peptide derivatives thereof, are known in the art (e.g., U.S. Pat. Nos. 5,574,010 and 5,552,520).

Exemplary Compounds: PYY Analog Polypeptides

Certain disclosed PYY analog polypeptides, including those of Table 3 below, exhibit one or more of: excellent solubility, stability, bioavailability, biological activity and specificity, and longer half-lives than those for endogenous PYY and known PYY analogs. Certain disclosed PYY analog polypeptides were developed to accommodate less frequent administration than is required for known PYY analogs. Certain disclosed PYY analog polypeptides were developed for administration via weekly or monthly injections. Certain disclosed PYY analog polypeptides were developed for administration via implantation of a delivery device comprising the PYY analog polypeptide, where the delivery device comprises a dose of the PYY analog polypeptide of up to 3 months, 6 months, 9 months, one year, 18 months or two years.

In some embodiments, an isolated polypeptide of the disclosure comprises an amino acid sequence selected from the group consisting of the following peptides listed in Table 3:

TABLE 3

Exemplary compounds: PYY analog polypeptides covalently bound to a lipophilic substituent, optionally via a spacer.

| Compound No. | Sequence | SEQ ID NO: |
|---|---|---|
| A1 | PKPEAPGK(γGlu-γGlu-dpeg-$CO(CH_2)_{18}CO_2H$)DASPEEWNRYYADLRHYLNWLTRQRY-($NH_2$) | SEQ ID NO: 1 |
| A2 | PKPEAPGK(γGlu-γGlu-$CO(CH_2)_{18}CO_2H$)DASPEEWNRYYADLRHYLNWLTRQRY-($NH_2$) | SEQ ID NO: 2 |
| A3 | PKPEAPGK(dpeg-dpeg-γGlu-$CO(CH_2)_{16}CO_2H$)DASPEEWNRYYADLRHYLNWLTRQRY-($NH_2$) | SEQ ID NO: 3 |
| A4 | K(γGlu-γGlu-$CO(CH_2)_{18}CO_2H$)PKPEAPGKDASPEEWNRYYADARHYLNWLTRQR-(n-methyl Y)-($NH_2$) | SEQ ID NO: 4 |
| A5 | PK(γGlu-γGlu-$CO(CH_2)_{18}CO_2H$)PEAPGKDASPEEWNRYYADARHYLNWLTRQR-(n-methyl Y)-($NH_2$) | SEQ ID NO: 5 |
| A6 | PKPK(γGlu-γGlu-$CO(CH_2)_{18}CO_2H$)APGKDASPEEWNRYYADARHYLNWLTRQR-(n-methyl Y)-($NH_2$) | SEQ ID NO: 6 |
| A7 | PKPEAPK(γGlu-γGlu-$CO(CH_2)_{18}CO_2H$)KDASPEEWNRYYADARHYLNWLTRQR-(n-methyl Y)-($NH_2$) | SEQ ID NO: 7 |
| A8 | PKPEAPGKDASPK(γGlu-γGlu-$CO(CH_2)_{18}CO_2H$)EWNRYYADARHYLNWLTRQR-(n-methyl Y)-($NH_2$) | SEQ ID NO: 8 |
| A9 | PKPEAPGKDASPEEWK(γGlu-γGlu-$CO(CH_2)_{18}CO_2H$)RYYADARHYLNWLTRQR-(n-methyl Y)-($NH_2$) | SEQ ID NO: 9 |
| A10 | PKPEAPGK(γGlu-γGlu-$CO(CH_2)_{18}CO_2H$)DASPEEWNRYYADLRHYLNWLTRQR-(n-methyl Y)-($NH_2$) | SEQ ID NO: 10 |
| A11 | PKPEAPGK(γGlu-γGlu-$CO(CH_2)_{18}CO_2H$)DASPEEWNRYYADLRHYLNWLTRQR-(homotyrosine)-($NH_2$) | SEQ ID NO: 11 |
| A12 | PKPEAPGK(γGlu-γGlu-$CO(CH_2)_{18}CO_2H$)DASPEEWNRYYADLRHYLNWLTRQRy-($NH_2$) | SEQ ID NO: 12 |
| A13 | PKPEAPGK(γGlu-γGlu-$CO(CH_2)_{18}CO_2H$)DASPEEWNRYYADLRHYLNWLTRQRF-($NH_2$) | SEQ ID NO: 13 |
| A14 | PKPEAPGKDASPEEWNRYYk(γGlu-γGlu-$CO(CH_2)_{18}CO_2H$)DLRHYLNWLTRQRF-($NH_2$) | SEQ ID NO: 14 |
| A15 | PKPEAPGk(γGlu-γGlu-$CO(CH_2)_{18}CO_2H$)DASPEEWNRYYADLRHYLNWLTRQRF-($NH_2$) | SEQ ID NO: 15 |
| A16 | PKPEAPGKDASPEEWNRYYK(γGlu-dpeg-dpeg-γGlu-$CO(CH_2)_{18}CO_2H$)DLRHYLNWLTRQRF-($NH_2$) | SEQ ID NO: 16 |
| A17 | PKPEAPGK(γGlu-dpeg-dpeg-γGlu-$CO(CH_2)_{18}CO_2H$)DASPEEWNRYYADLRHYLNWLTRQRF-($NH_2$) | SEQ ID NO: 17 |
| A18 | PKPEAPGk(γGlu-dpeg-dpeg-γGlu-$CO(CH_2)_{18}CO_2H$)DASPEEWNRYYADLRHYLNWLTRQRF-($NH_2$) | SEQ ID NO: 18 |

TABLE 3-continued

Exemplary compounds: PYY analog polypeptides covalently bound to a lipophilic substituent, optionally via a spacer.

| Compound No. | Sequence | SEQ ID NO: |
|---|---|---|
| A19 | PKPEKPGK(γGlu-γGlu-CO(CH$_2$)$_{18}$CO$_2$H)DASPEEWNRYYKDLRHYLNWLTRQRF-(NH$_2$) | SEQ ID NO: 19 |
| A20 | PKPEAPGK(γGlu-γGlu-CO(CH$_2$)$_{18}$CO$_2$H)DASPKEWNRYYKDLRHYLNWLTRQRF-(NH$_2$) | SEQ ID NO: 20 |
| A21 | PKPEAPGK(γGlu-γGlu-CO(CH$_2$)$_{18}$CO$_2$H)DASPEEWNRYYkDLRHYLNWLTRQRF-(NH$_2$) | SEQ ID NO: 21 |
| A22 | PKPEAPGK(γGlu-γGlu-CO(CH$_2$)$_{18}$CO$_2$H)DASPEEWNRYY-Dap-DLRHYLNWLTRQRF-(NH$_2$) | SEQ ID NO: 22 |
| A23 | PKPEAPGK(γGlu-γGlu-CO(CH$_2$)$_{18}$CO$_2$H)DASPEEWQRYYKDLRHYLNWLTRQRF-(NH$_2$) | SEQ ID NO: 23 |
| A24 | PKPEAPGK(γGlu-γGlu-CO(CH$_2$)$_{18}$CO$_2$H)DASPEEWDRYYKDLRHYLNWLTRQRF-(NH$_2$) | SEQ ID NO: 24 |
| A25 | PKPEAPGK(γGlu-γGlu-CO(CH$_2$)$_{18}$CO$_2$H)DASPEEWSRYYKDLRHYLNWLTRQRF-(NH$_2$) | SEQ ID NO: 25 |
| A26 | PKPEAPGK(γGlu-γGlu-CO(CH$_2$)$_{18}$CO$_2$H)DASPEEWTRYYKDLRHYLNWLTRQRF-(NH$_2$) | SEQ ID NO: 26 |
| A27 | PKPEKPGK(γGlu-γGlu-CO(CH$_2$)$_{18}$CO$_2$H)DASPKEWNRYYKDLRHYLNWLTRQRF-(NH$_2$) | SEQ ID NO: 27 |
| A28 | PKPEKPGKDASPKEWNRYYK(γGlu-γGlu-CO(CH$_2$)$_{18}$CO$_2$H)DLRHYLNWLTRQRF-(NH$_2$) | SEQ ID NO: 28 |
| A29 | PKPEKPGEDASPKEWNRYYK(γGlu-γGlu-CO(CH$_2$)$_{18}$CO$_2$H)DLRHYLNWLTRQRF-(NH$_2$) | SEQ ID NO: 29 |
| A30 | PKPEAPGK(γGlu-γGlu-CO(CH$_2$)$_{18}$CO$_2$H)DASPEEW-homoSer-RYYKDLRHYLNWLTRQRF-(NH$_2$) | SEQ ID NO: 30 |
| A31 | PKPEAPGK(γGlu-γGlu-CO(CH$_2$)$_{18}$CO$_2$H)DASPEEW-(alpha-methyl-Ser)-RYYKDLRHYLNWLTRQRF-(NH$_2$) | SEQ ID NO: 31 |
| A32 | PKPEAPGK(γGlu-γGlu-CO(CH$_2$)$_{16}$CO$_2$H)DASPEEWDRYYKDLRHYLNWLTRQRF-(NH$_2$) | SEQ ID NO: 32 |
| A33 | PKPEAPGK(γGlu-γGlu-CO(CH$_2$)$_{17}$CO$_2$H)DASPEEWDRYYKDLRHYLNWLTRQRF-(NH$_2$) | SEQ ID NO: 33 |
| A34 | PKPEKPGEDASPKEWDRYYK(γGlu-γGlu-CO(CH$_2$)$_{18}$CO$_2$H)DLRHYLNWLTRQRF-(NH$_2$) | SEQ ID NO: 34 |
| A35 | PKPEK(γGlu-γGlu-CO(CH$_2$)$_{16}$CO$_2$H)PGEDASPKEWDRYYKDLRHYLNWLTRQRF-(NH$_2$) | SEQ ID NO: 35 |
| A36 | PKPEK(γGlu-γGlu-CO(CH$_2$)$_{17}$CO$_2$H)PGEDASPKEWNRYYKDLRHYLNWLTRQRF-(NH$_2$) | SEQ ID NO: 36 |

TABLE 3-continued

| Compound No. | Sequence | SEQ ID NO: |
|---|---|---|
| | Exemplary compounds: PYY analog polypeptides covalently bound to a lipophilic substituent, optionally via a spacer. | |
| A37 | PKPEK(γGlu-γGlu-CO$(CH_2)_{18}CO_2H$)PGKDASPKEWNRYYKDLRHYLNWLTRQRF-($NH_2$) | SEQ ID NO: 37 |
| A38 | PKPEK(γGlu-γGlu-CO$(CH_2)_{16}CO_2H$)PGEDASPKEWNRYYKDLRHYLNWLTRQRF-($NH_2$) | SEQ ID NO: 38 |
| A39 | PKPEKPGK(γGlu-γGlu-CO$(CH_2)_{17}CO_2H$)DASPKEWE*RYYK*DLRHYLNWLTRQRF-($NH_2$) | SEQ ID NO: 39 |
| A40 | PKPEKPGK(γGlu-γGlu-CO$(CH_2)_{17}CO_2H$)DASPKEWD*RYYK*DLRHYLNWLTRQRF-($NH_2$) | SEQ ID NO: 40 |
| A41 | PKPEAPGK(γGlu-γGlu-CO$(CH_2)_{18}CO_2H$)DASPEEWE*RYYK*DLRHYLNWLTRQRF-($NH_2$) | SEQ ID NO: 41 |
| A42 | PKPEAPGK(γGlu-γGlu-CO$(CH_2)_{18}CO_2H$)DASPEEWD*RYYK*DLRHYLNWLTRQRF-($NH_2$) | SEQ ID NO: 42 |
| A43 | PKPEAPGK(γGlu-γGlu-CO$(CH_2)_{18}CO_2H$)DASPEEWK*RYYE*DLRHYLNWLTRQRF-($NH_2$) | SEQ ID NO: 43 |
| A44 | PKPEAPGK(γGlu-γGlu-CO$(CH_2)_{18}CO_2H$)DASPEEWK*RYYD*DLRHYLNWLTRQRF-($NH_2$) | SEQ ID NO: 44 |
| A45 | PKPEAPGK(γGlu-γGlu-CO$(CH_2)_{18}CO_2H$)D*ASPK*EWDRYYKDLRHYLNWLTRQRF-($NH_2$) | SEQ ID NO: 45 |
| A46 | PKPEAPGK(γGlu-γGlu-CO$(CH_2)_{18}CO_2H$)K*ASPE*EWDRYYKDLRHYLNWLTRQRF-($NH_2$) | SEQ ID NO: 46 |
| A47 | PKPEAPGK(γGlu-γGlu-CO$(CH_2)_{18}CO_2H$)DASPEEWDRYYKDD*RHYK*NWLTRQRF-($NH_2$) | SEQ ID NO: 47 |
| A48 | PKPEAPGK(γGlu-γGlu-CO$(CH_2)_{18}CO_2H$)DASPEEWDRYYKDK*RHYE*NWLTRQRF-($NH_2$) | SEQ ID NO: 48 |
| A49 | PKPEAPGK(γGlu-γGlu-CO$(CH_2)_{18}CO_2H$)DASPEEWNRYYADLRHYLNWLTRQR-(β-homo-Tyr)-($NH_2$) | SEQ ID NO: 49 |
| A50 | PKPEAPGKDASPEEWNRYYADLRHYLNWLTRK(γGlu-γGlu-CO$(CH_2)_{18}$CO2H)RF-($NH_2$) | SEQ ID NO: 50 |
| A51 | PKPEAPGKDASPEEWNRYYADLRHYLK(γGlu-γGlu-CO$(CH_2)_{18}CO_2H$)WLTRQRF-($NH_2$) | SEQ ID NO: 51 |
| A52 | PKPEAPGKDASPEEWNRYYADLRHK(γGlu-γGlu-CO$(CH_2)_{18}CO_2H$)LNWLTRQRF-($NH_2$) | SEQ ID NO: 52 |
| A53 | PKPEAPGKDASPEEWNRYYADLK(γGlu-γGlu-CO$(CH_2)_{18}CO_2H$)HYLNWLTRQRF-($NH_2$) | SEQ ID NO: 53 |
| A54 | PKPEAPGKDASPEEWNRYYK(γGlu-γGlu-CO$(CH_2)_{18}CO_2H$)DLRHYLNWLTRQRF-($NH_2$) | SEQ ID NO: 54 |

TABLE 3-continued

Exemplary compounds: PYY analog polypeptides covalently bound to a lipophilic substituent, optionally via a spacer.

| Compound No. | Sequence | SEQ ID NO: |
|---|---|---|
| A55 | PKPEAPGKDASPEEWK(γGlu-γGlu-CO(CH$_2$)$_{18}$CO$_2$H)RYYADLRHYLNWLTRQRF-(NH$_2$) | SEQ ID NO: 55 |
| A56 | PKPEAPGK(γGlu-γGlu-CO(CH$_2$)$_{18}$CO$_2$H)DASPEEWNRYYADLRHYLNWLTRQR-(4-pyridyl Ala)-(NH$_2$) | SEQ ID NO: 56 |
| A57 | PKPEAPGK(γGlu-γGlu-CO(CH$_2$)$_{18}$CO$_2$H)DASPEEWNRYYADLRHYLNWLTRQR-(3-pyridyl Ala)-(NH$_2$) | SEQ ID NO: 57 |
| A58 | PKPEAPGK(γGlu-γGlu-CO(CH$_2$)$_{18}$CO$_2$H)DASPEEWNRYYADLRHYLNWLTRQR-(4-methyl Phe)-(NH$_2$) | SEQ ID NO: 58 |
| A59 | PKPEAPGK(γGlu-γGlu-CO(CH$_2$)$_{18}$CO$_2$H)DASPEEWNRYYADLRHYLNWLTRQR-(4-carboxy Phe)-(NH$_2$) | SEQ ID NO: 59 |
| A60 | PKPEAPGK(γGlu-γGlu-CO(CH$_2$)$_{18}$CO$_2$H)DASPEEWNRYYADLRHYLNWLTRQR-(4-fluoro Phe)-(NH$_2$) | SEQ ID NO: 60 |
| A61 | PKPEAPGK(γGlu-γGlu-CO(CH$_2$)$_{18}$CO$_2$H)DASPEEWNRYYADLRHYLNWLTRQR-(homo-Phe)-(NH$_2$) | SEQ ID NO: 61 |
| A62 | PKPEAPGK(γGlu-γGlu-CO(CH$_2$)$_{18}$CO$_2$H)DASPEEWNRYYADLRHYLNWLTRQR-(n-methyl Phe)-(NH$_2$) | SEQ ID NO: 62 |
| A63 | PKPEAPK(γGlu-γGlu-CO(CH$_2$)$_{18}$CO$_2$H)KDASPEELNRYYADARHYLNWLTRQR-(n-methyl Tyr)-(NH$_2$) | SEQ ID NO: 63 |
| A64 | PKPEAPK(γGlu-γGlu-CO(CH$_2$)$_{18}$CO$_2$H)KDASPEELNRYYADARHYLNWLTRQRF-(NH$_2$) | SEQ ID NO: 64 |
| A65 | PKPEAPGKDASPEEWNRYYk(γGlu-dpeg-dpeg-γGlu-CO(CH$_2$)$_{18}$CO$_2$H)DLRHYLNWLTRQRF-(NH$_2$) | SEQ ID NO: 65 |
| A66 | PKPEAPGK(γGlu-γGlu-CO(CH$_2$)$_{18}$CO$_2$H)DKSPEEWNRYYKDLRHYLNWLTRQRF-(NH$_2$) | SEQ ID NO: 66 |
| A67 | PKPEAPGK(γGlu-γGlu-CO(CH$_2$)$_{18}$CO$_2$H)DASPEKWNRYYKDLRHYLNWLTRQRF-(NH$_2$) | SEQ ID NO: 67 |
| A68 | PKPEAPGK(γGlu-γGlu-CO(CH$_2$)$_{18}$CO$_2$H)DASPEEWNRKYKDLRHYLNWLTRQRF-(NH$_2$) | SEQ ID NO: 68 |
| A69 | PKPEAPGK(γGlu-γGlu-CO(CH$_2$)$_{18}$CO$_2$H)DASPEEWNRYKKDLRHYLNWLTRQRF-(NH$_2$) | SEQ ID NO: 69 |

TABLE 3-continued

| Exemplary compounds: PYY analog polypeptides covalently bound to a lipophilic substituent, optionally via a spacer. | | |
|---|---|---|
| Compound No. | Sequence | SEQ ID NO: |
| A70 | PKPEKPGKDASPK(γGlu-γGlu-$CO(CH_2)_{18}CO_2H$)EWNRYYKDLRHYLNWLTRQRF-($NH_2$) | SEQ ID NO: 70 |
| A71 | PKPEK(γGlu-γGlu-$CO(CH_2)_{18}CO_2H$)PGKDASPKEWNRYYKDLRHYLNWLTRQRF-($NH_2$) | SEQ ID NO: 71 |
| A72 | PKPEK(γGlu-γGlu-$CO(CH_2)_{18}CO_2H$)PGEDASPKEWNRYYKDLRHYLNWLTRQRF-($NH_2$) | SEQ ID NO: 72 |
| A73 | PKPEAPGK(γGlu-γGlu-$CO(CH_2)_{18}CO_2H$)DASPKEWNRYYKDLRHYLNWLTRQRF-($NH_2$) | SEQ ID NO: 73 |
| A74 | PKPEKPGK(γGlu-γGlu-$CO(CH_2)_{18}CO_2H$)DASPEEWNRYYKDLRHYLNWLTRQRF-($NH_2$) | SEQ ID NO: 74 |
| A75 | PKPEKPGK(γGlu-γGlu-$CO(CH_2)_{18}CO_2H$)DASPEEWSRYYKDLRHYLNWLTRQRF-($NH_2$) | SEQ ID NO: 75 |
| A76 | PKPEAPGK(γGlu-γGlu-$CO(CH_2)_{18}CO_2H$)DASPKEWDRYYKDLRHYLNWLTRQRF-($NH_2$) | SEQ ID NO: 76 |
| A77 | PKPEKPGEDASPEEWDRYYK(γGlu-γGlu-$CO(CH_2)_{18}CO_2H$)DLRHYLNWLTRQRF-($NH_2$) | SEQ ID NO: 77 |
| A78 | PKPEK(γGlu-γGlu-$CO(CH_2)_{18}CO_2H$)PGEDASPKEWDRYYKDLRHYLNWLTRQRF-($NH_2$) | SEQ ID NO: 78 |

Dap is Diaminopimelic Acid

Structural representations of certain peptides of Table 3 are provided below in Table 4:

TABLE 4

Chemical structures of exemplary peptides: PYY analog polypeptides comprising a lipophilic substituent via a spacer, two peptides of which further comprise a bridging moiety.

PKPEAPGK(γGlu-γGlu-$CO(CH_2)_{18}CO_2H$)DASPEEWNRYYADLRHLNWLTRQRY-($NH_2$)

A2

SEQ ID NO: 2

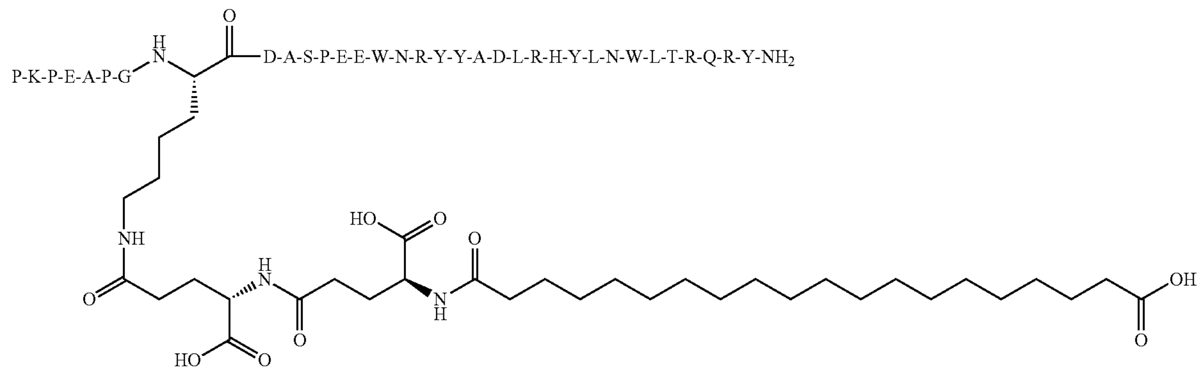

TABLE 4-continued

Chemical structures of exemplary peptides: PYY analog polypeptides comprising a lipophilic substituent via a spacer, two peptides of which further comprise a bridging moiety.

PKPEAPGK(γGly-γGlu-$CO(CH_2)_{18}CO_2H$)DASPEEWNRYYADLRHYLNWLTRQRF-($NH_2$)

A13

SEQ ID NO: 13

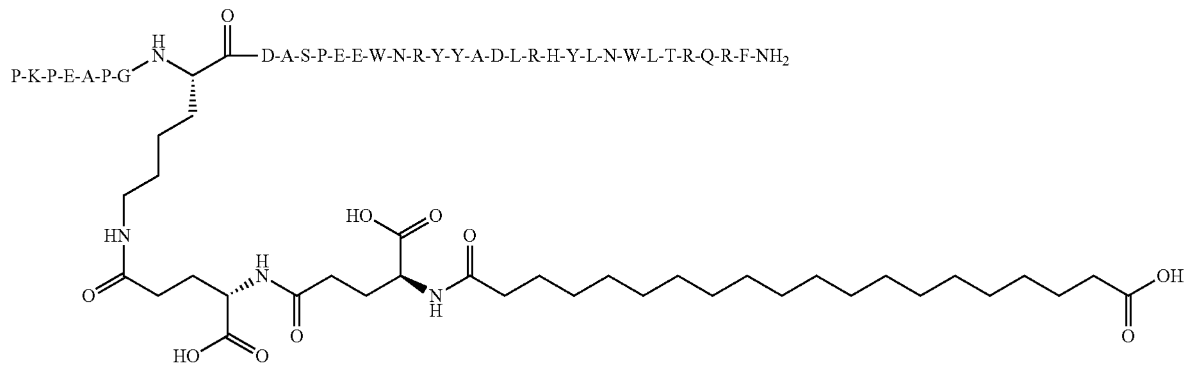

PKPEAPGK(γGlu-γGlu-$CO(CH_2)_{18}CO_2H$)DASPEEWDRYYKDLRHYLNWLTRQRF-($NH_2$)

A24

SEQ ID NO: 24

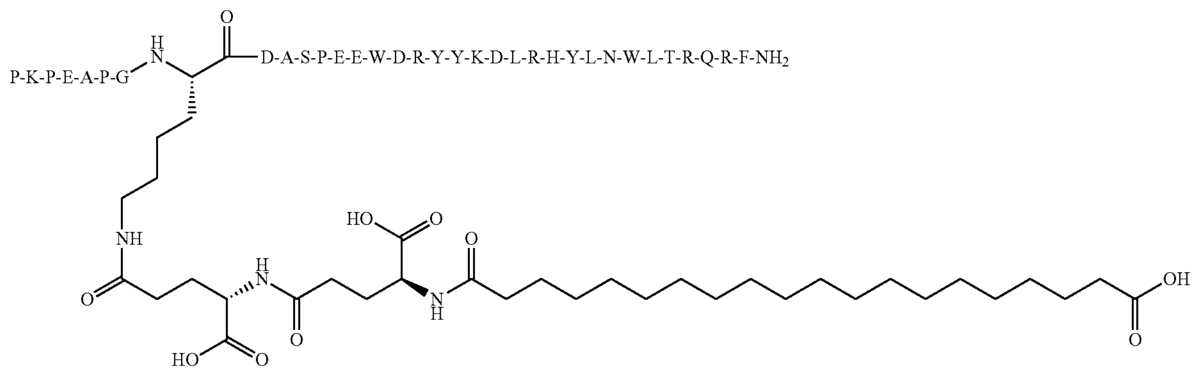

PKPEAPGK(γGlu-γGlu-$CO(CH_2)_{18}CO_2H$)DASPEEWD*RYYK*DLRHYLNWLTRQRF-($NH_2$)

A42

SEQ ID NO: 42

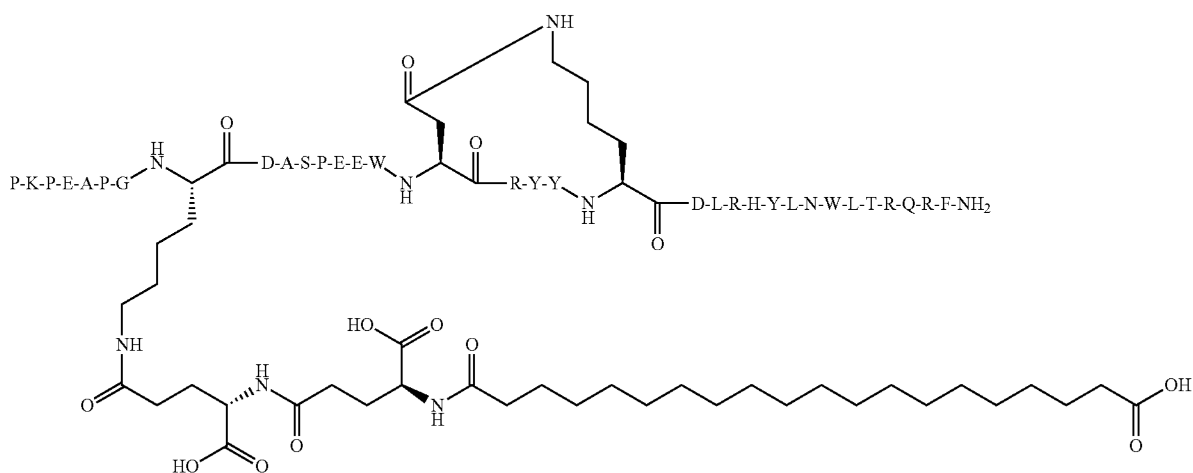

TABLE 4-continued

Chemical structures of exemplary peptides: PYY analog polypeptides comprising a lipophilic substituent via a spacer, two peptides of which further comprise a bridging moiety.

PKPEAPGK(γGlu-γGlu-CO$(CH_2)_{18}CO_2$H)DASPEEWK*RYYE*DLRHYLNWLTRQRF-$(NH_2)$
A43
SEQ ID NO: 43

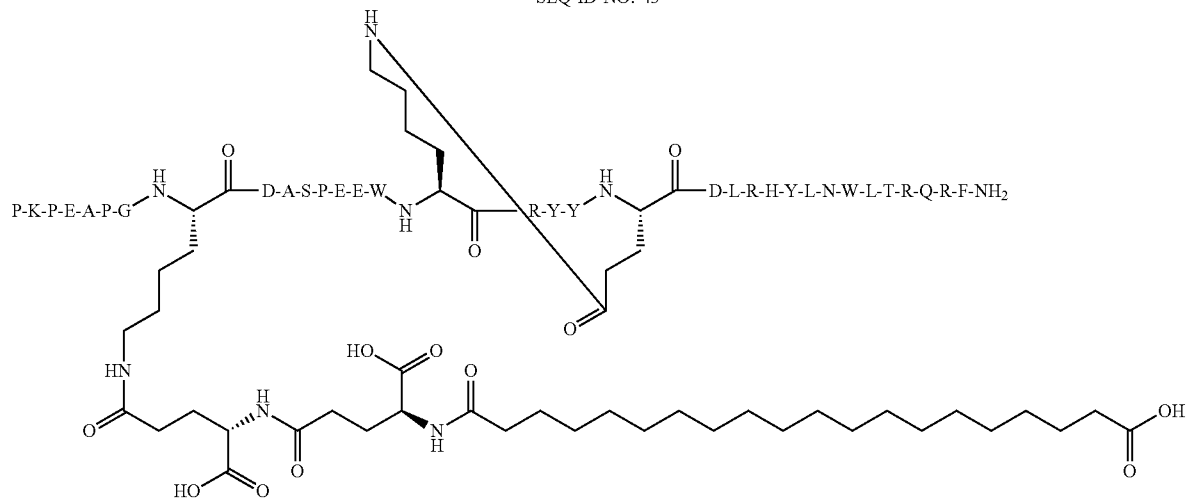

Notes:
each pairing of K* and E* and each pairing of K* and D* represent a covalent amide linkage derived from the amino sidechain of K* and the carboxy sidechain of E* or the caboxy sidechain of D* (with loss of a water molecule). For example, the segment - WD*RYYK*D- (SEQ ID NO: 807) represents:

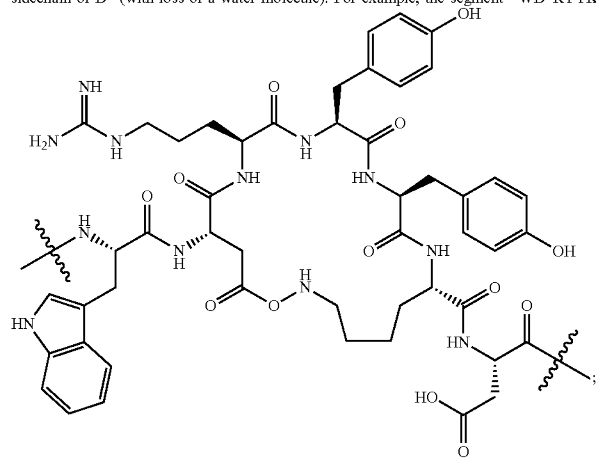

as used herein, dpeg represents —$COCH_2O(CH_2)_2O(CH_2)_2NH$—; and dpeg-dpeg represents —$COCH_2O(CH_2)_2O(CH_2)_2NH$—$COCH_2O(CH_2)_2O(CH_2)_2NH$—; and carboxy terminal amino acid, i.e. $F_{34}$, shown as —$F_{34}$—$(NH_2)$, depicts —NH—CH($CH_2$Ph)—$CONH_2$.

In some embodiments, the isolated polypeptide comprises an amino acid sequence selected from the group consisting of SEQ ID NOs: 1 to 78. or a pharmaceutically acceptable salt thereof.

In some embodiments, the isolated polypeptide comprises an amino acid sequence selected from the group consisting of SEQ ID NOs: 13, 24, 42 and 43 or a pharmaceutically acceptable salt thereof.

In some embodiments, the isolated polypeptide comprises an amino acid sequence of SEQ ID NO: 13 or a pharmaceutically acceptable salt thereof. In some embodiments, the isolated polypeptide comprises an amino acid sequence of SEQ ID NO: 24 or a pharmaceutically acceptable salt thereof. In some embodiments, the isolated polypeptide comprises an amino acid sequence of SEQ ID NO: 42 or a pharmaceutically acceptable salt thereof. In some embodiments, the isolated polypeptide comprises an amino acid sequence of SEQ ID NO: 43 or a pharmaceutically acceptable salt thereof.

In some embodiments, the present invention provides a compound set forth in Table 3, above, or a pharmaceutically acceptable salt thereof. In some embodiments, the present invention provides an isolated polypeptide that comprises an amino acid sequence selected from the group consisting of SEQ ID NOs: 1 to 78 or a pharmaceutically acceptable salt thereof. In some embodiments the pharmaceutically acceptable salt is an acetate salt. In some embodiments the pharmaceutically acceptable salt is a trifluoroacetic acid (TFA) salt. In some embodiments the pharmaceutically acceptable salt is a hydrochloric acid (HCl) salt.

In one embodiment, the compound is the isolated polypeptide comprising an amino acid sequence of SEQ ID NO: 13 or a pharmaceutically acceptable salt thereof. In some embodiments, the compound is the acetate salt of the isolated polypeptide comprising an amino acid sequence of SEQ ID NO: 13. In some embodiments, the compound is the TFA salt of the isolated polypeptide comprising an amino acid sequence of SEQ ID NO: 13. In some embodiments, the compound is the HCl salt of the isolated polypeptide comprising an amino acid sequence of SEQ ID NO: 13.

In one embodiment, the compound is the isolated polypeptide comprising an amino acid sequence of SEQ ID NO: 24 or a pharmaceutically acceptable salt thereof. In some embodiments, the compound is the acetate salt of the isolated polypeptide comprising an amino acid sequence of SEQ ID NO: 24. In some embodiments, the compound is the TFA salt of the isolated polypeptide comprising an amino acid sequence of SEQ ID NO: 24. In some embodiments, the compound is the HCl salt of the isolated polypeptide comprising an amino acid sequence of SEQ ID NO: 24.

In one embodiment, the compound is the isolated polypeptide comprising an amino acid sequence of SEQ ID NO: 42 or a pharmaceutically acceptable salt thereof. In some embodiments, the compound is the acetate salt of the isolated polypeptide comprising an amino acid sequence of SEQ ID NO: 42. In some embodiments, the compound is the TFA salt of the isolated polypeptide comprising an amino acid sequence of SEQ ID NO: 42. In some embodiments, the compound is the HCl salt of the isolated polypeptide comprising an amino acid sequence of SEQ ID NO: 42.

In one embodiment, the compound is the isolated polypeptide comprising an amino acid sequence of SEQ ID NO: 43 or a pharmaceutically acceptable salt thereof. In some embodiments, the compound is the acetate salt of the isolated polypeptide comprising an amino acid sequence of SEQ ID NO: 43. In some embodiments, the compound is the TFA salt of the isolated polypeptide comprising an amino acid sequence of SEQ ID NO: 43. In some embodiments, the compound is the HCl salt of the isolated polypeptide comprising an amino acid sequence of SEQ ID NO: 43.

In some embodiments, an isolated polypeptide of the disclosure comprises an amino acid sequence selected from the group consisting of the following peptides listed in Table 5:

TABLE 5

Exemplary compounds: PYY analog polypeptides optionally comprising a lipophilic substituent, optionally via a spacer; and optionally further comprising a bridging moiety.

| Compound No. | Sequence | SEQ ID NO: |
|---|---|---|
| B1 | PKPEAPGKDASPEEWNRYYADLRHYLNWLTRQRY-($NH_2$) | SEQ ID NO: 101 |
| B4 | KPKPEAPGKDASPEEWNRYYADARHYLNWLTRQR-(n-methyl Y)-($NH_2$) | SEQ ID NO: 104 |
| B5 | PKPEAPGKDASPEEWNRYYADARHYLNWLTRQR-(n-methyl Y)-($NH_2$) | SEQ ID NO: 105 |
| B6 | PKPKAPGKDASPEEWNRYYADARHYLNWLTRQR-(n-methyl Y)-($NH_2$) | SEQ ID NO: 106 |
| B7 | PKPEAPKKDASPEEWNRYYADARHYLNWLTRQR-(n-methyl Y)-($NH_2$) | SEQ ID NO: 107 |
| B8 | PKPEAPGKDASPKEWNRYYADARHYLNWLTRQR-(n-methyl Y)-($NH_2$) | SEQ ID NO: 108 |
| B9 | PKPEAPGKDASPEEWKRYYADARHYLNWLTRQR-(n-methyl Y)-($NH_2$) | SEQ ID NO: 109 |
| B10 | PKPEAPGKDASPEEWNRYYADLRHYLNWLTRQR-(n-methyl Y)-($NH_2$) | SEQ ID NO: 110 |
| B11 | PKPEAPGKDASPEEWNRYYADLRHYLNWLTRQR-(homotyrosine)-($NH_2$) | SEQ ID NO: 111 |
| B12 | PKPEAPGKDASPEEWNRYYADLRHYLNWLTRQRy-($NH_2$) | SEQ ID NO: 112 |
| B13 | PKPEAPGKDASPEEWNRYYADLRHYLNWLTRQRF-($NH_2$) | SEQ ID NO: 113 |
| B14 | PKPEAPGKDASPEEWNRYYkDLRHYLNWLTRQRF-($NH_2$) | SEQ ID NO: 114 |
| B15 | PKPEAPGkDASPEEWNRYYADLRHYLNWLTRQRF-($NH_2$) | SEQ ID NO: 115 |
| B16 | PKPEAPGKDASPEEWNRYYKDLRHYLNWLTRQRF-($NH_2$) | SEQ ID NO: 116 |
| B19 | PKPEKPGKDASPEEWNRYYKDLRHYLNWLTRQRF-($NH_2$) | SEQ ID NO: 119 |
| B20 | PKPEAPGKDASPKEWNRYYKDLRHYLNWLTRQRF-($NH_2$) | SEQ ID NO: 120 |

TABLE 5-continued

Exemplary compounds: PYY analog polypeptides optionally comprising a lipophilic substituent, optionally via a spacer; and optionally further comprising a bridging moiety.

| Compound No. | Sequence | SEQ ID NO: |
|---|---|---|
| B22 | PKPEAPGKDASPEEWNRYY-Dap-DLRHYLNWLTRQRF-($NH_2$) | SEQ ID NO: 122 |
| B23 | PKPEAPGKDASPEEWQRYYKDLRHYLNWLTRQRF-($NH_2$) | SEQ ID NO: 123 |
| B24 | PKPEAPGKDASPEEWDRYYKDLRHYLNWLTRQRF-($NH_2$) | SEQ ID NO: 124 |
| B25 | PKPEAPGKDASPEEWSRYYKDLRHYLNWLTRQRF-($NH_2$) | SEQ ID NO: 125 |
| B26 | PKPEAPGKDASPEEWTRYYKDLRHYLNWLTRQRF-($NH_2$) | SEQ ID NO: 126 |
| B27 | PKPEKPGKDASPKEWNRYYKDLRHYLNWLTRQRF-($NH_2$) | SEQ ID NO: 127 |
| B29 | PKPEKPGEDASPKEWNRYYKDLRHYLNWLTRQRF-($NH_2$) | SEQ ID NO: 129 |
| B30 | PKPEAPGKDASPEEW-homoSer-RYYKDLRHYLNWLTRQRF-($NH_2$) | SEQ ID NO: 130 |
| B31 | PKPEAPGKDASPEEW-(alpha-methyl-Ser)-RYYKDLRHYLNWLTRQRF-($NH_2$) | SEQ ID NO: 131 |
| B34 | PKPEKPGEDASPKEWDRYYKDLRHYLNWLTRQRF-($NH_2$) | SEQ ID NO: 134 |
| B39 | PKPEKPGKDASPKEWERYYKDLRHYLNWLTRQRF-($NH_2$) | SEQ ID NO: 139 |
| B40 | PKPEKPGKDASPKEWDRYYKDLRHYLNWLTRQRF-($NH_2$) | SEQ ID NO: 140 |
| B41 | PKPEAPGKDASPEEWERYYKDLRHYLNWLTRQRF-($NH_2$) | SEQ ID NO: 141 |
| B43 | PKPEAPGKDASPEEWKRYYEDLRHYLNWLTRQRF-($NH_2$) | SEQ ID NO: 143 |
| B44 | PKPEAPGKDASPEEWKRYYDDLRHYLNWLTRQRF-($NH_2$) | SEQ ID NO: 144 |
| B45 | PKPEAPGKDASPKEWDRYYKDLRHYLNWLTRQRF-($NH_2$) | SEQ ID NO: 145 |
| B46 | PKPEAPGKKASPEEWDRYYKDLRHYLNWLTRQRF-($NH_2$) | SEQ ID NO: 146 |
| B47 | PKPEAPGKDASPEEWDRYYKDDRHYKNWLTRQRF-($NH_2$) | SEQ ID NO: 147 |
| B48 | PKPEAPGKDASPEEWDRYYKDKRHYENWLTRQRF-($NH_2$) | SEQ ID NO: 148 |
| B49 | PKPEAPGKDASPEEWNRYYADLRHYLNWLTRQR-(β-homo Tyr)-($NH_2$) | SEQ ID NO: 149 |
| B50 | PKPEAPGKDASPEEWNRYYADLRHYLNWLTRKRF-($NH_2$) | SEQ ID NO: 150 |
| B51 | PKPEAPGKDASPEEWNRYYADLRHYLKWLTRQRF-($NH_2$) | SEQ ID NO: 151 |
| B52 | PKPEAPGKDASPEEWNRYYADLRHKLNWLTRQRF-($NH_2$) | SEQ ID NO: 152 |
| B53 | PKPEAPGKDASPEEWNRYYADLKHYLNWLTRQRF-($NH_2$) | SEQ ID NO: 153 |

TABLE 5-continued

Exemplary compounds: PYY analog polypeptides optionally comprising a lipophilic substituent, optionally via a spacer; and optionally further comprising a bridging moiety.

| Compound No. | Sequence | SEQ ID NO: |
|---|---|---|
| B55 | PKPEAPGKDASPEEWKRYYADLRHYLNWLTRQRF-($NH_2$) | SEQ ID NO: 155 |
| B56 | PKPEAPGKDASPEEWNRYYADLRHYLNWLTRQR-(4-pyridyl Ala)-($NH_2$) | SEQ ID NO: 156 |
| B57 | PKPEAPGKDASPEEWNRYYADLRHYLNWLTRQR-(3-pyridyl Ala)-($NH_2$) | SEQ ID NO: 157 |
| B58 | PKPEAPGKDASPEEWNRYYADLRHYLNWLTRQR-(4-methyl Phe)-($NH_2$) | SEQ ID NO: 158 |
| B59 | PKPEAPGKDASPEEWNRYYADLRHYLNWLTRQR-(4-carboxy Phe)-($NH_2$) | SEQ ID NO: 159 |
| B60 | PKPEAPGKDASPEEWNRYYADLRHYLNWLTRQR-(4-fluoro Phe)-($NH_2$) | SEQ ID NO: 160 |
| B61 | PKPEAPGKDASPEEWNRYYADLRHYLNWLTRQR-(homo Phe)-($NH_2$) | SEQ ID NO: 161 |
| B62 | PKPEAPGKDASPEEWNRYYADLRHYLNWLTRQR-(n-methyl Phe)-($NH_2$) | SEQ ID NO: 162 |
| B63 | PKPEAPKKDASPEELNRYYADARHYLNWLTRQR-(n-methyl Tyr)-($NH_2$) | SEQ ID NO: 163 |
| B64 | PKPEAPKKDASPEELNRYYADARHYLNWLTRQRF-($NH_2$) | SEQ ID NO: 164 |
| B66 | PKPEAPGKDKSPEEWNRYYKDLRHYLNWLTRQRF-($NH_2$) | SEQ ID NO: 166 |
| B67 | PKPEAPGKDASPEKWNRYYKDLRHYLNWLTRQRF-($NH_2$) | SEQ ID NO: 167 |
| B68 | PKPEAPGKDASPEEWNRKYKDLRHYLNWLTRQRF-($NH_2$) | SEQ ID NO: 168 |
| B69 | PKPEAPGKDASPEEWNRYKKDLRHYLNWLTRQRF-($NH_2$) | SEQ ID NO: 169 |
| B75 | PKPEKPGKDASPEEWSRYYKDLRHYLNWLTRQRF-($NH_2$) | SEQ ID NO: 175 |
| B77 | PKPEKPGEDASPEEWDRYYKDLRHYLNWLTRQRF-($NH_2$) | SEQ ID NO: 177 |
| B79 | PKPEAPGKDASPEEWDRYYKDLRHYLNWLTRQRY-($NH_2$) | SEQ ID NO: 179 |
| B80 | PKPEAPGDASPEEWDRYYKDLRHYLNWLTRQRF-($NH_2$) | SEQ ID NO: 180 |
| B81 | PKPEAPGDASPEEWKRYYEDLRHYLNWLTRQRF-($NH_2$) | SEQ ID NO: 181 |

In some embodiments, the isolated polypeptide comprises an amino acid sequence selected from the group consisting of SEQ ID NOs: 101 to 181. or a pharmaceutically acceptable salt thereof.

In some embodiments, the isolated polypeptide comprises an amino acid sequence selected from the group consisting of SEQ ID NOs: 113, 124, and 143 or a pharmaceutically acceptable salt thereof.

In some embodiments, the isolated polypeptide comprises an amino acid sequence of SEQ ID NO: 113 or a pharmaceutically acceptable salt thereof. In some embodiments, the isolated polypeptide comprises an amino acid sequence of SEQ ID NO: 124 or a pharmaceutically acceptable salt thereof. In some embodiments, the isolated polypeptide comprises an amino acid sequence of SEQ ID NO: 143 or a pharmaceutically acceptable salt thereof.

In some embodiments, the present invention provides a compound set forth in the Table 5, above, or a pharmaceutically acceptable salt thereof. In some embodiments, the present invention provides an isolated polypeptide that comprises an amino acid sequence selected from the group consisting of SEQ ID NOs: 101 to 181 or a pharmaceutically acceptable salt thereof. In some embodiments the pharmaceutically acceptable salt is an acetate salt. In some embodiments the pharmaceutically acceptable salt is a trifluoroacetic acid (TFA) salt. In some embodiments the pharmaceutically acceptable salt is a hydrochloric acid (HCl) salt.

In one embodiment, the compound is the isolated polypeptide comprising an amino acid sequence of SEQ ID NO: 113 or a pharmaceutically acceptable salt thereof. In some embodiments, the compound is the acetate salt of the isolated polypeptide comprising an amino acid sequence of SEQ ID NO: 113. In some embodiments, the compound is the TFA salt of the isolated polypeptide comprising an amino acid sequence of SEQ ID NO: 113. In some embodiments, the compound is the HCl salt of the isolated polypeptide comprising an amino acid sequence of SEQ ID NO: 113.

In one embodiment, the compound is the isolated polypeptide comprising an amino acid sequence of SEQ ID NO: 124 or a pharmaceutically acceptable salt thereof. In some embodiments, the compound is the acetate salt of the isolated polypeptide comprising an amino acid sequence of SEQ ID NO: 124. In some embodiments, the compound is the TFA salt of the isolated polypeptide comprising an amino acid sequence of SEQ ID NO: 124. In some embodiments, the compound is the HCl salt of the isolated polypeptide comprising an amino acid sequence of SEQ ID NO: 124.

In one embodiment, the compound is the isolated polypeptide comprising an amino acid sequence of SEQ ID NO: 143 or a pharmaceutically acceptable salt thereof. In some embodiments, the compound is the acetate salt of the isolated polypeptide comprising an amino acid sequence of SEQ ID NO: 143. In some embodiments, the compound is the TFA salt of the isolated polypeptide comprising an amino acid sequence of SEQ ID NO: 143. In some embodiments, the compound is the HCl salt of the isolated polypeptide comprising an amino acid sequence of SEQ ID NO: 143.

In some embodiments, an isolated polypeptide of the disclosure comprises an amino acid sequence selected from the group consisting of the following peptides listed in Table 6:

TABLE 6

Exemplary compounds: PYY analog polypeptides optionally covalently bound to a lipophilic substituent, optionally via a spacer

| Compound No. | Sequence | SEQ ID NO: |
|---|---|---|
| C39 | PKPEKPGKDASPKEWE*RYYK*DLRHYLNWLTRQRF-($NH_2$) | SEQ ID NO: 239 |
| C40 | PKPEKPGKDASPKEWD*RYYK*DLRHYLNWLTRQRF-($NH_2$) | SEQ ID NO: 240 |
| C41 | PKPEAPGKDASPEEWE*RYYK*DLRHYLNWLTRQRF-($NH_2$) | SEQ ID NO: 241 |
| C42 | PKPEAPGKDASPEEWD*RYYK*DLRHYLNWLTRQRF-($NH_2$) | SEQ ID NO: 242 |
| C43 | PKPEAPGKDASPEEWK*RYYE*DLRHYLNWLTRQRF-($NH_2$) | SEQ ID NO: 243 |
| C44 | PKPEAPGKDASPEEWK*RYYD*DLRHYLNWLTRQRF-($NH_2$) | SEQ ID NO: 244 |
| C45 | PKPEAPGKD*ASPK*EWDRYYKDLRHYLNWLTRQRF-($NH_2$) | SEQ ID NO: 245 |
| C46 | PKPEAPGKK*ASPE*EWDRYYKDLRHYLNWLTRQRF-($NH_2$) | SEQ ID NO: 246 |

TABLE 6-continued

Exemplary compounds: PYY analog polypeptides optionally covalently bound to a lipophilic substituent, optionally via a spacer

| Compound No. | Sequence | SEQ ID NO: |
|---|---|---|
| C47 | PKPEAPGKDASPEEWDRYYKDD*RHYK*NWLTRQRF-($NH_2$) | SEQ ID NO: 247 |
| C48 | PKPEAPGKDASPEEWDRYYKDK*RHYE*NWLTRQRF-($NH_2$) | SEQ ID NO: 248 |
| C80 | PKPEAPGDASPEEWD*RYYK*DLRHYLNWLTRQRF-($NH_2$) | SEQ ID NO: 280 |
| C81 | PKPEAPGDASPEEWK*RYYE*DLRHYLNWLTRQRF-($NH_2$) | SEQ ID NO: 281 |

Note:
Each pairing of K* and E* and each pairing of K* and D* represent a covalent amide of E* or the linkage derived from the amino sidechain of K* and the carboxy sidechain caboxy sidechain of D* (with loss of a water molecule).

In some embodiments, the isolated polypeptide comprises an amino acid sequence selected from the group consisting of SEQ ID NOs: 239, 240, 241, 242, 243, 244, 245, 246, 247, 248, 280, and 281 or a pharmaceutically acceptable salt thereof.

In some embodiments, the isolated polypeptide comprises an amino acid sequence of SEQ ID NO: 239 or a pharmaceutically acceptable salt thereof. In some embodiments, the isolated polypeptide comprises an amino acid sequence of SEQ ID NO: 240 or a pharmaceutically acceptable salt thereof. In some embodiments, the isolated polypeptide comprises an amino acid sequence of SEQ ID NO: 241 or a pharmaceutically acceptable salt thereof. In some embodiments, the isolated polypeptide comprises an amino acid sequence of SEQ ID NO: 242 or a pharmaceutically acceptable salt thereof. In some embodiments, the isolated polypeptide comprises an amino acid sequence of SEQ ID NO: 243 or a pharmaceutically acceptable salt thereof. In some embodiments, the isolated polypeptide comprises an amino acid sequence of SEQ ID NO: 244 or a pharmaceutically acceptable salt thereof. In some embodiments, the isolated polypeptide comprises an amino acid sequence of SEQ ID NO: 245 or a pharmaceutically acceptable salt thereof. In some embodiments, the isolated polypeptide comprises an amino acid sequence of SEQ ID NO: 246 or a pharmaceutically acceptable salt thereof. In some embodiments, the isolated polypeptide comprises an amino acid sequence of SEQ ID NO: 247 or a pharmaceutically acceptable salt thereof. In some embodiments, the isolated polypeptide comprises an amino acid sequence of SEQ ID NO: 248 or a pharmaceutically acceptable salt thereof. In some embodiments, the isolated polypeptide comprises an amino acid sequence of SEQ ID NO: 280 or a pharmaceutically acceptable salt thereof. In some embodiments, the isolated polypeptide comprises an amino acid sequence of SEQ ID NO: 281 or a pharmaceutically acceptable salt thereof.

In some embodiments the pharmaceutically acceptable salt is an acetate salt. In some embodiments the pharmaceutically acceptable salt is a trifluoroacetic acid (TFA) salt. In some embodiments the pharmaceutically acceptable salt is a hydrochloric acid (HCl) salt.

In one embodiment, the compound is the isolated polypeptide comprising an amino acid sequence of SEQ ID NO: 242 or a pharmaceutically acceptable salt thereof. In some embodiments, the compound is the acetate salt of the isolated polypeptide comprising an amino acid sequence of SEQ ID NO: 242. In some embodiments, the compound is the TFA salt of the isolated polypeptide comprising an amino acid sequence of SEQ ID NO: 242. In some embodiments, the compound is the HCl salt of the isolated polypeptide comprising an amino acid sequence of SEQ ID NO: 242.

In one embodiment, the compound is the isolated polypeptide comprising an amino acid sequence of SEQ ID NO: 243 or a pharmaceutically acceptable salt thereof. In some embodiments, the compound is the acetate salt of the isolated polypeptide comprising an amino acid sequence of SEQ ID NO: 243. In some embodiments, the compound is the TFA salt of the isolated polypeptide comprising an amino acid sequence of SEQ ID NO: 243. In some embodiments, the compound is the HCl salt of the isolated polypeptide comprising an amino acid sequence of SEQ ID NO: 243.

DESCRIPTION OF EXEMPLARY EMBODIMENTS

In certain embodiments, the present disclosure provides an isolated polypeptide comprising the amino acid sequence of SEQ ID NO: 90: $X_0PX_2PX_4X_5PX_7X_8X_9X_{10}SPX_{13}X_{14}X_{15}X_{16}RX_{18}X_{19}X_{20}DX_{22}X_{23}HX_{25}X_{26}X_{27}WLTRX_{32}RX_{34}$-(OH/$NH_2$) (SEQ ID NO: 90), or a pharmaceutically acceptable salt thereof, wherein:

$X_0$ is absent or K;
$X_2$ is K;
$X_4$ is E or K;
$X_5$ is A or K;
$X_7$ is G or K
$X_8$ is E, K, or k;
$X_9$ is D or K;
$X_{10}$ is A or K;
$X_{13}$ is E or K;
$X_{14}$ is E or K;
$X_{15}$ is L or W;
$X_{16}$ is D, E, K, N, Q, S, T, α-methylserine, or homoserine;
$X_{18}$ is K or Y;
$X_{19}$ is K or Y;
$X_{20}$ is A, D, E, K, k, or Dap,
$X_{22}$ is A, D, K, or L;
$X_{23}$ is K or R;
$X_{25}$ is K or Y;
$X_{26}$ is E, K, or L;
$X_{27}$ is K or N;
$X_{32}$ is K or Q;
$X_{34}$ is F, y, 3-pyridinylalanine, 4-pyridinylalanine, 4-carboxyphenylalanine, 4-fluorophenylalanine, 4-methylphenylalanine, N-methylphenylalanine, homophenylalanine, (3-homotyrosine, homotyrosine, or N-methyltyrosine;

wherein when $X_0$, $X_2$, $X_4$, $X_5$, $X_7$, $X_8$, $X_{13}$, $X_{20}$, $X_{23}$, $X_{25}$, $X_{27}$, or $X_{32}$ are K, the lysine residue is optionally covalently bound to a lipophilic substituent, optionally via a spacer, and wherein when $X_8$ or $X_{20}$ are k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_9$ and $X_{13}$ or at positions $X_{16}$ and $X_{20}$ or at positions $X_{22}$ and $X_{26}$.

In some embodiments, when $X_{15}$ is L, $X_{22}$ is A.

In some embodiment, when $X_{16}$ is N, $X_{20}$ is not A.

In some embodiments, when $X_8$ is E, $X_5$ is K and $X_{20}$ is K, and the lysine residue at either of $X_5$ or $X_{20}$ is covalently bound to a lipophilic substituent, optionally via a spacer.

In some embodiments, $X_8$ is K. In some embodiments, the lysine residue at the 8$^{th}$ position of the polypeptide sequence is covalently bound to a lipophilic substituent, optionally via a spacer.

In some embodiments, $X_{15}$ is W.

In some embodiments, $X_{34}$ is F.

In some embodiments, the peptide further comprises a lactam bridge formed via an amide bond between the side chains of a lysine and a glutamic acid at positions $X_9$ and $X_{13}$, respectively.

In some embodiments, the peptide further comprises a lactam bridge formed via an amide bond between the side chains of an aspartic acid and a lysine at positions $X_9$ and $X_{13}$, respectively.

In some embodiments, the peptide further comprises a lactam bridge formed via an amide bond between the side chains of a lysine and an aspartic acid at positions $X_{16}$ and $X_{20}$, respectively. In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively. In some embodiments, the peptide further comprises a lactam bridge formed via an amide bond between the side chains of a lysine and a glutamic acid at positions $X_{22}$ and $X_{26}$, respectively. In some embodiments, the peptide further comprises a lactam bridge formed via an amide bond between the side chains of an aspartic acid and a lysine at positions $X_{22}$ and $X_{26}$, respectively.

In some embodiments, $X_0$ is absent. In some embodiments, $X_0$ is K. In some embodiments, $X_0$ is K covalently bound to a lipophilic substituent, optionally via a spacer.

In some embodiments, $X_2$ is K. In some embodiments, $X_2$ is K covalently bound to a lipophilic substituent, optionally via a spacer.

In some embodiments, $X_4$ is E. In some embodiments, $X_4$ is K. In some embodiments, $X_4$ is K covalently bound to a lipophilic substituent, optionally via a spacer.

In some embodiments, $X_5$ is A. In some embodiments, $X_5$ is K. In some embodiments, $X_5$ is K covalently bound to a lipophilic substituent, optionally via a spacer.

In some embodiments, $X_7$ is G. In some embodiments, $X_7$ is K. In some embodiments, $X_7$ is K covalently bound to a lipophilic substituent, optionally via a spacer.

In some embodiments, $X_8$ is E. In some embodiments, $X_8$ is K. In some embodiments, $X_8$ is K covalently bound to a lipophilic substituent, optionally via a spacer. In some embodiments, $X_8$ is k. In some embodiments, $X_8$ is k covalently bound to a lipophilic substituent, optionally via a spacer.

As used herein, k refers to D-lysine.

In some embodiments, $X_9$ is D. In some embodiments, $X_9$ is K.

In some embodiments, $X_{10}$ is A. In some embodiments, $X_{10}$ is K. In some embodiments, $X_{10}$ is K covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{14}$ is E. In some embodiments, $X_{14}$ is K.

In some embodiments, $X_{15}$ is L. In some embodiments, $X_{15}$ is W.

In some embodiments, $X_{16}$ is D. In some embodiments, $X_{16}$ is E. In some embodiments, $X_{16}$ is K. In some embodiments, $X_{16}$ is N. In some embodiments, $X_{16}$ is Q. In some embodiments, $X_{16}$ is S. In some embodiments, $X_{16}$ is T. In some embodiments, $X_{16}$ is α-methylserine. In some embodiments, $X_{16}$ is homoserine.

In some embodiments, $X_{18}$ is K. In some embodiments, $X_{18}$ is Y.

In some embodiments, $X_{19}$ is K. In some embodiments, $X_{19}$ is Y.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer. In some embodiments, $X_{20}$ is Dap.

As used herein, Dap refers to diaminopimelic acid.

In some embodiments, $X_{22}$ is A. In some embodiments, $X_{22}$ is D. In some embodiments, $X_{22}$ is K. In some embodiments, $X_{22}$ is L.

In some embodiments, $X_{23}$ is K. In some embodiments, $X_{23}$ is K covalently bound to a lipophilic substituent, optionally via a spacer. In some embodiments, $X_{23}$ is R.

In some embodiments, $X_{25}$ is K. In some embodiments, $X_{25}$ is K covalently bound to a lipophilic substituent, optionally via a spacer. In some embodiments, $X_{25}$ is Y.

In some embodiments, $X_{26}$ is E. In some embodiments, $X_{26}$ is K. In some embodiments, $X_{26}$ is L.

In some embodiments, $X_{27}$ is K. In some embodiments, $X_{27}$ is K covalently bound to a lipophilic substituent, optionally via a spacer. In some embodiments, $X_{27}$ is N.

In some embodiments, $X_{32}$ is K. In some embodiments, $X_{32}$ is K covalently bound to a lipophilic substituent, optionally via a spacer. In some embodiments, $X_{32}$ is Q.

In some embodiments, $X_{34}$ is F. In some embodiments, $X_{34}$ is y. In some embodiments, $X_{34}$ is 3-pyridinylalanine. In some embodiments, $X_{34}$ is 4-pyridinylalanine. In some embodiments, $X_{34}$ is 4-carboxyphenylalanine. In some embodiments, $X_{34}$ is 4-fluorophenylalanine. In some embodiments, $X_{34}$ is 4-methylphenylalanine. In some embodiments, $X_{34}$ is N-methylphenylalanine. In some embodiments, $X_{34}$ is homophenylalanine. In some embodiments, $X_{34}$ is β-homotyrosine. In some embodiments, $X_{34}$ is homotyrosine. In some embodiments, $X_{34}$ is N-methyltyrosine.

As used herein, y refers to D-tyrosine.

In some embodiments, carboxy terminal amino acid, i.e. $X_{34}$, is —$X_{34}$—($NH_2$). In some embodiments, carboxy terminal amino acid $X_{34}$ is —$X_{34}$-(OH).

In some embodiments, certain amino acids represented by the consensus sequence of SEQ ID NO: 90 include the following:

In some embodiments, $X_5$ is A and $X_8$ is K covalently bound to a lipophilic substituent, optionally via a spacer. In some embodiments, $X_5$ is A and $X_{15}$ is W. In some embodiments, $X_5$ is A and $X_{16}$ is D. In some embodiments, $X_5$ is A and $X_{16}$ is K. In some embodiments, $X_5$ is A and $X_{16}$ is N. In some embodiments, $X_5$ is A and $X_{20}$ is K. In some embodiments, $X_5$ is A and $X_{20}$ is E. In some embodiments, $X_5$ is A and $X_{20}$ is A. In some embodiments, $X_5$ is A and $X_{34}$ is F.

In some embodiments, $X_5$ is K covalently bound to a lipophilic substituent, optionally via a spacer, and $X_8$ is E. In some embodiments, $X_5$ is K covalently bound to a lipophilic substituent, optionally via a spacer, and $X_{15}$ is W. In some embodiments, $X_5$ is K covalently bound to a lipophilic substituent, optionally via a spacer, and $X_{16}$ is N. In some embodiments, $X_5$ is K covalently bound to a lipophilic substituent, optionally via a spacer, and $X_{16}$ is D. In some embodiments, $X_5$ is K covalently bound to a lipophilic substituent, optionally via a spacer, and $X_{20}$ is K. In some embodiments, $X_5$ is K covalently bound to a lipophilic substituent, optionally via a spacer, and $X_{34}$ is F.

In some embodiments, $X_5$ is K and $X_8$ is E. In some embodiments, $X_5$ is K and $X_{15}$ is W. In some embodiments, $X_5$ is K and $X_{16}$ is N. In some embodiments, $X_5$ is K and $X_{16}$ is D. In some embodiments, $X_5$ is K and $X_{20}$ is K. In some embodiments, $X_5$ is K and $X_{20}$ is K covalently bound to a lipophilic substituent, optionally via a spacer. In some embodiments, $X_5$ is K and $X_{34}$ is F.

In some embodiments, $X_8$ is E and $X_{15}$ is W. In some embodiments, $X_8$ is E and $X_{16}$ is D. In some embodiments, $X_8$ is E and $X_{16}$ is N. In some embodiments, $X_8$ is E and $X_{20}$ is K. In some embodiments, $X_8$ is E and $X_{20}$ is K covalently bound to a lipophilic substituent, optionally via a spacer. In some embodiments, $X_8$ is E and $X_{34}$ is F.

In some embodiments, $X_8$ is K covalently bound to a lipophilic substituent, optionally via a spacer, and $X_{15}$ is W. In some embodiments, $X_8$ is K covalently bound to a lipophilic substituent, optionally via a spacer, and $X_{16}$ is D. In some embodiments, $X_8$ is K covalently bound to a lipophilic substituent, optionally via a spacer, and $X_{16}$ is K. In some embodiments, $X_8$ is K covalently bound to a lipophilic substituent, optionally via a spacer, and $X_{16}$ is N. In some embodiments, $X_8$ is K covalently bound to a lipophilic substituent, optionally via a spacer, and $X_{20}$ is K. In some embodiments, $X_8$ is K covalently bound to a lipophilic substituent, optionally via a spacer, and $X_{20}$ is E. In some embodiments, $X_8$ is K covalently bound to a lipophilic substituent, optionally via a spacer, and $X_{20}$ is A. In some embodiments, $X_8$ is K covalently bound to a lipophilic substituent, optionally via a spacer, and $X_{34}$ is F.

In some embodiments, $X_{15}$ is W and $X_{16}$ is D. In some embodiments, $X_{15}$ is W and $X_{16}$ is K. In some embodiments, $X_{15}$ is W and $X_{16}$ is N. In some embodiments, $X_{15}$ is W and $X_{20}$ is K. In some embodiments, $X_{15}$ is W and $X_{20}$ is E. In some embodiments, $X_{15}$ is W and $X_{20}$ is A. In some embodiments, $X_{15}$ is W and $X_{34}$ is F.

In some embodiments, $X_{16}$ is D and $X_{20}$ is K. In some embodiments, $X_{16}$ is D and $X_{34}$ is F.

In some embodiments, $X_{16}$ is K and $X_{20}$ is E. In some embodiments, $X_{16}$ is K and $X_{20}$ is D.

In some embodiments, $X_{16}$ is K and $X_{34}$ is F.

In some embodiments, $X_{16}$ is N and $X_{20}$ is A. In some embodiments, $X_{16}$ is N and $X_{20}$ is K.

In some embodiments, $X_{16}$ is N and $X_{34}$ is F.

In some embodiments, $X_{20}$ is K and $X_{34}$ is F.

In some embodiments, $X_{20}$ is E and $X_{34}$ is F.

In some embodiments, $X_{20}$ is A and $X_{34}$ is F.

In some embodiments, certain amino acids represented by the consensus sequence of SEQ ID NO: 90 include the following:

In some embodiments, $X_5$ is A, $X_8$ is K covalently bound to a lipophilic substituent, optionally via a spacer, and $X_{15}$ is W. In some embodiments, $X_5$ is A, $X_8$ is K covalently bound to a lipophilic substituent, optionally via a spacer, and $X_{16}$ is D. In some embodiments, $X_5$ is A, $X_8$ is K covalently bound to a lipophilic substituent, optionally via a spacer, and $X_{16}$ is K. In some embodiments, $X_5$ is A, $X_8$ is K covalently bound to a lipophilic substituent, optionally via a spacer, and $X_{16}$ is N. In some embodiments, $X_5$ is A, $X_8$ is K covalently bound to a lipophilic substituent, optionally via a spacer, and $X_{20}$ is K. In some embodiments, $X_5$ is A, $X_8$ is K covalently bound to a lipophilic substituent, optionally via a spacer, and $X_{20}$ is E. In some embodiments, $X_5$ is A, $X_8$ is K covalently bound to a lipophilic substituent, optionally via a spacer, and $X_{20}$ is A. In some embodiments, $X_5$ is A, $X_8$ is K covalently bound to a lipophilic substituent, optionally via a spacer, and $X_{34}$ is F.

In some embodiments, $X_5$ is A, $X_{15}$ is W, and $X_{16}$ is D. In some embodiments, $X_5$ is A, $X_{15}$ is W, and $X_{16}$ is D. In some embodiments, $X_5$ is A, $X_{15}$ is W, and $X_{16}$ is K. In some embodiments, $X_5$ is A, $X_{15}$ is W, and $X_{16}$ N. In some embodiments, $X_5$ is A, $X_{15}$ is W, and $X_{20}$ is K. In some embodiments, $X_5$ is A, $X_{15}$ is W, and $X_{20}$ is E. In some embodiments, $X_5$ is A, $X_{15}$ is W, and $X_{20}$ is A. In some embodiments, $X_5$ is A, $X_{15}$ is W, and $X_{34}$ is F.

In some embodiments, $X_5$ is A, $X_{16}$ is D, and $X_{20}$ is K. In some embodiments, $X_5$ is A, $X_{16}$ is D, and $X_{34}$ is F.

In some embodiments, $X_5$ is A, $X_{16}$ is K, and $X_{20}$ is E. In some embodiments, $X_5$ is A, $X_{16}$ is K, and $X_{20}$ is D. In some embodiments, $X_5$ is A, $X_{16}$ is K, and $X_{34}$ is F.

In some embodiments, $X_5$ is A, $X_{16}$ is N, and $X_{20}$ is A. In some embodiments, $X_5$ is A, $X_{16}$ is N, and $X_{20}$ is K. In some embodiments, $X_5$ is A, $X_{16}$ is N, and $X_{34}$ is F.

In some embodiments, $X_5$ is A, $X_{20}$ is K, and $X_{34}$ is F.

In some embodiments, $X_5$ is A, $X_{20}$ is E, and $X_{34}$ is F.

In some embodiments, $X_5$ is A, $X_{20}$ is A, and $X_{34}$ is F.

In some embodiments, $X_5$ is K covalently bound to a lipophilic substituent, optionally via a spacer, $X_8$ is E, and $X_{15}$ is W. In some embodiments, $X_5$ is K covalently bound to a lipophilic substituent, optionally via a spacer, $X_8$ is E, and $X_{16}$ is N. In some embodiments, $X_5$ is K covalently bound to a lipophilic substituent, optionally via a spacer, $X_8$ is E, and $X_{16}$ is D. In some embodiments, $X_5$ is K covalently bound to a lipophilic substituent, optionally via a spacer, $X_8$ is E, and $X_{20}$ is K. In some embodiments, $X_5$ is K covalently bound to a lipophilic substituent, optionally via a spacer, $X_8$ is E, and $X_{34}$ is F.

In some embodiments, $X_5$ is K, $X_8$ is E, and $X_{15}$ is W. In some embodiments, $X_5$ is K, $X_8$ is E, and $X_{16}$ is N. In some embodiments, $X_5$ is K, $X_8$ is E, and $X_{16}$ is D. In some embodiments, $X_5$ is K, $X_8$ is E, and $X_{20}$ is K covalently bound to a lipophilic substituent, optionally via a spacer. In some embodiments, $X_5$ is K, $X_8$ is E, and $X_{34}$ is F.

In some embodiments, $X_8$ is E, $X_{15}$ is W, and $X_{16}$ is N. In some embodiments, $X_8$ is E, $X_{15}$ is W, and $X_{20}$ is K. In some embodiments, $X_8$ is E, $X_{15}$ is W, and $X_{20}$ is K covalently bound to a lipophilic substituent, optionally via a spacer. In some embodiments, $X_8$ is E, $X_{15}$ is W, and $X_{34}$ is F.

In some embodiments, $X_8$ is K covalently bound to a lipophilic substituent, optionally via a spacer, $X_{15}$ is W, and $X_{16}$ is D. In some embodiments, $X_8$ is K covalently bound to a lipophilic substituent, optionally via a spacer, $X_{15}$ is W, and $X_{16}$ is K. In some embodiments, $X_8$ is K covalently bound to a lipophilic substituent, optionally via a spacer, $X_{15}$ is W, and $X_{16}$ is N. In some embodiments, $X_8$ is K covalently bound to a lipophilic substituent, optionally via a spacer, $X_{15}$ is W, and $X_{20}$ is K. In some embodiments, $X_8$ is K covalently bound to a lipophilic substituent, optionally via a spacer, $X_{15}$ is W, and $X_{20}$ is E. In some embodiments, $X_8$ is K covalently bound to a lipophilic substituent, optionally via a spacer, $X_{15}$ is W, and $X_{20}$ is A. In some embodiments, $X_8$ is K covalently bound to a lipophilic substituent, optionally via a spacer, $X_{15}$ is W, and $X_{34}$ is F.

In some embodiments, $X_8$ is K covalently bound to a lipophilic substituent, optionally via a spacer, $X_{16}$ is D, and $X_{20}$ is K. In some embodiments, $X_8$ is K covalently bound to a lipophilic substituent, optionally via a spacer, $X_{16}$ is D, and $X_{34}$ is F.

In some embodiments, $X_8$ is K covalently bound to a lipophilic substituent, optionally via a spacer, $X_{16}$ is K, and $X_{20}$ is E. In some embodiments, $X_8$ is K covalently bound to a lipophilic substituent, optionally via a spacer, $X_{16}$ is K, and $X_{20}$ is D. In some embodiments, $X_8$ is K covalently bound to a lipophilic substituent, optionally via a spacer, $X_{16}$ is K, and $X_{34}$ is F.

In some embodiments, $X_8$ is K covalently bound to a lipophilic substituent, optionally via a spacer, $X_{16}$ is N, and $X_{20}$ is A. In some embodiments, $X_8$ is K covalently bound to a lipophilic substituent, optionally via a spacer, $X_{16}$ is N, and $X_{20}$ is K. In some embodiments, $X_8$ is K covalently bound to a lipophilic substituent, optionally via a spacer, $X_{16}$ is N, and $X_{34}$ is F.

In some embodiments, $X_8$ is K covalently bound to a lipophilic substituent, optionally via a spacer, $X_{20}$ is K, and $X_{34}$ is F.

In some embodiments, $X_8$ is K covalently bound to a lipophilic substituent, optionally via a spacer, $X_{20}$ is E, and $X_{34}$ is F.

In some embodiments, $X_8$ is K covalently bound to a lipophilic substituent, optionally via a spacer, $X_{20}$ is A, and $X_{34}$ is F.

In some embodiments, $X_{15}$ is W, $X_{16}$ is D, and $X_{20}$ is K. In some embodiments, $X_{15}$ is W, $X_{16}$ is D, and $X_{34}$ is F.

In some embodiments, $X_{15}$ is W, $X_{16}$ is K, and $X_{20}$ is E. In some embodiments, $X_{15}$ is W, $X_{16}$ is K, and $X_{20}$ is D. In some embodiments, $X_{15}$ is W, $X_{16}$ is K, and $X_{34}$ is F.

In some embodiments, $X_{15}$ is W, $X_{16}$ is N, and $X_{20}$ is A. In some embodiments, $X_{15}$ is W, $X_{16}$ is N, and $X_{20}$ is K. In some embodiments, $X_{15}$ is W, $X_{16}$ is N, and $X_{34}$ is F.

In some embodiments, $X_{15}$ is W, $X_{20}$ is K, and $X_{34}$ is F.

In some embodiments, $X_{15}$ is W, $X_{20}$ is E, and $X_{34}$ is F.

In some embodiments, $X_{15}$ is W, $X_{20}$ is A, and $X_{34}$ is F.

In some embodiments, $X_{16}$ is D, $X_{20}$ is K, and $X_{34}$ is F.

In some embodiments, $X_{16}$ is K, $X_{20}$ is E, and $X_{34}$ is F.

In some embodiments, $X_{16}$ is K, $X_{20}$ is D, and $X_{34}$ is F.

In some embodiments, $X_{16}$ is N, $X_{20}$ is A, and $X_{34}$ is F.

In some embodiments, $X_{16}$ is N, $X_{20}$ is K, and $X_{34}$ is F.

In certain embodiments, the present disclosure provides an isolated polypeptide comprising the amino acid sequence of SEQ ID NO: 91: PKPE$X_5$P$X_7$$X_8$DASP$X_{13}$E$X_{15}$$X_{16}$RYY$X_{20}$D$X_{22}$RHYLNWLTRQR$X_{34}$-(OH/$NH_2$) (SEQ ID NO: 91), or a pharmaceutically acceptable salt thereof, wherein:

$X_5$ is A or K;

$X_7$ is G or K;

$X_8$ is E, K, or k;

$X_{13}$ is E or K;

$X_{15}$ is L or W;

$X_{16}$ is D, E, K, N, S, α-methylserine, or homoserine;

$X_{20}$ is A, D, E, K, or k, $X_{22}$ is A or L;

$X_{34}$ is F, 3-pyridinylalanine, 4-pyridinylalanine, 4-carboxyphenylalanine, 4-fluorophenylalanine, 4-methylphenylalanine, N-methylphenylalanine, homophenylalanine, β-homotyrosine, homotyrosine, or N-methyltyrosine;

wherein when $X_5$, $X_7$, $X_8$, $X_{13}$, or $X_{20}$ are K, the lysine residue is optionally covalently bound to a lipophilic substituent, optionally via a spacer, and wherein when $X_8$ or $X_{20}$ are k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

In some embodiments, when $X_{15}$ is L, $X_{22}$ is A.

In some embodiment, when $X_{16}$ is N, $X_{20}$ is not A.

In some embodiments, when $X_8$ is E, $X_5$ is K and $X_{20}$ is K, and the lysine residue at either of $X_5$ or $X_{20}$ is covalently bound to a lipophilic substituent, optionally via a spacer.

In some embodiments, $X_8$ is K. In some embodiments, the lysine residue at the $8^{th}$ position of the polypeptide sequence is covalently bound to a lipophilic substituent, optionally via a spacer.

In some embodiments, $X_{15}$ is W.

In some embodiments, $X_{34}$ is F.

In some embodiments, the peptide further comprises a lactam bridge formed via an amide bond between the side chains of a lysine and an aspartic acid at positions $X_{16}$ and $X_{20}$, respectively.

In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively.

In some embodiments, $X_5$ is A. In some embodiments, $X_5$ is K. In some embodiments, $X_5$ is K covalently bound to a lipophilic substituent, optionally via a spacer.

In some embodiments, $X_7$ is G. In some embodiments, $X_7$ is K. In some embodiments, $X_7$ is K covalently bound to a lipophilic substituent, optionally via a spacer.

In some embodiments, $X_8$ is E. In some embodiments, $X_8$ is K. In some embodiments, $X_8$ is K covalently bound to a lipophilic substituent, optionally via a spacer. In some embodiments, $X_8$ is k. In some embodiments, $X_8$ is k covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{15}$ is L. In some embodiments, $X_{15}$ is W.

In some embodiments, $X_{16}$ is D. In some embodiments, $X_{16}$ is E. In some embodiments, $X_{16}$ is K. In some embodiments, $X_{16}$ is N. In some embodiments, $X_{16}$ is S. In some embodiments, $X_{16}$ is α-methylserine. In some embodiments, $X_{16}$ is homoserine.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer.

In some embodiments, $X_{22}$ is A. In some embodiments, $X_{22}$ is L.

In some embodiments, $X_{34}$ is F. In some embodiments, $X_{34}$ is 3-pyridinylalanine. In some embodiments, $X_{34}$ is 4-pyridinylalanine. In some embodiments, $X_{34}$ is 4-carboxyphenylalanine. In some embodiments, $X_{34}$ is 4-fluorophenylalanine. In some embodiments, $X_{34}$ is 4-methylphenylalanine. In some embodiments, $X_{34}$ is N-methylphenylalanine. In some embodiments, $X_{34}$ is homophenylalanine. In some embodiments, $X_{34}$ is β-homotyrosine. In some embodiments, $X_{34}$ is homotyrosine. In some embodiments, $X_{34}$ is N-methyltyrosine.

In some embodiments, carboxy terminal amino acid, i.e. $X_{34}$, is —$X_{34}$—($NH_2$). In some embodiments, carboxy terminal amino acid $X_{34}$ is —$X_{34}$-(OH).

In some embodiments, certain amino acids represented by the consensus sequence of SEQ ID NO: 91 include the following:

In some embodiments, $X_5$ is A and $X_8$ is K covalently bound to a lipophilic substituent, optionally via a spacer. In some embodiments, $X_5$ is A and $X_{15}$ is W. In some embodiments, $X_5$ is A and $X_{16}$ is D. In some embodiments, $X_5$ is A and $X_{16}$ is K. In some embodiments, $X_5$ is A and $X_{16}$ is N. In some embodiments, $X_5$ is A and $X_{20}$ is K. In some embodiments, $X_5$ is A and $X_{20}$ is E. In some embodiments, $X_5$ is A and $X_{20}$ is A. In some embodiments, $X_5$ is A and $X_{34}$ is F.

In some embodiments, $X_5$ is K covalently bound to a lipophilic substituent, optionally via a spacer, and $X_8$ is E. In some embodiments, $X_5$ is K covalently bound to a lipophilic substituent, optionally via a spacer, and $X_{15}$ is W. In some embodiments, $X_5$ is K covalently bound to a lipophilic substituent, optionally via a spacer, and $X_{16}$ is N. In some embodiments, $X_5$ is K covalently bound to a lipophilic substituent, optionally via a spacer, and $X_{16}$ is D. In some embodiments, $X_5$ is K covalently bound to a lipophilic substituent, optionally via a spacer, and $X_{20}$ is K. In some embodiments, $X_5$ is K covalently bound to a lipophilic substituent, optionally via a spacer, and $X_{34}$ is F.

In some embodiments, $X_5$ is K and $X_8$ is E. In some embodiments, $X_5$ is K and $X_{15}$ is W. In some embodiments, $X_5$ is K and $X_{16}$ is N. In some embodiments, $X_5$ is K and $X_{16}$ is D. In some embodiments, $X_5$ is K and $X_{20}$ is K. In some embodiments, $X_5$ is K and $X_{20}$ is K covalently bound to a lipophilic substituent, optionally via a spacer. In some embodiments, $X_5$ is K and $X_{34}$ is F.

In some embodiments, $X_8$ is E and $X_{15}$ is W. In some embodiments, $X_8$ is E and $X_{16}$ is D. In some embodiments, $X_8$ is E and $X_{16}$ is N. In some embodiments, $X_8$ is E and $X_{20}$ is K. In some embodiments, $X_8$ is E and $X_{20}$ is K covalently bound to a lipophilic substituent, optionally via a spacer. In some embodiments, $X_8$ is E and $X_{34}$ is F.

In some embodiments, $X_8$ is K covalently bound to a lipophilic substituent, optionally via a spacer, and $X_{15}$ is W. In some embodiments, $X_8$ is K covalently bound to a lipophilic substituent, optionally via a spacer, and $X_{16}$ is D. In some embodiments, $X_8$ is K covalently bound to a lipophilic substituent, optionally via a spacer, and $X_{16}$ is K. In some embodiments, $X_8$ is K covalently bound to a lipophilic substituent, optionally via a spacer, and $X_{16}$ is N. In some embodiments, $X_8$ is K covalently bound to a lipophilic substituent, optionally via a spacer, and $X_{20}$ is K. In some embodiments, $X_8$ is K covalently bound to a lipophilic substituent, optionally via a spacer, and $X_{20}$ is E. In some embodiments, $X_8$ is K covalently bound to a lipophilic substituent, optionally via a spacer, and $X_{20}$ is A.

In some embodiments, $X_8$ is K covalently bound to a lipophilic substituent, optionally via a spacer, and $X_{34}$ is F.

In some embodiments, $X_{15}$ is W and $X_{16}$ is D. In some embodiments, $X_{15}$ is W and $X_{16}$ is K. In some embodiments, $X_{15}$ is W and $X_{16}$ is N. In some embodiments, $X_{15}$ is W and $X_{20}$ is K. In some embodiments, $X_{15}$ is W and $X_{20}$ is E. In some embodiments, $X_{15}$ is W and $X_{20}$ is A. In some embodiments, $X_{15}$ is W and $X_{34}$ is F.

In some embodiments, $X_{16}$ is D and $X_{20}$ is K. In some embodiments, $X_{16}$ is D and $X_{34}$ is F.

In some embodiments, $X_{16}$ is K and $X_{20}$ is E. In some embodiments, $X_{16}$ is K and $X_{20}$ is D.

In some embodiments, $X_{16}$ is K and $X_{34}$ is F.

In some embodiments, $X_{16}$ is N and $X_{20}$ is A. In some embodiments, $X_{16}$ is N and $X_{20}$ is K.

In some embodiments, $X_{16}$ is N and $X_{34}$ is F.

In some embodiments, $X_{20}$ is K and $X_{34}$ is F.

In some embodiments, $X_{20}$ is E and $X_{34}$ is F.

In some embodiments, $X_{20}$ is A and $X_{34}$ is F.

In some embodiments, certain amino acids represented by the consensus sequence of SEQ ID NO: 91 include the following:

In some embodiments, $X_5$ is A, $X_8$ is K covalently bound to a lipophilic substituent, optionally via a spacer, and $X_{15}$ is W. In some embodiments, $X_5$ is A, $X_8$ is K covalently bound to a lipophilic substituent, optionally via a spacer, and $X_{16}$ is D. In some embodiments, $X_5$ is A, $X_8$ is K covalently bound to a lipophilic substituent, optionally via a spacer, and $X_{16}$ is K. In some embodiments, $X_5$ is A, $X_8$ is K covalently bound to a lipophilic substituent, optionally via a spacer, and $X_{16}$ is N. In some embodiments, $X_5$ is A, $X_8$ is K covalently bound to a lipophilic substituent, optionally via a spacer, and $X_{20}$ is K. In some embodiments, $X_5$ is A, $X_8$ is K covalently bound to a lipophilic substituent, optionally via a spacer, and $X_{20}$ is E. In some embodiments, $X_5$ is A, $X_8$ is K covalently bound to a lipophilic substituent, optionally via a spacer, and $X_{20}$ is A. In some embodiments, $X_5$ is A, $X_8$ is K covalently bound to a lipophilic substituent, optionally via a spacer, and $X_{34}$ is F.

In some embodiments, $X_5$ is A, $X_{15}$ is W, and $X_{16}$ is D. In some embodiments, $X_5$ is A, $X_{15}$ is W, and $X_{16}$ is D. In some embodiments, $X_5$ is A, $X_{15}$ is W, and $X_{16}$ is K. In some embodiments, $X_5$ is A, $X_{15}$ is W, and $X_{16}$ N. In some embodiments, $X_5$ is A, $X_{15}$ is W, and $X_{20}$ is K. In some embodiments, $X_5$ is A, $X_{15}$ is W, and $X_{20}$ is E. In some embodiments, $X_5$ is A, $X_{15}$ is W, and $X_{20}$ is A. In some embodiments, $X_5$ is A, $X_{15}$ is W, and $X_{34}$ is F.

In some embodiments, $X_5$ is A, $X_{16}$ is D, and $X_{20}$ is K. In some embodiments, $X_5$ is A, $X_{16}$ is D, and $X_{34}$ is F.

In some embodiments, $X_5$ is A, $X_{16}$ is K, and $X_{20}$ is E. In some embodiments, $X_5$ is A, $X_{16}$ is K, and $X_{20}$ is D. In some embodiments, $X_5$ is A, $X_{16}$ is K, and $X_{34}$ is F.

In some embodiments, $X_5$ is A, $X_{16}$ is N, and $X_{20}$ is A. In some embodiments, $X_5$ is A, $X_{16}$ is N, and $X_{20}$ is K. In some embodiments, $X_5$ is A, $X_{16}$ is N, and $X_{34}$ is F.

In some embodiments, $X_5$ is A, $X_{20}$ is K, and $X_{34}$ is F.

In some embodiments, $X_5$ is A, $X_{20}$ is E, and $X_{34}$ is F.

In some embodiments, $X_5$ is A, $X_{20}$ is A, and $X_{34}$ is F.

In some embodiments, $X_5$ is K covalently bound to a lipophilic substituent, optionally via a spacer, $X_8$ is E, and $X_{15}$ is W. In some embodiments, $X_5$ is K covalently bound to a lipophilic substituent, optionally via a spacer, $X_8$ is E, and $X_{16}$ is N. In some embodiments, $X_5$ is K covalently bound to a lipophilic substituent, optionally via a spacer, $X_8$ is E, and $X_{16}$ is D. In some embodiments, $X_5$ is K covalently bound to a lipophilic substituent, optionally via a spacer, $X_8$ is E, and $X_{20}$ is K. In some embodiments, $X_5$ is K covalently bound to a lipophilic substituent, optionally via a spacer, $X_8$ is E, and $X_{34}$ is F.

In some embodiments, $X_5$ is K, $X_8$ is E, and $X_{15}$ is W. In some embodiments, $X_5$ is K, $X_8$ is E, and $X_{16}$ is N. In some embodiments, $X_5$ is K, $X_8$ is E, and $X_{16}$ is D. In some embodiments, $X_5$ is K, $X_8$ is E, and $X_{20}$ is K covalently bound to a lipophilic substituent, optionally via a spacer. In some embodiments, $X_5$ is K, $X_8$ is E, and $X_{34}$ is F.

In some embodiments, $X_8$ is E, $X_{15}$ is W, and $X_{16}$ is N. In some embodiments, $X_8$ is E, $X_{15}$ is W, and $X_{20}$ is K. In some embodiments, $X_8$ is E, $X_{15}$ is W, and $X_{20}$ is K covalently bound to a lipophilic substituent, optionally via a spacer. In some embodiments, $X_8$ is E, $X_{15}$ is W, and $X_{34}$ is F.

In some embodiments, $X_8$ is K covalently bound to a lipophilic substituent, optionally via a spacer, $X_{15}$ is W, and $X_{16}$ is D. In some embodiments, $X_8$ is K covalently bound to a lipophilic substituent, optionally via a spacer, $X_{15}$ is W, and $X_{16}$ is K. In some embodiments, $X_8$ is K covalently bound to a lipophilic substituent, optionally via a spacer, $X_{15}$ is W, and $X_{16}$ is N. In some embodiments, $X_8$ is K covalently bound to a lipophilic substituent, optionally via a spacer, $X_{15}$ is W, and $X_{20}$ is K. In some embodiments, $X_8$ is K covalently bound to a lipophilic substituent, optionally via a spacer, $X_{15}$ is W, and $X_{20}$ is E. In some embodiments, $X_8$ is K covalently bound to a lipophilic substituent, optionally via a spacer, $X_{15}$ is W, and $X_{20}$ is A. In some embodiments, $X_8$ is K covalently bound to a lipophilic substituent, optionally via a spacer, $X_{15}$ is W, and $X_{34}$ is F.

In some embodiments, $X_8$ is K covalently bound to a lipophilic substituent, optionally via a spacer, $X_{16}$ is D, and $X_{20}$ is K. In some embodiments, $X_8$ is K covalently bound to a lipophilic substituent, optionally via a spacer, $X_{16}$ is D, and $X_{34}$ is F.

In some embodiments, $X_8$ is K covalently bound to a lipophilic substituent, optionally via a spacer, $X_{16}$ is K, and $X_{20}$ is E. In some embodiments, $X_8$ is K covalently bound to a lipophilic substituent, optionally via a spacer, $X_{16}$ is K, and $X_{20}$ is D. In some embodiments, $X_8$ is K covalently bound to a lipophilic substituent, optionally via a spacer, $X_{16}$ is K, and $X_{34}$ is F.

In some embodiments, $X_8$ is K covalently bound to a lipophilic substituent, optionally via a spacer, $X_{16}$ is N, and $X_{20}$ is A. In some embodiments, $X_8$ is K covalently bound to a lipophilic substituent, optionally via a spacer, $X_{16}$ is N, and $X_{20}$ is K. In some embodiments, $X_8$ is K covalently bound to a lipophilic substituent, optionally via a spacer, $X_{16}$ is N, and $X_{34}$ is F.

In some embodiments, $X_8$ is K covalently bound to a lipophilic substituent, optionally via a spacer, $X_{20}$ is K, and $X_{34}$ is F.

In some embodiments, $X_8$ is K covalently bound to a lipophilic substituent, optionally via a spacer, $X_{20}$ is E, and $X_{34}$ is F.

In some embodiments, $X_8$ is K covalently bound to a lipophilic substituent, optionally via a spacer, $X_{20}$ is A, and $X_{34}$ is F.

In some embodiments, $X_{15}$ is W, $X_{16}$ is D, and $X_{20}$ is K. In some embodiments, $X_{15}$ is W, $X_{16}$ is D, and $X_{34}$ is F.

In some embodiments, $X_{15}$ is W, $X_{16}$ is K, and $X_{20}$ is E. In some embodiments, $X_{15}$ is W, $X_{16}$ is K, and $X_{20}$ is D. In some embodiments, $X_{15}$ is W, $X_{16}$ is K, and $X_{34}$ is F.

In some embodiments, $X_{15}$ is W, $X_{16}$ is N, and $X_{20}$ is A. In some embodiments, $X_{15}$ is W, $X_{16}$ is N, and $X_{20}$ is K. In some embodiments, $X_{15}$ is W, $X_{16}$ is N, and $X_{34}$ is F.

In some embodiments, $X_{15}$ is W, $X_{20}$ is K, and $X_{34}$ is F.

In some embodiments, $X_{15}$ is W, $X_{20}$ is E, and $X_{34}$ is F.

In some embodiments, $X_{15}$ is W, $X_{20}$ is A, and $X_{34}$ is F. In some embodiments, $X_{16}$ is D, $X_{20}$ is K, and $X_{34}$ is F. In some embodiments, $X_{16}$ is K, $X_{20}$ is E, and $X_{34}$ is F. In some embodiments, $X_{16}$ is K, $X_{20}$ is D, and $X_{34}$ is F. In some embodiments, $X_{16}$ is N, $X_{20}$ is A, and $X_{34}$ is F. In some embodiments, $X_{16}$ is N, $X_{20}$ is K, and $X_{34}$ is F.

In certain embodiments, the present disclosure provides an isolated polypeptide comprising the amino acid sequence of SEQ ID NO: 92: PKPE$X_5$P$X_7X_8$DASP$X_{13}$E$X_{15}X_{16}$ RYY$X_{20}$ D$X_{22}$RHYLNWLTRQR$X_{34}$-(OH/$NH_2$) (SEQ ID NO: 92), or a pharmaceutically acceptable salt thereof, wherein:

$X_5$ is A or K;

$X_7$ is G or K;

$X_8$ is E, K, or k;

$X_{13}$ is E or K;

$X_{15}$ is L or W;

$X_{16}$ is D, E, K, S, α-methyl serine, or homoserine;

$X_{20}$ is A, D, E, K, or k, $X_{22}$ is A or L;

$X_{34}$ is F, 3-pyridinylalanine, 4-pyridinylalanine, 4-carboxyphenylalanine, 4-fluorophenylalanine, 4-methylphenylalanine, N-methylphenylalanine, homophenylalanine, β-homotyrosine, homotyrosine, or N-methyltyrosine;

wherein when $X_5$, $X_7$, $X_8$, $X_{13}$, or $X_{20}$ are K, the lysine residue is optionally covalently bound to a lipophilic substituent, optionally via a spacer, and wherein when $X_8$ or $X_{20}$ are k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

In some embodiments, when $X_{15}$ is L, $X_{22}$ is A.

In some embodiments, when $X_8$ is E, $X_5$ is K and $X_{20}$ is K, and the lysine residue at either of $X_5$ or $X_{20}$ is covalently bound to a lipophilic substituent, optionally via a spacer.

In some embodiments, $X_8$ is K. In some embodiments, the lysine residue at the $8^{th}$ position of the polypeptide sequence is covalently bound to a lipophilic substituent, optionally via a spacer.

In some embodiments, $X_{15}$ is W.

In some embodiments, $X_{34}$ is F.

In some embodiments, the peptide further comprises a lactam bridge formed via an amide bond between the side chains of a lysine and an aspartic acid at positions $X_{16}$ and $X_{20}$, respectively.

In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively.

In some embodiments, $X_5$ is A. In some embodiments, $X_5$ is K. In some embodiments, $X_5$ is K covalently bound to a lipophilic substituent, optionally via a spacer.

In some embodiments, $X_7$ is G. In some embodiments, $X_7$ is K. In some embodiments, $X_7$ is K covalently bound to a lipophilic substituent, optionally via a spacer.

In some embodiments, $X_8$ is E. In some embodiments, $X_8$ is K. In some embodiments, $X_8$ is K covalently bound to a lipophilic substituent, optionally via a spacer. In some embodiments, $X_8$ is k. In some embodiments, $X_8$ is k covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{15}$ is L. In some embodiments, $X_{15}$ is W.

In some embodiments, $X_{16}$ is D. In some embodiments, $X_{16}$ is E. In some embodiments, $X_{16}$ is K. In some embodiments, $X_{16}$ is S. In some embodiments, $X_{16}$ is α-methylserine. In some embodiments, $X_{16}$ is homoserine.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer.

In some embodiments, $X_{22}$ is A. In some embodiments, $X_{22}$ is L.

In some embodiments, $X_{34}$ is F. In some embodiments, $X_{34}$ is 3-pyridinylalanine. In some embodiments, $X_{34}$ is 4-pyridinylalanine. In some embodiments, $X_{34}$ is 4-carboxyphenylalanine. In some embodiments, $X_{34}$ is 4-fluorophenylalanine. In some embodiments, $X_{34}$ is 4-methylphenylalanine. In some embodiments, $X_{34}$ is N-methylphenylalanine. In some embodiments, $X_{34}$ is homophenylalanine. In some embodiments, $X_{34}$ is β-homotyrosine. In some embodiments, $X_{34}$ is homotyrosine. In some embodiments, $X_{34}$ is N-methyltyrosine.

In some embodiments, carboxy terminal amino acid, i.e. $X_{34}$, is —$X_{34}$—($NH_2$). In some embodiments, carboxy terminal amino acid $X_{34}$ is —$X_{34}$-(OH).

In some embodiments, certain amino acids represented by the consensus sequence of SEQ ID NO: 92 include the following:

In some embodiments, $X_5$ is A and $X_8$ is K covalently bound to a lipophilic substituent, optionally via a spacer. In some embodiments, $X_5$ is A and $X_{15}$ is W. In some embodiments, $X_5$ is A and $X_{16}$ is D. In some embodiments, $X_5$ is A and $X_{16}$ is K. In some embodiments, $X_5$ is A and $X_{20}$ is K. In some embodiments, $X_5$ is A and $X_{20}$ is E. In some embodiments, $X_5$ is A and $X_{20}$ is A. In some embodiments, $X_5$ is A and $X_{34}$ is F.

In some embodiments, $X_5$ is K covalently bound to a lipophilic substituent, optionally via a spacer, and $X_8$ is E. In some embodiments, $X_5$ is K covalently bound to a lipophilic substituent, optionally via a spacer, and $X_{15}$ is W. In some embodiments, $X_5$ is K covalently bound to a lipophilic substituent, optionally via a spacer, and $X_{16}$ is D. In some embodiments, $X_5$ is K covalently bound to a lipophilic substituent, optionally via a spacer, and $X_{20}$ is K. In some embodiments, $X_5$ is K covalently bound to a lipophilic substituent, optionally via a spacer, and $X_{34}$ is F.

In some embodiments, $X_5$ is K and $X_8$ is E. In some embodiments, $X_5$ is K and $X_{15}$ is W. In some embodiments, $X_5$ is K and $X_{16}$ is D. In some embodiments, $X_5$ is K and $X_{20}$ is K. In some embodiments, $X_5$ is K and $X_{20}$ is K covalently bound to a lipophilic substituent, optionally via a spacer. In some embodiments, $X_5$ is K and $X_{34}$ is F.

In some embodiments, $X_8$ is E and $X_{15}$ is W. In some embodiments, $X_8$ is E and $X_{16}$ is D. In some embodiments, $X_8$ is E and $X_{20}$ is K. In some embodiments, $X_8$ is E and $X_{20}$ is K covalently bound to a lipophilic substituent, optionally via a spacer. In some embodiments, $X_8$ is E and $X_{34}$ is F.

In some embodiments, $X_8$ is K covalently bound to a lipophilic substituent, optionally via a spacer, and $X_{15}$ is W. In some embodiments, $X_8$ is K covalently bound to a lipophilic substituent, optionally via a spacer, and $X_{16}$ is D. In some embodiments, $X_8$ is K covalently bound to a lipophilic substituent, optionally via a spacer, and $X_{16}$ is K. In some embodiments, $X_8$ is K covalently bound to a lipophilic substituent, optionally via a spacer, and $X_{20}$ is K. In some embodiments, $X_8$ is K covalently bound to a lipophilic substituent, optionally via a spacer, and $X_{20}$ is E. In some embodiments, $X_8$ is K covalently bound to a lipophilic substituent, optionally via a spacer, and $X_{20}$ is A. In some embodiments, $X_8$ is K covalently bound to a lipophilic substituent, optionally via a spacer, and $X_{34}$ is F.

In some embodiments, $X_{15}$ is W and $X_{16}$ is D. In some embodiments, $X_{15}$ is W and $X_{16}$ is K. In some embodiments, $X_{15}$ is W and $X_{20}$ is K. In some embodiments, $X_{15}$ is W and $X_{20}$ is E. In some embodiments, $X_{15}$ is W and $X_{20}$ is A. In some embodiments, $X_{15}$ is W and $X_{34}$ is F.

In some embodiments, $X_{16}$ is D and $X_{20}$ is K. In some embodiments, $X_{16}$ is D and $X_{34}$ is F.

In some embodiments, $X_{16}$ is K and $X_{20}$ is E. In some embodiments, $X_{16}$ is K and $X_{20}$ is D. In some embodiments, $X_{16}$ is K and $X_{34}$ is F.

In some embodiments, $X_{20}$ is K and $X_{34}$ is F.

In some embodiments, $X_{20}$ is E and $X_{34}$ is F.

In some embodiments, $X_{20}$ is A and $X_{34}$ is F.

In some embodiments, certain amino acids represented by the consensus sequence of SEQ ID NO: 92 include the following:

In some embodiments, $X_5$ is A, $X_8$ is K covalently bound to a lipophilic substituent, optionally via a spacer, and $X_{15}$ is W. In some embodiments, $X_5$ is A, $X_8$ is K covalently bound to a lipophilic substituent, optionally via a spacer, and $X_{16}$ is D. In some embodiments, $X_5$ is A, $X_8$ is K covalently bound to a lipophilic substituent, optionally via a spacer, and $X_{16}$ is K. In some embodiments, $X_5$ is A, $X_8$ is K covalently bound to a lipophilic substituent, optionally via a spacer, and $X_{20}$ is K. In some embodiments, $X_5$ is A, $X_8$ is K covalently bound to a lipophilic substituent, optionally via a spacer, and $X_{20}$ is E. In some embodiments, $X_5$ is A, $X_8$ is K covalently bound to a lipophilic substituent, optionally via a spacer, and $X_{20}$ is A. In some embodiments, $X_5$ is A, $X_8$ is K covalently bound to a lipophilic substituent, optionally via a spacer, and $X_{34}$ is F.

In some embodiments, $X_5$ is A, $X_{15}$ is W, and $X_{16}$ is D. In some embodiments, $X_5$ is A, $X_{15}$ is W, and $X_{16}$ is D. In some embodiments, $X_5$ is A, $X_{15}$ is W, and $X_{16}$ is K. In some embodiments, $X_5$ is A, $X_{15}$ is W, and $X_{20}$ is K. In some embodiments, $X_5$ is A, $X_{15}$ is W, and $X_{20}$ is E. In some embodiments, $X_5$ is A, $X_{15}$ is W, and $X_{20}$ is A. In some embodiments, $X_5$ is A, $X_{15}$ is W, and $X_{34}$ is F.

In some embodiments, $X_5$ is A, $X_{16}$ is D, and $X_{20}$ is K. In some embodiments, $X_5$ is A, $X_{16}$ is D, and $X_{34}$ is F.

In some embodiments, $X_5$ is A, $X_{16}$ is K, and $X_{20}$ is E. In some embodiments, $X_5$ is A, $X_{16}$ is K, and $X_{20}$ is D. In some embodiments, $X_5$ is A, $X_{16}$ is K, and $X_{34}$ is F.

In some embodiments, $X_5$ is A, $X_{20}$ is K, and $X_{34}$ is F.

In some embodiments, $X_5$ is A, $X_{20}$ is E, and $X_{34}$ is F.

In some embodiments, $X_5$ is A, $X_{20}$ is A, and $X_{34}$ is F.

In some embodiments, $X_5$ is K covalently bound to a lipophilic substituent, optionally via a spacer, $X_8$ is E, and $X_{15}$ is W. In some embodiments, $X_5$ is K covalently bound to a lipophilic substituent, optionally via a spacer, $X_8$ is E, and $X_{16}$ is D. In some embodiments, $X_5$ is K covalently bound to a lipophilic substituent, optionally via a spacer, $X_8$ is E, and $X_{20}$ is K. In some embodiments, $X_5$ is K covalently bound to a lipophilic substituent, optionally via a spacer, $X_8$ is E, and $X_{34}$ is F.

In some embodiments, $X_5$ is K, $X_8$ is E, and $X_{15}$ is W. In some embodiments, $X_5$ is K, $X_8$ is E, and $X_{16}$ is D. In some embodiments, $X_5$ is K, $X_8$ is E, and $X_{20}$ is K covalently bound to a lipophilic substituent, optionally via a spacer. In some embodiments, $X_5$ is K, $X_8$ is E, and $X_{34}$ is F.

In some embodiments, $X_8$ is E, $X_{15}$ is W, and $X_{20}$ is K. In some embodiments, $X_8$ is E, $X_{15}$ is W, and $X_{20}$ is K covalently bound to a lipophilic substituent, optionally via a spacer. In some embodiments, $X_8$ is E, $X_{15}$ is W, and $X_{34}$ is F.

In some embodiments, $X_8$ is K covalently bound to a lipophilic substituent, optionally via a spacer, $X_{15}$ is W, and $X_{16}$ is D. In some embodiments, $X_8$ is K covalently bound to a lipophilic substituent, optionally via a spacer, $X_{15}$ is W, and $X_{16}$ is K. In some embodiments, $X_8$ is K covalently bound to a lipophilic substituent, optionally via a spacer, $X_{15}$ is W, and $X_{20}$ is K. In some embodiments, $X_8$ is K covalently bound to a lipophilic substituent, optionally via a spacer, $X_{15}$ is W, and $X_{20}$ is E. In some embodiments, $X_8$ is K covalently bound to a lipophilic substituent, optionally via a spacer, $X_{15}$ is W, and $X_{20}$ is A. In some embodiments, $X_8$ is K covalently bound to a lipophilic substituent, optionally via a spacer, $X_{15}$ is W, and $X_{34}$ is F.

In some embodiments, $X_8$ is K covalently bound to a lipophilic substituent, optionally via a spacer, $X_{16}$ is D, and $X_{20}$ is K. In some embodiments, $X_8$ is K covalently bound to a lipophilic substituent, optionally via a spacer, $X_{16}$ is D, and $X_{34}$ is F.

In some embodiments, $X_8$ is K covalently bound to a lipophilic substituent, optionally via a spacer, $X_{16}$ is K, and $X_{20}$ is E. In some embodiments, $X_8$ is K covalently bound to a lipophilic substituent, optionally via a spacer, $X_{16}$ is K, and $X_{20}$ is D. In some embodiments, $X_8$ is K covalently bound to a lipophilic substituent, optionally via a spacer, $X_{16}$ is K, and $X_{34}$ is F.

In some embodiments, $X_8$ is K covalently bound to a lipophilic substituent, optionally via a spacer, $X_{20}$ is K, and $X_{34}$ is F.

In some embodiments, $X_8$ is K covalently bound to a lipophilic substituent, optionally via a spacer, $X_{20}$ is E, and $X_{34}$ is F.

In some embodiments, $X_8$ is K covalently bound to a lipophilic substituent, optionally via a spacer, $X_{20}$ is A, and $X_{34}$ is F.

In some embodiments, $X_{15}$ is W, $X_{16}$ is D, and $X_{20}$ is K. In some embodiments, $X_{15}$ is W, $X_{16}$ is D, and $X_{34}$ is F.

In some embodiments, $X_{15}$ is W, $X_{16}$ is K, and $X_{20}$ is E. In some embodiments, $X_{15}$ is W, $X_{16}$ is K, and $X_{20}$ is D. In some embodiments, $X_{15}$ is W, $X_{16}$ is K, and $X_{34}$ is F.

In some embodiments, $X_{15}$ is W, $X_{20}$ is K, and $X_{34}$ is F.

In some embodiments, $X_{15}$ is W, $X_{20}$ is E, and $X_{34}$ is F.

In some embodiments, $X_{15}$ is W, $X_{20}$ is A, and $X_{34}$ is F.

In some embodiments, $X_{16}$ is D, $X_{20}$ is K, and $X_{34}$ is F.

In some embodiments, $X_{16}$ is K, $X_{20}$ is E, and $X_{34}$ is F.

In some embodiments, $X_{16}$ is K, $X_{20}$ is D, and $X_{34}$ is F.

In certain embodiments, the present disclosure provides an isolated polypeptide comprising the amino acid sequence of SEQ ID NO: 93: PKPE$X_5$P$X_7X_8$DASP$X_{13}$E$X_{15}X_{16}$RYY$X_{20}$D$X_{22}$RHYLNWLTRQR$X_{34}$-(OH/$NH_2$) (SEQ ID NO: 93), or a pharmaceutically acceptable salt thereof, wherein:

$X_5$ is A or K;

$X_7$ is G or K;

$X_8$ is E, K, or k;

$X_{13}$ is E or K;

$X_{15}$ is L or W;

$X_{16}$ is D, E, K, N, S, α-methylserine, or homoserine;

$X_{20}$ is D, E, K, or k, $X_{22}$ is A or L;

$X_{34}$ is F, 3-pyridinylalanine, 4-pyridinylalanine, 4-carboxyphenylalanine, 4-fluorophenylalanine, 4-methylphenylalanine, N-methylphenylalanine, homophenylalanine, β-homotyrosine, homotyrosine, or N-methyltyrosine;

wherein when $X_5$, $X_7$, $X_8$, $X_{13}$, or $X_{20}$ are K, the lysine residue is optionally covalently bound to a lipophilic substituent, optionally via a spacer, and wherein when $X_8$ or $X_{20}$ are k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

In some embodiments, when $X_{15}$ is L, $X_{22}$ is A.

In some embodiments, when $X_8$ is E, $X_5$ is K and $X_{20}$ is K, and the lysine residue at either of $X_5$ or $X_{20}$ is covalently bound to a lipophilic substituent, optionally via a spacer.

In some embodiments, $X_8$ is K. In some embodiments, the lysine residue at the $8^{th}$ position of the polypeptide sequence is covalently bound to a lipophilic substituent, optionally via a spacer.

In some embodiments, $X_{15}$ is W.

In some embodiments, $X_{34}$ is F.

In some embodiments, the peptide further comprises a lactam bridge formed via an amide bond between the side chains of a lysine and an aspartic acid at positions $X_{16}$ and $X_{20}$, respectively. In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively.

In some embodiments, $X_5$ is A. In some embodiments, $X_5$ is K. In some embodiments, $X_5$ is K covalently bound to a lipophilic substituent, optionally via a spacer.

In some embodiments, $X_7$ is G. In some embodiments, $X_7$ is K. In some embodiments, $X_7$ is K covalently bound to a lipophilic substituent, optionally via a spacer.

In some embodiments, $X_8$ is E. In some embodiments, $X_8$ is K. In some embodiments, $X_8$ is K covalently bound to a lipophilic substituent, optionally via a spacer. In some embodiments, $X_8$ is k. In some embodiments, $X_8$ is k covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{15}$ is L. In some embodiments, $X_{15}$ is W.

In some embodiments, $X_{16}$ is D. In some embodiments, $X_{16}$ is E. In some embodiments, $X_{16}$ is K. In some embodiments, $X_{16}$ is N. In some embodiments, $X_{16}$ is S. In some embodiments, $X_{16}$ is α-methylserine. In some embodiments, $X_{16}$ is homoserine.

In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer.

In some embodiments, $X_{22}$ is A. In some embodiments, $X_{22}$ is L.

In some embodiments, $X_{34}$ is F. In some embodiments, $X_{34}$ is 3-pyridinylalanine. In some embodiments, $X_{34}$ is 4-pyridinylalanine. In some embodiments, $X_{34}$ is 4-carboxyphenylalanine. In some embodiments, $X_{34}$ is 4-fluorophenylalanine. In some embodiments, $X_{34}$ is 4-methylphenylalanine. In some embodiments, $X_{34}$ is N-methylphenylalanine. In some embodiments, $X_{34}$ is homophenylalanine. In some embodiments, $X_{34}$ is β-homotyrosine. In some embodiments, $X_{34}$ is homotyrosine. In some embodiments, $X_{34}$ is N-methyltyrosine.

In some embodiments, carboxy terminal amino acid, i.e. $X_{34}$, is —$X_{34}$—($NH_2$). In some embodiments, carboxy terminal amino acid $X_{34}$ is —$X_{34}$-(OH).

In some embodiments, certain amino acids represented by the consensus sequence of SEQ ID NO: 93 include the following:

In some embodiments, $X_5$ is A and $X_8$ is K covalently bound to a lipophilic substituent, optionally via a spacer. In some embodiments, $X_5$ is A and $X_{15}$ is W. In some embodiments, $X_5$ is A and $X_{16}$ is D. In some embodiments, $X_5$ is A and $X_{16}$ is K. In some embodiments, $X_5$ is A and $X_{16}$ is N. In some embodiments, $X_5$ is A and $X_{20}$ is K. In some embodiments, $X_5$ is A and $X_{20}$ is E. In some embodiments, $X_5$ is A and $X_{34}$ is F.

In some embodiments, $X_5$ is K covalently bound to a lipophilic substituent, optionally via a spacer, and $X_8$ is E. In some embodiments, $X_5$ is K covalently bound to a lipophilic substituent, optionally via a spacer, and $X_{15}$ is W. In some embodiments, $X_5$ is K covalently bound to a lipophilic substituent, optionally via a spacer, and $X_{16}$ is N. In some embodiments, $X_5$ is K covalently bound to a lipophilic substituent, optionally via a spacer, and $X_{16}$ is D. In some embodiments, $X_5$ is K covalently bound to a lipophilic substituent, optionally via a spacer, and $X_{20}$ is K. In some embodiments, $X_5$ is K covalently bound to a lipophilic substituent, optionally via a spacer, and $X_{34}$ is F.

In some embodiments, $X_5$ is K and $X_8$ is E. In some embodiments, $X_5$ is K and $X_{15}$ is W. In some embodiments, $X_5$ is K and $X_{16}$ is N. In some embodiments, $X_5$ is K and $X_{16}$ is D. In some embodiments, $X_5$ is K and $X_{20}$ is K. In some embodiments, $X_5$ is K and $X_{20}$ is K covalently bound to a lipophilic substituent, optionally via a spacer. In some embodiments, $X_5$ is K and $X_{34}$ is F.

In some embodiments, $X_8$ is E and $X_{15}$ is W. In some embodiments, $X_8$ is E and $X_{16}$ is D.

In some embodiments, $X_8$ is E and $X_{16}$ is N. In some embodiments, $X_8$ is E and $X_{20}$ is K. In some embodiments, $X_8$ is E and $X_{20}$ is K covalently bound to a lipophilic substituent, optionally via a spacer. In some embodiments, $X_8$ is E and $X_{34}$ is F.

In some embodiments, $X_8$ is K covalently bound to a lipophilic substituent, optionally via a spacer, and $X_{15}$ is W. In some embodiments, $X_8$ is K covalently bound to a lipophilic substituent, optionally via a spacer, and $X_{16}$ is D. In some embodiments, $X_8$ is K covalently bound to a lipophilic substituent, optionally via a spacer, and $X_{16}$ is K. In some embodiments, $X_8$ is K covalently bound to a lipophilic substituent, optionally via a spacer, and $X_{16}$ is N. In some embodiments, $X_8$ is K covalently bound to a lipophilic substituent, optionally via a spacer, and $X_{20}$ is K. In some embodiments, $X_8$ is K covalently bound to a lipophilic substituent, optionally via a spacer, and $X_{20}$ is E. In some embodiments, $X_8$ is K covalently bound to a lipophilic substituent, optionally via a spacer, and $X_{34}$ is F.

In some embodiments, $X_{15}$ is W and $X_{16}$ is D. In some embodiments, $X_{15}$ is W and $X_{16}$ is K. In some embodiments, $X_{15}$ is W and $X_{16}$ is N. In some embodiments, $X_{15}$ is W and $X_{20}$ is K. In some embodiments, $X_{15}$ is W and $X_{20}$ is E. In some embodiments, $X_{15}$ is W and $X_{34}$ is F.

In some embodiments, $X_{16}$ is D and $X_{20}$ is K. In some embodiments, $X_{16}$ is D and $X_{34}$ is F. In some embodiments, $X_{16}$ is K and $X_{20}$ is E. In some embodiments, $X_{16}$ is K and $X_{20}$ is D.

In some embodiments, $X_{16}$ is K and $X_{34}$ is F.

In some embodiments, $X_{16}$ is N and $X_{20}$ is K. In some embodiments, $X_{16}$ is N and $X_{34}$ is F.

In some embodiments, $X_{20}$ is K and $X_{34}$ is F.

In some embodiments, $X_{20}$ is E and $X_{34}$ is F.

In some embodiments, certain amino acids represented by the consensus sequence of SEQ ID NO: 93 include the following:

In some embodiments, $X_5$ is A, $X_8$ is K covalently bound to a lipophilic substituent, optionally via a spacer, and $X_{15}$ is W. In some embodiments, $X_5$ is A, $X_8$ is K covalently bound to a lipophilic substituent, optionally via a spacer, and $X_{16}$ is D. In some embodiments, $X_5$ is A, $X_8$ is K covalently bound to a lipophilic substituent, optionally via a spacer, and $X_{16}$ is K. In some embodiments, $X_5$ is A, $X_8$ is K covalently bound to a lipophilic substituent, optionally via a spacer, and $X_{16}$ is N. In some embodiments, $X_5$ is A, $X_8$ is K covalently bound to a lipophilic substituent, optionally via a spacer, and $X_{20}$ is K. In some embodiments, $X_5$ is A, $X_8$ is K covalently bound to a lipophilic substituent, optionally via a spacer, and $X_{20}$ is E. In some embodiments, $X_5$ is A, $X_8$ is K covalently bound to a lipophilic substituent, optionally via a spacer, and $X_{34}$ is F.

In some embodiments, $X_5$ is A, $X_{15}$ is W, and $X_{16}$ is D. In some embodiments, $X_5$ is A, $X_{15}$ is W, and $X_{16}$ is D. In some embodiments, $X_5$ is A, $X_{15}$ is W, and $X_{16}$ is K. In some embodiments, $X_5$ is A, $X_{15}$ is W, and $X_{16}$ N. In some embodiments, $X_5$ is A, $X_{15}$ is W, and $X_{20}$ is K. In some embodiments, $X_5$ is A, $X_{15}$ is W, and $X_{20}$ is E. In some embodiments, $X_5$ is A, $X_{15}$ is W, and $X_{34}$ is F.

In some embodiments, $X_5$ is A, $X_{16}$ is D, and $X_{20}$ is K. In some embodiments, $X_5$ is A, $X_{16}$ is D, and $X_{34}$ is F.

In some embodiments, $X_5$ is A, $X_{16}$ is K, and $X_{20}$ is E. In some embodiments, $X_5$ is A, $X_{16}$ is K, and $X_{20}$ is D. In some embodiments, $X_5$ is A, $X_{16}$ is K, and $X_{34}$ is F.

In some embodiments, $X_5$ is A, $X_{16}$ is N, and $X_{20}$ is K. In some embodiments, $X_5$ is A, $X_{16}$ is N, and $X_{34}$ is F.

In some embodiments, $X_5$ is A, $X_{20}$ is K, and $X_{34}$ is F.

In some embodiments, $X_5$ is A, $X_{20}$ is E, and $X_{34}$ is F.

In some embodiments, $X_5$ is K covalently bound to a lipophilic substituent, optionally via a spacer, $X_8$ is E, and $X_{15}$ is W. In some embodiments, $X_5$ is K covalently bound to a lipophilic substituent, optionally via a spacer, $X_8$ is E, and $X_{16}$ is N. In some embodiments, $X_5$ is K covalently bound to a lipophilic substituent, optionally via a spacer, $X_8$ is E, and $X_{16}$ is D. In some embodiments, $X_5$ is K covalently bound to a lipophilic substituent, optionally via a spacer, $X_8$ is E, and $X_{20}$ is K. In some embodiments, $X_5$ is K covalently bound to a lipophilic substituent, optionally via a spacer, $X_8$ is E, and $X_{34}$ is F.

In some embodiments, $X_5$ is K, $X_8$ is E, and $X_{15}$ is W. In some embodiments, $X_5$ is K, $X_8$ is E, and $X_{16}$ is N. In some embodiments, $X_5$ is K, $X_8$ is E, and $X_{16}$ is D. In some embodiments, $X_5$ is K, $X_8$ is E, and $X_{20}$ is K covalently bound to a lipophilic substituent, optionally via a spacer.

In some embodiments, $X_5$ is K, $X_8$ is E, and $X_{34}$ is F.

In some embodiments, $X_8$ is E, $X_{15}$ is W, and $X_{16}$ is N. In some embodiments, $X_8$ is E, $X_{15}$ is W, and $X_{20}$ is K. In some embodiments, $X_8$ is E, $X_{15}$ is W, and $X_{20}$ is K covalently bound to a lipophilic substituent, optionally via a spacer. In some embodiments, $X_8$ is E, $X_{15}$ is W, and $X_{34}$ is F.

In some embodiments, $X_8$ is K covalently bound to a lipophilic substituent, optionally via a spacer, $X_{15}$ is W, and $X_{16}$ is D. In some embodiments, $X_8$ is K covalently bound to a lipophilic substituent, optionally via a spacer, $X_{15}$ is W, and $X_{16}$ is K. In some embodiments, $X_8$ is K covalently bound to a lipophilic substituent, optionally via a spacer, $X_{15}$ is W, and $X_{16}$ is N. In some embodiments, $X_8$ is K covalently bound to a lipophilic substituent, optionally via a spacer, $X_{15}$ is W, and $X_{20}$ is K. In some embodiments, $X_8$ is K covalently bound to a lipophilic substituent, optionally via a spacer, $X_{15}$ is W, and $X_{20}$ is E. In some embodiments, $X_8$ is K covalently bound to a lipophilic substituent, optionally via a spacer, $X_{15}$ is W, and $X_{34}$ is F.

In some embodiments, $X_8$ is K covalently bound to a lipophilic substituent, optionally via a spacer, $X_{16}$ is D, and $X_{20}$ is K. In some embodiments, $X_8$ is K covalently bound to a lipophilic substituent, optionally via a spacer, $X_{16}$ is D, and $X_{34}$ is F.

In some embodiments, $X_8$ is K covalently bound to a lipophilic substituent, optionally via a spacer, $X_{16}$ is K, and $X_{20}$ is E. In some embodiments, $X_8$ is K covalently bound to a lipophilic substituent, optionally via a spacer, $X_{16}$ is K, and $X_{20}$ is D. In some embodiments, $X_8$ is K covalently bound to a lipophilic substituent, optionally via a spacer, $X_{16}$ is K, and $X_{34}$ is F.

In some embodiments, $X_8$ is K covalently bound to a lipophilic substituent, optionally via a spacer, $X_{16}$ is N, and $X_{20}$ is K. In some embodiments, $X_8$ is K covalently bound to a lipophilic substituent, optionally via a spacer, $X_{16}$ is N, and $X_{34}$ is F.

In some embodiments, $X_8$ is K covalently bound to a lipophilic substituent, optionally via a spacer, $X_{20}$ is K, and $X_{34}$ is F.

In some embodiments, $X_8$ is K covalently bound to a lipophilic substituent, optionally via a spacer, $X_{20}$ is E, and $X_{34}$ is F.

In some embodiments, $X_{15}$ is W, $X_{16}$ is D, and $X_{20}$ is K. In some embodiments, $X_{15}$ is W, $X_{16}$ is D, and $X_{34}$ is F.

In some embodiments, $X_{15}$ is W, $X_{16}$ is K, and $X_{20}$ is E. In some embodiments, $X_{15}$ is W, $X_{16}$ is K, and $X_{20}$ is D. In some embodiments, $X_{15}$ is W, $X_{16}$ is K, and $X_{34}$ is F.

In some embodiments, $X_{15}$ is W, $X_{16}$ is N, and $X_{20}$ is K. In some embodiments, $X_{15}$ is W, $X_{16}$ is N, and $X_{34}$ is F.

In some embodiments, $X_{15}$ is W, $X_{20}$ is K, and $X_{34}$ is F.

In some embodiments, $X_{15}$ is W, $X_{20}$ is E, and $X_{34}$ is F.

In some embodiments, $X_{16}$ is D, $X_{20}$ is K, and $X_{34}$ is F.

In some embodiments, $X_{16}$ is K, $X_{20}$ is E, and $X_{34}$ is F.

In some embodiments, $X_{16}$ is K, $X_{20}$ is D, and $X_{34}$ is F.

In some embodiments, $X_{16}$ is N, $X_{20}$ is K, and $X_{34}$ is F.

In certain embodiments, the present invention provides an isolated polypeptide comprising the amino acid sequence of SEQ ID NO: 94: PKPE$X_5$PG$X_8$DASP$X_{13}$EW$X_{16}$RYY$X_{20}$D$X_{22}$RHYLNWLTRQR$X_{34}$-(OH/$NH_2$) (SEQ ID NO: 94), or a pharmaceutically acceptable salt thereof, wherein:

$X_5$ is A or K;

$X_8$ is E, K, or k;

$X_{13}$ is E or K;

$X_{16}$ is D, E, K, or N;

$X_{20}$ is A, D, E, K, or k, $X_{22}$ is A or L;

$X_{34}$ is F or N-methyltyrosine;

wherein when $X_5$, $X_8$, $X_{13}$, or $X_{20}$ are K, the lysine residue is optionally covalently bound to a lipophilic substituent, optionally via a spacer, and wherein when $X_8$ or $X_{20}$ are k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

In some embodiment, when $X_{16}$ is N, $X_{20}$ is not A.

In some embodiments, when $X_8$ is E, $X_5$ is K and $X_{20}$ is K, and the lysine residue at either of $X_5$ or $X_{20}$ is covalently bound to a lipophilic substituent, optionally via a spacer.

In some embodiments, $X_8$ is K. In some embodiments, the lysine residue at the $8^{th}$ position of the polypeptide sequence is covalently bound to a lipophilic substituent, optionally via a spacer.

In some embodiments, $X_{34}$ is F.

In some embodiments, the peptide further comprises a lactam bridge formed via an amide bond between the side chains of a lysine and an aspartic acid at positions $X_{16}$ and $X_{20}$, respectively. In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively.

In some embodiments, $X_5$ is A. In some embodiments, $X_5$ is K. In some embodiments, $X_5$ is K covalently bound to a lipophilic substituent, optionally via a spacer.

In some embodiments, $X_8$ is E. In some embodiments, $X_8$ is K. In some embodiments, $X_8$ is K covalently bound to a lipophilic substituent, optionally via a spacer. In some embodiments, $X_8$ is k. In some embodiments, $X_8$ is k covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{16}$ is D. In some embodiments, $X_{16}$ is E. In some embodiments, $X_{16}$ is K. In some embodiments, $X_{16}$ is N.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer.

In some embodiments, $X_{22}$ is A. In some embodiments, $X_{22}$ is L.

In some embodiments, $X_{34}$ is F. In some embodiments, $X_{34}$ is N-methyltyrosine.

In some embodiments, carboxy terminal amino acid, i.e. $X_{34}$, is —$X_{34}$—($NH_2$). In some embodiments, carboxy terminal amino acid $X_{34}$ is —$X_{34}$-(OH).

In some embodiments, certain amino acids represented by the consensus sequence of SEQ ID NO: 94 include the following:

In some embodiments, $X_5$ is A and $X_8$ is K covalently bound to a lipophilic substituent, optionally via a spacer. In some embodiments, $X_5$ is A and $X_{16}$ is D. In some embodiments, $X_5$ is A and $X_{16}$ is K. In some embodiments, $X_5$ is A and $X_{16}$ is N. In some embodiments, $X_5$ is A and $X_{20}$ is K. In some embodiments, $X_5$ is A and $X_{20}$ is E. In some embodiments, $X_5$ is A and $X_{20}$ is A. In some embodiments, $X_5$ is A and $X_{34}$ is F.

In some embodiments, $X_5$ is K covalently bound to a lipophilic substituent, optionally via a spacer, and $X_8$ is E. In some embodiments, $X_5$ is K covalently bound to a lipophilic substituent, optionally via a spacer, and $X_{16}$ is N. In some embodiments, $X_5$ is K covalently bound to a lipophilic substituent, optionally via a spacer, and $X_{16}$ is D. In some embodiments, $X_5$ is K covalently bound to a lipophilic substituent, optionally via a spacer, and $X_{20}$ is K. In some embodiments, $X_5$ is K covalently bound to a lipophilic substituent, optionally via a spacer, and $X_{34}$ is F.

In some embodiments, $X_5$ is K and $X_8$ is E. In some embodiments, $X_5$ is K and $X_{16}$ is N. In some embodiments, $X_5$ is K and $X_{16}$ is D. In some embodiments, $X_5$ is K and $X_{20}$ is K. In some embodiments, $X_5$ is K and $X_{20}$ is K covalently bound to a lipophilic substituent, optionally via a spacer. In some embodiments, $X_5$ is K and $X_{34}$ is F.

In some embodiments, $X_8$ is E and $X_{16}$ is D. In some embodiments, $X_8$ is E and $X_{16}$ is N. In some embodiments, $X_8$ is E and $X_{20}$ is K. In some embodiments, $X_8$ is E and $X_{20}$ is K covalently bound to a lipophilic substituent, optionally via a spacer. In some embodiments, $X_8$ is E and $X_{34}$ is F.

In some embodiments, $X_8$ is K covalently bound to a lipophilic substituent, optionally via a spacer, and $X_{16}$ is D. In some embodiments, $X_8$ is K covalently bound to a lipophilic substituent, optionally via a spacer, and $X_{16}$ is K. In some embodiments, $X_8$ is K covalently bound to a lipophilic substituent, optionally via a spacer, and $X_{16}$ is N. In some embodiments, $X_8$ is K covalently bound to a lipophilic substituent, optionally via a spacer, and $X_{20}$ is K. In some embodiments, $X_8$ is K covalently bound to a lipophilic substituent, optionally via a spacer, and $X_{20}$ is E. In some embodiments, $X_8$ is K covalently bound to a lipophilic substituent, optionally via a spacer, and $X_{20}$ is A. In some embodiments, $X_8$ is K covalently bound to a lipophilic substituent, optionally via a spacer, and $X_{34}$ is F.

In some embodiments, $X_{16}$ is D and $X_{20}$ is K. In some embodiments, $X_{16}$ is D and $X_{34}$ is F. In some embodiments, $X_{16}$ is K and $X_{20}$ is E. In some embodiments, $X_{16}$ is K and $X_{20}$ is D.

In some embodiments, $X_{16}$ is K and $X_{34}$ is F.

In some embodiments, $X_{16}$ is N and $X_{20}$ is A. In some embodiments, $X_{16}$ is N and $X_{20}$ is K.

In some embodiments, $X_{16}$ is N and $X_{34}$ is F.

In some embodiments, $X_{20}$ is K and $X_{34}$ is F.

In some embodiments, $X_{20}$ is E and $X_{34}$ is F.

In some embodiments, $X_{20}$ is A and $X_{34}$ is F.

In some embodiments, certain amino acids represented by the consensus sequence of SEQ ID NO: 94 include the following:

In some embodiments, $X_5$ is A, $X_8$ is K covalently bound to a lipophilic substituent, optionally via a spacer, and $X_{16}$ is D. In some embodiments, $X_5$ is A, $X_8$ is K covalently bound to a lipophilic substituent, optionally via a spacer, and $X_{16}$ is K. In some embodiments, $X_5$ is A, $X_8$ is K covalently bound to a lipophilic substituent, optionally via a spacer, and $X_{16}$ is N. In some embodiments, $X_5$ is A, $X_8$ is K covalently bound to a lipophilic substituent, optionally via a spacer, and $X_{20}$ is K. In some embodiments, $X_5$ is A, $X_8$ is K covalently bound to a lipophilic substituent, optionally via a spacer, and $X_{20}$ is E. In some embodiments, $X_5$ is A, $X_8$ is K covalently bound to a lipophilic substituent, optionally via a spacer, and $X_{20}$ is A. In some embodiments, $X_5$ is A, $X_8$ is K covalently bound to a lipophilic substituent, optionally via a spacer, and $X_{34}$ is F.

In some embodiments, $X_5$ is A, $X_{16}$ is D, and $X_{20}$ is K. In some embodiments, $X_5$ is A, $X_{16}$ is D, and $X_{34}$ is F.

In some embodiments, $X_5$ is A, $X_{16}$ is K, and $X_{20}$ is E. In some embodiments, $X_5$ is A, $X_{16}$ is K, and $X_{20}$ is D. In some embodiments, $X_5$ is A, $X_{16}$ is K, and $X_{34}$ is F.

In some embodiments, $X_5$ is A, $X_{16}$ is N, and $X_{20}$ is A. In some embodiments, $X_5$ is A, $X_{16}$ is N, and $X_{20}$ is K. In some embodiments, $X_5$ is A, $X_{16}$ is N, and $X_{34}$ is F.

In some embodiments, $X_5$ is A, $X_{20}$ is K, and $X_{34}$ is F.

In some embodiments, $X_5$ is A, $X_{20}$ is E, and $X_{34}$ is F.

In some embodiments, $X_5$ is A, $X_{20}$ is A, and $X_{34}$ is F.

In some embodiments, $X_5$ is K covalently bound to a lipophilic substituent, optionally via a spacer, $X_8$ is E, and $X_{16}$ is N. In some embodiments, $X_5$ is K covalently bound to a lipophilic substituent, optionally via a spacer, $X_8$ is E, and $X_{16}$ is D. In some embodiments, $X_5$ is K covalently bound to a lipophilic substituent, optionally via a spacer, $X_8$ is E, and $X_{20}$ is K. In some embodiments, $X_5$ is K covalently bound to a lipophilic substituent, optionally via a spacer, $X_8$ is E, and $X_{34}$ is F.

In some embodiments, $X_5$ is K, $X_8$ is E, and $X_{16}$ is N. In some embodiments, $X_5$ is K, $X_8$ is E, and $X_{16}$ is D. In some embodiments, $X_5$ is K, $X_8$ is E, and $X_{20}$ is K covalently bound to a lipophilic substituent, optionally via a spacer. In some embodiments, $X_5$ is K, $X_8$ is E, and $X_{34}$ is F.

In some embodiments, $X_8$ is K covalently bound to a lipophilic substituent, optionally via a spacer, $X_{16}$ is D, and $X_{20}$ is K. In some embodiments, $X_8$ is K covalently bound to a lipophilic substituent, optionally via a spacer, $X_{16}$ is D, and $X_{34}$ is F.

In some embodiments, $X_8$ is K covalently bound to a lipophilic substituent, optionally via a spacer, $X_{16}$ is K, and $X_{20}$ is E. In some embodiments, $X_8$ is K covalently bound to a lipophilic substituent, optionally via a spacer, $X_{16}$ is K, and $X_{20}$ is D. In some embodiments, $X_8$ is K covalently bound to a lipophilic substituent, optionally via a spacer, $X_{16}$ is K, and $X_{34}$ is F.

In some embodiments, $X_8$ is K covalently bound to a lipophilic substituent, optionally via a spacer, $X_{16}$ is N, and $X_{20}$ is A. In some embodiments, $X_8$ is K covalently bound to a lipophilic substituent, optionally via a spacer, $X_{16}$ is N, and $X_{20}$ is K. In some embodiments, $X_8$ is K covalently bound to a lipophilic substituent, optionally via a spacer, $X_{16}$ is N, and $X_{34}$ is F.

In some embodiments, $X_8$ is K covalently bound to a lipophilic substituent, optionally via a spacer, $X_{20}$ is K, and $X_{34}$ is F.

In some embodiments, $X_8$ is K covalently bound to a lipophilic substituent, optionally via a spacer, $X_{20}$ is E, and $X_{34}$ is F.

In some embodiments, $X_8$ is K covalently bound to a lipophilic substituent, optionally via a spacer, $X_{20}$ is A, and $X_{34}$ is F.

In some embodiments, $X_{16}$ is D, $X_{20}$ is K, and $X_{34}$ is F.

In some embodiments, $X_{16}$ is K, $X_{20}$ is E, and $X_{34}$ is F.

In some embodiments, $X_{16}$ is K, $X_{20}$ is D, and $X_{34}$ is F.

In some embodiments, $X_{16}$ is N, $X_{20}$ is A, and $X_{34}$ is F.

In some embodiments, $X_{16}$ is N, $X_{20}$ is K, and $X_{34}$ is F.

In certain embodiments, the present disclosure provides an isolated polypeptide comprising the amino acid sequence of SEQ ID NO: 95: PKPE$X_5$PGK$_8$DASP$X_{13}$EW$X_{16}$ RYY$X_{20}$ DLRHYLNWLTRQRF-(OH/$NH_2$) (SEQ ID NO: 95), or a pharmaceutically acceptable salt thereof, wherein:

$X_5$ is A or K;

$X_{13}$ is E or K;

$X_{16}$ is D, E, K, or N;

$X_{20}$ is A, D, E, K, or k; and wherein when $X_5$, $X_{13}$, or $X_{20}$ are K, the lysine residue is optionally covalently bound to a lipophilic substituent, optionally via a spacer, wherein $K_8$ is optionally covalently bound to a lipophilic substituent, optionally via a spacer, and wherein when $X_{20}$ is k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

In some embodiment, when $X_{16}$ is N, $X_{20}$ is not A.

In some embodiments, K is covalently bound to a lipophilic substituent, optionally via a spacer.

In some embodiments, the peptide further comprises a lactam bridge formed via an amide bond between the side chains of a lysine and an aspartic acid at positions $X_{16}$ and $X_{20}$, respectively. In some embodiments, the peptide further comprises a lactam bridge formed via an amide bond between the side chains of a lysine and a glutamic acid at positions $X_{16}$ and $X_{20}$, respectively. In some embodiments, the peptide further comprises a lactam bridge formed via an amide bond between the side chains of an aspartic acid and a lysine at positions $X_{16}$ and $X_{20}$, respectively. In some embodiments, the peptide further comprises a lactam bridge formed via an amide bond between the side chains of a glutamic acid and a lysine at positions $X_{16}$ and $X_{20}$, respectively.

In some embodiments, $X_5$ is A. In some embodiments, $X_5$ is K. In some embodiments, $X_5$ is K covalently bound to a lipophilic substituent, optionally via a spacer.

In some embodiments, $K_8$ is unsubstituted. In some embodiments, $K_8$ is covalently bound to a lipophilic substituent, optionally via a spacer.

In some embodiments, $X_{13}$ is E. In some embodiments, $X_{13}$ is K. In some embodiments, $X_{13}$ is K covalently bound to a lipophilic substituent, optionally via a spacer.

In some embodiments, $X_{16}$ is D. In some embodiments, $X_{16}$ is E. In some embodiments, $X_{16}$ is K. In some embodiments, $X_{16}$ is N.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a lipophilic substituent, optionally via a spacer. In some embodiments, $X_{20}$ is k. In some embodiments, $X_{20}$ is k covalently bound to a lipophilic substituent, optionally via a spacer.

In some embodiments, carboxy terminal amino acid, i.e. $F_{34}$, is —$F_{34}$—($NH_2$). In some embodiments, carboxy terminal amino acid $F_{34}$ is —$F_{34}$-(OH).

In some embodiments, certain amino acids represented by the consensus sequence of SEQ ID NO: 95 include the following:

In some embodiments, $X_5$ is A and $K_8$ is covalently bound to a lipophilic substituent, optionally via a spacer. In some embodiments, $X_5$ is A and $X_{16}$ is D. In some embodiments, $X_5$ is A and $X_{16}$ is K. In some embodiments, $X_5$ is A and $X_{16}$ is N. In some embodiments, $X_5$ is A and $X_{20}$ is K. In some embodiments, $X_5$ is A and $X_{20}$ is E. In some embodiments, $X_5$ is A and $X_{20}$ is A.

In some embodiments, $X_5$ is K covalently bound to a lipophilic substituent, optionally via a spacer, and $X_{16}$ is N. In some embodiments, $X_5$ is K covalently bound to a lipophilic substituent, optionally via a spacer, and $X_{16}$ is D. In some embodiments, $X_5$ is K covalently bound to a lipophilic substituent, optionally via a spacer, and $X_{20}$ is K.

In some embodiments, $X_5$ is K and $X_{16}$ is N. In some embodiments, $X_5$ is K and $X_{16}$ is D. In some embodiments, $X_5$ is K and $X_{20}$ is K. In some embodiments, $X_5$ is K and $X_{20}$ is K covalently bound to a lipophilic substituent, optionally via a spacer.

In some embodiments, $K_8$ is covalently bound to a lipophilic substituent, optionally via a spacer, and $X_{16}$ is D. In some embodiments, $K_8$ is covalently bound to a lipophilic substituent, optionally via a spacer, and $X_{16}$ is K. In some embodiments, $K_8$ is covalently bound to a lipophilic substituent, optionally via a spacer, and $X_{16}$ is N. In some embodiments, $K_8$ is covalently bound to a lipophilic substituent, optionally via a spacer, and $X_{20}$ is K. In some embodiments, $K_8$ is covalently bound to a lipophilic substituent, optionally via a spacer, and $X_{20}$ is E. In some embodiments, $K_8$ is covalently bound to a lipophilic substituent, optionally via a spacer, and $X_{20}$ is A.

In some embodiments, $X_{16}$ is D and $X_{20}$ is K.

In some embodiments, $X_{16}$ is K and $X_{20}$ is E. In some embodiments, $X_{16}$ is K and $X_{20}$ is D.

In some embodiments, $X_{16}$ is N and $X_{20}$ is A. In some embodiments, $X_{16}$ is N and $X_{20}$ is K.

In some embodiments, certain amino acids represented by the consensus sequence of SEQ ID NO: 95 include the following:

In some embodiments, $X_5$ is A, $K_8$ is covalently bound to a lipophilic substituent, optionally via a spacer, and $X_{16}$ is D. In some embodiments, $X_5$ is A, $K_8$ is covalently bound to a lipophilic substituent, optionally via a spacer, and $X_{16}$ is K. In some embodiments, $X_5$ is A, $K_8$ is covalently bound to a lipophilic substituent, optionally via a spacer, and $X_{16}$ is N. In some embodiments, $X_5$ is A, $K_8$ is covalently bound to a lipophilic substituent, optionally via a spacer, and $X_{20}$ is K. In some embodiments, $X_5$ is A, $K_8$ is covalently bound to a lipophilic substituent, optionally via a spacer, and $X_{20}$ is E. In some embodiments, $X_5$ is A, $K_8$ is covalently bound to a lipophilic substituent, optionally via a spacer, and $X_{20}$ is A.

In some embodiments, $X_5$ is A, $X_{16}$ is D, and $X_{20}$ is K.

In some embodiments, $X_5$ is A, $X_{16}$ is K, and $X_{20}$ is E. In some embodiments, $X_5$ is A, $X_{16}$ is K, and $X_{20}$ is D.

In some embodiments, $X_5$ is A, $X_{16}$ is N, and $X_{20}$ is A. In some embodiments, $X_5$ is A, $X_{16}$ is N, and $X_{20}$ is K.

In some embodiments, $K_8$ is covalently bound to a lipophilic substituent, optionally via a spacer, $X_{16}$ is D, and $X_{20}$ is K.

In some embodiments, $K_8$ is covalently bound to a lipophilic substituent, optionally via a spacer, $X_{16}$ is K, and $X_{20}$ is E. In some embodiments, $K_8$ is covalently bound to a lipophilic substituent, optionally via a spacer, $X_{16}$ is K, and $X_{20}$ is D.

In some embodiments, $K_8$ is covalently bound to a lipophilic substituent, optionally via a spacer, $X_{16}$ is N, and $X_{20}$ is A. In some embodiments, $K_8$ is covalently bound to a lipophilic substituent, optionally via a spacer, $X_{16}$ is N, and $X_{20}$ is K.

Conjugation of a Lipophilic Substituent to any of the Peptides, Optionally Via a Spacer In some embodiments, any of the disclosed polypeptides is optionally substituted with one or more lipophilic substituents each optionally via a spacer, wherein "lipophilic substituent" and "spacer" are defined herein. In some embodiments, any of the disclosed polypeptides, comprising an amino acid sequence selected from the group consisting of amino acid sequences represented by any of the consensus sequences of SEQ ID NO: 1 through SEQ ID NO: 78 either comprises one or more lipophilic substituents each optionally via a spacer, or can be modified, or further modified, by covalent attachment of one or more lipophilic substituents each optionally via a spacer. In some embodiments, any of the disclosed polypeptides, comprising an amino acid sequence selected from the group consisting of amino acid sequences represented by any of the consensus sequences of SEQ ID NO: 101 through SEQ ID NO: 181 can be modified by covalent attachment of one or more lipophilic substituents each optionally via a spacer. In some embodiments, any of the disclosed polypeptides, comprising an amino acid sequence selected from the group consisting of amino acid sequences represented by any of the consensus sequences of SEQ ID NO: 239, 240, 241, 242, 243, 244, 245, 246, 247, 248, 280, or 281 can be modified by covalent attachment of one or more lipophilic substituents each optionally via a spacer. In some embodiments, the lipophilic substituent may be attached to an amino group of the polypeptide (e.g., an ε-amino group of a lysine residue) by means of a carboxyl group of the lipophilic substituent, or optionally an amino group of the spacer, wherein a carboxyl group of the spacer forms an amide bond with an ε-amino group of a lysine residue.

Lipophilic Substituent

Conjugation of one or more "lipophilic substituents", each optionally via a "spacer," to any of the disclosed polypeptides of this invention is intended to prolong the action of the polypeptide by facilitating binding to serum albumin and delayed renal clearance of the conjugated polypeptide. As used herein, a "lipophilic substituent" comprises a substituent comprising 4 to 40 carbon atoms, 8 to 25 carbon atoms, 12 to 22 carbon atoms, or 6 to 20 carbon atoms. The lipophilic substituent may be attached to an amino group of the polypeptide (e.g., an ε-amino group of a lysine residue) by means of a carboxyl group of the lipophilic substituent, or optionally an amino group of the spacer, which carboxyl group of the spacer in turn forms an amide bond with an amino group of the amino acid (e.g., lysine) residue to which it is attached. In some embodiments, the polypeptide comprises three, two, or preferably one lipophilic substituent each with or without an optional spacer, which is defined in greater detail below.

In some embodiments, the lipophilic substituent comprises a straight-chain or branched alkyl group. In some embodiments, the lipophilic substituent is an acyl group of a straight-chain or branched fatty acid. In some embodiments, the lipophilic substituent is an acyl group of a straight-chain or branched fatty acid, further substituted with one or more carboxylic acid and/or hydroxamic acid groups.

In some embodiments, the polypeptide comprises three, two, or preferably one lipophilic substituents each without an optional spacer. In some embodiments, the lipophilic substituent is $—CO(CH_2)_{16}CO_2H$. In some embodiments, the lipophilic substituent is $—CO(CH_2)_{18}CO_2H$. In some embodiments, the lipophilic substituent is $—CO(CH_2)_{20}CO_2H$.

In some embodiments, the polypeptide comprises three, two, or preferably one lipophilic substituents each without an optional spacer. In some embodiments, the lipophilic substituent is a monovalent group of Formula I:

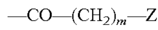

$—CO—(CH_2)_m—Z$ Formula I wherein

Z is $—CH_3$ or $—CO_2H$; and m is from 4 to 24, which lipophilic substituent forms an amide bond between an amino group (e.g., ε-amino group of a lysine) of the disclosed polypeptide and a CO— group of the lipophilic substituent.

In some embodiments, Z is $—CO_2H$. In some embodiments, m is from 14 to 20. In some embodiments, the lipophilic substituent is covalently bound to the isolated polypeptide via a spacer. In some embodiments, the lipophilic substituent, $—CO—(CH_2)_m—Z$, is linked to an amino group of the isolated polypeptide via the spacer, wherein the spacer forms a bridge between the amino group of the isolated polypeptide and a CO— group of the lipophilic substituent.

In some embodiments, m is selected from the group consisting of 4-20, 8-20, 12-20, 14-20, 16-20, 14, 16, 18, and 20.

In some embodiments, Z is $—CO_2H$, and the lipophilic substituent has the formula $—CO—(CH_2)_m—CO_2H$. In some embodiments, $—CO—(CH_2)_m—Z$ is selected from the group consisting of $—CO—(CH_2)_4—CO_2H$, $—CO—(CH_2)_5—CO_2H$, $—CO—(CH_2)_6—CO_2H$, $—CO—(CH_2)_7—CO_2H$, $—CO—(CH_2)_8—CO_2H$, $—CO—(CH_2)_9—CO_2H$, $—CO—(CH_2)_{10}—CO_2H$, $—CO—(CH_2)_U—CO_2H$, $—CO—(CH_2)_{12}—CO_2H$, $—CO—(CH_2)_{13}—CO_2H$, $—CO—(CH_2)_{14}—CO_2H$, $—CO—(CH_2)_{15}—CO_2H$, $—CO—(CH_2)_{16}—CO_2H$, $—CO—(CH_2)_{17}—CO_2H$, $—CO—(CH_2)_{18}—CO_2H$, $—CO—(CH_2)_{19}—CO_2H$, $—CO—(CH_2)_{20}—CO_2H$.

In some embodiments, the lipophilic substituent is $—CO—(CH_2)_{14}—CO_2H$. In some embodiments, the lipophilic substituent is $—CO—(CH_2)_{16}—CO_2H$. In some embodiments, the lipophilic substituent is $—CO—(CH_2)_{18}—CO_2H$. In some embodiments, the lipophilic substituent is $—CO—(CH_2)_{20}—CO_2H$.

In some embodiments, Z is $—CH_3$, and the lipophilic substituent has the formula $—CO—(CH_2)_m—CH_3$. In some embodiments, $—CO—(CH_2)_m—Z$ is selected from the group consisting of $—CO—(CH_2)_4—CH_3$, $—CO—(CH_2)_5—CH_3$, $—CO—(CH_2)_6—CH_3$, $—CO—(CH_2)_7—CH_3$, $—CO—(CH_2)_8—CH_3$, $—CO—(CH_2)_9—CH_3$, $—CO—(CH_2)_{10}—CH_3$, $—CO—(CH_2)_U—CH_3$, $—CO—(CH_2)_{12}—CH_3$, $—CO—(CH_2)_{13}—CH_3$, $—CO—(CH_2)_{14}—CH_3$, $—CO—(CH_2)_{15}—CH_3$, $—CO—(CH_2)_{16}—CH_3$, $—CO—(CH_2)_{17}—CH_3$, $—CO—(CH_2)_{18}—CH_3$, $—CO—(CH_2)_{19}—CH_3$, and $—CO—(CH_2)_{20}—CH_3$.

Lipophilic Substituent & Spacer

In some embodiments, the lipophilic substituent is attached to the parent peptide by means of a "spacer." In some embodiments, provided herein is any of the disclosed polypeptides, comprising an amino acid sequence selected from the group consisting of amino acid sequences represented by any of the consensus sequences of SEQ ID NO:1 through SEQ ID NO: 143, comprising a lipophilic substituent, wherein the lipophilic substituent is linked to the ε-amino group of a lysine via a spacer, which spacer forms a bridge between an amino group of the disclosed polypeptide and a CO— group of the lipophilic substituent.

In some embodiments, the spacer comprises one or more amino acids, for example, single amino acid such as Glu, Asp, Gly or Lys, dipeptide such as 2(Glu), Glu-Gly, or polypeptide such as 3(Glu), 4(Glu) (SEQ ID NO: 814), 2(Glu)-Gly etc. In some embodiments, when the spacer comprises one or more amino acids, e.g., Glu, Asp, Gly or Lys, one carboxyl group of the spacer may form an amide bond with an amino group of the disclosed polypeptide, and an amino group of the spacer may form an amide bond with a carboxyl group of the lipophilic substituent.

In some embodiments, when the spacer comprises Glu or Asp, that further include a carboxylic acid-terminating sidechain, the terminal carboxyl group of the sidechain of the Glu or Asp-containing spacer may form an amide bond with an amino group of the disclosed polypeptide, and an amino group of the Glu or Asp-containing spacer may form an amide bond with a carboxyl group of the lipophilic substituent, i.e., γGlu or βAsp.

In some embodiments, the spacer is -γGlu-γGlu-. In some embodiments, the spacer is -γGlu-γGlu-dpeg-. In some embodiments, the spacer is -dpeg-dpeg-γGlu-. In some embodiments, the spacer is -γGlu-dpeg-dpeg-γGlu-. In some embodiments, the spacer is -γGlu-γGlu-dpeg-γGlu-γGlu-. In some embodiments, the spacer is $—[COCH_2(OCH_2CH_2)_2NH]_2$-γGlu-.

In some embodiments, the polypeptide comprises three, two, or preferably one lipophilic substituent each with a spacer. In some non-limiting embodiments, the lipophilic substituent and spacer form a monovalent group selected from the group consisting of those listed in Table 7:

TABLE 7

| representative lipophilic substituent and spacer moieties |
|---|
| -γGlu-γGlu-$CO(CH_2)_{16}CO_2H$ |
| -γGlu-γGlu-$CO(CH_2)_{17}CO_2H$ |
| -γGlu-γGlu-$CO(CH_2)_{18}CO_2H$ |
| -γGlu-γGlu-dpeg-$CO(CH_2)_{16}CO_2H$ |
| -γGlu-γGlu-dpeg-$CO(CH_2)_{18}CO_2H$ |
| -γGlu-γGlu-dpeg-γGlu-$CO(CH_2)_{16}CO_2H$ |
| -γGlu-γGlu-dpeg-γGlu-$CO(CH_2)_{18}CO_2H$ |
| -γGlu-γGlu-dpeg-γGlu-γGlu-$CO(CH_2)_{16}CO_2H$ |
| -γGlu-γGlu-dpeg-γGlu-γGlu-$CO(CH_2)_{18}CO_2H$ |
| -γGlu-γGlu-dpeg-dpeg-$CO(CH_2)_{16}CO_2H$ |
| -γGlu-γGlu-dpeg-dpeg-$CO(CH2)_{18}CO_2H$ |
| -γGlu-γGlu-dpeg-dpeg-γGlu-$CO(CH_2)_{16}CO_2H$ |
| -γGlu-γGlu-dpeg-dpeg-γGlu-$CO(CH_2)_{18}CO_2H$ |
| -γGlu-γGlu-γGlu-$CO(CH_2)_{16}CO_2H$ |
| -γGlu-γGlu-γGlu-$CO(CH_2)_{18}CO_2H$ |
| -dpeg-dpeg-γGlu-$CO(CH_2)_{16}CO_2H$ |
| -dpeg-dpeg-γGlu-$CO(CH_2)_{18}CO_2H$ |

TABLE 7-continued

| representative lipophilic substituent and spacer moieties |
|---|
| -γGlu-dpeg-dpeg-γGlu-$CO(CH_2)_{16}CO_2H$ |
| -γGlu-dpeg-dpeg-γGlu-$CO(CH_2)_{18}CO_2H$ |
| -γGlu-γGlu-γGlu-dpeg-$CO(CH_2)_{16}CO_2H$ |
| -γGlu-γGlu-γGlu-dpeg-$CO(CH_2)_{18}CO_2H$ |
| -γGlu-dpeg-$CO(CH_2)_{16}CO_2H$ |
| -γGlu-dpeg-$CO(CH_2)_{18}CO_2H$ |
| —$[COCH_2(OCH_2CH_2)_2NH]_2$-γGlu-$CO(CH_2)_{16}CO_2H$ |

Preferably, the lipophilic substituent and spacer are attached to an amino group of the polypeptide. In particular, a carboxyl group of the lipophilic substituent, or optionally a carboxyl group of the spacer, forms an amide bond with an ε-amino group of a lysine residue. The lysine residue bound to the lipophilic substituent, optionally via a spacer, may be L-lysine or D-lysine. Structural representations of representative spacer moieties and lipophilic substituents are provided in Table 8:

TABLE 8
| Structures of Representative Spacers Moieties & Lipophillic Substituents Bound to Lysine |
| --- |
| 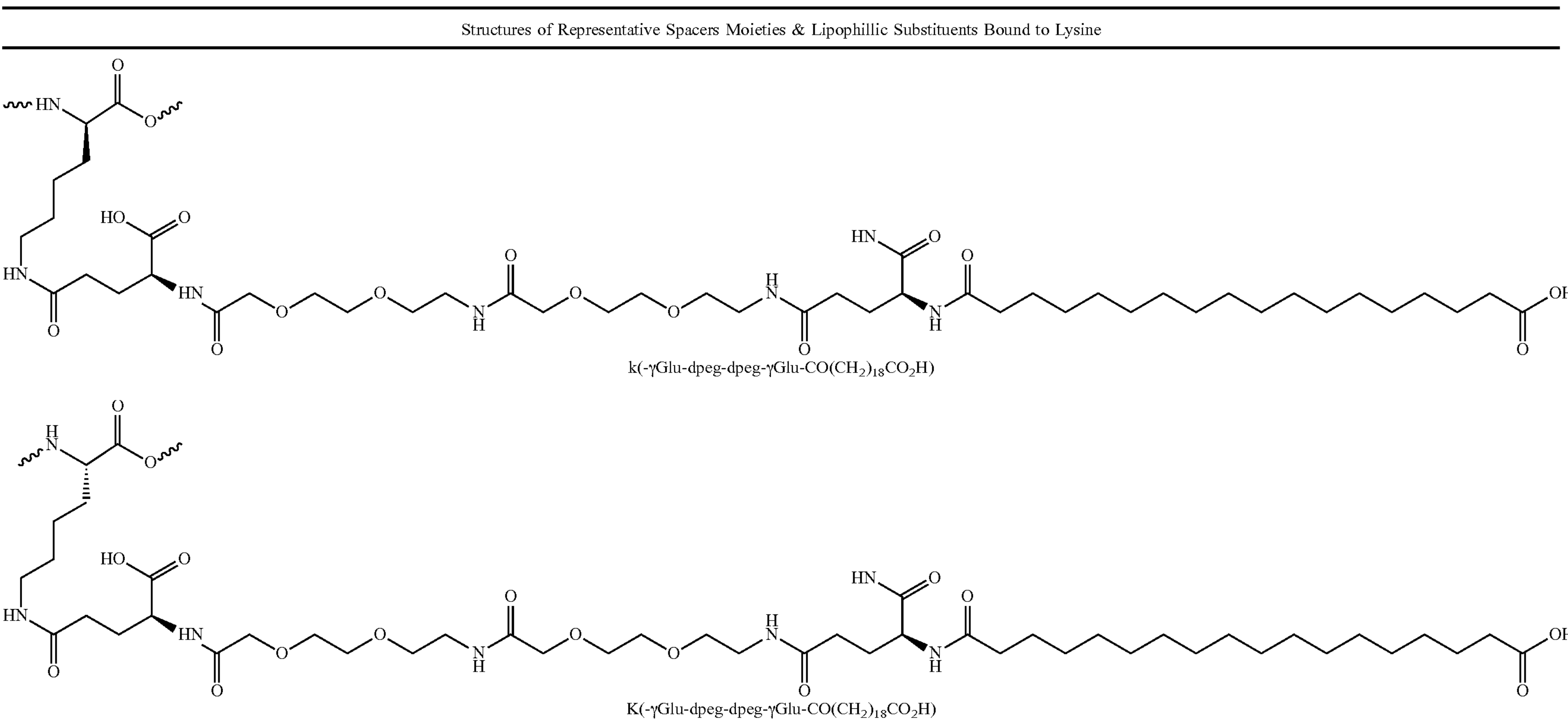 |
| k(-γGlu-dpeg-dpeg-γGlu-CO$(CH_2)_{18}CO_2H$) |
| K(-γGlu-dpeg-dpeg-γGlu-CO$(CH_2)_{18}CO_2H$) |

TABLE 8-continued
Structures of Representative Spacers Moieties & Lipophillic Substituents Bound to Lysine
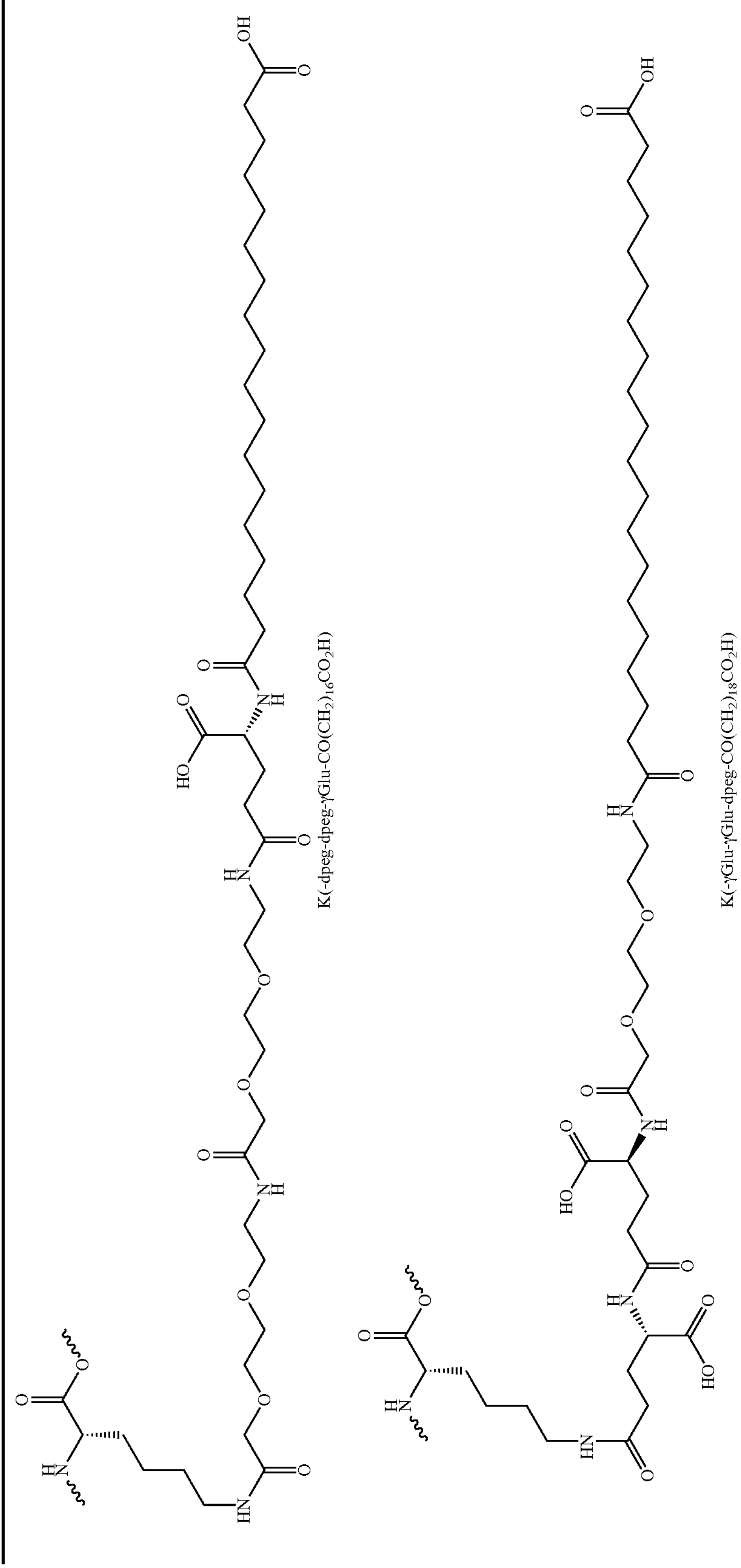

TABLE 8-continued
| Structures of Representative Spacers Moieties & Lipophillic Substituents Bound to Lysine |
| --- |
| 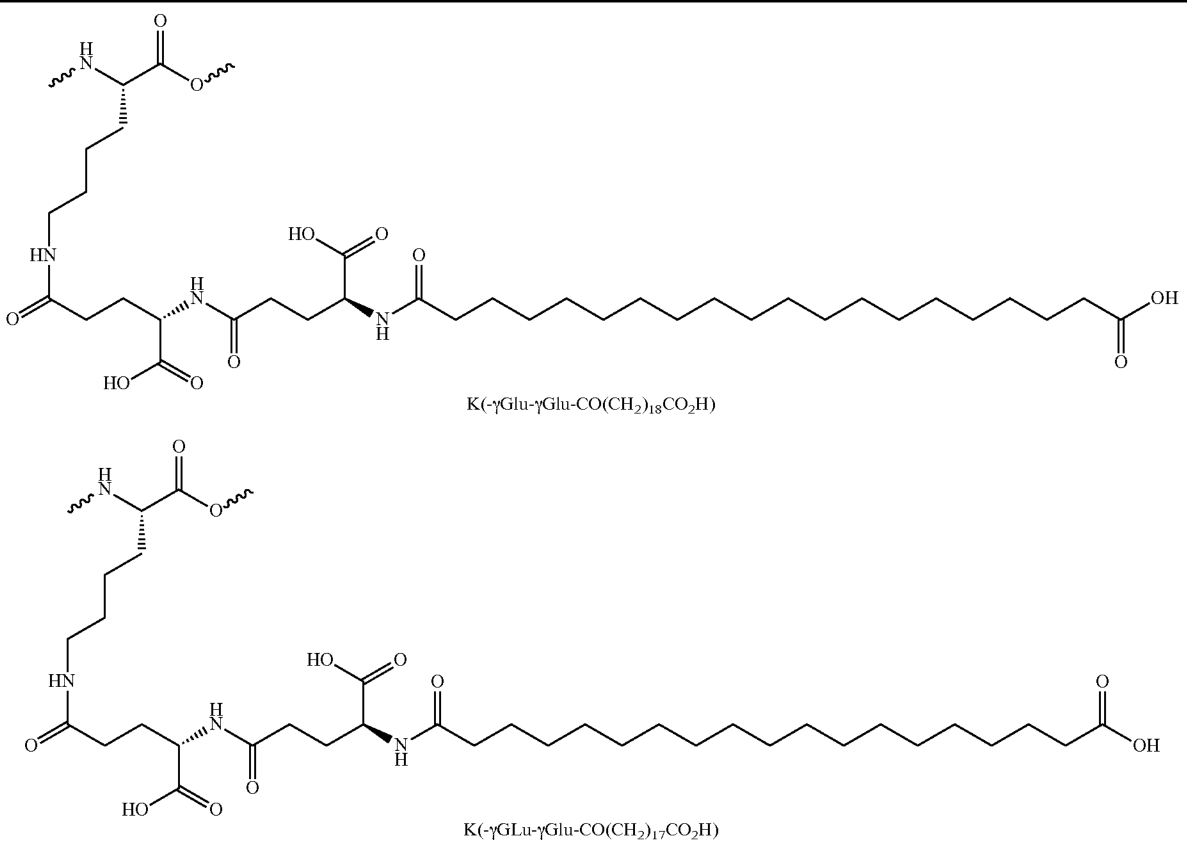 |
| K(-γGlu-γGlu-CO$(CH_2)_{18}CO_2H$) |
| K(-γGLu-γGlu-CO$(CH_2)_{17}CO_2H$) |

TABLE 8-continued

| Structures of Representative Spacers Moieties & Lipophillic Substituents Bound to Lysine |
| --- |
| K(-γGlu-γGlu-CO$(CH_2)_{16}CO_2H$) |
| K(-γGlu-γGlu-CO$(CH_2)_{18}CO_2H$)-P |

In some embodiments, the lipophilic substituent and spacer form a monovalent group of Formula II:

$$—(Y)_n—CO—(CH_2)_m—Z \quad \text{Formula II}$$

wherein

Y is selected from the group consisting of γGlu, Asp, Lys and Gly;

Z is $—CH_3$ or $—CO_2H$;

m is from 4 to 24; and n is from 1 to 10.

In some embodiments, Z is $—CO_2H$. In some embodiments, m is from 14 to 20. In some embodiments, Y is γGlu. In some embodiments, n is from 1 to 5.

In some embodiments, Y is selected from the group consisting of γGlu and Gly. In some embodiments, Y is γGlu. In some embodiments, Y is Gly.

In some embodiments, the polypeptide comprises three, two, or preferably one lipophilic substituent each with a spacer. In some embodiments, the lipophilic substituent and spacer are a monovalent group of Formula III:

$$—(V)_r—(Y)_n—CO—(CH_2)_m—Z \quad \text{Formula III}$$

wherein,

V is $—[COCH_2(OCH_2CH_2)_tNH]—$;

Y is selected from the group consisting of γGlu, Asp, and Gly;

Z is $—CH_3$ or $—CO_2H$;

m is from 4 to 24;

n is from 1 to 10;

r is from 1 to 6; and t is from 1 to 6.

In some embodiments, Z is $—CO_2H$. In some embodiments, Z is $—CH_3$.

In some embodiments, Y is γGlu. In some embodiments, Y is Asp. In some embodiments, Y is Gly.

In some embodiments, m is selected from the group consisting of 4-20, 8-20, 12-20, 14-20, 16-20, 14, 16, 18, and 20. In some embodiments, m is from 14 to 20.

In some embodiments, n is selected from the group consisting of 1, 2, 3, 4, 5, 6, 7, 8, 9 and 10. In some embodiments, n is from 1 to 5. In some embodiments, n is 1. In some embodiments, n is 2. In some embodiments, n is 3. In some embodiments, n is 4. In some embodiments, n is 5.

In some embodiments, r is from 1 to 3. In some embodiments, r is 1. In some embodiments, r is 2. In some embodiments, r is 3. In some embodiments, r is 4. In some embodiments, r is 5.

In some embodiments, t is from 1 to 3. In some embodiments, t is selected from the group consisting of 1, 2, 3, 4, 5 and 6.

In some embodiments, Y is γGlu; Z is $—CO_2H$; m is 16; n is 1; r is 2; and t is 2.

In an embodiment, $—(V)_r—(Y)_n—$ is $—[COCH_2(OCH_2CH_2)_2NH]2$-γGlu-.

In some embodiments, the polypeptide comprises three, two, or preferably one lipophilic substituent each with a spacer. In some embodiments, the lipophilic substituent and spacer are a monovalent group of Formula IV:

$$—(Y1)_{n1}\text{-(dpeg)}_r\text{-}(Y2)_{n2}—CO—(CH_2)_m—Z \quad \text{Formula IV}$$

wherein

Z is $—CH_3$ or $—CO_2H$;

m is from 4 to 24;

Y1 is selected from the group consisting of γGlu, Asp, and Gly;

Y2 is selected from the group consisting of γGlu, Asp, and Gly;

dpeg is $—[CO(CH_2)O(CH_2)_2O(CH_2)NH]—$;

r is from 1 to 8;

n1 is from 0 to 10; and n2 is from 0 to 10.

In some embodiments, Z is $—CO_2H$. In some embodiments, Z is $—CH_3$.

In some embodiments, m is selected from the group consisting of 4-20, 8-20, 12-20, 14-20, 16-20, 14, 16, 18, and 20. In some embodiments, m is from 14 to 20.

In some embodiments, Y1 is γGlu. In some embodiments, Y1 is Asp. In some embodiments, Y1 is Gly.

In some embodiments, Y2 is γGlu. In some embodiments, Y2 is Asp. In some embodiments, Y2 is Gly.

In some embodiments, n1 is selected from the group consisting of 0, 1, 2, 3, 4, 5, 6, 7, 8, 9 and 10. In some embodiments, n1 is from 0 to 3. In some embodiments, n1 is 0. In some embodiments, n1 is 1. In some embodiments, n1 is 2. In some embodiments, n1 is 3. In some embodiments, n1 is 4. In some embodiments, n1 is 5.

In some embodiments, n2 is selected from the group consisting of 0, 1, 2, 3, 4, 5, 6, 7, 8, 9 and 10. In some embodiments, n2 is from 0 to 3. In some embodiments, n2 is 0. In some embodiments, n2 is 1. In some embodiments, n2 is 2. In some embodiments, n2 is 3. In some embodiments, n2 is 4. In some embodiments, n2 is 5.

In some embodiments, r is from 1 to 3. In some embodiments, r is 1. In some embodiments, r is 2. In some embodiments, r is 3. In some embodiments, r is 4. In some embodiments, r is 5.

In some embodiments, r is 6. In some embodiments, r is 7. In some embodiments, r is 8.

In some embodiments, r is 1, n1 is 2, and n2 is 0.

In some embodiments, r is 1, n1 is 2, and n2 is 2.

In some embodiments, Y1 is γGlu and Y2 is γGlu.

In some embodiments, Y1 is γGlu and n2 is 0.

In some embodiments, Y1 is γGlu, r is 1, n1 is 2, and n2 is 0.

In some embodiments, $—(Y1)_{n1}\text{-(dpeg)}_r\text{-}(Y2)_{n2}$- is selected from the group consisting of -γGlu-γGlu-dpeg-, -γGlu-γGlu-dpeg-γGlu-γGlu-, -γGlu-γGlu-dpeg-γGlu-, -γGlu-γGlu-dpeg-dpeg-, -γGlu-γGlu-dpeg-dpeg-γGlu-, -dpeg-dpeg-γGlu-, -γGlu-γGlu-γGlu-dpeg-, and -γGlu-dpeg-.

In some embodiments, the polypeptide comprises three, two, or preferably one lipophilic substituent each with a spacer. In some embodiments, the lipophilic substituent and spacer are a monovalent group of Formula V:

$$\text{-}(\gamma Glu)_n\text{-}CO—(CH_2)_m—Z \quad \text{Formula V}$$

wherein

Z is $—CH_3$ or $—CO_2H$;

m is from 4 to 24; and n is from 1 to 10 ("$(\gamma Glu)_n$", where n is from 1 to 10 disclosed as SEQ ID NO: 808).

In some embodiments, Z is $—CH_3$. In some embodiments, Z is $—CO_2H$.

In some embodiments, m is from 14 to 20.

In some embodiments, m is selected from the group consisting of 4-20, 8-20, 12-20, 14-20, 16-20, 14, 16, 18, and 20.

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, the polypeptide comprises three, two, or preferably one lipophilic substituent each with a spacer. In some embodiments, the lipophilic substituent and spacer are a monovalent group of Formula VI:

$$-(\gamma Glu)_n-(Gly)-CO—(CH_2)_m—Z \quad \text{Formula VI}$$

wherein

Z is $—CH_3$ or $—CO_2H$;

m is from 4 to 24; and n is from 1 to 10 ("$(\gamma Glu)_n$-(Gly)", where n is from 1 to 10 disclosed as SEQ ID NO: 809).

In some embodiments, $(\gamma Glu)_n$ is selected from the group consisting of γGlu; 2(γGlu); 3(γGlu); 4(γGlu) (SEQ ID NO: 810); and 5(γGlu) (SEQ ID NO: 811). In some embodiments, -$(\gamma Glu)_n$-(Gly)- is selected from the group consisting of 2(γGlu),Gly; and 3(γGlu),Gly (SEQ ID NO: 812).

In some embodiments, the polypeptide comprises three, two, or preferably one lipophilic substituent each with a spacer. In some embodiments, the lipophilic substituent and spacer are a monovalent group of Formula VII:

$$-(Gly)-(\gamma Glu)_n-(CO—(CH_2)_m—Z \quad \text{Formula VII}$$

wherein

Z is $—CH_3$ or $—CO_2H$;

m is from 4 to 24; and n is from 1 to 10 ("-(Gly)-$(\gamma Glu)_n$", where n is from 1 to 10 disclosed as SEQ ID NO: 813).

In some embodiments, certain variables represented in certain of the preceding Formulae include the following:

In some embodiments, Z is $—CH_3$. In some embodiments, Z is $—CO_2H$.

In some embodiments, m is selected from the group consisting of 4-20, 8-20, 12-20, 14-20, 16-20, 14, 16, 18, and 20.

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, n is 1 and Z is $—CO_2H$. In some embodiments, n is 1 and Z is $—CH_3$. In some embodiments, n is 2 and Z is $—CO_2H$. In some embodiments, n is 2 and Z is $—CH_3$. In some embodiments, n is 3 and Z is $—CO_2H$. In some embodiments, n is 3 and Z is $—CH_3$. In some embodiments, n is 4 and Z is $—CO_2H$. In some embodiments, n is 4 and Z is $—CH_3$. In some embodiments, n is 5 and Z is $—CO_2H$. In some embodiments, n is 5 and Z is $—CH_3$.

In some embodiments, n is 1, Z is $—CO_2H$, and m is 14-20. In some embodiments, n is 1, Z is $—CO_2H$, and m is 14. In some embodiments, n is 1, Z is $—CO_2H$, and m is 16. In some embodiments, n is 1, Z is $—CO_2H$, and m is 18.

In some embodiments, n is 1, Z is $—CH_3$, and m is 14-20. In some embodiments, n is 1, Z is $—CH_3$ and m is 14. In some embodiments, n is 1, Z is $—CH_3$, and m is 16. In some embodiments, n is 1, Z is $—CH_3$, and m is 18.

In some embodiments, n is 2, Z is $—CO_2H$, and m is 14-20. In some embodiments, n is 2, Z is $—CO_2H$, and m is 14. In some embodiments, n is 2, Z is $—CO_2H$, and m is 16. In some embodiments, n is 2, Z is $—CO_2H$, and m is 18.

In some embodiments, n is 2, Z is $—CH_3$, and m is 14-20. In some embodiments, n is 2, Z is $—CH_3$ and m is 14. In some embodiments, n is 2, Z is $—CH_3$, and m is 16. In some embodiments, n is 2, Z is $—CH_3$, and m is 18.

In some embodiments, n is 3, Z is $—CO_2H$, and m is 14-20. In some embodiments, n is 3, Z is $—CO_2H$, and m is 14. In some embodiments, n is 3, Z is $—CO_2H$, and m is 16. In some embodiments, n is 3, Z is $—CO_2H$, and m is 18.

In some embodiments, n is 3, Z is $—CH_3$, and m is 14-20. In some embodiments, n is 3, Z is $—CH_3$ and m is 14. In some embodiments, n is 3, Z is $—CH_3$, and m is 16. In some embodiments, n is 3, Z is $—CH_3$, and m is 18.

In some embodiments, n is 4, Z is $—CO_2H$, and m is 14-20. In some embodiments, n is 4, Z is $—CO_2H$, and m is 14. In some embodiments, n is 4, Z is $—CO_2H$, and m is 16. In some embodiments, n is 4, Z is $—CO_2H$, and m is 18.

In some embodiments, n is 4, Z is $—CH_3$, and m is 14-20. In some embodiments, n is 4, Z is $—CH_3$ and m is 14. In some embodiments, n is 4, Z is $—CH_3$, and m is 16. In some embodiments, n is 4, Z is $—CH_3$, and m is 18.

In some embodiments, n is 5, Z is $—CO_2H$, and m is 14-20. In some embodiments, n is 5, Z is $—CO_2H$, and m is 14. In some embodiments, n is 5, Z is $—CO_2H$, and m is 16. In some embodiments, n is 5, Z is $—CO_2H$, and m is 18.

In some embodiments, n is 5, Z is $—CH_3$, and m is 14-20. In some embodiments, n is 5, Z is $—CH_3$ and m is 14. In some embodiments, n is 5, Z is $—CH_3$, and m is 16. In some embodiments, n is 5, Z is $—CH_3$, and m is 18.

In some embodiments, the polypeptide comprises three, two, or preferably one lipophilic substituent each with a spacer. In some embodiments, the lipophilic substituent and spacer are a monovalent group of Formula VIII:

$$—(Y1)_{n1}—(V)_r—(Y2)_{n2}—CO—(CH_2)_m—Z \quad \text{Formula VIII}$$

wherein

Z is $—CH_3$ or $—CO_2H$;

m is from 4 to 24;

Y1 is selected from the group consisting of γGlu, Asp, and Gly;

Y2 is selected from the group consisting of γGlu, Asp, and Gly;

V is $—[COCH_2(OCH_2CH_2)_tNH]—$;

r is from 1 to 6;

n1 is from 0 to 10;

n2 is from 0 to 10; and t is from 1 to 6.

In some embodiments, the polypeptide comprises three, two, or preferably one lipophilic substituent each with a spacer. In some embodiments, the lipophilic substituent and spacer are a monovalent group of Formula IX:

$$—(Y)_n—(V)_r—CO—(CH_2)_m—Z \quad \text{Formula IX}$$

wherein

Z is $—CH_3$ or $—CO_2H$;

m is from 4 to 24;

Y is selected from the group consisting of γGlu, Asp, and Gly;

V is $—[COCH_2(OCH_2CH_2)_tNH]—$;

r is from 1 to 6; and n is from 1 to 10; and t is from 1 to 6.

In some embodiments, the polypeptide comprises three, two, or preferably one lipophilic substituent each with a spacer. In some embodiments, the lipophilic substituent and spacer are a monovalent group of Formula X:

$$-(dpeg)_r-(Y2)_{n2}—CO—(CH_2)_m—Z \quad \text{Formula X}$$

wherein

Z is $—CH_3$ or $—CO_2H$;

m is from 4 to 24;

dpeg is $—[CO(CH_2)O(CH_2)_2O(CH_2)NH]—$;

Y2 is selected from the group consisting of γGlu, Asp, and Gly;

r is from 1 to 8; and n2 is from 0 to 10.

In some embodiments, -(dpeg)$_r$-(Y2)$_{n2}$— is selected from the group consisting of dpeg,γGlu; and dpeg,dpeg,γGlu.

In an embodiment, -(dpeg)$_r$-(Y2)$_{n2}$- is -dpeg-dpeg-γGlu-.

In some embodiments, the polypeptide comprises three, two, or preferably one lipophilic substituent each with a spacer. In some embodiments, the lipophilic substituent and spacer are a monovalent group of Formula XI:

—(Y1)$_{n1}$-(dpeg)$_r$-CO—(CH$_2$)$_m$—Z     Formula XI wherein

Z is —$CH_3$ or —$CO_2H$;

m is from 4 to 24;

Y1 is selected from the group consisting of γGlu, Asp, and Gly;

dpeg is —[CO(CH$_2$)O(CH$_2$)$_2$O(CH$_2$)NH]

r is from 1 to 8; and n1 is from 0 to 10.

In some embodiments, Z is —$CO_2H$.

In some embodiments, m is selected from the group consisting of 4-20, 8-20, 12-20, 14-20, 16-20, 14, 16, 18, and 20. In some embodiments, m is from 14 to 20.

In some embodiments, Y1 is γGlu. In some embodiments, Y1 is Asp. In some embodiments, Y1 is Gly.

In some embodiments, n1 is selected from the group consisting of 0, 1, 2, 3, 4, 5, 6, 7, 8, 9 and 10. In some embodiments, n1 is from 0 to 3. In some embodiments, n1 is 0. In some embodiments, n1 is 1. In some embodiments, n1 is 2. In some embodiments, n1 is 3. In some embodiments, n1 is 4. In some embodiments, n1 is 5.

In some embodiments, r is from 1 to 3. In some embodiments, r is 1. In some embodiments, r is 2. In some embodiments, r is 3. In some embodiments, r is 4. In some embodiments, r is 5.

In some embodiments, r is 6. In some embodiments, r is 7. In some embodiments, r is 8.

In some embodiments, r is 1 and n1 is 2.

In some embodiments, Y1 is γGlu, r is 1, and n1 is 2.

In some embodiments, —(Y1)$_{n1}$-(dpeg)$_r$- is selected from the group consisting of -γGlu-γGlu-dpeg-, -γGlu-γGlu-dpeg-dpeg-, -γGlu-γGlu-γGlu-dpeg-, and -γGlu-dpeg-.

Further Exemplary Spacers

In some embodiments, the spacer comprises a bivalent group of Formula XII:

—N(R$_1$)(CHR$_2$)$_p$CO—[N(R$_3$)((CH$_2$)$_2$O(CH$_2$)$_2$O)$_q$(CH$_2$)CO—]$_r$     Formula XII wherein each $R_1$ and $R_3$ is hydrogen or $C_1$-$C_4$ alkyl;

each $R_2$ is H or $CO_2H$;

p is 1, 2, 3, 4, 5 or 6;

q is 1, 2 or 3;

r is 0 or 1.

which spacer forms a bridge between an amino group of the disclosed polypeptide and a CO— group of the lipophilic substituent.

In some embodiments, the spacer comprises a bivalent group of Formula XIII:

[—N(R$_3$)((CH$_2$)$_2$O(CH$_2$)$_2$O)$_q$(CH$_2$)CO-]$_r$     Formula XIII wherein each $R_3$ is hydrogen or $C_1$-$C_4$ alkyl;

q is 1, 2 or 3;

r is 0 or 1.

which spacer forms a bridge between an amino group of the disclosed polypeptide and a CO— group of the lipophilic substituent.

In some embodiments, certain variables represented in certain Formulae include the following:

In some embodiments, each $R_1$ is hydrogen. In some embodiments, each $R_3$ is hydrogen. In some embodiments, each $R_1$ and each $R_3$ are hydrogen.

In some embodiments, at least one $R_2$ is $CO_2H$. In some embodiments, one $R_2$ is $CO_2H$.

In some embodiments, p is 1. In some embodiments, p is 2. In some embodiments, p is 3.

In some embodiments, p is 4. In some embodiments, p is 5. In some embodiments, p is 6.

In some embodiments, q is 1. In some embodiments, q is 2. In some embodiments, q is 3.

In some embodiments, r is 0. In some embodiments, r is 1.

In some embodiments, the spacer is γ-glutamyl, i.e., —NH(CHCO$_2$H)(CH$_2$)$_2$CO—. In some embodiments, the spacer is γ-aminobutanoyl, i.e., —NH(CH$_2$)$_3$CO—. In some embodiments, the spacer is β-asparagyl, i.e., —NH(CHCO$_2$H)(CH$_2$)CO—. In some embodiments, the spacer is —NH(CH$_2$)$_2$CO—. In some embodiments, the spacer is glycyl. In some embodiments, the spacer is β-alanyl.

In some embodiments, the spacer is —NHCH(CO$_2$H)(CH$_2$)$_2$CO—[N(R$_3$)((CH$_2$)$_2$O(CH$_2$)$_2$O)$_q$(CH$_2$)CO-]$_r$. In some embodiments, the spacer is —NH(CH$_2$)$_3$CO—[N(R$_3$)((CH$_2$)$_2$O(CH$_2$)$_2$O)$_q$(CH$_2$)CO-]$_r$. In some embodiments, the spacer is —NHCH(CO$_2$H)(CH$_2$)$_2$CO—NH((CH$_2$)$_2$O(CH$_2$)$_2$O)$_2$(CH$_2$)CO—. In some embodiments, the spacer is —NH(CH$_2$)$_3$CO—NH((CH$_2$)$_2$O(CH$_2$)$_2$O)$_2$(CH$_2$)CO—. In some embodiments, the spacer is —NHCH(CO$_2$H)CH$_2$CO—[N(R$_3$)((CH$_2$)$_2$O(CH$_2$)$_2$O)$_q$(CH$_2$)CO-]$_r$. In some embodiments, the spacer is —NH(CH$_2$)$_2$CO—[N(R$_3$)((CH$_2$)$_2$O(CH$_2$)$_2$O)$_q$(CH$_2$)CO-]$_r$.

In some embodiments, the spacer comprises a bivalent group of Formula XIV:

—(Y)$_n$—     Formula XIV wherein

Y is selected from the group consisting of γGlu, Asp, Lys and Gly;

n is from 1 to 10.

In some embodiments, Y is selected from the group consisting of γGlu and Gly. In some embodiments, Y is γGlu. In some embodiments, Y is Gly.

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XV:

-(γGlu)$_n$-     Formula XV wherein n is from 1 to 10 ("(γGlu)$_n$", where n is from 1 to 10 disclosed as SEQ ID NO: 808).

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XVI:

-(γGlu)$_n$-(Gly)- Formula XVI wherein n is from 1 to 10 ("(γGlu)$_n$-(Gly)", where n is from 1 to 10 disclosed as SEQ ID NO: 809).

In some embodiments, (γGlu)$_n$ is selected from the group consisting of γGlu; 2(γGlu); 3(γGlu); 4(γGlu) (SEQ ID NO: 810); and 5(γGlu) (SEQ ID NO: 811). In some embodiments, -(γGlu)$_n$-(Gly)- is selected from the group consisting of 2(γGlu),Gly; and 3(γGlu),Gly (SEQ ID NO: 812).

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XVII:

-(Gly)-(γGlu)$_n$- Formula XVII wherein n is from 1 to 10 ("-(Gly)-(γGlu)$_n$", where n is from 1 to 10 disclosed as SEQ ID NO: 813).

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, the spacer comprises a bivalent group of Formula XVIII:

—(V)$_r$—(Y)$_n$— Formula XVIII wherein

Y is selected from the group consisting of γGlu, Asp, and Gly;

V is —[COCH$_2$(OCH$_2$CH$_2$)$_t$NH]—;

r is from 1 to 6;

n is from 1 to 10; and t is from 1 to 6.

In some embodiments, Y is γGlu. In some embodiments, Y is Asp. In some embodiments, Y is Gly.

In some embodiments, n is selected from the group consisting of 1, 2, 3, 4, 5, 6, 7, 8, 9 and 10. In some embodiments, n is from 1 to 5. In some embodiments, n is 1. In some embodiments, n is 2. In some embodiments, n is 3. In some embodiments, n is 4. In some embodiments, n is 5.

In some embodiments, r is from 1 to 3. In some embodiments, r is 1. In some embodiments, r is 2. In some embodiments, r is 3. In some embodiments, r is 4. In some embodiments, r is 5.

In some embodiments, t is from 1 to 3. In some embodiments, t is selected from the group consisting of 1, 2, 3, 4, 5 and 6.

In an embodiment, —(V)$_r$—(Y)$_n$— is —[COCH$_2$(OCH$_2$CH$_2$)$_2$NH]2-γGlu-.

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XIX:

—(Y1)$_{n1}$-(dpeg)$_r$-(Y2)$_{n2}$— Formula XIX wherein

Y1 is selected from the group consisting of γGlu, Asp, and Gly;

Y2 is selected from the group consisting of γGlu, Asp, and Gly;

dpeg is —[CO(CH$_2$)O(CH$_2$)$_2$O(CH$_2$)NH]

r is from 1 to 8;

n1 is from 0 to 10; and n2 is from 0 to 10.

In some embodiments, Y1 is γGlu. In some embodiments, Y1 is Asp. In some embodiments, Y1 is Gly.

In some embodiments, Y2 is γGlu. In some embodiments, Y2 is Asp. In some embodiments, Y2 is Gly.

In some embodiments, n1 is selected from the group consisting of 0, 1, 2, 3, 4, 5, 6, 7, 8, 9 and 10. In some embodiments, n1 is from 0 to 3. In some embodiments, n1 is 0. In some embodiments, n1 is 1. In some embodiments, n1 is 2. In some embodiments, n1 is 3. In some embodiments, n1 is 4. In some embodiments, n1 is 5.

In some embodiments, n2 is selected from the group consisting of 0, 1, 2, 3, 4, 5, 6, 7, 8, 9 and 10. In some embodiments, n2 is from 0 to 3. In some embodiments, n2 is 0. In some embodiments, n2 is 1. In some embodiments, n2 is 2. In some embodiments, n2 is 3. In some embodiments, n2 is 4. In some embodiments, n2 is 5.

In some embodiments, r is from 1 to 3. In some embodiments, r is 1. In some embodiments, r is 2. In some embodiments, r is 3. In some embodiments, r is 4. In some embodiments, r is 5.

In some embodiments, r is 6. In some embodiments, r is 7. In some embodiments, r is 8.

In some embodiments, r is 1, n1 is 2, and n2 is 0.

In some embodiments, r is 1, n1 is 2, and n2 is 2.

In some embodiments, Y1 is γGlu and Y2 is γGlu.

In some embodiments, Y1 is γGlu and n2 is 0.

In some embodiments, Y1 is γGlu, r is 1, n1 is 2, and n2 is 0.

In some embodiments, —(Y1)$_{n1}$-(dpeg)$_r$-(Y2)$_{n2}$- is selected from the group consisting of -γGlu-γGlu-dpeg-, -γGlu-γGlu-dpeg-γGlu-γGlu-, -γGlu-γGlu-dpeg-γGlu-, -γGlu-γGlu-dpeg-dpeg-, -γGlu-γGlu-dpeg-dpeg-γGlu-, -dpeg-dpeg-γGlu-, -γGlu-γGlu-γGlu-dpeg-, and -γGlu-dpeg-.

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

Accordingly, in some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent, and optionally comprises a spacer.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent of Formula I.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent of Formula I and a spacer selected from the group consisting of those described by Formula XII, XIII, XIV, XV, XVI, XVII, XVIII, and XIX.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 157 and SEQ ID NOs: 239, 240, 241, 242, 243, 244, 245, 246, 247, 248, 280, and 281, wherein the isolated peptide further comprises a lipophilic substituent and a spacer selected from the group consisting of those described by Formula I, II, III, IV, V, VI, VII, VIII, IX, X, and XI.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent and a spacer selected from the group consisting of those described by Formula I.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent and a spacer selected from the group consisting of those described by Formula II.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent and a spacer selected from the group consisting of those described by Formula III.

In some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 101 through SEQ ID NO: 181 and SEQ ID NOs: 239, 240, 241, 242, 243, 244, 245, 246, 247, 248, 280, and 281, wherein the isolated peptide further comprises a lipophilic substituent and a spacer selected from the group consisting of those described by Formula IV. As used herein, $(\gamma Glu)_2$ and 2(γGlu) both mean -(γGlu)-(γGlu)- or —CO$(CH_2)_2CH(CO_2H)NH$—CO$(CH_2)_2CH(CO_2H)NH$—; $(\gamma Glu)_3$ and 3(γGlu) both mean -(γGlu)-(γGlu)-(γGlu)- or —CO$(CH_2)_2CH(CO_2H)NH$—CO$(CH_2)_2CH(CO_2H)NH$—CO$(CH_2)_2CH(CO_2H)NH$—; etc.; where a variable is present more than once in a given formula, each occurrence of that variable is independently determined. For example, for group —$(Y)_3$-, where Y may be γGlu, Asp, Lys, or Gly, each Y is independently selected to be one of the four amino acids. Accordingly, by non-limiting example, —$(Y)_3$— may be -(γGlu)-(γGlu)-(γGlu)-, -(γGlu)-(Asp)-(γGlu)-, -(Gly)-(Asp)-(γGlu)-, or -(Gly)-(γGlu)-(γGlu)-.

Bridging Moiety

In some embodiments, any of the disclosed polypeptides is optionally substituted with one or more bridging moieties. As used herein, the term "bridging moiety" means a covalent bond or any bivalent linker or moiety that joins two sidechains of two separate amino acid residues. In some embodiments, any of the disclosed polypeptides is optionally substituted with one or more lactam bridging moieties. As used herein, the term "lactam bridging moiety" means a lactam bridge or lactam bond that joins amino-containing and carboxy-containing sidechains of two separate amino acid residues. In some embodiments, the lactam bridging moiety is formed between a lysine residue and an aspartic acid residue, and the amino-containing sidechain of lysine and the carboxy-containing sidechain of aspartic acid are covalently joined, with loss of water, to form a lactam bridging moiety. In some embodiments, the lactam bridging moiety is formed between a lysine residue and a glutamic acid residue, and the amino-containing sidechain of lysine and the carboxy-containing sidechain of glutamic acid are covalently joined, with loss of water, to form a lactam bridging moiety. In some embodiments, the lactam bridging moiety is formed between two amino acids that are spaced three, four, or five residues apart on the peptide. In some embodiments, the lactam bridging moiety is formed between two amino acids that are spaced four residues apart on the peptide.

Polypeptide Intermediates & General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry; Reactions, Mechanisms, and Structure*, M. B. Smith and J. March, 5th Edition, John Wiley & Sons, 2001, *Comprehensive Organic Transformations*, R. C. Larock, 2nd Edition, John Wiley & Sons, 1999, and *Protecting Groups in Organic Synthesis*, T. W.

Greene and P. G. M. Wuts, 3rd edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitable hydroxyl protecting groups include, but are not limited to, esters (e.g., acetyl, benzyl), allyl ethers, ethers, silyl ethers, alkyl ethers, arylalkyl ethers, benzyl ethers and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl) ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkyl silyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (Boc), ethyloxycarbonyl, methyloxycarbonyl, trichloroethyloxycarbonyl, allyloxycarbonyl (Alloc), benzyloxocarbonyl (Cbz), allyl, phthalimide, benzyl (Bn), dimethyl-2,6-dioxocyclohex-1-ylidene)ethyl (Dmb), 1-(4,4-dimethyl-2,6-dioxocyclohex-1-ylidene)-3-methylbutyl (ivDde), fluorenylmethylcarbonyl (Fmoc), formyl, acetyl, chloroacetyl, dichloroacetyl, trichloroacetyl, phenylacetyl, trifluoroacetyl, benzoyl, and the like.

In certain embodiments, the present invention also relates to synthetic peptide intermediates of disclosed PYY analogs. In some embodiments, a polypeptide intermediate of the disclosure is an isolated polypeptide comprising the amino acid sequence of any of SEQ ID NO: 101 through SEQ ID NO: 181 or SEQ ID NOs: 239, 240, 241, 242, 243, 244, 245, 246, 247, 248, 280, and 281, wherein at least one amino acid is covalently bound to a protecting group. In some embodiments, a polypeptide intermediate of the disclosure is an isolated polypeptide comprising the amino acid sequence of any of SEQ ID NO: 101 through SEQ ID NO: 181 or SEQ ID NOs: 239, 240, 241, 242, 243, 244, 245, 246, 247, 248, 280, and 281, wherein at least one amino acid is covalently bound to a spacer as defined herein, wherein the spacer is further covalently bound to a protecting group or a hydrogen atom. In some embodiments, the polypeptide intermediate comprises a lysine residue bound to a protecting group via the amino group of its sidechain. In some embodiments, the lysine residue is covalently bound to a Alloc or ivDde. In some embodiments, the polypeptide intermediate comprises an aspartic acid residue bound to a protecting group via the carboxyl group of its sidechain. In some embodiments, the aspartic acid residue is covalently bound to an allyl group. In some embodiments, the polypeptide intermediate comprises a glutamic acid residue bound to a protecting group via the carboxyl group of its sidechain. In some embodiments, the glutamic acid residue is covalently bound to an allyl group.

Exemplary Polypeptide Intermediates

The compounds of this invention may be prepared or isolated in general by synthetic and/or semi-synthetic methods known to those skilled in the art for analogous compounds and by methods described in detail in the Examples, herein.

In certain embodiments, the present invention also relates to synthetic peptide intermediates of disclosed PYY analogs. In some embodiments, a polypeptide intermediate of the disclosure is an isolated polypeptide comprising the amino acid sequence of SEQ ID NO: 390: $X_0PX_2PX_4X_5PX_7X_8X_9X_{10}$ $SPX_{13}X_{14}$ $X_{15}X_{16}RX_{18}X_{19}X_{20}DX_{22}X_{23}HX_{25}$ $X_{26}X_{27}$ $WLTRX_{32}RX_{34}$-(OH/$NH_2$) (SEQ ID NO: 390), or a pharmaceutically acceptable salt thereof, wherein:

$X_0$ is absent or K;
$X_2$ is K;
$X_4$ is E or K;
$X_5$ is A or K;
$X_7$ is G or K
$X_8$ is E, K, or k;
$X_9$ is D or K;
$X_{10}$ is A or K;
$X_{13}$ is E or K;
$X_{14}$ is E or K;
$X_{15}$ is L or W;
$X_{16}$ is D, E, K, N, Q, S, T, α-methylserine, or homoserine;
$X_{18}$ is K or Y;
$X_{19}$ is K or Y;
$X_{20}$ is A, D, E, K, k, or Dap,
$X_{22}$ is A, D, K, or L;
$X_{23}$ is K or R;
$X_{25}$ is K or Y;
$X_{26}$ is E, K, or L;
$X_{27}$ is K or N;
$X_{32}$ is K or Q;
$X_{34}$ is F, y, 3-pyridinylalanine, 4-pyridinylalanine, 4-carboxyphenylalanine, 4-fluorophenylalanine, 4-methylphenylalanine, N-methylphenylalanine, homophenylalanine, β-homotyrosine, homotyrosine, or N-methyltyrosine;

wherein when $X_0$, $X_2$, $X_4$, $X_5$, $X_7$, $X_8$, $X_{13}$, $X_{20}$, $X_{23}$, $X_{25}$, $X_{27}$, or $X_{32}$ are K, the lysine residue is optionally covalently bound to a protecting group or to a spacer optionally bound to a protecting group, and wherein when $X_8$ or $X_{20}$ are k, the D-lysine residue is optionally covalently bound to a protecting group or to a spacer optionally bound to a protecting group.

In some embodiments, when $X_{15}$ is L, $X_{22}$ is A.

In some embodiment, when $X_{16}$ is N, $X_{20}$ is not A.

In some embodiments, when $X_8$ is E, $X_5$ is K and $X_{20}$ is K.

In some embodiments, $X_8$ is K. In some embodiments, $X_8$ is K covalently bound to a protecting group. In some embodiments, $X_8$ is K covalently bound to a spacer optionally bound to a protecting group.

In some embodiments, $X_{15}$ is W.

In some embodiments, $X_{34}$ is F.

In some embodiments, $X_0$ is absent. In some embodiments, $X_0$ is K. In some embodiments, $X_0$ is K covalently bound to a protecting group. In some embodiments, $X_0$ is K covalently bound to a spacer optionally bound to a protecting group.

In some embodiments, $X_2$ is K. In some embodiments, $X_2$ is K covalently bound to a protecting group. In some embodiments, $X_2$ is K covalently bound to a spacer optionally bound to a protecting group.

In some embodiments, $X_4$ is E. In some embodiments, $X_4$ is K. In some embodiments, $X_4$ is K covalently bound to a protecting group. In some embodiments, $X_4$ is K covalently bound to a spacer optionally bound to a protecting group.

In some embodiments, $X_5$ is A. In some embodiments, $X_5$ is K. In some embodiments, $X_5$ is K covalently bound to a protecting group. In some embodiments, $X_5$ is K covalently bound to a spacer optionally bound to a protecting group.

In some embodiments, $X_7$ is G. In some embodiments, $X_7$ is K. In some embodiments, $X_7$ is K covalently bound to a protecting group. In some embodiments, $X_7$ is K covalently bound to a spacer optionally bound to a protecting group.

In some embodiments, $X_8$ is E. In some embodiments, $X_8$ is K. In some embodiments, $X_8$ is K covalently bound to a protecting group. In some embodiments, $X_8$ is K covalently bound to a spacer optionally bound to a protecting group. In some embodiments, $X_8$ is k. In some embodiments, $X_8$ is k covalently bound to a protecting group. In some embodiments, $X_8$ is k covalently bound to a spacer optionally bound to a protecting group.

In some embodiments, $X_9$ is D. In some embodiments, $X_9$ is K.

In some embodiments, $X_{10}$ is A. In some embodiments, $X_{10}$ is K. In some embodiments, $X_{10}$ is K covalently bound to a protecting group. In some embodiments, $X_{10}$ is K covalently bound to a spacer optionally bound to a protecting group.

In some embodiments, $X_{13}$ is E. In some embodiments, $X_{13}$ is K. In some embodiments, $X_{13}$ is K covalently bound to a protecting group. In some embodiments, $X_{13}$ is K covalently bound to a spacer optionally bound to a protecting group.

In some embodiments, $X_{14}$ is E. In some embodiments, $X_{14}$ is K.

In some embodiments, $X_{15}$ is L. In some embodiments, $X_{15}$ is W.

In some embodiments, $X_{16}$ is D. In some embodiments, $X_{16}$ is E. In some embodiments, $X_{16}$ is K. In some embodiments, $X_{16}$ is N. In some embodiments, $X_{16}$ is Q. In some embodiments, $X_{16}$ is S. In some embodiments, $X_{16}$ is T. In some embodiments, $X_{16}$ is α-methylserine. In some embodiments, $X_{16}$ is homoserine.

In some embodiments, $X_{18}$ is K. In some embodiments, $X_{18}$ is Y.

In some embodiments, $X_{19}$ is K. In some embodiments, $X_{19}$ is Y.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a protecting group. In some embodiments, $X_{20}$ is K covalently bound to a spacer optionally bound to a protecting group. In some embodiments, $X_{20}$ is k. In some embodiments, $X_{20}$ is k covalently bound to a protecting group. In some embodiments, $X_{20}$ is k covalently bound to a spacer optionally bound to a protecting group. In some embodiments, $X_{20}$ is Dap.

In some embodiments, $X_{22}$ is A. In some embodiments, $X_{22}$ is D. In some embodiments, $X_{22}$ is K. In some embodiments, $X_{22}$ is L.

In some embodiments, $X_{23}$ is K. In some embodiments, $X_{23}$ is K covalently bound to a protecting group. In some embodiments, $X_{23}$ is K covalently bound to a spacer optionally bound to a protecting group. In some embodiments, $X_{23}$ is R.

In some embodiments, $X_{25}$ is K. In some embodiments, $X_{25}$ is K covalently bound to a protecting group. In some embodiments, $X_{25}$ is K covalently bound to a spacer optionally bound to a protecting group. In some embodiments, $X_{25}$ is Y.

In some embodiments, $X_{26}$ is E. In some embodiments, $X_{26}$ is K. In some embodiments, $X_{26}$ is L.

In some embodiments, $X_{27}$ is K. In some embodiments, $X_{27}$ is K covalently bound to a protecting group. In some embodiments, $X_{27}$ is K covalently bound to a spacer optionally bound to a protecting group. In some embodiments, $X_{27}$ is N.

In some embodiments, $X_{32}$ is K. In some embodiments, $X_{32}$ is K covalently bound to a protecting group. In some embodiments, $X_{32}$ is K covalently bound to a spacer optionally bound to a protecting group. In some embodiments, $X_{32}$ is Q.

In some embodiments, $X_{34}$ is F. In some embodiments, $X_{34}$ is y. In some embodiments, $X_{34}$ is 3-pyridinylalanine. In some embodiments, $X_{34}$ is 4-pyridinylalanine. In some embodiments, $X_{34}$ is 4-carboxyphenylalanine. In some embodiments, $X_{34}$ is 4-fluorophenylalanine. In some embodiments, $X_{34}$ is 4-methylphenylalanine. In some embodiments, $X_{34}$ is N-methylphenylalanine. In some embodiments, $X_{34}$ is homophenylalanine. In some embodiments, $X_{34}$ is β-homotyrosine. In some embodiments, $X_{34}$ is homotyrosine. In some embodiments, $X_{34}$ is N-methyltyrosine.

In some embodiments, a polypeptide intermediate of the disclosure is an isolated polypeptide comprising the amino acid sequence of SEQ ID NO: SEQ ID NO: 394: PKPEX$_5$PGX$_8$DASPX$_{13}$EWX$_{16}$RYYX$_{20}$DX$_{22}$RHYLNWLTRQRX$_{34}$-(OH/NH$_2$) (SEQ ID NO: 394), or a pharmaceutically acceptable salt thereof, wherein:

$X_5$ is A or K;

$X_8$ is E, K, or k;

$X_{13}$ is E or K;

$X_{16}$ is D, E, K, or N;

$X_{20}$ is A, D, E, K, or k, $X_{22}$ is A or L;

$X_{34}$ is F or N-methyltyrosine;

wherein when $X_5$, $X_8$, $X_{13}$, or $X_{20}$ are K, the lysine residue is optionally covalently bound to a protecting group or to a spacer optionally bound to a protecting group, and wherein when $X_8$ or $X_{20}$ are k, the D-lysine residue is optionally covalently bound to a protecting group or to a spacer optionally bound to a protecting group.

In some embodiment, when $X_{16}$ is N, $X_{20}$ is not A.

In some embodiments, when $X_8$ is E, $X_5$ is K and $X_{20}$ is K.

In some embodiments, $X_8$ is K. In some embodiments, $X_8$ is K covalently bound to a protecting group. In some embodiments, $X_8$ is K covalently bound to a spacer optionally bound to a protecting group.

In some embodiments, $X_{34}$ is F.

In some embodiments, $X_5$ is A. In some embodiments, $X_5$ is K. In some embodiments, $X_5$ is K covalently bound to a protecting group. In some embodiments, $X_5$ is K covalently bound to a spacer optionally bound to a protecting group.

In some embodiments, $X_8$ is E. In some embodiments, $X_8$ is K. In some embodiments, $X_8$ is K covalently bound to a protecting group. In some embodiments, $X_8$ is K covalently bound to a spacer optionally bound to a protecting group. In some embodiments, $X_8$ is k. In some embodiments, $X_8$ is k covalently bound to a protecting group. In some embodiments, $X_8$ is k covalently bound to a spacer optionally bound to a protecting group.

In some embodiments, $X_{13}$ is E. In some embodiments, $X_{13}$ is K. In some embodiments, $X_{13}$ is K covalently bound to a protecting group. In some embodiments, $X_{13}$ is K covalently bound to a spacer optionally bound to a protecting group.

In some embodiments, $X_{16}$ is D. In some embodiments, $X_{16}$ is E. In some embodiments, $X_{16}$ is K. In some embodiments, $X_{16}$ is N.

In some embodiments, $X_{20}$ is A. In some embodiments, $X_{20}$ is D. In some embodiments, $X_{20}$ is E. In some embodiments, $X_{20}$ is K. In some embodiments, $X_{20}$ is K covalently bound to a protecting group. In some embodiments, $X_{20}$ is K covalently bound to a spacer optionally bound to a protecting group. In some embodiments, $X_{20}$ is k. In some embodiments, $X_{20}$ is k covalently bound to a protecting group. In some embodiments, $X_{20}$ is k covalently bound to a spacer optionally bound to a protecting group.

In some embodiments, $X_{22}$ is A. In some embodiments, $X_{22}$ is L.

In some embodiments, $X_{34}$ is F. In some embodiments, $X_{34}$ is N-methyltyrosine.

In some embodiments, an isolated polypeptide of the disclosure comprises an amino acid sequence selected form the group consisting of the following peptides listed in Tables 9, 10, 11, and 12.

TABLE 9

Exemplary polypeptide intermediates of SEQ ID NOs: 24, 42, and 43.

Intermediate to A24 (SEQ ID NO: 24):

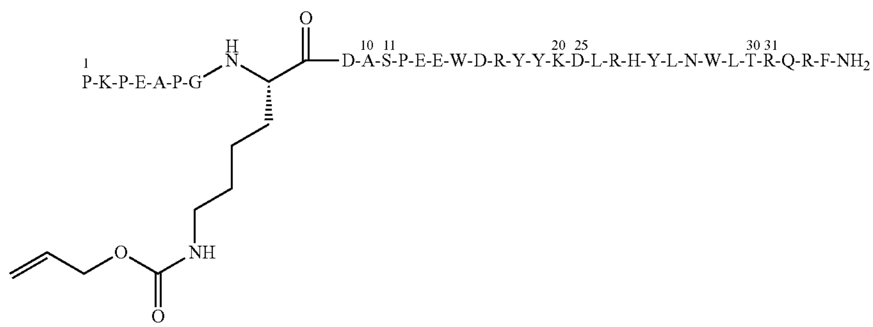

SEQ ID NO: 524 (F24)

Intermediate to A42 (SEQ ID NO: 42):

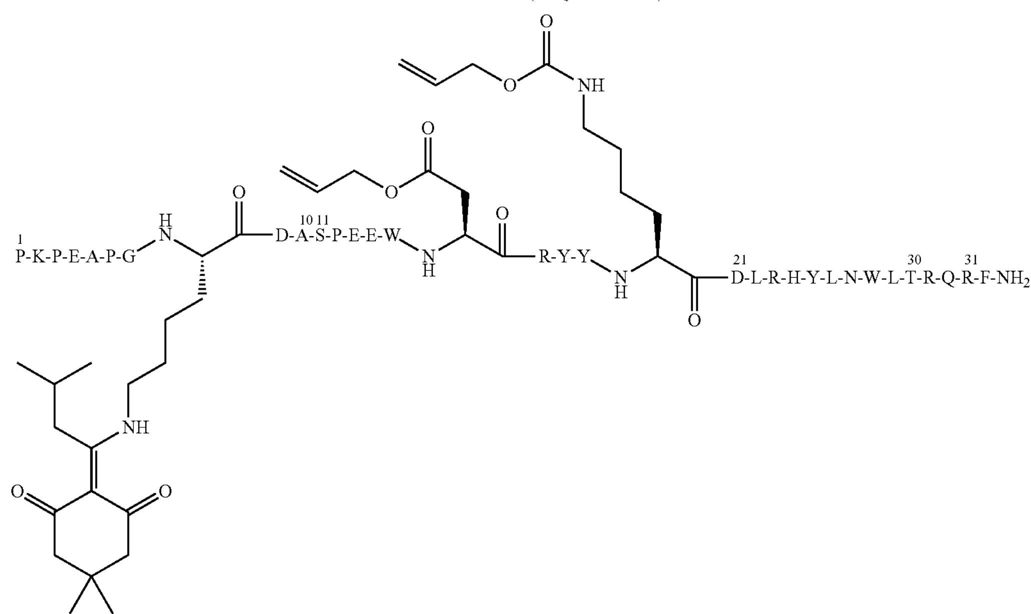

SEQ ID NO: 742 (H42)

TABLE 9-continued

Exemplary polypeptide intermediates of SEQ ID NOs: 24, 42, and 43.

Intermediate to A43 (SEQ ID NO: 43)

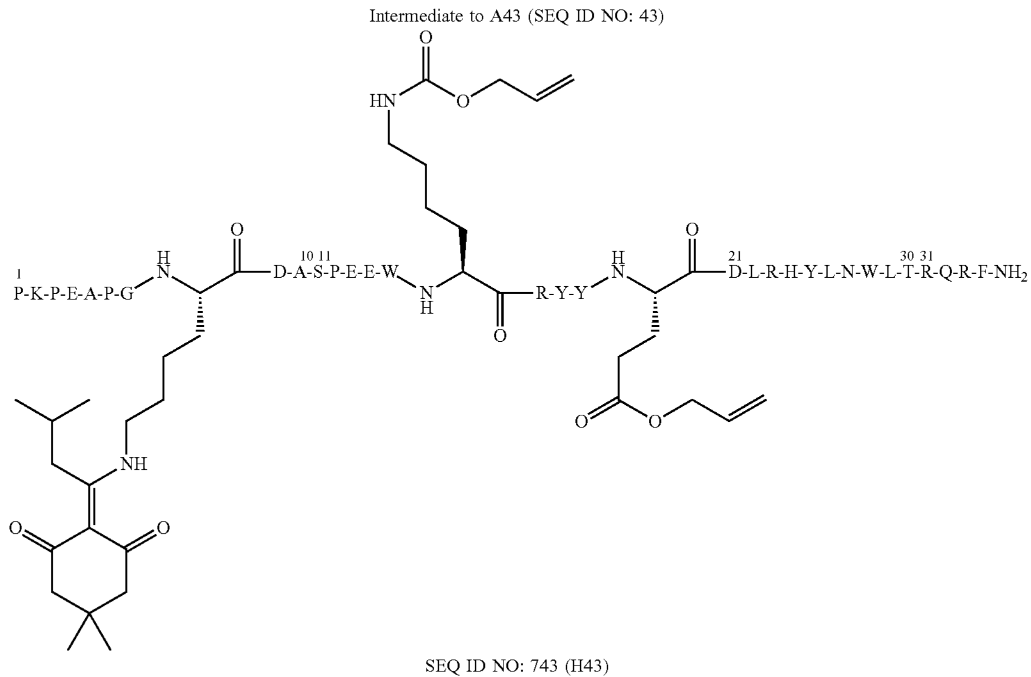

SEQ ID NO: 743 (H43)

TABLE 10

Compound A24 and exemplary polypeptide intermediates thereof

| Compound No. | Sequence | SEQ ID NO: |
|---|---|---|
| A24 | PKPEAPGK(γGlu-γGlu-CO$(CH_2)_{18}CO_2H$) DASPEEWDRYYKDLRHYLNWLTRQRF-$(NH_2)$ | SEQ ID NO: 24 |
| D24 | PKPEAPGK(γGlu-γGlu)DASPEEWDRYYKD LRHYLNWLTRQRF-$(NH_2)$ | SEQ ID NO: 324 |
| E24 | PKPEAPGK(γGlu)DASPEEWDRYYKDLRHYL NWLTRQRF-$(NH_2)$ | SEQ ID NO: 424 |
| B24 | PKPEAPGKDASPEEWDRYYKDLRHYLNWLTRQ RF-$(NH_2)$ | SEQ ID NO: 124 |
| F24 | PKPEAPGK(alloc)DASPEEWDRYYKDLRHY LNWLTRQRF-$(NH_2)$ | SEQ ID NO: 524 |

Notes:
alloc = allyloxycarbonyl protecting group

In some embodiments, the present invention provides a peptide intermediate of Compound A24 (SEQ ID NO: 24). In some embodiments, the peptide intermediate of Compound A24 comprises at least one amino acid covalently bound to a protecting group. In some embodiments, the peptide intermediate of Compound A24 comprises a lysine residue bound to a protecting group via the amino group of its sidechain. In some embodiments, the lysine residue is covalently bound to a Alloc or ivDde. In some embodiments, the peptide intermediate of Compound A24 comprises an aspartic acid residue bound to a protecting group via the carboxyl group of its sidechain. In some embodiments, the aspartic acid residue is covalently bound to an allyl group. In some embodiments, the peptide intermediate of Compound A24 comprises a glutamic acid residue bound to a protecting group via the carboxyl group of its sidechain. In some embodiments, the glutamic acid residue is covalently bound to an allyl group. In some embodiments, the peptide intermediate of Compound A24 comprises at least one amino acid covalently bound to a spacer as defined herein, wherein the spacer is further covalently bound to a protecting group or a hydrogen atom. In some embodiments, the present invention provides a peptide intermediate set forth in the Table 10, above. In some embodiments, the peptide intermediate is a peptide having the amino acid sequence of SEQ ID NO: 324. In some embodiments, the peptide intermediate is a peptide having the amino acid sequence of SEQ ID NO: 424. In some embodiments, the peptide intermediate is a peptide having the amino acid sequence of SEQ ID NO: 124. In some embodiments, the peptide intermediate is a peptide having the amino acid sequence of SEQ ID NO: 524.

In some embodiments, the present invention provides a method for preparing compounds of the invention, such as Compound A24 (SEQ ID NO: 24), comprising the step of acylating a polypeptide intermediates, such as Compound D24 (SEQ ID NO: 324), with the following activated acyl group, $(LG)CO(CH_2)_{zz}CO_2H$, wherein ZZ is from 14 to 22 and LG is a leaving group, as defined herein, as exemplified below in Scheme 1:

Scheme 1

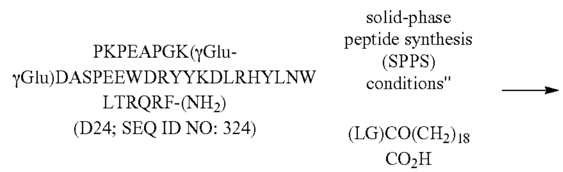

-continued

PKPEAPGK(γGlu-γGlu-$CO(CH_{12})_{18}CO_2H$)DASPEEWDRYYKDLRHYLNWLTRQRF-($NH_2$)
(A24; SEQ ID NO: 24)

TABLE 11

Compound A42 and exemplary polypeptide intermediates thereof.

| Compound No. | Sequence | SEQ ID NO: |
|---|---|---|
| A42 | PKPEAPGK(γGlu-γGlu-$CO(CH_2)_{18}CO_2H$)DASPEEWD*RYYK*DLRHYLNWLTRQRF-($NH_2$) | SEQ ID NO: 42 |
| D42 | PKPEAPGK(γGlu-γGlu)DASPEEWD*RYYK*DLRHYLNWLTRQRF-($NH_2$) | SEQ ID NO: 342 |
| E42 | PKPEAPGK(γGlu)DASPEEWD*RYYK*DLRHYLNWLTRQRF-($NH_2$) | SEQ ID NO: 442 |
| C42 | PKPEAPGKDASPEEWD*RYYK*DLRHYLNWLTRQRF-($NH_2$) | SEQ ID NO: 242 |
| F42 | PKPEAPGK(ivDde)DASPEEWD*RYYK*DLRHYLNWLTRQRF-($NH_2$) | SEQ ID NO: 542 |
| G42 | PKPEAPGK(ivDde)DASPEEWDRYYKDLRHYLNWLTRQRF-($NH_2$) | SEQ ID NO: 642 |
| H42 | PKPEAPGK(ivDde)DASPEEWD(allyl)RYYK(alloc)DLRHYLNWLTRQRF-($NH_2$) | SEQ ID NO: 742 |

Notes:
Each pairing of K* and D* represents a covalent amide linkage derived from the amino sidechain of K* and the carboxy sidechain of D* (with loss of a water molecule).
alloc = allyloxycarbonyl protecting group
allyl = allyl (CH2═CH-CH2 ) protecting group
ivDde = 1-(4,4-dimethyl-2,6-dioxocyclohex-1-ylidene)-3-methylbutyl protecting group In some embodiments, the present invention provides a peptide intermediate of Compound A42 (SEQ ID NO: 42). In some embodiments, the peptide intermediate of Compound A42 comprises at least one amino acid covalently bound to a protecting group. In some embodiments, the peptide intermediate of Compound A42 comprises a lysine residue bound to a protecting group via the amino group of its sidechain. In some embodiments, the lysine residue is covalently bound to a Alloc or ivDde. In some embodiments, the peptide intermediate of Compound A42 comprises an aspartic acid residue bound to a protecting group via the carboxyl group of its sidechain. In some embodiments, the aspartic acid residue is covalently bound to an allyl group. In some embodiments, the peptide intermediate of Compound A42 comprises a glutamic acid residue bound to a protecting group via the carboxyl group of its sidechain. In some embodiments, the glutamic acid residue is covalently bound to an allyl group. In some embodiments, the peptide intermediate of Compound A42 comprises at least one amino acid covalently bound to a spacer as defined herein, wherein the spacer is further covalently bound to a protecting group or a hydrogen atom. In some embodiments, the present invention provides a peptide intermediate set forth in the Table 11, above. In some embodiments, the peptide intermediate is a peptide having the amino acid sequence of SEQ ID NO: 342. In some embodiments, the peptide intermediate is a peptide having the amino acid sequence of SEQ ID NO: 442. In some embodiments, the peptide intermediate is a peptide having the amino acid sequence of SEQ ID NO: 242. In some embodiments, the peptide intermediate is a peptide having the amino acid sequence of SEQ ID NO: 542. In some embodiments, the peptide intermediate is a peptide having the amino acid sequence of SEQ ID NO: 642. In some embodiments, the peptide intermediate is a peptide having the amino acid sequence of SEQ ID NO: 742.

In some embodiments, the present invention provides a method for preparing compounds of the invention, such as Compound A42 (SEQ ID NO: 42), comprising the step of acylating a polypeptide intermediates, such as Compound D42 (SEQ ID NO: 342), with the following activated acyl group, $(LG)CO(CH_2)_{zz}CO_2H$, wherein ZZ is from 14 to 22 and LG is a leaving group, as defined herein, as exemplified below in Scheme 2:

Scheme 2

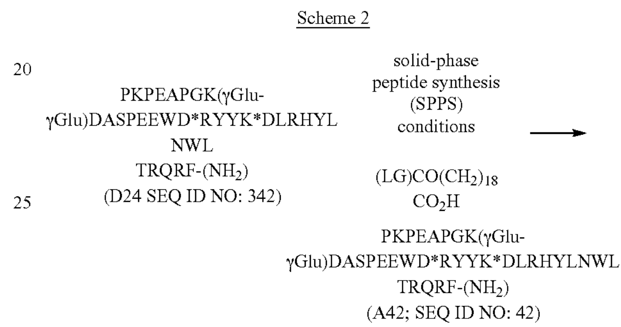

TABLE 12

Compound A43 and exemplary polypeptide intermediates thereof.

| Compound No. | Sequence | SEQ ID NO: |
|---|---|---|
| A43 | PKPEAPGK(γGlu-γGlu-$CO(CH_2)_{18}CO_2H$)DASPEEWK*RYYE*DLRHYLNWLTRQRF-($NH_2$) | SEQ ID NO: 43 |
| D43 | PKPEAPGK(γGlu-γGlu)DASPEEWK*RYYE*DLRHYLNWLTRQRF-($NH_2$) | SEQ ID NO: 343 |
| E43 | PKPEAPGK(γGlu)DASPEEWK*RYYE*DLRHYLNWLTRQRF-($NH_2$) | SEQ ID NO: 443 |
| C43 | PKPEAPGKDASPEEWK*RYYE*DLRHYLNWLTRQRF-($NH_2$) | SEQ ID NO: 243 |
| F43 | PKPEAPGK(ivDde)DASPEEWK*RYYE*DLRHYLNWLTRQRF-($NH_2$) | SEQ ID NO: 543 |
| G43 | PKPEAPGK(ivDde)DASPEEWKRYYEDLRHYLNWLTRQRF-($NH_2$) | SEQ ID NO: 643 |
| H43 | PKPEAPGK(ivDde)DASPEEWK(alloc)RYYE(allyl)DLRHYLNWLTRQRF-($NH_2$) | SEQ ID NO 743 |

Notes:
Each pairing of K* and E* represents a covalent amide linkage derived from the amino sidechain of K* and the carboxy sidechain of E* (with loss of a water molecule).
alloc = allyloxycarbonyl protecting group
allyl = allyl (CH2═CH—CH2—) protecting group
ivDde = 1-(4,4-dimethyl-2,6-dioxocyclohex-1-ylidene)-3-methylbutyl protecting group In some embodiments, the present invention provides a peptide intermediate of Compound A43 (SEQ ID NO: 43). In some embodiments, the peptide intermediate of Compound A43 comprises at least one amino acid covalently bound to a protecting group. In some embodiments, the peptide intermediate of Compound A43 comprises a lysine residue bound to a protecting group via the amino group of its sidechain. In some embodiments, the lysine residue is covalently bound to a Alloc or ivDde. In some embodiments, the peptide intermediate of Compound A43 comprises an aspartic acid residue bound to a protecting group via the carboxyl group of its sidechain. In some embodiments, the aspartic acid residue is covalently bound to an allyl group. In some embodiments, the peptide intermediate of Compound A43 comprises a glutamic acid residue bound to a protecting group via the carboxyl group of its sidechain. In some embodiments, the glutamic acid residue is covalently bound to an allyl group. In some embodiments, the peptide intermediate of Compound A43 comprises at least one amino acid covalently bound to a spacer as defined herein, wherein the spacer is further covalently bound to a protecting group or a hydrogen atom. In some embodiments, the present invention provides a peptide intermediate set forth in the Table 12, above. In some embodiments, the peptide intermediate is a peptide having the amino acid sequence of SEQ ID NO: 343. In some embodiments, the peptide intermediate is a peptide having the amino acid sequence of SEQ ID NO: 443. In some embodiments, the peptide intermediate is a peptide having the amino acid sequence of SEQ ID NO: 243. In some embodiments, the peptide intermediate is a peptide having the amino acid sequence of SEQ ID NO: 543. In some embodiments, the peptide intermediate is a peptide having the amino acid sequence of SEQ ID NO: 643. In some embodiments, the peptide intermediate is a peptide having the amino acid sequence of SEQ ID NO: 743.

In some embodiments, the present invention provides a method for preparing compounds of the invention, such as Compound A43 (SEQ ID NO: 43), comprising the step of acylating a polypeptide intermediates, such as Compound D43 (SEQ ID NO: 343), with the following activated acyl group, $(LG)CO(CH_2)_{zz}CO_2H$, wherein ZZ is from 14 to 22 and LG is a leaving group, as defined herein, as exemplified below in Scheme 3:

Scheme 3

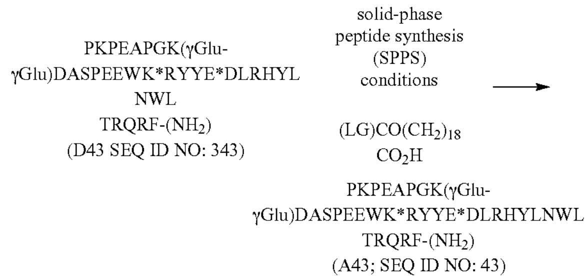

Methods of Use

According to another embodiment, the invention relates to a method of treating metabolic disease or disorder in a subject in need of treatment, comprising providing the subject with an effective amount of a PYY analog polypeptide of the disclosure or a pharmaceutical composition thereof. Metabolic diseases or disorders include type 1 diabetes, type 2 diabetes, and obesity. Additionally, the invention relates to a method of effecting weight loss in a subject, including a diabetic subject, comprising providing the subject with an effective amount of a PYY analog polypeptide of the disclosure. In certain embodiments, the invention also relates to methods of treating nonalcoholic fatty liver disease (NAFLD) and/or nonalcoholic steatohepatitis (NASH).

In some embodiments, provided is a method of treating obesity in a human subject, providing weight loss to the human subject, or suppressing appetite in the human subject, comprising administering to the subject any of the polypeptides disclosed herein, a pharmaceutical composition comprising any of the disclosed polypeptides, or an osmotic delivery device comprising any of the disclosed polypeptides.

In some embodiments, provided is a method of treating diabetes in a human subject, comprising administering to the subject any of the polypeptides disclosed herein, a pharmaceutical composition comprising any of the disclosed polypeptides, or an osmotic delivery device comprising any of the disclosed polypeptides. In some embodiments, the diabetes is type 1 diabetes. In some embodiments, the diabetes is type 2 diabetes.

In some embodiments, provided is a method of treating nonalcoholic fatty liver disease (NAFLD) in a human subject, comprising administering to the subject any of the polypeptides disclosed herein, a pharmaceutical composition comprising any of the disclosed polypeptides, or an osmotic delivery device comprising any of the disclosed polypeptides.

In some embodiments, provided is a method of treating nonalcoholic steatohepatitis (NASH) in a human subject, comprising administering to the subject any of the polypeptides disclosed herein, a pharmaceutical composition comprising any of the disclosed polypeptides, or an osmotic delivery device comprising any of the disclosed polypeptides.

PYY analog polypeptides of the disclosure are particularly useful for the treatment of diabetes, the method comprising providing a diabetic subject with an effective amount of a PYY analog polypeptide. In some embodiments, a PYY analog polypeptide of the disclosure is used for the treatment of a subject with type 1 or type 2 diabetes to control, or reduce, concentrations of blood sugar in the subject, where blood sugar levels can be monitored or approximated based on measured blood concentrations of glycated hemoglobin (hemoglobin A1c, HbA1c).

(i) In some embodiments, a PYY analog polypeptide of the disclosure is used for the treatment of a subject with type 1 diabetes;

(ii) In some embodiments, a PYY analog polypeptide of the disclosure is used for the treatment of a subject with type 2 diabetes;

(iii) In some embodiments, a PYY analog polypeptide of the disclosure is used for the treatment of obesity; and (iv) In some embodiments, a PYY analog polypeptide of the disclosure is used to provide weight loss to a subject, such as a diabetic subject, (v) In some embodiments, a PYY analog polypeptide of the disclosure is used for the treatment of nonalcoholic fatty liver disease (NAFLD), (vi) In some embodiments, a PYY analog polypeptide of the disclosure is used for the treatment of nonalcoholic steatohepatitis (NASH), wherein the PYY analog polypeptide of usage (i), (ii), (iii), (iv), (v) or (vi) comprises any isolated polypeptide of this disclosure including those represented by any of the consensus sequences of SEQ ID NO: 1 through SEQ ID NO: 78, or a pharmaceutically acceptable salt thereof.

In some embodiments, the PYY analog polypeptide of usage (i), (ii), (iii), (iv), (v) or (vi) comprises any isolated polypeptide of this disclosure including those selected from the group consisting of SEQ ID NOs: 13, 24, 42 and 43 or a pharmaceutically acceptable salt thereof.

In some embodiments, the PYY analog polypeptide of usage (i), (ii), (iii), (iv), (v) or (vi) comprises the isolated polypeptide of SEQ ID NO: 13 or a pharmaceutically acceptable salt thereof. In some embodiments, the PYY analog polypeptide of usage (i), (ii), (iii), (iv), (v) or (vi) comprises the isolated polypeptide of SEQ ID NO: 24 or a pharmaceutically acceptable salt thereof. In some embodiments, the PYY analog polypeptide of usage (i), (ii), (iii), (iv), (v) or (vi) comprises the isolated polypeptide of SEQ ID NO: 42 or a pharmaceutically acceptable salt thereof. In some embodiments, the PYY analog polypeptide of usage (i), (ii), (iii), (iv), (v) or (vi) comprises the isolated polypeptide of SEQ ID NO: 43 or a pharmaceutically acceptable salt thereof.

In some embodiments, the PYY analog polypeptide is used for the treatment of a subject with type 1 diabetes wherein the isolated polypeptide is of SEQ ID NO: 13 or a pharmaceutically acceptable salt thereof. In some embodiments, the PYY analog polypeptide is used for the treatment of a subject with type 1 diabetes wherein the isolated polypeptide is of SEQ ID NO: 24 or a pharmaceutically acceptable salt thereof. In some embodiments, the PYY analog polypeptide is used for the treatment of a subject with type 1 diabetes wherein the isolated polypeptide is of SEQ ID NO: 42 or a pharmaceutically acceptable salt thereof. In some embodiments, the PYY analog polypeptide is used for the treatment of a subject with type 1 diabetes wherein the isolated polypeptide is of SEQ ID NO: 43 or a pharmaceutically acceptable salt thereof.

In some embodiments, the PYY analog polypeptide is used for the treatment of a subject with type 2 diabetes wherein the isolated polypeptide is of SEQ ID NO: 13 or a pharmaceutically acceptable salt thereof. In some embodiments, the PYY analog polypeptide is used for the treatment of a subject with type 2 diabetes wherein the isolated polypeptide is of SEQ ID NO: 24 or a pharmaceutically acceptable salt thereof. In some embodiments, the PYY analog polypeptide is used for the treatment of a subject with type 2 diabetes wherein the isolated polypeptide is of SEQ ID NO: 42 or a pharmaceutically acceptable salt thereof. In some embodiments, the PYY analog polypeptide is used for the treatment of a subject with type 2 diabetes wherein the isolated polypeptide is of SEQ ID NO: 43 or a pharmaceutically acceptable salt thereof.

In some embodiments, the PYY analog polypeptide is used for the treatment of a subject with obesity wherein the isolated polypeptide is of SEQ ID NO: 13 or a pharmaceutically acceptable salt thereof. In some embodiments, the PYY analog polypeptide is used for the treatment of a subject with obesity wherein the isolated polypeptide is of SEQ ID NO: 24 or a pharmaceutically acceptable salt thereof. In some embodiments, the PYY analog polypeptide is used for the treatment of a subject with obesity wherein the isolated polypeptide is of SEQ ID NO: 42 or a pharmaceutically acceptable salt thereof. In some embodiments, the PYY analog polypeptide is used for the treatment of a subject with obesity wherein the isolated polypeptide is of SEQ ID NO: 43 or a pharmaceutically acceptable salt thereof.

In some embodiments, the PYY analog polypeptide is used to provide weight loss to a subject wherein the isolated polypeptide is of SEQ ID NO: 13 or a pharmaceutically acceptable salt thereof. In some embodiments, the PYY analog polypeptide is used to provide weight loss to a subject wherein the isolated polypeptide is of SEQ ID NO: 23 or a pharmaceutically acceptable salt thereof. In some embodiments, the PYY analog polypeptide is used to provide weight loss to a subject wherein the isolated polypeptide is of SEQ ID NO: 42 or a pharmaceutically acceptable salt thereof. In some embodiments, the PYY analog polypeptide is used to provide weight loss to a subject wherein the isolated polypeptide is of SEQ ID NO: 43 or a pharmaceutically acceptable salt thereof.

In some embodiments, the PYY analog polypeptide is used for the treatment of a subject with NAFLD wherein the isolated polypeptide is of SEQ ID NO: 13 or a pharmaceutically acceptable salt thereof. In some embodiments, the PYY analog polypeptide is used for the treatment of a subject with NAFLD wherein the isolated polypeptide is of SEQ ID NO: 24 or a pharmaceutically acceptable salt thereof. In some embodiments, the PYY analog polypeptide is used for the treatment of a subject with NAFLD wherein the isolated polypeptide is of SEQ ID NO: 42 or a pharmaceutically acceptable salt thereof. In some embodiments, the PYY analog polypeptide is used for the treatment of a subject with NAFLD wherein the isolated polypeptide is of SEQ ID NO: 43 or a pharmaceutically acceptable salt thereof.

In some embodiments, the PYY analog polypeptide is used for the treatment of a subject with NASH wherein the isolated polypeptide is of SEQ ID NO: 13 or a pharmaceutically acceptable salt thereof. In some embodiments, the PYY analog polypeptide is used for the treatment of a subject with NASH wherein the isolated polypeptide is of SEQ ID NO: 24 or a pharmaceutically acceptable salt thereof. In some embodiments, the PYY analog polypeptide is used for the treatment of a subject with NASH wherein the isolated polypeptide is of SEQ ID NO: 42 or a pharmaceutically acceptable salt thereof. In some embodiments, the PYY analog too polypeptide is used for the treatment of a subject with NASH wherein the isolated polypeptide is of SEQ ID NO: 43 or a pharmaceutically acceptable salt thereof.

Certain PYY analog polypeptides of the disclosure, while capable of eliciting anorectic and weight-loss effects when administered in combination with a GLP-1 receptor agonist, can induce dose-dependent orexigenic and weight-gain effects when administered alone. This property of select PYY analog polypeptides of the disclosure is useful in the treatment of a variety of wasting disorders. Accordingly, in some embodiments, a PYY analog polypeptide of the disclosure is used for the treatment of anorexia nervosa, sarcopenia, frailty, cachexia, and the like. In some embodiments, the PYY analog is SEQ ID NO: 13. In some embodiments, the PYY analog is SEQ ID NO: 24.

The terms “patient” or “subject” as used herein, refer to a rodent or an animal, preferably a mammal, and most preferably a human.

Combinations

In some embodiments, a PYY analog polypeptide of the disclosure is co-formulated in combination with a second agent. In some embodiments, a PYY analog polypeptide of the disclosure is co-formulated in combination with a second agent, wherein the second agent is an incretin mimetic. In some embodiments, a PYY analog polypeptide of the disclosure is co-formulated in combination with a second agent, wherein the second agent is an insulinotropic compound.

The phrase “incretin mimetics” as used herein includes, but is not limited to GLP-1 peptide; GLP-1 (7-36); GLP-1 receptor agonists; peptide derivatives of GLP-1; peptide analogs of GLP-1; exenatide; exenatide having the amino acid sequence of exendin-4 (the naturally-occurring form of exenatide; exenatide-LAR; lixisenatide; liraglutide; semaglutide; dulaglutide; albiglutide; taspoglutide; tirzepatide (Eli Lilly's LY3298176 or Y-(Aib)-EGTFTSDYSI-(Aib)-LDKIAQ-[diacid-gamma-Glu-$(AEEA)_2$-Lys]-AF-VQWLIAGGPSSGAPPPS-$NH_2$) SEQ ID NO: 805); glucagon as well as peptide analogs and peptide derivatives thereof; glucagon like polypeptide-2 (GLP-2); PYY as well as peptide analogs and peptide derivatives thereof; PYY(3-36); oxyntomodulin as well as peptide analogs and peptide derivatives thereof); amylin as well as peptide analogs and peptide derivatives thereof; and gastric inhibitory peptide (GIP). Incretin mimetics are also referred to herein as "insulinotropic peptides." Incretin mimetics which target the GLP-1 receptor are also known in the literature as "GLP-1 receptor agonists" or "GLP-1 agonists," with both terms being used interchangeably herein.

Some embodiments of the present invention comprise use of a disclosed PYY analog polypeptide of the present invention in combination with a second therapeutic agent, such as a second polypeptide, such as, by way of, non-limiting example, insulinotropic peptides. In some embodiments, a pharmaceutical composition comprising a PYY analog polypeptide in combination with a second agent is used to treat type 2 diabetes.

In some embodiments, provided is a pharmaceutical composition comprising any of the isolated polypeptides as disclosed herein. In some embodiments, provided is a pharmaceutical composition comprising any of the isolated polypeptides as disclosed herein and further comprising a second polypeptide. In some embodiments, the second polypeptide is a glucagon analog. In some embodiments, the second polypeptide is an amylin analog. In a preferred embodiment, the second polypeptide is a GLP-1 receptor agonist.

The term "GLP-1" refers to a polypeptide, glucagon-like peptide-1(7-36)amide, a 30-residue peptide hormone released from intestinal L cells following nutrient consumption. GLP-1 has the amino acid sequence of (HAE-GTFTSDVS SYLEGQAAKEFIAWLVKGR-$NH_2$), SEQ ID NO: 801. GLP-1 is a regulatory peptide that binds to the extracellular region of the GLP-1 receptor (GLP-1R), a G-coupled protein receptor on β cell and via adenyl cyclase activity and production of cAMP stimulates the insulin response to the nutrients that are absorbed from the gut [Baggio 2007, "Biology of incretins: GLP-1 and GIP," Gastroenterology, vol. 132(6):2131-57; Holst 2008, "The incretin system and its role in type 2 diabetes mellitus," Mol Cell Endocrinology, vol. 297(1-2): 127-36], The effects of GLP-1R agonism are multiple. GLP-1 maintains glucose homeostasis by enhancing endogenous glucose dependent insulin secretion, rendering the P cells glucose competent and sensitive to GLP-1, suppressing glucagon release, restoring first and second phase insulin secretion, slowing gastric emptying, decreasing food intake, and increasing satiety [Holst 2008 Mol. Cell Endocrinology; Kjems 2003 "The influence of GLP-1 on glucose-stimulated insulin secretion: effects on beta-cell sensitivity in type 2 and nondiabetic subjects," Diabetes, vol. 52(2): 380-86; Holst 2013 "Incretin hormones and the satiation signal," Int J Obes (Lond), vol. 37(9): 1161-69; Seufert 2014, "The extra-pancreatic effects of GLP-1 receptor agonists: a focus on the cardiovascular, gastrointestinal and central nervous systems," Diabetes Obes Metab, vol. 16(8): 673-88], The risk of hypoglycemia is minimal given the mode of action of GLP-1.

Glucagon-like peptide-1 (7-36)amide (GLP-1) is a 30-residue peptide hormone released from intestinal L cells following nutrient consumption. It potentiates the glucose-induced secretion of insulin from pancreatic beta cells, increases insulin expression, inhibits beta-cell apoptosis, promotes beta-cell neogenesis, reduces glucagon secretion, delays gastric emptying, promotes satiety and increases peripheral glucose disposal. These multiple effects have generated a great deal of interest in the discovery of long-lasting agonists of the GLP-1 receptor (GLP-1R) in order to treat type 2 diabetes. The term "exenatide" as used herein includes, but is not limited to exenatide, exenatide having the amino acid sequence of (HGEGTFTSDLSKQMEEE-AVRLFIEWLKNGGPSSGAPPPS-$NH_2$), SEQ ID NO: 802, native exendin-4, exenatide peptides, exenatide peptide analogs, and exenatide peptide derivatives.

Endogenous GLP-1 is released from the gut in response to nutrient ingestion. Following food intake and digestion, carbohydrates and fats appear in the lumen of the gut, which stimulate a so-called incretin effect, the release of incretins such as GLP-1 from intestinal L-cells. GLP-1, once released, targets the pancreas where it enhances secretion of insulin in a "glucose dependent manner." In other words, this GLP-1-mediated effect upon insulin persists when glucose levels are high yet safely dissipates as glucose levels fall. GLP-1 activity thus self-regulates to reduce the risk of hypoglycemia (the condition by which glucose levels drop dangerously low). Since GLP-1 has a short elimination half-life ($t_{1/2}$) of less than five minutes, this endogenous peptide is unsuitably short-lived for use as a therapeutic.

Synthetic analogs of GLP-1 have been designed to have longer half-lives and similarly enhance secretion of insulin in a glucose dependent manner like endogenous GLP-1, for use in the treatment of type 2 diabetes and for providing weight loss.

Numerous GLP-1 receptor agonists (e.g., GLP-1 peptide derivatives and peptide analogs) demonstrating insulinotropic action are known in the art (see, e.g., U.S. Pat. Nos. 5,118,666; 5,120,712; 5,512,549; 5,545,618; 5,574,008; 5,574,008; 5,614,492; 5,958,909; 6,191,102; 6,268,343; 6,329,336; 6,451,974; 6,458,924; 6,514,500; 6,593,295; 6,703,359; 6,706,689; 6,720,407; 6,821,949; 6,849,708; 6,849,714; 6,887,470; 6,887,849; 6,903,186; 7,022,674; 7,041,646; 7,084,243; 7,101,843; 7,138,486; 7,141,547; 7,144,863; and 7,199,217), as well as in clinical trials (e.g., taspoglutide and albiglutide).

Certain GLP-1 receptor agonists, including Bydureon® (exenatide), marketed by AstraZeneca of Cambridge, U.K.; Trulicity® (dulaglutide), marketed by Eli Lilly and Co., of Indianapolis, Ind., U.S.A.; and Victoza® (liraglutide), Ozempic® (injectable semaglutide) & Rybelsus® (orally administered semaglutide), marketed by Novo Nordisk A/S of Bagsvserd, Denmark, have each been approved by numerous regulatory authorities, including the United States Food and Drug Administration (U.S. FDA) and European Medicines Agency (EMA) for the treatment of patients suffering from type 2 diabetes. These marketed GLP-1 receptor agonists were developed and formulated for injectable and/or oral administration to patients. However, patient adherence to injectable and orally administered therapies for type 2 diabetes is notoriously poor which prohibits many patients from realizing a full and lasting therapeutic potential of GLP-1 receptor agonists. Many patients skip or cease periodic self-administrations of prescribed injectable and orally administered GLP-1 receptor agonists and thus fail to adequately treat and control their own type 2 diabetic condition.

The PYY analog polypeptides of the disclosure in combination with a GLP-1 receptor agonist have been found to deliver bariatric surgery-like efficacy for weight loss. The observation that improved glycemic control following Roux-en-Y gastric bypass surgery (RYGB) in obese or obese T2D patients precedes the weight loss seen following RYGB, suggests that surgical rearrangement of the gut leads to physiological adaptations beyond those driven by weight loss alone. Indeed, RYGB leads to enhanced post-prandial secretion of GLP-1 and PYY, both of which are released from L-cells lining the distal gut. The gut peptide hormones GLP-1 and peptide tyrosine-tyrosine (PYY) each play a role in whole body energy balance through several overlapping biological responses to energy input. These responses principally include potentiation of glucose-induced insulin secretion, inhibition of gastric emptying, inducing satiety, and inhibition of food intake.

Accordingly, combinations of a PYY analog polypeptide of the disclosure together with a GLP-1 receptor agonist are suitable for the treatment of the diseases and disorders disclosed herein. In some embodiments, the GLP-1 receptor agonist is a long acting GLP-1 receptor agonist.

Oxyntomodulin is a naturally occurring 37 amino acid peptide hormone found in the colon that has been found to suppress appetite and facilitate weight loss (Wynne K, et al., Int J Obes (Lond) 30(12): 1729-36(2006)). The sequence of oxyntomodulin, as well as peptide analogs and peptide derivatives thereof, are known in the art (e.g., Bataille D, et al., Peptides 2(Suppl 2):41-44 (1981); and U.S. Patent Publication Nos. 2005/0070469 and 2006/0094652).

Gastric Inhibitory Peptide (GIP) is an insulinotropic peptide hormone (Efendic, S., et al., Horm Metab Res. 36:742-6 (2004)) and is secreted by the mucosa of the duodenum and jejunum in response to absorbed fat and carbohydrate that stimulate the pancreas to secrete insulin. GIP circulates as a biologically active 42-amino acid peptide. GIP is also known as glucose-dependent insulinotropic protein. GIP is a 42-amino acid gastrointestinal regulatory peptide that stimulates insulin secretion from pancreatic beta cells in the presence of glucose (Tseng, C., et al., PNAS 90:1992-1996 (1993)). The sequence of GIP, as well as peptide analogs and peptide derivatives thereof, are known in the art (e.g., Meier J. J., Diabetes Metab Res Rev. 21(2):91-117 (2005) and Efendic S., Horm Metab Res. 36(11-12):742-6 (2004)).

Glucagon is a peptide hormone, produced by alpha cells of the pancreas, which raises the concentration of glucose in the bloodstream. Its effect is opposite that of insulin, which lowers the glucose concentration. The pancreas releases glucagon when the concentration of glucose in the bloodstream falls too low. Glucagon causes the liver to convert stored glycogen into glucose, which is released into the bloodstream. High blood glucose levels stimulate the release of insulin. Insulin allows glucose to be taken up and used by insulin-dependent tissues. Thus, glucagon and insulin are part of a feedback system that keeps blood glucose levels at a stable level.

Human amylin, or islet amyloid polypeptide (IAPP), is a 37-residue polypeptide hormone. Amylin is co-secreted with insulin from pancreatic β-cells in the ratio of approximately 100:1 (insulimamylin). Pro-islet amyloid polypeptide (i.e., pro-IAPP) is produced in the pancreatic β-cells as a 67 amino acid, 7404 Dalton pro-peptide that undergoes post-translational modifications including protease cleavage to produce the 37-residue amylin. Loss of β-cell function that occurs early in type 1 diabetics and can occur late in type 2 diabetics leads to deficiencies in the secretion of insulin and amylin.

Amylin functions as part of the endocrine pancreas, those cells within the pancreas that synthesize and secrete hormones. Amylin contributes to glycemic control; it is secreted from the pancreatic islets into the blood circulation and is cleared by peptidases in the kidney. Amylin's metabolic function is well-characterized as an inhibitor of the appearance of nutrients, such as glucose, in the plasma. It thus functions as a synergistic partner to insulin, a peptide that regulates blood glucose levels and coordinates the body's distribution and uptake of glucose. Insulin's role in the body is, among other things, to prevent blood glucose levels from rising too high, particularly after a meal.

Amylin is believed to play a role in glycemic regulation by slowing gastric emptying and promoting satiety (i.e., feeling of fullness), thereby preventing post-prandial (i.e., after-meal) spikes in blood glucose levels. The overall effect is to slow the rate of appearance of glucose in the blood after eating. Amylin also lowers the secretion of glucagon by the pancreas. Glucagon's role in the body is, among other things, to prevent blood glucose levels dropping too low. This is significant because certain type 1 diabetics, for example, are prone to secrete excess amounts of the blood glucose-raising glucagon just after meals.

For numerous reasons, human amylin, having a half-life in serum of about 13 minutes, is not amenable for use as a therapeutic agent. Rather, pramlintide (Symlin®, developed by Amylin Pharmaceuticals, Inc., San Diego, Calif., USA and marketed by AstraZeneca pic, Cambridge, UK) was developed as a synthetic analogue of human amylin for the treatment of patients with types 1 or 2 diabetes, who use meal-time insulin but cannot achieve desired glycemic control despite optimal insulin therapy. Pramlintide differs from human amylin in 3 of its 37 amino acids. These modifications provide pramlintide a longer half-life of approximately 48 minutes in humans and reduce its propensity to aggregate, a characteristic found of human amylin. Further analogues of human amylin have been disclosed such as those in U.S. patent application Ser. No. 16/598,915 (corresponding to PCT International Application No. PCT/US2019/055696), both filed Oct. 10, 2019.

Implantable Delivery

In some embodiments, provided is an osmotic delivery device, as described herein, comprising any of the long acting PYY analog polypeptides, as disclosed herein, or a pharmaceutical composition comprising any of the long acting PYY analog polypeptides.

In some embodiments, the osmotic delivery device comprises an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a suspension formulation, wherein the second chamber comprises the suspension formulation and the suspension formulation is flowable and comprises the isolated polypeptide; and a diffusion moderator inserted in the second open end of the reservoir, the diffusion moderator adjacent the suspension formulation.

An implantable, osmotic delivery device typically includes a reservoir having at least one orifice through which the suspension formulation is delivered. The suspension formulation may be stored within the reservoir. In a preferred embodiment, the implantable, drug delivery device is an osmotic delivery device, wherein delivery of the drug is osmotically driven. Some osmotic delivery devices and their component parts have been described, for example, the DUROS® delivery device or similar devices (see, e.g., U.S. Pat. Nos. 5,609,885; 5,728,396; 5,985,305; 5,997,527; 6,113,938; 6,132,420; 6,156,331; 6,217,906; 6,261,584; 6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; and 7,112,335; 7,163,688; U.S. Patent Publication Nos. 2005/0175701, 2007/0281024, 2008/0091176, and 2009/0202608).

The osmotic delivery device typically consists of a cylindrical reservoir which contains the osmotic engine, piston, and drug formulation. The reservoir is capped at one end by a controlled-rate, semi-permeable membrane and capped at the other end by a diffusion moderator through which suspension formulation, comprising the drug, is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The osmotic device releases a drug at a predetermined rate based on the principle of osmosis. Extracellular fluid enters the osmotic delivery device through a semi-permeable membrane directly into a salt engine that expands to drive the piston at a slow and even delivery rate. Movement of the piston forces the drug formulation to be released through the orifice or exit port at a predetermined shear rate. In one embodiment of the present invention, the reservoir of the osmotic device is loaded with a suspension formulation wherein the device is capable of delivering the suspension formulation to a subject over an extended period of time (e.g., about 1, about 3, about 6, about 9, about 10, and about 12 months) at a pre-determined, therapeutically effective delivery rate.

The release rate of the drug from the osmotic delivery device typically provides a subject with a predetermined target dose of a drug, for example, a therapeutically effective daily dose delivered over the course of a day; that is, the release rate of the drug from the device, provides substantial steady-state delivery of the drug at a therapeutic concentration to the subject.

Typically, for an osmotic delivery device, the volume of a beneficial agent chamber comprising the beneficial agent formulation is between about 100 μl to about 1000 μl, more preferably between about 120 μl and about 500 μl, more preferably between about 150 μl and about 200 μl.

Typically, the osmotic delivery device is implanted within the subject, for example, subdermally or subcutaneously to provide subcutaneous drug delivery. The device(s) can be implanted subdermally or subcutaneously into either or both arms (e.g., in the inside, outside, or back of the upper arm) or the abdomen. Preferred locations in the abdominal area are under the abdominal skin in the area extending below the ribs and above the belt line. To provide a number of locations for implantation of one or more osmotic delivery device within the abdomen, the abdominal wall can be divided into 4 quadrants as follows: the upper right quadrant extending at least 2-3 centimeters below the right ribs, e.g., at least about 5-8 centimeters below the right ribs, and at least 2-3 centimeters to the right of the midline, e.g., at least about 5-8 centimeters to the right of the midline; the lower right quadrant extending at least 2-3 centimeters above the belt line, e.g., at least about 5-8 centimeters above the belt line, and at least 2-3 centimeters to the right of the midline, e.g., at least about 5-8 centimeters to the right of the midline; the upper left quadrant extending at least 2-3 centimeters below the left ribs, e.g., at least about 5-8 centimeters below the left ribs, and at least 2-3 centimeters to the left of the midline, e.g., at least about 5-8 centimeters to the left of the midline; and the lower left quadrant extending at least 2-3 centimeters above the belt line, e.g., at least about 5-8 centimeters above the belt line, and at least 2-3 centimeters to the left of the midline, e.g., at least about 5-8 centimeters to the left of the midline. This provides multiple available locations for implantation of one or more devices on one or more occasions. Implantation and removal of osmotic delivery devices are generally carried out by medical professionals using local anesthesia (e.g., lidocaine).

Termination of treatment by removal of an osmotic delivery device from a subject is straightforward, and provides the important advantage of immediate cessation of delivery of the drug to the subject.

Preferably, the osmotic delivery device has a fail-safe mechanism to prevent an inadvertent excess or bolus delivery of drug in a theoretical situation like the plugging or clogging of the outlet (diffusion moderator) through which the drug formulation is delivered. To prevent an inadvertent excess or bolus delivery of drug the osmotic delivery device is designed and constructed such that the pressure needed to partially or wholly dislodge or expel the diffusion moderator from the reservoir exceeds the pressure needed to partially or wholly dislodge or expel the semi-permeable membrane to the extent necessary to de-pressurize the reservoir. In such a scenario, pressure would build within the device until it would push the semi-permeable membrane at the other end outward, thereby releasing the osmotic pressure. The osmotic delivery device would then become static and no longer deliver the drug formulation provided that the piston is in a sealing relationship with the reservoir.

A dose and delivery rate can be selected to achieve a desired blood concentration of a drug generally within less than about 6 half-lives of the drug within the subject after implantation of the device. The blood concentration of the drug is selected to give the optimal therapeutic effects of the drug while avoiding undesirable side effects that may be induced by excess concentration of the drug, while at the same time avoiding peaks and troughs that may induce side effects associated with peak or trough plasma concentrations of the drug.

The suspension formulations may also be used in infusion pumps, for example, the ALZET® (DURECT Corporation, Cupertino, Calif.) osmotic pumps which are miniature, infusion pumps for the continuous dosing of laboratory animals (e.g., mice and rats).

Modes of Administration

In some embodiments, the method comprises providing a PYY analog polypeptide of the disclosure or a pharmaceutical composition thereof, to a subject in need of treatment, via injection. In some embodiments, the method comprises providing a PYY analog polypeptide of the disclosure or a pharmaceutical composition thereof, formulated for oral administration, to a subject in need of treatment.

In some embodiments, the method comprises providing a PYY analog polypeptide of the disclosure or a pharmaceutical composition thereof, to a subject in need of treatment, via implantation. In some embodiments, the method comprises providing continuous delivery of a PYY analog polypeptide, to a subject in need of treatment, from an osmotic delivery device. The delivery device, such as an osmotic delivery device, comprises sufficient PYY analog polypeptide of the disclosure for continuous administration for up to 3 months, 6 months, 9 months, 12 months, 18 months or 24 months. As such, continuous administration of a PYY analog polypeptide of the disclosure via osmotic delivery device eliminates daily, or multiple daily dosing of marketed PYY analog polypeptides.

The substantial steady-state delivery of the PYY analog polypeptide from the osmotic delivery device is continuous over an administration period. In some embodiments, the subject or patient is a human subject or human patient.

In some embodiments of the present invention, the administration period is, for example, at least about 3 months, at least about 3 months to about a year, at least about 4 months to about a year, at least about 5 months to about a year, at least about 6 months to about a year, at least about 8 months to about a year, at least about 9 months to about a year, at least about 10 months to about a year, at least about one year to about two years, at least about two years to about three years.

In further embodiments, the treatment methods of the present invention provide significant decrease in the subject's fasting plasma glucose concentration after implantation of the osmotic delivery device in the subject (relative to the subject's fasting plasma glucose concentration before implantation of the osmotic delivery device) that is achieved within about 7 days, 6 days, 5 days, 4 days, 3 days, 2 days, 1 day or less after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

In some embodiments, the present invention relates to a method of treating a disease or condition in a subject in need of treatment. The method comprises providing continuous delivery of a drug from an osmotic delivery device, wherein substantial steady-state delivery of the drug at therapeutic concentrations is achieved in the subject. The substantial steady-state delivery of the drug from the osmotic delivery device is continuous over an administration period of at least about 3 months. The drug has a known or determined half-life in a typical subject. Humans are preferred subjects for the practice of the present invention. The present invention includes a drug effective for treatment of the disease or condition, as well as an osmotic delivery device comprising the drug for use in the present methods of treating the disease or condition in a subject in need of treatment. Advantages of the present invention include mitigation of peak-associated drug toxicities and attenuation of sub-optimal drug therapy associated with troughs.

In some embodiments, the substantial steady-state delivery of a drug at therapeutic concentrations is achieved within a period of about 1 month, 7 days, 5 days, 3 days or 1 day after implantation of the osmotic delivery device in the subject.

The invention also provides a method for promoting weight loss in a subject in need thereof, a method for treating excess weight or obesity in a subject in need thereof, and/or a method for suppressing appetite in a subject in need thereof. The method comprises providing delivery of an isolated PYY analog polypeptide. In some embodiments, the isolated PYY analog polypeptide is continuously delivered from an implantable osmotic delivery device. In some embodiments, substantial steady-state delivery of the PYY analog polypeptide from the osmotic delivery device is achieved and is substantially continuous over an administration period. In some embodiments, the subject is human.

The present invention includes an osmotic delivery device comprising a PYY analog polypeptide for use in the present methods in a subject in need of treatment. The subject may have type 2 diabetes. The subject in need thereof may have a baseline HbA1c % of greater than 10.0%, i.e., a high baseline (HBL) subject. The subject may not have previously received a drug for treating type 2 diabetes mellitus.

In further embodiments, the treatment methods of the present invention provide significant decrease in the subject's fasting plasma glucose concentration after implantation of the osmotic delivery device in the subject (relative to the subject's fasting plasma glucose concentration before implantation of the osmotic delivery device) that is achieved within about 7 days or less after implantation of the osmotic delivery device in the subject, within about 6 days or less after implantation of the osmotic delivery device in the subject, within about 5 days or less after implantation of the osmotic delivery device in the subject, within about 4 days or less after implantation of the osmotic delivery device in the subject, within about 3 days or less after implantation of the osmotic delivery device in the subject, within about 2 days or less after implantation of the osmotic delivery device in the subject, or within about 1 day or less after implantation of the osmotic delivery device in the subject. In preferred embodiments of the present invention, the significant decrease in the subject's fasting plasma glucose concentration after implantation of the osmotic delivery device, relative to the subject's fasting plasma glucose concentration before implantation, is achieved within about 2 days or less, preferably within about 1 day or less after implantation of the osmotic delivery device in the subject, or more preferably within about 1 day after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

In embodiments of all aspects of the present invention relating to methods of treating a disease or condition in a subject, an exemplary osmotic delivery device comprises the following: an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a drug formulation or suspension formulation comprising the drug, wherein the second chamber comprises the drug formulation or suspension formulation and the drug formulation or suspension formulation is flowable; and a diffusion moderator inserted in the second open end of the reservoir, the diffusion moderator adjacent the suspension formulation. In preferred embodiments, the reservoir comprises titanium or a titanium alloy.

In embodiments of all aspects of the present invention relating to methods of treating a disease or condition in a subject, the drug formulation can comprise the drug and a vehicle formulation. Alternatively, suspension formulations are used in the methods and can, for example, comprise a particle formulation comprising the drug and a vehicle formulation. Vehicle formulations for use in forming the suspension formulations of the present invention can, for example, comprise a solvent and a polymer.

The reservoir of the osmotic delivery devices may, for example, comprise titanium or a titanium alloy.

In embodiments of all aspects of the present invention the implanted osmotic delivery device can be used to provide subcutaneous delivery.

In embodiments of all aspects of the present invention the continuous delivery can, for example, be zero-order, controlled continuous delivery.

Pharmaceutical Compositions

According to another embodiment, the invention provides a pharmaceutical composition comprising a compound, i.e., isolated polypeptide, of this invention or a pharmaceutically acceptable derivative thereof and a pharmaceutically acceptable carrier, adjuvant, or vehicle.

In some embodiments, provided is a pharmaceutical composition comprising any of the disclosed polypeptides formulated as pharmaceutically acceptable salts thereof, such as a trifluoroacetate salt, acetate salt or hydrochloride salt. In some embodiments, provided is a pharmaceutical composition comprising any of the disclosed polypeptides formulated as a trifluoroacetate salt. In some embodiments, provided is a pharmaceutical composition comprising any of the disclosed polypeptides formulated as an acetate salt. In some embodiments, provided is a pharmaceutical composition comprising any of the disclosed polypeptides formulated as a hydrochloride salt.

The term "pharmaceutically acceptable carrier, adjuvant, or vehicle" refers to a non-toxic carrier, adjuvant, or vehicle that does not destroy the pharmacological activity of the compound with which it is formulated.

As used herein, the term "pharmaceutically acceptable carrier" is intended to include any and all solvents, polymers, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Representative pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, provided is a pharmaceutical composition comprising a pharmaceutically acceptable derivative of any of the disclosed polypeptides formulated as pharmaceutically acceptable salts thereof, such as a trifluoroacetate salt, acetate salt or hydrochloride salt. A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

The pharmaceutical composition comprises a drug and may be formulated as a "particle formulation" as described in greater detail below. The pharmaceutical composition and/or particle formulation may include stabilizing components (also referred to herein as "excipients"). Examples of stabilizing components include, but are not limited to, carbohydrates, antioxidants, amino acids, buffers, inorganic compounds, and surfactants.

The amount of compound in compositions of this invention is such that is effective to measurably activate one or more PYY receptors (e.g., human, rat, monkey etc), in a biological sample or in a patient. In certain embodiments, the amount of compound in compositions of this invention is such that is effective to measurably activate human PYY receptors in the absence or presence of human serum albumin, in a biological sample or in a patient. In certain embodiments, a composition of this invention is formulated for administration to a patient in need of such composition. In some embodiments, a composition of this invention is formulated for injectable administration to a patient. In some embodiments, a composition of this invention is formulated for administration to a patient via an implantable delivery device such as an osmotic deliver device.

The isolated polypeptides of the disclosure (also referred to herein as "active compounds"), and derivatives, fragments, analogs and homologs thereof, can be incorporated into pharmaceutical compositions suitable for administration. Such compositions typically comprise the isolated polypeptide, or a pharmaceutically acceptable salt thereof, and a pharmaceutically acceptable carrier.

A pharmaceutical composition of the invention is formulated to be compatible with its intended route of administration. Examples of routes of administration include parenteral, (e.g., intravenous, intradermal, subdermal, subcutaneous), oral (e.g., inhalation), transdermal (i.e., topical), transmucosal, rectal, or combinations thereof. In some embodiments, a pharmaceutical composition or an isolated polypeptide of the disclosure is formulated for administration by topical administration. In some embodiments, a pharmaceutical composition or an isolated polypeptide of the disclosure is formulated for administration by inhalation administration. In some embodiments, the pharmaceutical composition is formulated for administration by a device or other suitable delivery mechanism that is suitable for subdermal or subcutaneous implantation and delivers the pharmaceutical composition subcutaneously. In some embodiments, the pharmaceutical composition is formulated for administration by an implant device that is suitable for subdermal or subcutaneous implantation and delivers the pharmaceutical composition subcutaneously. In some embodiments, the pharmaceutical composition is formulated for administration by an osmotic delivery device, e.g., an implantable osmotic delivery device, that is suitable for subdermal or subcutaneous placement or other implantation and delivers the pharmaceutical composition subcutaneously. Solutions or suspensions used for parenteral application, intradermal application, subdermal application, subcutaneous application, or combinations thereof can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Drug Particle Formulations

Compounds, i.e., isolated polypeptides or pharmaceutically acceptable salts thereof, for use in the practice of the present invention are typically added to particle formulations, which are used to make polypeptide-containing particles that are uniformly suspended, dissolved or dispersed in a suspension vehicle to form a suspension formulation. In some embodiments, the PYY analog polypeptide is formulated in a particle formulation and converted (e.g., spray dried) to particles. In some embodiments, the particles comprising the PYY analog polypeptide are suspended in a vehicle formulation, resulting in a suspension formulation of vehicle and suspended particles comprising the PYY analog polypeptide.

Preferably, particle formulations are formable into particles using processes such as spray drying, lyophilization, desiccation, freeze-drying, milling, granulation, ultrasonic drop creation, crystallization, precipitation, or other techniques available in the art for forming particles from a mixture of components. In one embodiment of the invention the particles are spray dried. The particles are preferably substantially uniform in shape and size.

In some embodiments, the present invention provides drug particle formulations for pharmaceutical use. The particle formulation typically comprises a drug and includes one or more stabilizing component (also referred to herein as "excipients"). Examples of stabilizing components include, but are not limited to, carbohydrates, antioxidants, amino acids, buffers, inorganic compounds, and surfactants. The amounts of stabilizers in the particle formulation can be determined experimentally based on the activities of the stabilizers and the desired characteristics of the formulation, in view of the teachings of the present specification.

In any of the embodiments, the particle formulation may comprise about 50 wt % to about 90 wt % drug, about 50 wt % to about 85 wt % drug, about 55 wt % to about 90 wt % drug, about 60 wt % to about 90 wt % drug, about 65 wt % to about 85 wt % drug, about 65 wt % to about 90 wt % drug, about 70 wt % to about 90 wt % drug, about 70 wt % to about 85 wt % drug, about 70 wt % to about 80 wt % drug, or about 70 wt % to about 75 wt % drug.

Typically, the amount of carbohydrate in the particle formulation is determined by aggregation concerns. In general, the carbohydrate amount should not be too high so as to avoid promoting crystal growth in the presence of water due to excess carbohydrate unbound to drug.

Typically, the amount of antioxidant in the particle formulation is determined by oxidation concerns, while the amount of amino acid in the formulation is determined by oxidation concerns and/or formability of particles during spray drying.

Typically, the amount of buffer in the particle formulation is determined by pre-processing concerns, stability concerns, and formability of particles during spray drying. Buffer may be required to stabilize drug during processing, e.g., solution preparation and spray drying, when all stabilizers are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinsitol). Suitable carbohydrates include disaccharides and/or non-reducing sugars, such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteine, thioglycerol, thioglycolic acid, thiosorbitol, butylated hydroxanisol, butylated hydroxyltoluene, and propyl gallate. Further, amino acids that readily oxidize can be used as antioxidants, for example, cysteine, methionine, and tryptophan.

Examples of amino acids that may be included in the particle formulation include, but are not limited to, arginine, methionine, glycine, histidine, alanine, leucine, glutamic acid, iso-leucine, L-threonine, 2-phenylamine, valine, norvaline, proline, phenylalanine, tryptophan, serine, asparagines, cysteine, tyrosine, lysine, and norleucine. Suitable amino acids include those that readily oxidize, e.g., cysteine, methionine, and tryptophan.

Examples of buffers that may be included in the particle formulation include, but are not limited to, citrate, histidine, succinate, phosphate, maleate, tris, acetate, carbohydrate, and gly-gly. Suitable buffers include citrate, histidine, succinate, and tris.

Examples of inorganic compounds that may be included in the particle formulation include, but are not limited to, NaCl, $Na_2SO_4$, $NaHCO_3$, KCl, $KH_2PO_4$, $CaCl_2$, and $MgCl_2$.

In addition, the particle formulation may include other stabilizers/excipients, such as surfactants and salts. Examples of surfactants include, but are not limited to, Polysorbate 20, Polysorbate 80, PLURONIC® (BASF Corporation, Mount Olive, N.J.) F68, and sodium dodecyl sulfate (SDS). Examples of salts include, but are not limited to, sodium chloride, calcium chloride, and magnesium chloride.

The particles are typically sized such that they can be delivered via an implantable osmotic delivery device. Uniform shape and size of the particles typically helps to provide a consistent and uniform rate of release from such a delivery device; however, a particle preparation having a non-normal particle size distribution profile may also be used. For example, in a typical implantable osmotic delivery device having a delivery orifice, the size of the particles is less than about 30%, more preferably is less than about 20%, more preferably is less than about than 10%, of the diameter of the delivery orifice. In an embodiment of the particle formulation for use with an osmotic delivery system, wherein the delivery orifice diameter of the implant is about 0.5 mm, particle sizes may be, for example, less than about 150 microns to about 50 microns. In an embodiment of the particle formulation for use with an osmotic delivery system, wherein the delivery orifice diameter of the implant is about 0.1 mm, particle sizes may be, for example, less than about 30 microns to about 10 microns. In one embodiment, the orifice is about 0.25 mm (250 microns) and the particle size is about 2 microns to about 5 microns.

Those of ordinary skill in the art will appreciate that a population of particles follow principles of particle size distribution. Widely used, art-recognized methods of describing particle size distributions include, for example, average diameters and D values, such as the D50 value, which is commonly used to represent the mean diameter of the range of the particle sizes of a given sample.

Particles of a particle formulation have diameters of between about 2 microns to about 150 microns, e.g., less than 150 microns in diameter, less than 100 microns in diameter, less than 50 microns in diameter, less than 30 microns in diameter, less than 10 microns in diameter, less than microns in diameter, and about 2 microns in diameter. Preferably, particles have diameters of between about 2 microns and about 50 microns.

Particles of a particle formulation comprising an isolated PYY analog polypeptide have average diameters of between about 0.3 microns to about 150 microns. Particles of a particle formulation comprising an isolated PYY analog polypeptide have average diameters of between about 2 microns to about 150 microns, e.g., less than 150 microns in average diameter, less than 100 microns in average diameter, less than 50 microns in average diameter, less than 30 microns in average diameter, less than 10 microns in average diameter, less than 5 microns in average diameter, and about 2 microns in average diameter. In some embodiments, particles have average diameters of between about 0.3 microns and 50 microns, for example, between about 2 microns and about 50 microns. In some embodiments, the particles have an average diameter between 0.3 microns and 50 microns, for example, between about 2 microns and about 50 microns, where each particle is less than about 50 microns in diameter.

Typically, the particles of the particle formulations, when incorporated in a suspension vehicle, do not settle in less than about 3 months, preferably do not settle in less than about 6 months, more preferably do not settle in less than about 12 months, more preferably do not settle in less than about 24 months at delivery temperature, and most preferably do not settle in less than about 36 months at delivery temperature. The suspension vehicles typically have a viscosity of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise. Generally speaking, smaller particles tend to have a lower settling rate in viscous suspension vehicles than larger particles. Accordingly, micron- to nano-sized particles are typically desirable. In viscous suspension formulation, particles of about 2 microns to about 7 microns of the present invention will not settle for at least 20 years at room temperature based on simulation modeling studies. In an embodiment of the particle formulation of the present invention, for use in an implantable osmotic delivery device, comprises particles of sizes less than about 50 microns, more preferably less than about 10 microns, more preferably in a range from about 2 microns to about 7 microns.

In summary, disclosed polypeptides, or pharmaceutically acceptable salts thereof, are formulated into dried powders in solid state particles, which preserve maximum chemical and biological stability of the drug. Particles offers long-term storage stability at high temperature, and therefore, allows delivery to a subject of stable and biologically effective drug for extended periods of time. Particles are suspended in suspension vehicles for administration to patients.

Particle Suspensions in Vehicles

In one aspect, the suspension vehicle provides a stable environment in which the drug particle formulation is dispersed. The drug particle formulations are chemically and physically stable (as described above) in the suspension vehicle. The suspension vehicle typically comprises one or more polymer and one or more solvent that form a solution of sufficient viscosity to uniformly suspend the particles comprising the drug. The suspension vehicle may comprise further components, including, but not limited to, surfactants, antioxidants, and/or other compounds soluble in the vehicle.

The viscosity of the suspension vehicle is typically sufficient to prevent the drug particle formulation from settling during storage and use in a method of delivery, for example, in an implantable, osmotic delivery device. The suspension vehicle is biodegradable in that the suspension vehicle disintegrates or breaks down over a period of time in response to a biological environment, while the drug particle is dissolved in the biological environment and the active pharmaceutical ingredient (i.e., the drug) in the particle is absorbed.

In embodiments, the suspension vehicle is a "single-phase" suspension vehicle, which is a solid, semisolid, or liquid homogeneous system that is physically and chemically uniform throughout.

The solvent in which the polymer is dissolved may affect characteristics of the suspension formulation, such as the behavior of drug particle formulation during storage. A solvent may be selected in combination with a polymer so that the resulting suspension vehicle exhibits phase separation upon contact with the aqueous environment. In some embodiments of the invention, the solvent may be selected in combination with the polymer so that the resulting suspension vehicle exhibits phase separation upon contact with the aqueous environment having less than approximately about 10% water.

The solvent may be an acceptable solvent that is not miscible with water. The solvent may also be selected so that the polymer is soluble in the solvent at high concentrations, such as at a polymer concentration of greater than about 30%. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain (C8 to C24) aliphatic alcohols, esters, or mixtures thereof. The solvent used in the suspension vehicle may be "dry," in that it has a low moisture content. Preferred solvents for use in formulation of the suspension vehicle include lauryl lactate, lauryl alcohol, benzyl benzoate, and mixtures thereof.

Examples of polymers for formulation of the suspension vehicles of the present invention include, but are not limited to, a polyester (e.g., polylactic acid and polylacticpolyglycolic acid), a polymer comprising pyrrolidones (e.g., polyvinylpyrrolidone having a molecular weight ranging from approximately 2,000 to approximately 1,000,000), ester or ether of an unsaturated alcohol (e.g., vinyl acetate), polyoxyethylenepolyoxypropylene block copolymer, or mixtures thereof. Polyvinylpyrrolidone can be characterized by its K-value (e.g., K-17), which is a viscosity index. In one embodiment, the polymer is polyvinylpyrrolidone having a molecular weight of 2,000 to 1,000,000. In a preferred embodiment, the polymer is polyvinylpyrrolidone K-17 (typically having an approximate average molecular weight range of 7,900-10,800). The polymer used in the suspension vehicle may include one or more different polymers or may include different grades of a single polymer. The polymer used in the suspension vehicle may also be dry or have a low moisture content.

Generally speaking, a suspension vehicle for use in the present invention may vary in composition based on the desired performance characteristics. In one embodiment, the suspension vehicle may comprise about 40 wt % to about 80 wt % polymer(s) and about 20 wt % to about 60 wt % solvent(s). Preferred embodiments of a suspension vehicle include vehicles formed of polymer(s) and solvent(s) combined at the following ratios: about 25 wt % solvent and about 75 wt % polymer; about 50 wt % solvent and about 50 wt % polymer; about 75 wt % solvent and about 25 wt % polymer. Accordingly, in some embodiments, the suspension vehicle may comprise selected components and in other embodiments consist essentially of selected components.

The suspension vehicle may exhibit Newtonian behavior. The suspension vehicle is typically formulated to provide a viscosity that maintains a uniform dispersion of the particle formulation for a predetermined period of time. This helps facilitate making a suspension formulation tailored to provide controlled delivery of the drug contained in the drug particle formulation. The viscosity of the suspension vehicle may vary depending on the desired application, the size and type of the particle formulation, and the loading of the particle formulation in the suspension vehicle. The viscosity of the suspension vehicle may be varied by altering the type or relative amount of the solvent or polymer used.

The suspension vehicle may have a viscosity ranging from about 100 poise to about 1,000,000 poise, preferably from about 1,000 poise to about 100,000 poise. In preferred embodiments, the suspension vehicles typically have a viscosity, at 33° C., of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise, at 33° C. The viscosity may be measured at 33° C., at a shear rate of 10-4/sec, using a parallel plate rheometer.

The suspension vehicle may exhibit phase separation when contacted with the aqueous environment; however, typically the suspension vehicle exhibits substantially no phase separation as a function of temperature. For example, at a temperature ranging from approximately 0° C. to approximately 70° C. and upon temperature cycling, such as cycling from 4° C. to 37° C. to 4° C., the suspension vehicle typically exhibits no phase separation.

The suspension vehicle may be prepared by combining the polymer and the solvent under dry conditions, such as in a dry box. The polymer and solvent may be combined at an elevated temperature, such as from approximately 40° C. to approximately 70° C., and allowed to liquefy and form the single phase. The ingredients may be blended under vacuum to remove air bubbles produced from the dry ingredients. The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. Differential scanning calorimetry (DSC) may be used to verify that the suspension vehicle is a single phase. Further, the components of the vehicle (e.g., the solvent and/or the polymer) may be treated to substantially reduce or substantially remove peroxides (e.g., by treatment with methionine; see, e.g., U.S., Patent Application Publication No. 2007-0027105).

The drug particle formulation is added to the suspension vehicle to form a suspension formulation. In some embodiments, the suspension formulation may comprise a drug particle formulation and a suspension vehicle and in other embodiments consist essentially of a drug particle formulation and a suspension vehicle.

The suspension formulation may be prepared by dispersing the particle formulation in the suspension vehicle. The suspension vehicle may be heated and the particle formulation added to the suspension vehicle under dry conditions. The ingredients may be mixed under vacuum at an elevated temperature, such as from about 40° C. to about 70° C. The ingredients may be mixed at a sufficient speed, such as from about 40 rpm to about 120 rpm, and for a sufficient amount of time, such as about 15 minutes, to achieve a uniform dispersion of the particle formulation in the suspension vehicle. The mixer may be a dual helix blade or other suitable mixer. The resulting mixture may be removed from the mixer, sealed in a dry container to prevent water from contaminating the suspension formulation, and allowed to cool to room temperature before further use, for example, loading into an implantable, drug delivery device, unit dose container, or multiple-dose container.

The suspension formulation typically has an overall moisture content of less than about 10 wt %, preferably less than about 5 wt %, and more preferably less than about 4 wt %.

In preferred embodiments, the suspension formulations of the present invention are substantially homogeneous and flowable to provide delivery of the drug particle formulation from the osmotic delivery device to the subject.

In summary, the components of the suspension vehicle provide biocompatibility. Components of the suspension vehicle offer suitable chemico-physical properties to form stable suspensions of drug particle formulations. These properties include, but are not limited to, the following: viscosity of the suspension; purity of the vehicle; residual moisture of the vehicle; density of the vehicle; compatibility with the dry powders; compatibility with implantable devices; molecular weight of the polymer; stability of the vehicle; and hydrophobicity and hydrophilicity of the vehicle. These properties can be manipulated and controlled, for example, by variation of the vehicle composition and manipulation of the ratio of components used in the suspension vehicle.

The suspension formulations described herein may be used in an implantable, osmotic delivery device to provide zero-order, continuous, controlled, and sustained delivery of a compound over an extended period of time, such as over weeks, months, or up to about one year or more. Such an implantable osmotic delivery device is typically capable of delivering the suspension formulation, comprising the drug, at a desired flow rate over a desired period of time. The suspension formulation may be loaded into the implantable, osmotic delivery device by conventional techniques.

EXAMPLES

The following examples are put forth so as to provide those of ordinary skill in the art with a complete disclosure and description of how to practice the present invention, and are not intended to limit the scope of what the inventors regard as the invention. Efforts have been made to ensure accuracy with respect to numbers used (e.g., amounts, concentrations, and percent changes) but some experimental errors and deviations should be accounted for. Unless indicated otherwise, temperature is in degrees Centigrade and pressure is at or near atmospheric.

Example 1: Generation of a Long Acting PYY Analog Polypeptides

Long acting PYY analogs of the invention, as provided in Table 3, were synthesized on a Prelude peptide synthesizer (Protein Technologies Inc., Tucson, Ariz.)) by solid-phase methods using Fmoc strategy with N-[(dimethylamino)-1H-1,2,3-triazolo-[4,5-b]pyridin-1-ylmethylene]-N-methylmethanaminium hexafluorophosphate N-oxide (HATU) or 2-(6-chloro-1-H-benzotriazole-1-yl)-1,1,3,3-tetramethylaminium hexafluorophosphate (HCTU) activation (5-fold molar excess to amino acid) in N,N-dimethylformamide (DMF), and N'N-diisopropylethylamine (DIEA) was used as base. A 20% piperidine/DMF solution was used for Fmoc deprotection. The resin used was Rink Amide MB HA LL (Novabiochem) with loading of (0.30-0.40) mmol/g on a (20-400) μmol scale.

Upon completion of solid phase synthesis of the linear polypeptide, the resin was washed with dichloromethane (DCM) and dried under vacuum for 30 minutes. For analogs containing the allyloxycarbonyl (Alloc) protecting group, removal was accomplished via a solution of $Pd(PPh_3)_3$ in (chloroform/acetic acid/n-methyl-morpholine, 37:2:1). For analogs containing the tert-butyloxycarbonyl (BOC)-Lys-fluorenylmethyloxycarbonyl (Fmoc)-OH, the Fmoc protecting group was removed using 20% piperidine/DMF. The resulting Fmoc-deprotected resin was washed with DMF (6×30 secs). Next, elongation of the spacer region was carried out in step-wise manner with the manual addition of each building block under pre-activation conditions. Addition of the lipophilic substituent (also referred to as “acyl chain”) was carried out under solid-phase peptide synthesis (SPPS) conditions with no pre-activation step. Final deprotection and cleavage of the peptide from the solid support were performed by treatment of the resin with (95% TFA, 2% water, 2% thioanisole, and 1% triisopropylsilane) for 2-3 hours. The cleaved peptide was precipitated using cold diethyl ether. The diethyl ether layer was decanted, and the solids triturated again with cold diethyl ether and pelleted by centrifugation.

For analogs containing a lactam bridge, the appropriate allyl-protected amino acid building blocks were installed under normal solid-phase conditions as described above. Also, Fmoc-Lys-ε-1-(4,4-dimethyl-2,6-dioxocyclohex-1-ylidene)-3-methylbutyl(ivDde)-OH was installed as a handle to later incorporate the acyl spacer and side-chain. Upon completion of the linear peptide the allyl-protecting groups were removed as described above. Lactam-bridge formation was afforded via solid-phase protocol using benzotriazol-1-yl-oxytripyrrolidinophosphonium hexafluorophosphate (PyBOP, 0.5 M) activation and DIEA as the base. Deprotection of the Fmoc & ivDde groups was afforded via 4% solution of hydrazine in DMF. The resulting de-protected resin was washed with DMF (6×30 secs). Elongation of the spacer region and addition of a lipophilic substituent was carried out as described in the preceding paragraphs. Final deprotection and cleavage of the peptide from the solid support was performed by treatment of the resin with (95% TFA, 2% water, 2% thioanisole, and 1% triisopropylsilane) for 2-3 hours. The cleaved peptide was precipitated using cold diethyl ether. The diethyl ether was decanted, and the solids triturated again with cold diethyl ether and pelleted by centrifugation.

The crude product was next dissolved in a solution of acetonitrile (ACN)/$H_2O$, 0.1% TFA. A 10% solution of acetic acid was added to each solution of crude peptide product and allowed to stir until analysis via LC/MS indicated removal of any $CO_2$ adducts. The solution was frozen and lyophilized. Purification was afforded via the methods described in Example 2.

Example 2: Purification and Characterization of Long Acting PYY Analog Polypeptides, i.e., Linear Polypeptide, without any Lipophilic Substituent and Optional Spacer The product of Example 1 was lyophilized and analyzed by electrospray ionization-liquid chromatography/mass spectrometry (ESI-LC/MS) and analytical high-pressure liquid chromatography (HPLC) and was demonstrated to be pure (>98%). Mass results were consistent with calculated values.

Characterizations of peptide analogs were performed via C18 HPLC and LC/MS analysis (Acquity SQD Waters Corp, Milford, Mass.) and UV detection provided by dual absorbance signals at 215 nm and 280 nm, using one of Method A, Method B, Method C or Method D.

Method A, LC/MS conditions: performed using a Phenomenex HPLC Aeris™ Peptide XB C18 column, 1.7 pm, 2.1×100 mm or Acquity BEH300 or BEH130 CT8 column, 1.77 pm. 2.1×100 mm using 5-65% acetonitrile/water with 0.05% TFA over 30 minutes with a flow rate 0.5 mL/min, λ—215 nm, 280 nm.

Method B, C18 HPLC conditions: HPLC analysis was conducted on an Acquity BEH130, C18 column, 1.7 μm, 100×2.10 mm column at 25° C. 5-65% acetonitrile/water with 0.05% TFA over 30 minutes, flow rate 0.5 mL/min, λ—215 nm, 280 nm.

Method C, HPLC conditions: HPLC analysis was conducted on an Acquity BEH130, C18 column, 1.7 μm, 100×2.10 mm column at 25° C. 5-65% acetonitrile/water with 0.05% TFA over 20 minutes, flow rate 0.5 mL/min, λ—215 nm, 280 nm.

Method D, HPLC conditions: HPLC analysis was conducted on an Acquity BEH130, C18 column, 1.7 μm, 100×2.10 mm column at 25° C. 5-65% acetonitrile/water with 0.05% TFA over 10 minutes, flow rate 0.5 mL/min, λ—215 nm, 280 nm. 5.0 μL of sample was injected using a PLNO (partial loop w/needle over-fill) injection mode.

Polypeptide analogs without a lipophilic substituent and optional spacer are sometimes referred to herein as “linear polypeptides.” Polypeptide analogs having at least one covalently bound lipophilic substituent and optional spacer are sometimes referred to herein as “conjugated polypeptides.” Table 13 provides characterization data for exemplary long acting PYY analog polypeptides of the disclosure.

Polypeptide analogs without a lipophilic substituent and optional spacer are sometimes referred to herein as “linear polypeptides.” Polypeptide analogs having at least one covalently bound lipophilic substituent and optional spacer are sometimes referred to herein as “conjugated polypeptides.”

TABLE 13

Exemplary compounds: PYY analog polypeptides

| Compound No. | SEQ ID NO: | Parent MW | Calculated Mass (Parent MW) M + 3 | Observed Mass (Parent MW) M + 3 | Calculated Mass (Parent MW) M + 4 | Observed Mass (Parent MW) M + 4 |
|---|---|---|---|---|---|---|
| A1 | SEQ ID NO: 1 | 4948.58 | 1650.53 | 1651.7 | — | — |
| A2 | SEQ ID NO: 2 | 4803.43 | 1602.14 | 1603.4 | — | — |
| A3 | SEQ ID NO: 3 | 4936.57 | 1646.52 | 1647.7 | — | — |
| A4 | SEQ ID NO: 4 | 4903.55 | 1637.2 | 1635.52 | — | — |
| A5 | SEQ ID NO: 5 | 4775.37 | 1595 | 1592.79 | — | — |
| A6 | SEQ ID NO: 6 | 4774.43 | 1594 | 1592.48 | — | — |
| A7 | SEQ ID NO: 7 | 4846.5 | 1617.9 | 1616.5 | — | — |
| A8 | SEQ ID NO: 8 | 4774.43 | 1593.5 | 1592.48 | — | — |
| A9 | SEQ ID NO: 9 | 4789.44 | 1599.2 | 1597.48 | — | — |
| A10 | SEQ ID NO: 10 | 4817.45 | 1606.82 | 1608.6 | — | — |
| A11 | SEQ ID NO: 11 | 4817.45 | 1606.82 | 1608.5 | — | — |
| A12 | SEQ ID NO: 12 | 4803.43 | 1602.14 | 1603.4 | — | — |
| A13 | SEQ ID NO: 13 | 4787.43 | 1596.81 | 1598.9 | — | — |

TABLE 13-continued

| Exemplary compounds: PYY analog polypeptides | | | | | | |
|---|---|---|---|---|---|---|
| Compound No. | SEQ ID NO: | Parent MW | Calculated Mass (Parent MW) M + 3 | Observed Mass (Parent MW) M + 3 | Calculated Mass (Parent MW) M + 4 | Observed Mass (Parent MW) M + 4 |
| A14 | SEQ ID NO: 14 | 4844.52 | 1615.84 | 1617.8 | — | — |
| A15 | SEQ ID NO: 15 | 4787.43 | 1596.81 | 1597.5 | — | — |
| A16 | SEQ ID NO: 16 | 5134.84 | 1712.61 | 1714.3 | — | — |
| A17 | SEQ ID NO: 17 | 5077.74 | 1693.58 | 1694.7 | — | — |
| A18 | SEQ ID NO: 18 | 5134.84 | 1712.61 | 1714.2 | — | — |
| A19 | SEQ ID NO: 19 | 4901.62 | 1634.87 | 1637.2 | — | — |
| A20 | SEQ ID NO: 20 | 4844.57 | 1615.85 | 1617.8 | — | — |
| A21 | SEQ ID NO: 21 | 4844.52 | 1615.84 | 1617.1 | — | — |
| A22 | SEQ ID NO: 22 | 4802.44 | 1601.81 | 1603.2 | — | — |
| A23 | SEQ ID NO: 23 | 4858.55 | 1620.52 | 1622.4 | — | — |
| A24 | SEQ ID NO: 24 | 4845.51 | 1616.17 | 1617.8 | — | — |
| A25 | SEQ ID NO: 25 | 4817.5 | 1606.83 | 1608.4 | — | — |
| A26 | SEQ ID NO: 26 | 4831.52 | 1611.51 | 1612.4 | — | — |
| A27 | SEQ ID NO: 27 | 4900.68 | — | — | 1226.17 | 1227.1 |
| A28 | SEQ ID NO: 28 | 4900.68 | — | — | 1226.17 | 1227.1 |
| A29 | SEQ ID NO: 29 | 4901.62 | — | — | 1226.41 | 1227.1 |
| A30 | SEQ ID NO: 30 | 4831.52 | — | — | 1208.88 | 1209.8 |
| A31 | SEQ ID NO: 31 | 4831.52 | — | — | 1208.88 | 1209.8 |
| A32 | SEQ ID NO: 32 | 4817.45 | — | — | 1205.36 | 1206.5 |
| A33 | SEQ ID NO: 33 | 4831.48 | 1611.49 | 1612.6 | — | — |
| A34 | SEQ ID NO: 34 | 4902.6 | 1635.2 | 1637 | — | — |
| A35 | SEQ ID NO: 35 | 4874.55 | 1625.85 | 1626.1 | — | — |
| A36 | SEQ ID NO: 36 | 4887.59 | 1630.2 | 1631.7 | — | — |
| A37 | SEQ ID NO: 37 | 4900.68 | 1634.56 | 1635.9 | — | — |
| A38 | SEQ ID NO: 38 | 4873.57 | 1626.1 | 1626.1 | — | — |
| A39 | SEQ ID NO: 39 | 4897.68 | — | — | 1225.42 | 1226.3 |
| A40 | SEQ ID NO: 40 | 4883.65 | — | — | 1221.91 | 1222.7 |
| A41 | SEQ ID NO: 41 | 4841.52 | — | — | 1211.38 | 1212.7 |
| A42 | SEQ ID NO: 42 | 4827.49 | — | — | 1207.87 | 1208.9 |
| A43 | SEQ ID NO: 43 | 4841.52 | — | — | 1211.38 | 1212.7 |
| A44 | SEQ ID NO: 44 | 4827.49 | — | — | 1207.87 | 1209 |
| A49 | SEQ ID NO: 49 | 4817.45 | 1606.82 | 1607.7 | — | — |
| A50 | SEQ ID NO: 50 | 4787.47 | 1596.82 | 1598.6 | — | — |
| A51 | SEQ ID NO: 51 | 4801.5 | 1601.5 | 1602.4 | — | — |
| A52 | SEQ ID NO: 52 | 4752.43 | 1585.14 | 1587.5 | — | — |
| A53 | SEQ ID NO: 53 | 4759.41 | 1587.47 | 1588.4 | — | — |
| A54 | SEQ ID NO: 54 | 4844.52 | 1615.84 | 1617.7 | — | — |
| A55 | SEQ ID NO: 55 | 4801.5 | 1601.5 | 1603.1 | — | — |

"—" = not determined

Example 3: Stability and Solubility of Long Acting PYY Analog Polypeptides

The analog polypeptides described herein were tested for solubility in saline or in aqueous (DI water) at room temperature. Samples were visually inspected for clarity of the sample, any appearance of turbidity or haziness. The results of this analysis are shown in Table 14.

Several Long-acting PYY analog analogs described herein were tested, as the trifluoro acetate salt, for stability in aqueous (i.e., in DI water) or in saline (at 1 mg/ml solution. These analog polypeptides were incubated at 37° C., and samples were withdrawn at various time intervals and analyzed by LC/MS and HPLC determination of purity and mass of the parent peptide and extent of any degradation products. The purity results of these analyses are shown in Table 14 and are considered indicative of stability.

TABLE 14

| Solubility and Stability of long-acting PYY Analog Polypeptides | | | | | |
|---|---|---|---|---|---|
| Compound No. | Salt form | Solubility (in Water, RT) mg/mL | Stability (37° C./RT, T0: Mar. 25, 2020 | Stability (37° C./RT, 14 days) | Stability (37° C./RT, 28 days) |
| A1 | TFA | 58 | 98 | — | — |
| A3 | TFA | 48 | 96.3 | — | — |
| A10 | TFA | 53 | 94.2 | — | — |
| A13 | TFA | 40 | 93.9 | — | — |
| A14 | TFA | 79 | 94.2 | — | — |
| A18 | TFA | 95 | 94.5 | — | — |
| A19 | TFA | 59 | 88.8 | — | — |
| A20 | TFA | 103 | 98.6 | — | — |
| A21 | TFA | 114 | 96.4 | — | — |
| A22 | TFA | 57 | 96.1 | — | — |
| A24 | TFA | 90 | 98.1 | — | — |
| A24 | Acetate | <0.8 | 97.7 | — | — |
| A25 | TFA | 37 | 97.6 | — | — |
| A26 | TFA | 68 | 99.8 | — | — |
| A39 | TFA | 16 | 95.9 | — | — |
| A40 | TFA | 27 | 98.1 | — | — |
| A41 | TFA | 26 | 95.7 | — | — |
| A42 | TFA | 53 | 98 | — | — |

"—" = not determined

Example 4: Human and Rat NPY Receptor Functional Assay

The NPY family of G-protein coupled receptors include Y1, Y2, Y4, and Y5 in humans and rats. Each receptor binds a pharmacologically distinct set of endogenous peptide agonist hormones or neurotransmitters belonging to the NPY family, and include neuropeptide Y (NPY), peptide tyrosine-tyrosine (PYY), and pancreatic polypeptide (PP). While NPY and PYY (1-36) bind Y1, Y2, and Y5 receptors with relative high affinity, PYY (3-36) selectively binds the Y2 receptor, and PP is selective for the Y4 receptor. Following agonist binding, the receptor-G protein complex activates a downstream intracellular signaling cascade which leads to inhibition of adenylate cyclase and a reduction in intracellular cAMP levels.

Cell Handling and CAMP Accumulation Assays

HEK-CNG cells stably expressing the human or rat Y1, Y2, Y4 or Y5 receptors (Codex Biosolutions) were used to characterize the functional potency of peptide agonists using the ActOne™ membrane potential dye kit (Codex Biosolutions). In addition to each NPY receptor, each cell line encodes a proprietary exogenous Cyclic Nucleotide-Gated (CNG) channel (Codex Biosolutions). The channel is activated by elevated intracellular levels of cAMP, resulting in ion flux and cell membrane depolarization which can be detected with a calcium sensitive dye or fluorescent membrane potential (MP) dye. Cells were carried in growth media containing 90% DMEM, 10% FBS, 250 mcg/mL G418 and 1 mcg/mL puromycin for no more than 15 passages.

Prior to testing, cells were counted and dispensed at 14,000 cells per well (Y1, Y4 and Y5) or 28,000 cells per well (Y2) into black 384 well Poly-D-Lysine plates at 20 mcL per well. Covered plates were then incubated at room temperature for 30 minutes followed by an overnight incubation at 37° C. in 5% $CO_2$. The following day, media was removed and wells were washed once with 40 mcL Dulbecco's phosphate buffered saline. Twenty microliters of DMEM followed by 20 mcL of dye loading solution containing IX ACTOne™ membrane potential dye dilution buffer, IX ACTOne™ membrane potential dye solution (Codex Biosolutions) and 50 mcM of the phosphodiesterase inhibitor Ro20-1724 was added to each well, covered and pre-incubated at room temperature for 2 hours in the dark. During this pre-incubation, experimental peptides and standards (NPY for Y1 and Y5, PYY (3-36) for Y2, and PP for Y4) were serially diluted over 12 concentrations to a 5× concentration (ranging from 5×10-7 M to 5×10-13 M) in agonist dilution buffer containing IX DPBS, 0.5% casein, 125 mcM Ro20-1724 and 1.5 mcM isoproterenol to stimulate b1/b2-adrenoreceptor mediated cAMP production. Following the pre-incubation, an initial read (Ex530/Em590) was performed on a Flexstation 3 fluorescent plate reader (Molecular Devices, Sunnyvale, Calif.). Ten microliters of experimental peptide or peptide standard was added in triplicate to wells and incubated for 50 minutes at room temperature in the dark. Following this incubation step, plates were read again as before (final read).

Data Analysis and Interpretation

NPY receptor activation, leading to a reduction in intracellular cAMP levels, is detected as a decrease in isoproteranol induced fluorescent signal. Peptide standard and experimental values were initially transformed in excel using the formula: final read/initial read. Transformed values were then normalized to receptor specific standard values (1×10-13M minimum and 1×10-7 M maximum) using the formula: (test value−standard minavg)/(standard maxavg−standard minavg)*100. Normalized experimental values represent a baseline corrected percentage of the receptor-system max response produced by the control peptide for each assay (NPY for Y1R and Y5R, PYY(3-36) for Y2R, and PP for Y4R). Analogs whose activity was ≤70% of the control peptide maximum are identified as partial agonists. Normalized data was analyzed from triplicate tests and used to estimate the EC50 for each test peptide on each receptor. Data was fit in GraphPad Prism software (v8.2.1) using a 3-parameter logistic curve model: Y=Bottom+(Top-Bottom)/(1+10^((Log EC50−X))). EC50 values were converted to pEC50 values using the formula: pEC50=−Log(EC50). All reported values met the curve fitting parameter $r^2$≥0.8.

The results of these analyses are reported in Table 15.

TABLE 15

Activity of PYY analog polypeptides against PYY Receptors

| Compound No. | NPY1R pEC50 | NPY2R pEC50 | NPY4R pEC50 | NPY5R pEC50 |
|---|---|---|---|---|
| PYY (3-36) | 8.5 | 10.3 | <7.0 | 9.4 |
| A1 | 9.1* | 10.5 | 8.8 | 8.8 |
| A2 | 9.3* | 10.5 | 9.2 | 8.9 |
| A3 | 9.1* | 10.7 | 9.1 | 9 |
| A4 | nr | 8.7 | inactive | 7.3 |
| A5 | nr | 7.7 | inactive | 8 |
| A6 | nr | 8.9 | inactive | 7.7 |
| A7 | nr | 9.7 | inactive | 6 |
| A8 | nr | 9.6 | inactive | 7.1 |
| A9 | nr | 9.6 | inactive | 6 |
| A10 | 8.4* | 9.7 | inactive | 7.7 |
| A11 | nr | 9.5 | inactive | 7.1 |
| A12 | nr | 9.7 | inactive | 7.1 |
| A13 | inactive | 10.2 | inactive | 8.7 |
| A19 | nr | 10.5 | nr | 8.7 |
| A20 | nr | 10.5 | nr | 8.7 |
| A21 | nr | 10.4 | nr | 8.3 |
| A22 | nr | 10.5 | nr | 8.7 |
| A23 | nr | 10.4 | nr | 8.6 |
| A24 | inactive | 10.5 | inactive | 8.7 |
| A25 | nr | 10.9 | nr | 8.4 |
| A26 | nr | 10.7 | nr | 8.5 |
| A14 | 8.5* | 10.1 | nr | 8.3 |
| A15 | 9.6* | 10.2 | nr | 8 |
| A16 | nr | 10.2 | nr | 9.1 |
| A17 | 8.3* | 10.2 | nr | 8.7 |
| A18 | nr | 10.3 | nr | 9.3 |
| A27 | nr | 10.7 | nr | 8.9 |
| A28 | nr | 10.5 | nr | 8.8 |
| A29 | nr | 10.9 | nr | 9 |
| A30 | nr | 10.3 | nr | 8.5 |
| A31 | nr | 10.4 | nr | 8.7 |
| A32 | nr | 10.8 | nr | 9 |
| A33 | nr | 10.4 | nr | 8.9 |
| A34 | nr | 10.2 | nr | 8.8 |
| A35 | nr | 10.5 | nr | 9.1 |
| A36 | nr | 10.9 | nr | 8.7 |
| A37 | nr | 10.8 | nr | 8.6 |
| A38 | 8.6* | 11.1 | nr | 8.4 |
| A39 | 9.1* | 10.4 | nr | 8.9 |
| A40 | nr | 10.1 | nr | 9 |
| A41 | nr | 10.5 | nr | 9.3* |
| A42 | nr | 10.3 | nr | 9.1 |
| A43 | 9.2* | 10.5 | nr | 8.5 |
| A44 | 8.1* | 9.7 | nr | 9.2 |
| A49 | nr | 7.6 | inactive | 6 |
| A50 | nr | 6 | inactive | 6 |
| A51 | nr | 6 | inactive | 6 |
| A52 | nr | 8.4 | inactive | 8 |
| A53 | nr | 8.7 | inactive | 7.3 |
| A54 | nr | 7.7 | inactive | 8.0 |
| A55 | nr | 8.9 | inactive | 7.7 |
| A56 | nr | 9.7 | inactive | inactive |
| A57 | nr | 9.6 | inactive | 7.1 |
| A58 | 8.8* | 10.3 | inactive | 8.8 |

TABLE 15-continued

| Activity of PYY analog polypeptides against PYY Receptors | | | | |
|---|---|---|---|---|
| Compound No. | NPY1R pEC50 | NPY2R pEC50 | NPY4R pEC50 | NPY5R pEC50 |
| A59 | nr | 8.8 | inactive | 6 |
| A60 | 8.9* | 10.3 | inactive | 8.6 |
| A61 | 8.6* | 10 | inactive | 8.3 |
| A62 | 8.1* | 9.4 | inactive | 8.2 |
| A63 | nr | 7.5 | inactive | 6 |
| A64 | nr | 8.6 | inactive | 7.9 |
| A65 | 8.0* | 10.2 | nr | 8.6 |
| A66 | nr | 10.3 | nr | 8.3 |
| A67 | nr | 10.3 | nr | 8.5 |
| A68 | nr | 9.7 | nr | 7.9 |
| A69 | nr | 10 | nr | 8.3 |
| A70 | nr | 10.4 | nr | 8.7 |
| A71 | nr | 10.7 | nr | 8.8 |
| A72 | 9.0* | 10.8 | nr | 8.8 |
| A73 | nr | 10.3 | nr | 8.6 |
| A74 | 9.3* | 10.3 | nr | 9 |
| A75 | nr | 10.6 | nr | 9.3 |
| A76 | 10.6* | 10.4 | nr | 8.9 |
| A77 | nr | 10.3 | nr | 9.2 |
| A78 | nr | 10.2 | nr | 8.5 |

*maximal response ≤70% when compared to NPY maximal response on NPY1R.
nr; not reported Example 5: In Vitro Metabolic Stability Pharmacokinetics Studies (T½) of PYY Analogs Rat and Human Kidney Brush Border Membranes In vitro incubations in kidney brush border membrane (kBBM) preparations were used to characterize the ability of peptides to resist degradation by proteases and peptidases in the systemic circulation. kBBM were selected because they contain a high concentration of a diverse set of proteases and peptidases, many of which are present throughout the body. Generally, peptides with low in vivo CL are stable in this assay, while peptides with high in vivo CL are unstable in this assay.

Brush border membranes from rat and human kidney tissue were prepared via centrifugation and stored at −70° C. Thawed stocks of rat or human kBBM were diluted to the appropriate concentration in 25 mM HEPES buffer (pH 7.4) containing 1% casein and aliquoted into a 96-well plate. The kBBM solutions were pre-warmed for 10 minutes at 37° C. Reactions were initiated by the addition of test peptide (1 mcM final concentration) also dissolved in 25 mM HEPES buffer (pH 7.4) containing 1% casein. The final concentration of kBBM in each incubation was 50 meg protein/mL. Reactions were maintained at 37° C. in a shaking water bath. At 0, 0.25, 0.5, 1.0, 2.0, and 4.0 h post-initiation, 30 mcL of the reaction mixture was removed and placed into a 96-well plate containing 120 mcL of ice-cold methanol containing 2.5% formic acid. Quenched samples were centrifuged at 2178×g for 10 min and then a portion of the supernatants were transferred to a clean 96-well plate and diluted 1:1 with water. Samples were analyzed by UPLC-MS/MS. The results of these analyses are shown in Tables 16, 17, and 18.

Human Subcutaneous Tissue Homogenates

In vitro incubations in subcutaneous (SC) tissue homogenates were used to characterize the ability of peptides to resist pre-systemic degradation by proteases and peptidases after SC administration. In vivo nonclinical studies have shown that peptidase activity in the SC space can limit the bioavailability of a peptide after SC administration. Peptides with high SC bioavailability are stable in this assay, while peptides with low SC bioavailability are unstable in this assay.

Human SC tissue was homogenized in cold 25 mM HEPES buffer (pH 7.4, 10-fold volume based on sample weight), and then filtered through a double layer of cheesecloth. The filtrates were aliquoted, flash frozen on a methanol/dry ice bath and stored at −80° C. The protein concentration of each pooled batch was determined using the BCA protein assay. Thawed stocks of human SC tissue homogenates were diluted to 1.0 mg protein/mL in 25 mM HEPES buffer (pH 7.4) and aliquoted into a 96-well plate. The diluted SC homogenates were pre-warmed for 10 minutes at 37° C. Reactions were initiated by the addition of test peptide (10 mcM final concentration) also dissolved in 25 mM HEPES buffer (pH 7.4). Reactions were maintained at 37° C. in a shaking water bath. At 0, 0.25, 0.5, 1.0, 2.0, and 4.0 h post-initiation, 50 mcL of the reaction mixture was removed and placed into a 96-well plate containing 150 mcL of ice-cold methanol containing 2.5% formic acid. Quenched samples were centrifuged at 2178×g for 10 min and then a portion of the supernatants were transferred to a clean 96-well plate and diluted 1:10 with water. Samples were analyzed by UPLC-MS/MS. The results of these analyses are shown in Tables 16, 17, and 18.

Fraction Unbound ($f_u$) in Plasma

Conventional methods of measuring plasma protein binding, such as equilibrium dialysis, ultrafiltration and ultracentrifugation, are not reliable with peptides because of their tendency to adsorb to the surface of plastic tubing, dialysis membranes and molecular weight cut-off filters. As a result, the extent to which acylated peptides bind to serum albumin was evaluated using surface plasmon resonance (SPR). The utility of this technique to provide a reasonable estimation of the fraction of a drug bound to plasma protein has been demonstrated in the literature. The results of this analysis for compounds A13 (SEQ ID NO: 24) and A24 (SEQ ID NO: 24) are shown in Tables 17 and 18. The estimated half life of compounds A13 and A24 in humans based off this data is approximately 4 days, each.

TABLE 16

| Metabolic stability pharmacokinetics of PYY analog polypeptides | | | |
|---|---|---|---|
| Compound No. | rkBBM t½(hr) | hkBBM t½(hr) | (H)SC tissue stability t½(hr) |
| A27 | — | 10 | 0.2 |
| A28 | — | 5.2 | 0.2 |
| A29 | — | 8.7 | 1.1 |
| A35 | — | 5.6 | 1.3 |
| A21 | >12 | >12 | 2.5 |
| A26 | >12 | >12 | 4 |
| A14 | >12 | >12 | 4.5 |
| A23 | >12 | >12 | 4.5 |
| A25 | >12 | >12 | 4.7 |
| A34 | — | 6.7 | 4.9 |
| A30 | — | >12 | 5.1 |
| A31 | — | >12 | 5.6 |
| A22 | >12 | >12 | 7.2 |
| A16 | >12 | >12 | 7.3 |
| A15 | >12 | >12 | 9.6 |
| A17 | >12 | >12 | 9.7 |
| A33 | — | >12 | 9.9 |
| A12 | >12 | — | 10.2 |
| A2 | >12 | >12 | 10.6 |
| A24 | >12 | >12 | 10.8 |
| A13 | >12 | >72 | 10.8 |
| A10 | >12 | >72 | 11.2 |
| A11 | >12 | — | >12 |

TABLE 17

| Metabolic stability pharmacokinetics and fraction unbound of PYY analog compound A13 | | | |
|---|---|---|---|
| | kBBM t½(hr) | SC tissue stability t½(hr) | % $f_u$ |
| Rat | >12 | 2.9 | 0.68% |
| Monkey | >12 | ND | 0.43% |
| Human | >72 | 10.8 | 0.44% |

ND = not determined

TABLE 18

| Metabolic stability pharmacokinetics and fraction unbound of PYY analog compound A24 | | | |
|---|---|---|---|
| | kBBM t½(hr) | SC tissue stability t½(hr) | % $f_u$ |
| Rat | >12 | 7.1 | 0.27% |
| Monkey | ND | ND | 0.17% |
| Human | >12 | 10.8 | 0.22% |

ND = not determined

Example 6: Pharmacokinetic Analysis of PYY Analog Polypeptides

Intravenous infusion of long-acting PYY analog polypeptides to assess clearance (CL) of peptides Peptides were dissolved in 0.05% Tween-20 in PBS (pH7.4) and administered as a 1-hour subcutaneous infusion to non-fasted male Sprague-Dawley rats (n=3 per group) at a final dose of 0.033 mg/kg via a cannula placed into the femoral vein. Formulations were administered at a rate of 0.150 mL/h/kg. Blood samples (approximately 250 μL) were collected for pharmacokinetic analysis via a jugular vein cannula at 0.25, 0.5, 0.75, 1, 1.17, 1.33, 1.5, 2, 4, 8, 24, 48, 72, 96, and 120 hr post-start of infusion into microtainer tubes containing $K_2$EDTA as anticoagulant and 25 μL of a protease inhibitor cocktail. Plasma was prepared by centrifugation and stored at −80° C. until analysis.

Subcutaneous Bolus Injection of Long-Acting PYY Analog Polypeptides to Assess Bioavailability (F) of Polypeptides Peptides were dissolved in sterile saline and administered to non-fasted male Sprague-Dawley rats (n=3 per group) at a dose of 0.1 mg/kg via a single bolus injection into the subcutaneous space between the scapulae. Blood samples (approximately 250 μL) were collected for pharmacokinetic analysis via a jugular vein cannula at 0.083, 0.25, 0.5, 1, 2, 4, 8, 24, 48, 72, 96, and 120 hr post-dose into microtainer tubes containing $K_2$EDTA as anticoagulant and 25 μL of a protease inhibitor cocktail. Plasma was prepared by centrifugation and stored at −80° C. until analysis.

Plasma Sample Preparation for Pharmacokinetic Studies

A 70 μL aliquot of each plasma sample was placed into to a 96-well plate. To each well was added 210 μL of 0.1% TFA in 2:1 ethanol:acetonitrile containing an appropriate internal standard. Plates were vortex mixed for 10 min at 1300 rpm, and then centrifuged for 10 min at 500×g. Supernatants (210 μL) were placed into a clean 96-well plate and evaporated under a nitrogen stream at 45° C. Residues were reconstituted in 80 μL of 20% acetonitrile (aq) containing 0.1% formic acid.

LC/MS quantification of PYY Polypeptides in Plasma

All calibration standards were prepared in control rat plasma containing $K_2$EDTA and protease inhibitor cocktail.

Figure 4:
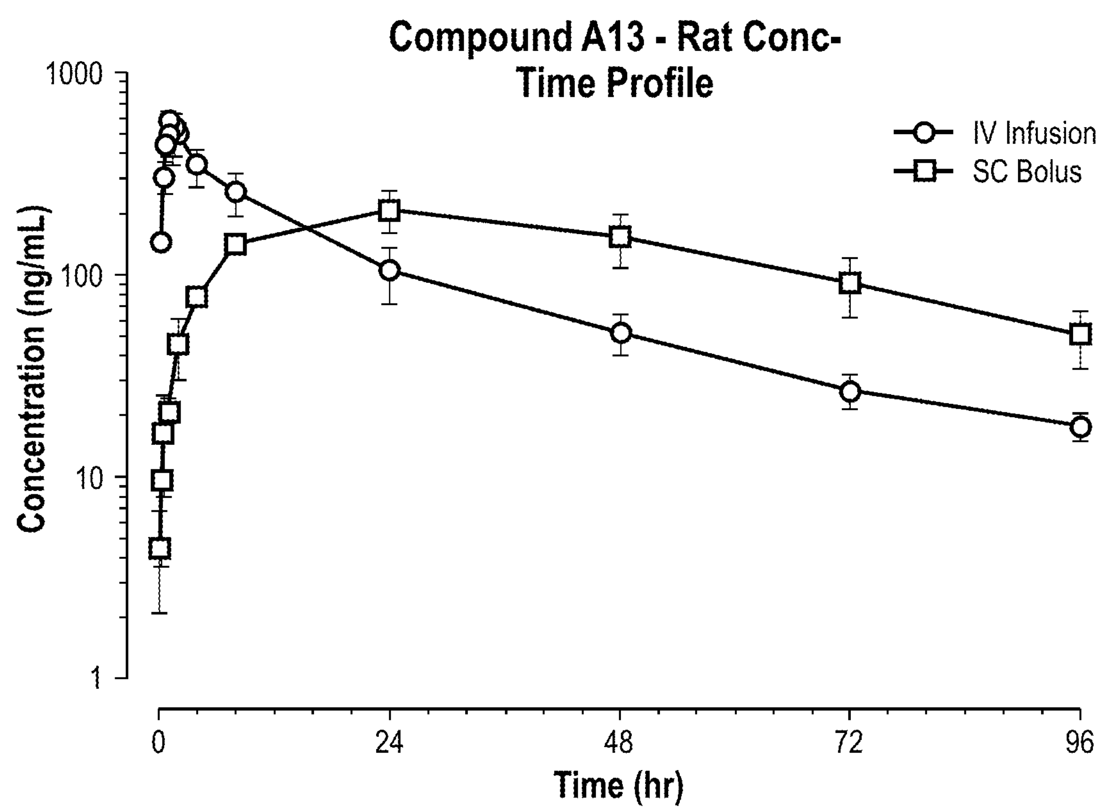
FIG. 4 depicts the change in plasma concentration of A13 following bolus or intravenous infusion.
Figure 5:
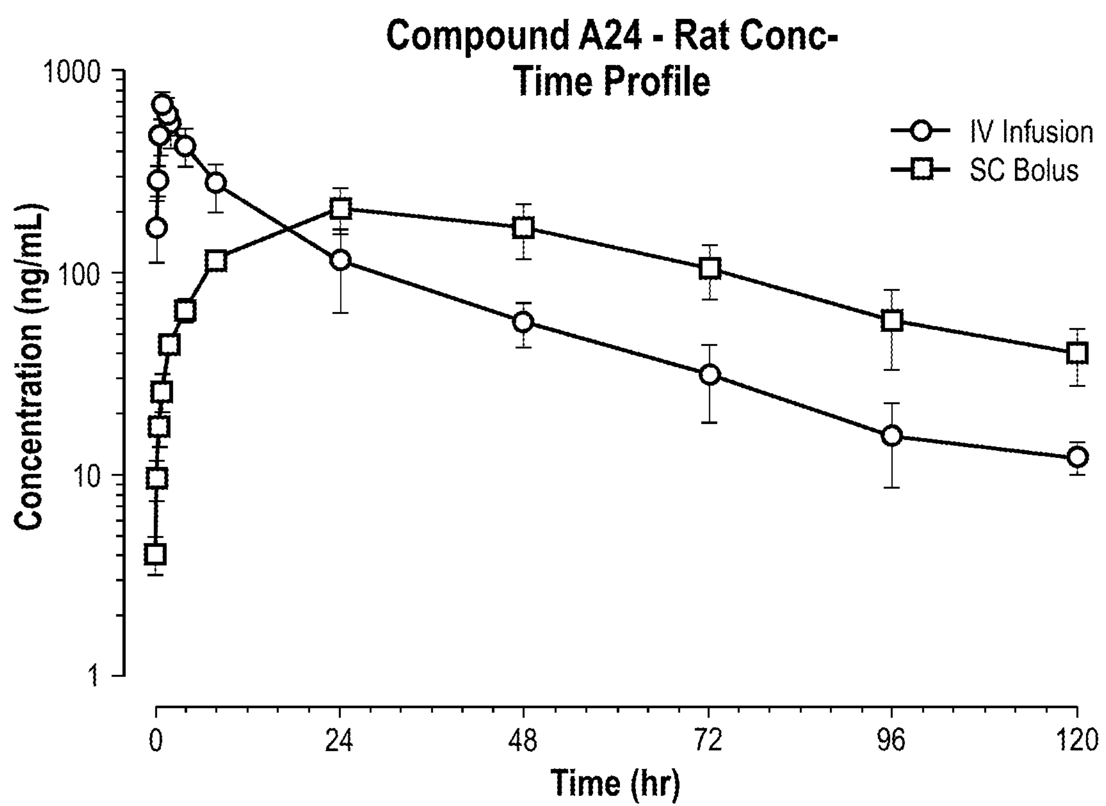
FIG. 5 depicts the change in plasma concentration of A24 following bolus or intravenous infusion.

Samples and standards were analyzed by electrospray ionization (ESI) UPLC-MS/MS using a system consisting of a CTC HTS PAL auto-injector (Leap, Carrboro, N.C.), an Agilent Infinity 1290 system with column oven (Palo Alto, Calif.), a Valeo switching valve (Houston, Tex.), and a Sciex TripleTOF® 5600 mass spectrometer (Framingham, Mass.). Samples were injected onto a 2.1×50 mm reverse phase C18 analytical column, typically a Waters CORTECS UPLC C18+, 1.6 μm (Waters Corporation, Milford, Mass.) or similar. Chromatographic separation was achieved with a gradient method using water containing 0.1% formic acid (A) and acetonitrile containing 0.1% formic acid (B) as mobile phase. Initial conditions consisted of 95% A and 5% B. The organic component was increased to 95% B over a period of 3-4 minutes, depending on the peptide. Typical flow rates were 550 μL/min. The column temperature was held constant at 45° C. Peptides were quantified by monitoring one or more product ions produced from a multiply charged parent ion. The results of these analyses are provided in Table 19. Comprehensive pharmacokinetic and ADME profiles for compounds A13 (SEQ ID NO: 13) and A24 (SEQ ID NO: 24) are shown in Tables 20 and 21, respectively. The change in plasma concentration of A13 and A24 following bolus and intravenous infusion are presented in FIGS. 4 and 5.

TABLE 19

| Quantification of PYY in plasma | | | |
|---|---|---|---|
| Compound No. | CL (mL/min/kg) | IV $t_{1/2}$ (hr) | F (%) |
| A2 | 0.0749 | 26.6 | 46.2 |
| A7 | 0.326 | 6.44 | 66.7 |
| A10 | 0.0600 | 43.2 | 58.7 |
| A13 | 0.0589 | 32.4 | 51.4 |
| A24 | 0.0564 | 28.7 | 49.8 |
| A25 | 0.0696 | 16.2 | 28.4 |

TABLE 20

| Pharmacokinetic and ADME profile of compound A13 in a rat model | | | | | | | |
|---|---|---|---|---|---|---|---|
| Route | Dose (mg/kg) | CL (mL/min/kg) | $V_{ss}$ (mL/kg) | $T_{1/2}$ (hr) | $T_{max}$ (hr) | $C_{max}$ (ng/mL) | F (%) |
| IV infusion | 0.033 | 0.0589 | 119 | 32.4 | ND | ND | ND |
| SC bolus | 0.100 | ND | ND | 30.9 | 24 | 211 | 51.4 |

ND = not determined

TABLE 21

| Pharmacokinetic and ADME profile of compound A24 in a rat model | | | | | | | |
|---|---|---|---|---|---|---|---|
| Route | Dose (mg/kg) | CL (mL/min/kg) | $V_{ss}$ (mL/kg) | $T_{1/2}$ (hr) | $T_{max}$ (hr) | $C_{max}$ (ng/mL) | F (%) |
| IV infusion | 0.033 | 0.0564 | 101 | 28.7 | ND | ND | ND |
| SC bolus | 0.100 | ND | ND | 33.5 | 24 | 210 | 49.8 |

ND = not determined

Figure 6:
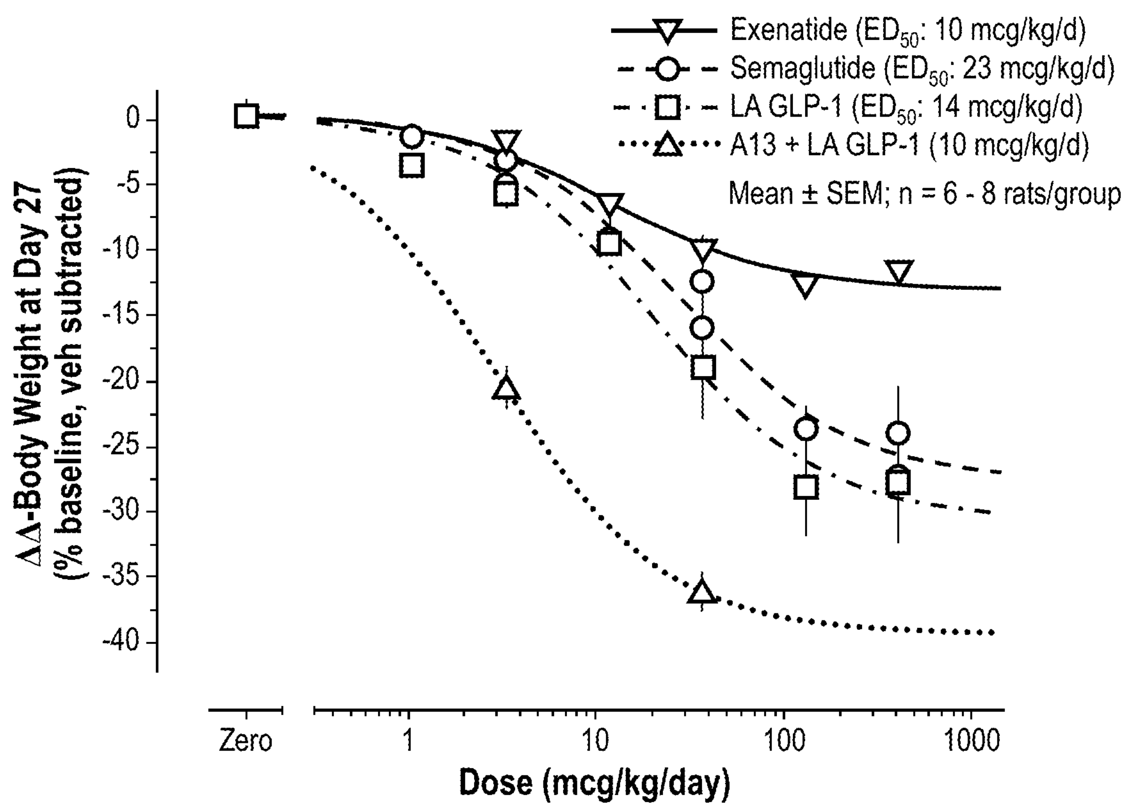
FIG. 6 is a graph depicting weight loss in the diet-induced-obese rat model of obesity and highlighting that the combination of the PYY analog peptide A13 with a long acting GLP-1 receptor agonist is significantly more effective and potent than the industry benchmarks exenatide or semaglutide alone.

Example 7a: Weight-Loss Efficacy of PYY Analog in Combination with a Long-Acting GLP-1 Receptor Agonist in LE DIO Rats Chronic weight loss efficacy studies were conducted in a rodent model for obesity Long Evans (LE) diet-induced obese (DIO) rat to investigate the efficacy and durability of long acting PYY analog(s) singly and in combination with a long acting GLP-1 analog (LA GLP-1). Male LE DIO rats were used (Envigo Laboratories, Inc., Indianapolis, Ind.) and beginning at weaning, the rats were fed a high fat chow (Teklad TD 95217, 40% kcal from fat, Harlan Laboratories, Madison, Wis.). The rats were housed 1 per cage and given ad libitum access to high fat diet (Harlan TD.95217) and water, maintained on a 12 hr light/dark cycle from 5:00 AM to 5:00 PM at 21° C. and 50% relative humidity and allowed to acclimate for at least 10 days post shipping prior to use. Rats were 16-18 weeks old at the start of the study. All procedures were performed in compliance with the Animal Welfare Act, USDA regulations and approved by the Mispro Institutional Animal Care and Use Committee. Animals were randomized into treatment groups according to body weight and fat mass (n=8 rats/group). DIO LE rats were dosed by subcutaneous (SC) injection with every other day dosing (eod) with either a long acting PYY and/or GLP-1 receptor agonist polypeptide at the specified doses or vehicle control (saline). The mean weight loss (%)±SEM from baseline and vehicle control (ΔΔ) results from the chronic combination studies of compound A13 (SEQ ID NO: 13) with the LA GLP-1 are shown in FIG. 1. Comparative data with respect to exenatide and semaglutide is provided in FIG. 6.

Figure 8:
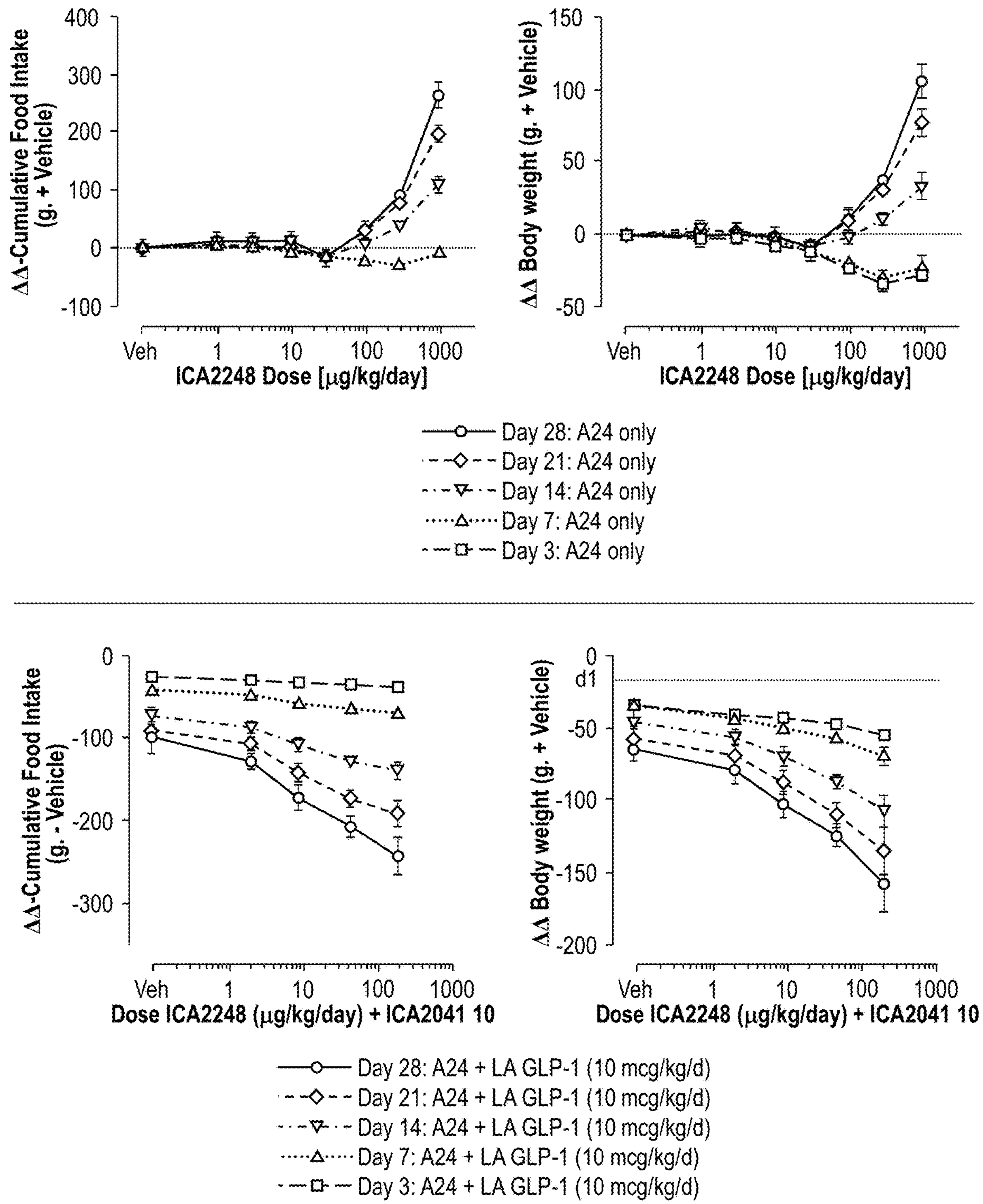
FIG. 8 is a panel of graphs depicting changes in food intake (ΔΔ g) over different durations of treatment with different doses (left panels) and corresponding changes in body weight (ΔΔ g, right panels) in the diet-induced-obese rat model of obesity. The upper panels correspond to repeated administrations of the PYY analog A24 alone, while the lower panels correspond to combined administrations of the PYY analog A24 and a long acting GLP-1 receptor agonist.

Example 7b: Weight-Gain Efficacy of PYY Analog Administered Alone in LE DIO Rats The experiments described in Example 7a where responses to a long-acting PYY agonist in combination with a long-acting GLP-1 agonist were analyzed were separately analyzed in LE DIO rats that received a long-acting PYY agonist (compound A24; SEQ ID NO: 24) alone. Surprisingly, in contrast to the synergistic reduction in food intake and synergistic weight loss of the combination of compound A24 (SEQ ID NO: 24) and the long acting GLP-1 receptor agonist shown as the lower panels in FIG. 8, the PYY agonist alone invoked a dose-dependent increase in food intake and gain in body weight as shown in the upper panels of FIG. 8. A similar pattern of increase in food intake and weight gain was also observed with another long-acting PYY agonist (compound A13; SEQ ID NO: 13) when administered alone. The orexigenic (food intake-stimulating) and weight-gain effects of both PYY agonists (A13 and A24) administered alone contrast with previously-described patterns of weight change with similarly-selective (Y2) PYY agonists. This is the first example of an agent, orexigenic on its own, that when combined with a GLP-1 agonist, promotes an anorectic effect more profound than that observed with the GLP-1 agonist on its own.

The orexigenic effect of SEQ ID NO: 13 and SEQ ID NO: 24 is not easily ascribed to the long duration of effect per se of these peptides. Other selective PYY agonists whose duration of effect was enhanced by, for example, PEGylation or by linking to Fmoc exhibited only anorectic effects and not orexigenic effects. Similarly, the orexigenic effects of these peptides are not easily ascribed to albumin-binding per se, since PYY-albumin conjugates do not exhibit this effect and are only anorectic. Nor have acylated PYY agonists that reversibly bind albumin been previously reported to stimulate food intake and weight gain.

The orexigenic effect of the class of PYY agonists typified by compounds A13 and A24 (see upper left panel of FIG. 8) will be useful in certain conditions of pathogenic weight loss or loss of body energy content. Examples of such conditions include anorexia nervosa, a condition for which there are few pharmacologic options, and which is associated with ~10% mortality, principally in young people. Other examples include forms of cachexia, associated with, and complicating the treatment of malignancy. Another example is "frailty", or the malnutrition of aging. The component of this condition represented by loss of muscle mass, termed sarcopenia, has been implicated in multiple age-related morbidities and degradation of quality of life, including loss of mobility, propensity of major bone fracture, and slow recovery of such fractures.

Figure 9:
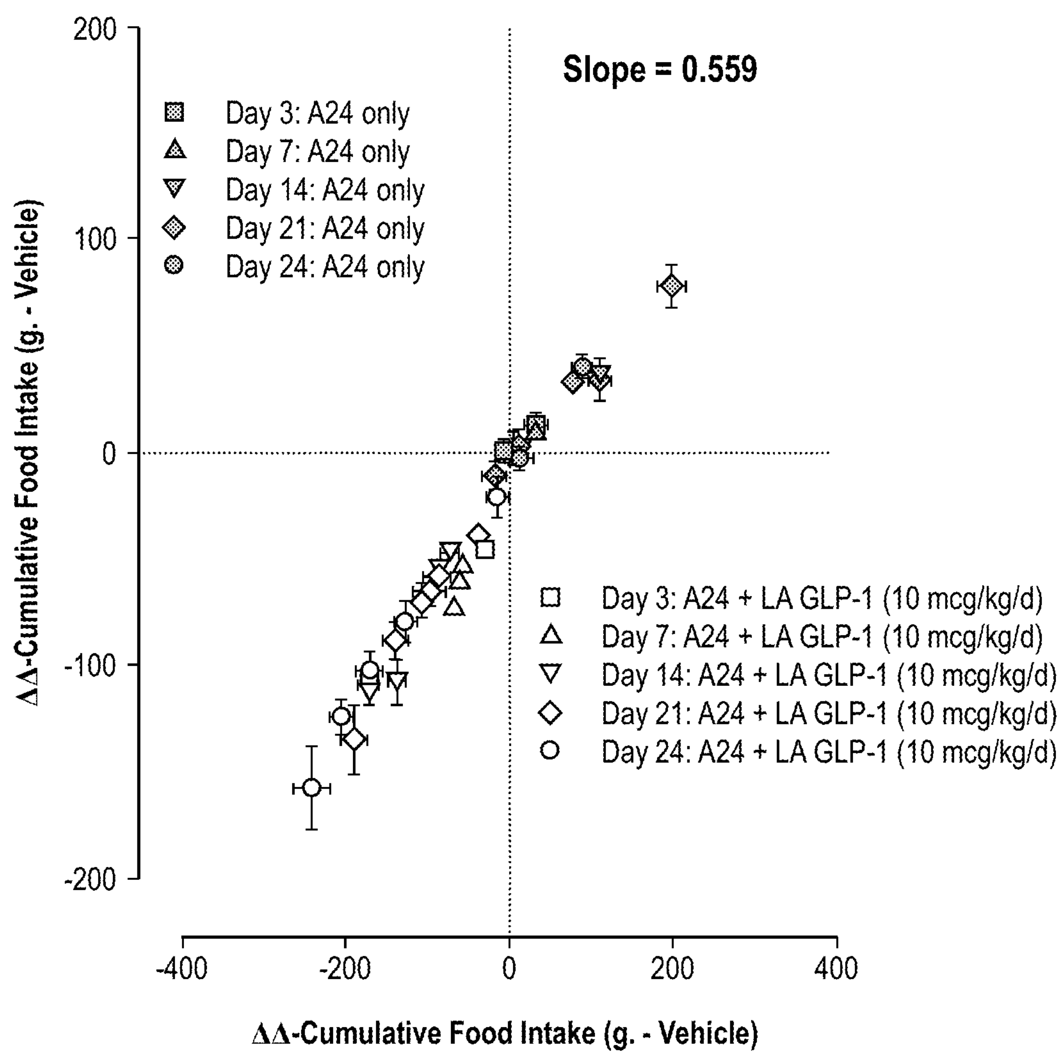
FIG. 9 replots the Y-dimension data from FIG. 8 on XY axes. Changes in body weight (ΔΔ g, Y-axis) are plotted as a function of changes in food intake (ΔΔ g, X-axis). The good fit of the relationship ($R^2$ 0.82) indicates that effects on food intake are highly predictive of effects on body weight. The slope of the relationship indicates, in this animal model, that any given change in cumulative food intake (increase or decrease) over a given period will result in a corresponding change in body weight approximately 56% as great.

Such therapeutically useful weight gain effects of the class of PYY agonists typified by compounds A13 and A24 (see upper right panel of FIG. 8 and upper right quadrant of FIG. 9) can be invoked with these agents administered singly, or in combination with other agents that invoke beneficial effects via separate mechanisms. Examples of separate beneficial agents include orexigenic agents, such as ghrelin and/or motilin agonists, or agents that promote muscle growth, such as anabolic steroids and activators of the growth hormone/inulin-like growth factor axis. Combinations that are beneficial for the abovementioned conditions do not include a PYY agonist typified by compounds A13 and A24 in association with a GLP-1 receptor agonist, since such a combination is associated with loss of body weight (lower panels of FIG. 8 and lower left quadrant of FIG. 9).

Figure 2:
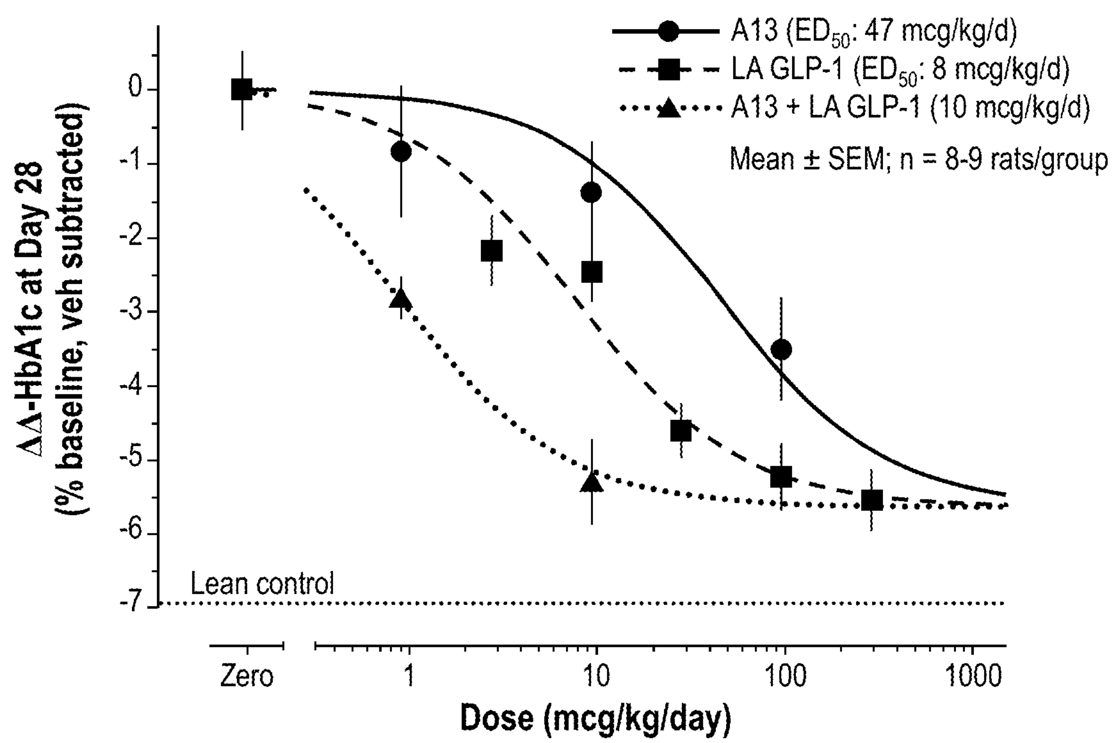
FIG. 2 depicts mean HbA1c (%) from baseline and vehicle control (ΔΔ %) of a long acting PYY analog in combination with a long acting GLP-1 analog
Figure 3:
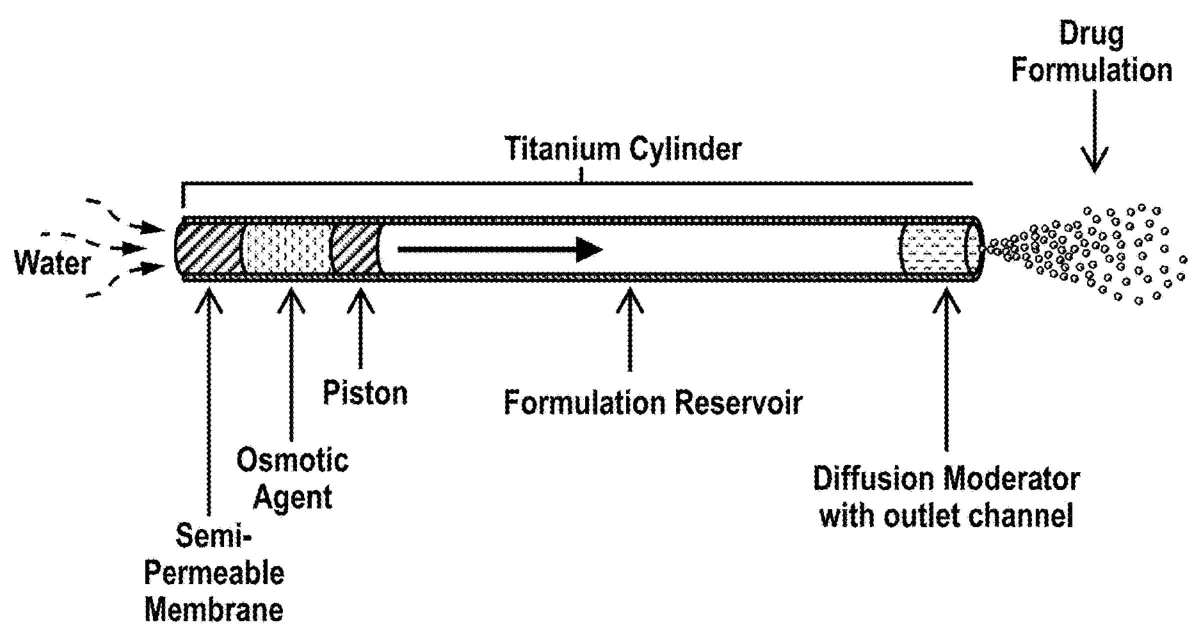
FIG. 3 depicts a cross-sectional diagram of a representative osmotic mini-pump for drug delivery.
Figure 7:
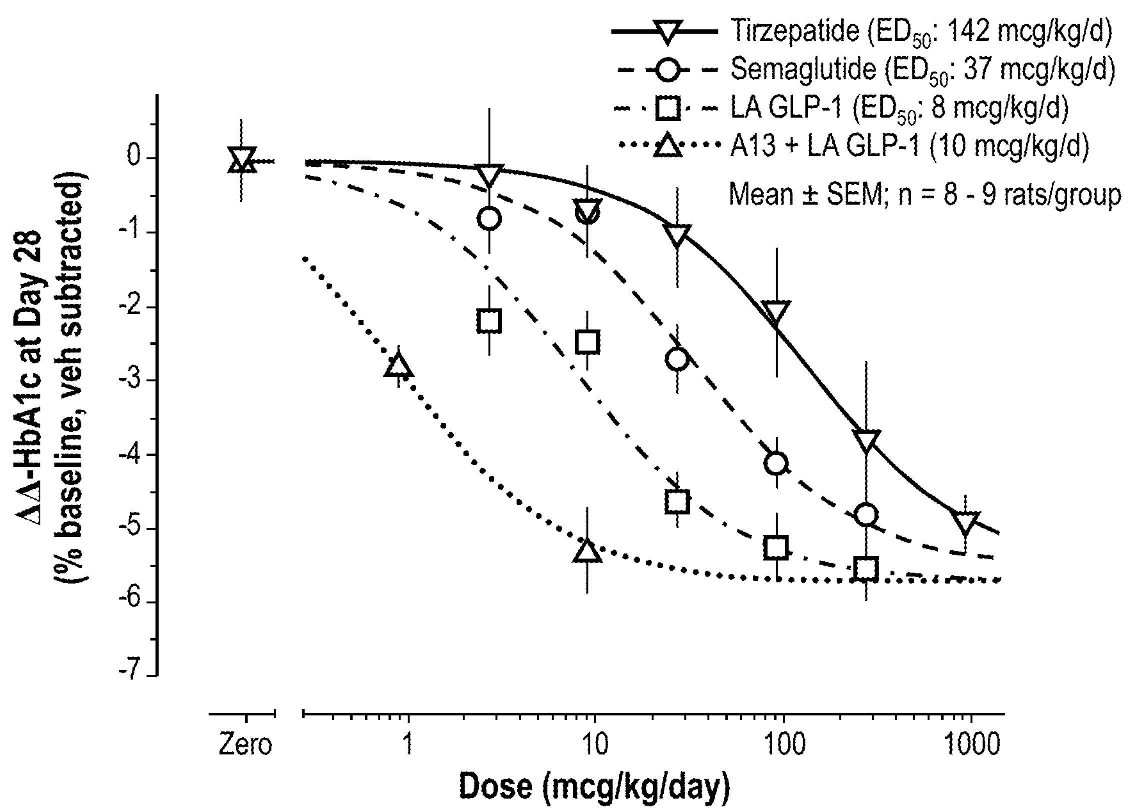
FIG. 7 is a graph depicting the antidiabetic effect in a Zucker diabetic fatty (ZDF) rat model of type 2 diabetes and highlighting that the combination of the PYY analog peptide A13 with a long acting GLP-1 receptor agonist is significantly more effective and potent than tirzepatide and semaglutide alone.

Example 8: Anti-Diabetic Efficacy PYY Analogs in in Combination with a GLP-1 Agonist in ZDF Rats Chronic studies were conducted to determine the antidiabetic effects of continuous administration of a PYY analog polypeptide in combination with a GLP-1 receptor agonist on HbA1c (a primary anti-diabetic parameter) after 27 days of treatment in Zucker Diabetic Fatty (ZDF) rats. Male ZDF rats were obtained at six (6) weeks of age (Charles River, Raleigh, N.C.) and used on study at eight (8) weeks old. Upon receipt, the rats were housed one animal per cage with free access to Purina 5008 chow (Lab Diet, St. Louis, Mo.) and water, maintained on a 12-hour light/dark cycle from 5:00 AM to 5:00 PM at 21° C. and 50% relative humidity and allowed to acclimate for nine (9) days before the start of the study. Blood samples were taken as pre-bleeds (Day −3) via tail vein to measure glucose levels and HbA1c. The ZDF rats were randomized into treatment groups (n=10/group) with similar mean HbA1c and glucose. They were subcutaneously (SC) implanted with Alzet osmotic mini-pumps (two (2) pumps/animal) containing either specified doses of PYY analog polypeptide and/or GLP-1 receptor agonist (10 mcg/kg/day) or vehicle (20% DMSO in water) (n=10 animals/treatment group). PYY analog whose PK supported every other day dosing were dosed by SC injection instead of mini-pump administration. All other procedures were the same as described for previous example. Blood samples were taken again on Days 14 and 27 (end of study) to measure glucose levels and HbA1c. Final whole blood samples were collected by cardiac puncture under isoflurane anesthesia (Day 27). HbA1c analysis was performed by using a Carolina Chemistries CLC720i Clinical Chemistry analyzer (Mindray Inc., Mahwah, N.Y.) with the protocol and method parameters as described by the manufacturer. HbA1c results expressed as the mean % change from baseline and vehicle control (ΔΔ) from the chronic combination studies of Compound A13 (SEQ ID NO: 13) with the GLP-1 receptor agonist are shown in FIG. 2. Comparative data with respect to tirzepatide and semaglutide is provided in FIG. 7.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polypeptide, comprising the amino acid sequence of SEQ ID NO: 90:

$X_0PX_2PX_4X_5PX_7X_8X_9X_{10}SPX_{13}X_{14}X_{15}X_{16}$ $RX_{18}X_{19}X_{20}$ $DX_{22}X_{23}$ $HX_{25}X_{26}X_{27}WLTRX_{32}RX_{34}$-(OH/$NH_2$) (SEQ ID NO: 90), or a pharmaceutically acceptable salt thereof, wherein:

$X_0$ is absent or K;
$X_2$ is K;
$X_4$ is E or K;
$X_5$ is A or K;
$X_7$ is G or K
$X_8$ is E, K, or k;
$X_9$ is D or K;
$X_{10}$ is A or K;
$X_{13}$ is E or K;
$X_{14}$ is E or K;
$X_{15}$ is L or W;
$X_{16}$ is D, E, K, N, Q, S, T, α-methylserine, or homoserine;
$X_{18}$ is K or Y;
$X_{19}$ is K or Y;
$X_{20}$ is A, D, E, K, k, or Dap,
$X_{22}$ is A, D, K, or L;
$X_{23}$ is K or R;
$X_{25}$ is K or Y;
$X_{26}$ is E, K, or L;
$X_{27}$ is K or N;
$X_{32}$ is K or Q;
$X_{34}$ is F, y, 3-pyridinylalanine, 4-pyridinylalanine, 4-carboxyphenylalanine, 4-fluorophenylalanine, 4-methylphenylalanine, N-methylphenylalanine, homophenylalanine, β-homotyrosine, homotyrosine, or N-methyltyrosine;

wherein when $X_0$, $X_2$, $X_4$, $X_5$, $X_7$, $X_8$, $X_{13}$, $X_{20}$, $X_{23}$, $X_{25}$, $X_{27}$, or $X_{32}$ are K, the lysine residue is optionally covalently bound to a lipophilic substituent, optionally via a spacer, and wherein when $X_8$ or $X_{20}$ are k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_9$ and $X_{13}$ or at positions $X_{16}$ and $X_{20}$ or at positions $X_{22}$ and $X_{26}$.

2. The isolated polypeptide of claim 1, comprising the amino acid sequence of SEQ ID NO: 95:

$PKPEX_5PGK_8DASPX_{13}EWX_{16}RYYX_{20}$DLRHYLNWL-TRQRF-(OH/$NH_2$) (SEQ ID NO: 95), or a pharmaceutically acceptable salt thereof, wherein:

$X_5$ is A or K;
$X_{13}$ is E or K;
$X_{16}$ is D, E, K, or N;
$X_{20}$ is A, D, E, K, or k; and wherein when $X_5$, $X_{13}$, or $X_{20}$ are K, the lysine residue is optionally covalently bound to a lipophilic substituent, optionally via a spacer, wherein $K_8$ is optionally covalently bound to a lipophilic substituent, optionally via a spacer, and wherein when $X_{20}$ is k, the D-lysine residue is optionally covalently bound to a lipophilic substituent, optionally via a spacer, provided that the polypeptide comprises at least one residue covalently bound to lipophilic substituent, optionally via a spacer; and wherein the polypeptide optionally further comprises a lactam bridge formed via an amide bond between the side chains of a lysine and an aspartic acid or between the side chains of a lysine and a glutamic acid, wherein the residues that form the lactam bridge are located at positions $X_{16}$ and $X_{20}$.

3. The isolated polypeptide of claim 1, wherein when $X_{15}$ is L, $X_{22}$ is A.

4. The isolated polypeptide of claim 1, wherein when $X_{16}$ is N, $X_{20}$ is not A.

5. The isolated polypeptide of claim 1, wherein when $X_8$ is E, $X_5$ is K and $X_{20}$ is K, and the lysine residue at either of $X_5$ or $X_{20}$ is covalently bound to a lipophilic substituent, optionally via a spacer.

6. The isolated polypeptide of claim 1, wherein $X_{34}$ is F.

7. The isolated polypeptide of claim 1, wherein $X_8$ is K covalently bound to a lipophilic substituent, optionally via a spacer.

8. The isolated polypeptide of claim 1, wherein the lipophilic substituent is covalently bound to the isolated polypeptide via a spacer, and wherein the lipophilic substituent and spacer are of Formula II:

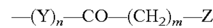

$$—(Y)_n—CO—(CH_2)_m—Z \quad \text{Formula II}$$

wherein,
Y is selected from the group consisting of γGlu, Asp, Lys and Gly;
Z is $—CH_3$ or $—CO_2H$;
m is from 4 to 24; and
n is from 1 to 10.

9. The isolated polypeptide of claim 8, wherein Y is γGlu, and n is 2.

10. An isolated polypeptide comprising the amino acid sequence of any of SEQ ID NOs: 1 to 78, or a pharmaceutically acceptable salt thereof.

11. The isolated polypeptide of claim 10 comprising the amino acid sequence of SEQ ID NO: 13, or a pharmaceutically acceptable salt thereof.

12. The isolated polypeptide of claim 10 comprising the amino acid sequence of SEQ ID NO: 24, or a pharmaceutically acceptable salt thereof.

13. The isolated polypeptide of claim 10 comprising the amino acid sequence of SEQ ID NO: 42, or a pharmaceutically acceptable salt thereof.

14. The isolated polypeptide of claim 10 comprising the amino acid sequence of SEQ ID NO: 43, or a pharmaceutically acceptable salt thereof.

15. A pharmaceutical composition comprising the isolated polypeptide of claim 1, or a pharmaceutically acceptable salt thereof, and a pharmaceutically acceptable adjuvant, carrier, or vehicle.

16. A pharmaceutical combination comprising the isolated polypeptide of claim 1, or a pharmaceutically acceptable salt thereof, and a GLP-1 receptor agonist.

17. An osmotic delivery device, comprising the isolated polypeptide of claim 1.

18. A method of treating obesity in a human subject, providing weight loss to the human subject, or suppressing appetite in the human subject, comprising administering to the subject a pharmaceutical composition comprising the isolated polypeptide of claim 1.

19. A method of treating diabetes in a human subject, comprising administering to the subject a pharmaceutical composition comprising the isolated polypeptide of claim 1.

20. A method of treating nonalcoholic fatty liver disease (NAFLD) and/or nonalcoholic steatohepatitis (NASH) in a human subject, comprising administering to the subject a pharmaceutical composition comprising the isolated polypeptide of claim 1.

* * * * *